United States Patent
Diels et al.

(10) Patent No.: US 10,017,509 B2
(45) Date of Patent: Jul. 10, 2018

(54) MACROCYLIC PYRIMIDINE DERIVATIVES

(71) Applicant: Janssen Pharmaceutica NV, Beerse (BE)

(72) Inventors: Gaston Stanislas Marcella Diels, Beerse (BE); Bruno Schoentjes, Ville d'Avray (FR); Matthias Luc Aime Versele, Leuven (BE); Didier Jean-Claude Berthelot, La Neuville Chant d'Oisel (FR); Marc Willems, Vosselaar (BE); Marcel Viellevoye, Breda (NL); Werner Constant Johan Embrechts, Beerse (BE); Berthold Wroblowski, Vosselaar (BE); Lieven Meerpoel, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/300,956

(22) PCT Filed: Apr. 2, 2015

(86) PCT No.: PCT/EP2015/057399
§ 371 (c)(1),
(2) Date: Sep. 30, 2016

(87) PCT Pub. No.: WO2015/150555
PCT Pub. Date: Oct. 8, 2015

(65) Prior Publication Data
US 2017/0022202 A1     Jan. 26, 2017

(30) Foreign Application Priority Data

Apr. 3, 2014  (EP) .................................. 14163443
Sep. 5, 2014  (EP) .................................. 14183747

(51) Int. Cl.
*C07D 471/22* (2006.01)
*C07D 498/22* (2006.01)

(52) U.S. Cl.
CPC ......... *C07D 471/22* (2013.01); *C07D 498/22* (2013.01)

(58) Field of Classification Search
CPC .......................... C07D 471/22; C07D 498/22
See application file for complete search history.

(56) References Cited

FOREIGN PATENT DOCUMENTS

| | | |
|---|---|---|
| CN | 101360751 A | 2/2009 |
| CN | 101365703 A | 2/2009 |
| WO | WO 2004/078682 A2 | 9/2004 |
| WO | 2004084898 A1 | 10/2004 |
| WO | 2004105765 A1 | 12/2004 |
| WO | 2005058318 A1 | 6/2005 |
| WO | 2005058913 A1 | 6/2005 |
| WO | 2006061415 A1 | 6/2006 |
| WO | 2006061417 A3 | 6/2006 |
| WO | 2007003525 A3 | 1/2007 |
| WO | WO 2007/058627 A1 | 5/2007 |
| WO | WO 2007/059628 A1 | 5/2007 |
| WO | 2008155421 A3 | 12/2008 |
| WO | 2009016132 A1 | 2/2009 |
| WO | 2009112439 A1 | 9/2009 |
| WO | WO 2009112439 * | 9/2009 |
| WO | 2009150230 A1 | 12/2009 |
| WO | 2010138666 A1 | 12/2010 |
| WO | 2011008788 A1 | 1/2011 |
| WO | 2011051282 A1 | 5/2011 |

OTHER PUBLICATIONS

Ben-Zvi, Han, et al., Hydroxychloroquine: From Malaria to Auto-immunity, Clinic Rev Allerg Immunol, Jan. 8, 2011, 145-153, 42.
Browne, Gareth, et al., Regulation of peptide-chain elongation in mammalian cells, European Journal of Biochemistry, Oct. 3, 2002, 5360-5368, 269.
Burger, Matthew, et al., Synthesis and in Vitro and in Vivo Evaluation of Phosphoinositide-3-kinase Inhibitors, Medicinal Chemistry Letters, Oct. 13, 2010, 34-38, 2.
Goto, Jiro, et al., Studies of 7,B-[2-(Aminoaryl)Acetamido]-Cephalosporin Derivatives—I. Synthesis and Structure-Activity Relationships in the Aminopyridine Series, The journal of antibiotics, Dec. 8, 1983, 532-542, vol. XXXVII No. 5.
Sato, Hiroki, et al., Structure-Activity Relationships of 1-Methyl-2-(5-phenylpyrrolidin-3-ylthio)carbapenems, Bioorganic & Medicinal Chemistry, Nov. 30, 2001, 1595-1610, 10.
Jin, Shengkan, et al., Metabolic catastrophe as a means to cancer cell death, Journal of Cell Science, Oct. 17, 2006, 379-383, 120(3).
Kavalali, Ege, T., et al., Synaptic Mechanisms Underlying Rapid Antidepressant Action of Ketamine, Am J Psychiatry, Nov. 2012, 1150-1156, 169.

(Continued)

*Primary Examiner* — Bruck Kifle

(57) ABSTRACT

The present invention relates to substituted macrocylic pyrimidine derivatives of Formula (I)

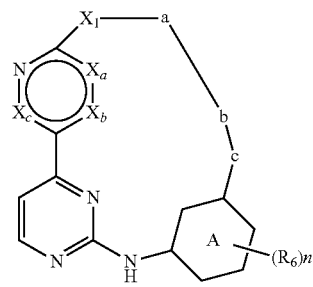

wherein the variables have the meaning defined in the claims. The compounds according to the present invention have EF2K inhibitory activity and optionally also Vps34 inhibitory activity. The invention further relates to processes for preparing such novel compounds, pharmaceutical compositions comprising said compounds as an active ingredient as well as the use of said compounds as a medicament.

12 Claims, No Drawings

(56) References Cited

OTHER PUBLICATIONS

Leprivier, Gabriel, et al., The eEF2 Kinase Confers Resistance to Nutrient Deprivation by Blocking Translation Elongation, Cell, May 23, 2013, 1064-1079, 153.

Maiuri, MC., et al., Control of autophagy by oncogenes and tumor suppressor genes, cell Death and Differentiation, Sep. 19, 2008, 87-93, 16.

O'Neill, Paul M., et al., The Effect of Fluorine Substitution on the Metabolism and Antimalarial Activity of Amodiaquine, Journal of Medical Chemistry, Nov. 19, 1993, 37, 37.

Parry, Paul R., et al., Functionalized Pyridylboronic Acids and Their Suzuki Cross-Coupling Reactions to Yield Novel Heteroarylpyridines, Journal of Organic Chemistry, 2002, pp. 7541-7543, vol. 67.

Amaravadi, Ravi, K., Principles and Current Strategies for Targeting Autophagy for Cancer Treatment, Clin Cancer Res, Feb. 15, 2011, 654-666, 17(4).

Thompson, Mark J., et al., Design, Synthesis, and Structure-Activity Relationship of Indole-3-glyoxylamide Libraries Possessing Highly Potent Activity in a Cell Line Model of Prion Disease, Journal of Medicinal Chemistry, Oct. 20, 2009, 7503-7511, 7503-7511.

Halt, William, et al., A Matterof Life or Death (or Both): Understanding Autophagy in Cancer, Clin cancer Research, Apr. 1, 2006, 1961-1965, 12(7).

Poulsen, Anders, et al., Journal of Molecular Modeling, Springer, DE, vol. 19, No. 1, pp. 119-130 XP035158034.

\* cited by examiner

MACROCYLIC PYRIMIDINE DERIVATIVES

CROSS REFERENCE TO RELATED APPLICATIONS

This application is a national stage application of International Patent Application No. PCT/EP2015/057399, filed 2 Apr. 2015, which claims priority from EPO Patent Application No. 14183747.6, filed 5 Sep. 2014 and EPO Patent Application No. 14163443.6, filed 3 Apr. 2014. The complete disclosures of the aforementioned related patent applications are hereby incorporated herein by reference for all purposes.

FIELD OF THE INVENTION

The present invention relates to substituted macrocylic pyrimidine derivatives having EF2K inhibitory activity and optionally also Vps34 inhibitory activity. The invention further relates to processes for preparing such compounds, pharmaceutical compositions comprising said compounds as an active ingredient as well as the use of said compounds as a medicament.

BACKGROUND OF THE INVENTION

In all eukaryotic cell types, protein elongation is a critical and energetically expensive step in the synthesis of new proteins. The rate of protein elongation is therefore strictly regulated to coordinate the availability of resources (energy, amino acids) with the demand for newly synthesised proteins. Eukaryotic elongation factor 2 (EF2) is essential for protein elongation: its affinity for the ribosome, and hence protein elongation rate, is controlled by its phosphorylation state. Phosphorylation of eEF2 at Threonine 56 by the elongation factor 2 kinase (EF2K or eEF2K) decreases the affinity of EF2 for the ribosome, and reduces protein elongation rates (Browne et al., *Eur J Biochem.* 2002, 269(22): 5360-5368). This regulation is critical under various forms of cellular stress, such as nutrient limitation and hypoxia, or conditions of increased energy expenditure, such as muscle exercise. In addition, local subcellular regulation of EF2 phosphorylation by EF2K at nerve growth cones or at the synapse ensures preferential translation of certain nerve growth factors and neurotransmitters. Dysregulation of EF2 (Thr56) phosphorylation has been associated with several devastating pathologies, including cancer and depression. Tumour cells often experience various forms of stress (hypoxia, nutrient deprivation), and therefore activate eEF2K activity to balance protein elongation rates with the high demand for de novo protein synthesis. Indeed, EF2 is highly phosphoryated in tumour tissue compared to normal tissue as an adaptive response to nutrient limitation (Leprivier et al., *Cell* 2013, 153(5):1064-1079). Deregulation of this control through inhibition of eEF2K is thought to fatally increase energy expenditure in tumour cells, and represent an anti-tumour strategy through induction of metabolic crisis (Hait et al., *Clin Cancer Res.* 2006, 12:1961-1965; Jin et al., *J Cell Sci.* 2007, 120(3):379-83; Leprivier et al., *Cell* 2013, 153(5):1064-1079). Increased local translation of synaptic proteins such as BDNF (brain-derived neurotrophic factor) plays a critical role in the fast-acting anti-depressant activity of NMDA (N-Methyl-D-aspartic acid) antagonists (such as ketamine); reduced phosphorylation levels of EF2 are thought to be critical to enable BDNF translation, and hence EF2K inhibition has been proposed as a fast-acting anti-depressant therapy (Kavalali et al., *Am J Psychiatry* 2012, 169(11):1150-1156). Consistent with its role under hypoxia and starvation, EF2K is activated by direct phosphorylation by AMPK, whereas EF2K is regulated through inhibitory phosphorylation by growth and cell cycle kinases, such as S6K and CDK2. In addition, EF2K is a Ca2+/calmodulin-dependent kinase; this regulation may be key for the synaptic regulation of EF2K. (Browne et al., *Eur J Biochem.* 2002, 269(22):5360-5368).

EF2K is an atypical kinase: the primary sequence of its catalytic domain is only remotely related to that of canonical kinases, such as serine/threonine kinases, tyrosine kinases, or lipid kinases. Compounds with EF2K inhibitory activity, may prevent the stress-induced phosphorylation of eEF2 in cells and in xenografted tumours in mice. In addition to strict regulation of protein synthesis under cellular stress as described above, many cell types utilize autophagy as a recycling mechanism to cope with low nutrient availability, hypoxia and other forms of cellular stress. Autophagy is a catabolic process, in which cytosolic content, including proteins, protein aggregates and entire organelles are engulfed in vesicles (autophagosomes) which fuse to lysosomes to enable degradation of macromolecules to recuperate building blocks (amino acids, fatty acids, nucleotides) and energy (Hait et al., *Clin Cancer Res.* 2006, 12:1961-1965). The double membrane of autophagosomes critically consists of phosphatidylinositol-(3)-phosphate [PI(3)P], the product of the class III PI3K, Vps34 (also called PIK3C3). Vps34, and the adaptor protein, Beclin1, are both essential for autophagy in mammalian cells (Amaravadi et al., *Clin Cancer Res.* 2011, 17:654-666). Autophagy is upregulated in tumors, and inhibition of autophagy using the lysosomotropic agent, chloroquine (which inhibits the fusion of lysosomes to autophagosomes), or RNAi approaches can impair tumorigenesis. Moreover, inhibition of autophagy has been shown to sensitize tumors to chemotherapeutic agents, radiation, proteasome inhibitors, and kinase inhibitors (such as the receptor tyrosine kinases EGFR, class I PI3K, mTOR, and Akt) (Amaravadi et al., *Clin Cancer Res.* 2011, 17:654-666). The clinical utility of chloroquine in treating patients with malaria, rheumatoid arthritis, lupus and HIV suggest potential utility of autophagy inhibitors for those pathologies as well (Ben-Zvi et al., *Clin Rev Allergy Immunol.* 2012, 42(2):145-53). Inhibition of the class III PI3K, Vps34, may inhibit autophagy in cancer cells under stress. Moreover it was found that cancer cells, partially deficient in autophagy through knockdown of Beclin, are especially sensitive to Vps34 inhibition, suggesting that autophagy-deficient tumors (e.g. because of mono-allelic deletion of beclin1, as frequently found in breast, ovarian and prostate cancer, or other genetic lesions (Maiuri et al., *Cell Death Differ.* 2009, 16(1):87-93) may be most susceptible to Vps34 inhibition.

WO 2009/112439 describes 4-aryl-2-anilino-pyrimidines as PLK kinase inhibitors.

There is a strong need for novel compounds which have EF2K inhibitory activity and optionally also have Vps34 inhibitory activity, thereby opening new avenues for the treatment of cancer. It is an object of the present invention to overcome or ameliorate at least one of the disadvantages of the prior art, or to provide a useful alternative. It is accordingly an object of the present invention to provide such novel compounds.

SUMMARY OF THE INVENTION

It has been found that the compounds of the present invention have EF2K inhibitory activity and optionally also have Vps34 inhibitory activity. The compounds according to the invention and the pharmaceutical compositions comprising such compounds may be useful for treating or preventing, in particular treating, diseases such as cancer, depression, and memory and learning disorders. In particular, the compounds according to the present invention and the pharmaceutical compositions thereof may be useful in the treatment of a haematological malignancy or solid tumour. In a specific embodiment said solid tumour is selected from the group consisting of glioblastoma, medulloblastoma, prostate cancer, breast cancer, ovarian cancer and colorectal cancer, and the like.

This invention concerns compounds of Formula (I)

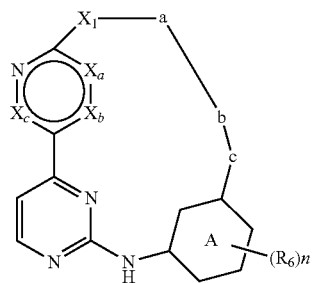

(I)

tautomers and stereochemically isomeric forms thereof, wherein $X_a$, $X_b$ and $X_c$ each independently represent CH or N;

—$X_1$— represents —(CHR$_{12}$)$_s$—NR$_1$—$X_e$—C$_{1-4}$alkanediyl-(SO$_2$)$_{p3}$— or —(CH$_2$)$_s$—O—$X_e$—C$_{1-4}$alkanediyl-(SO$_2$)$_{p3}$—; wherein each of said C$_{1-4}$alkanediyl moieties are optionally substituted with hydroxyl or hydroxyC$_{1-4}$alkyl;

—$X_e$— represents —C(R$_2$)$_2$— or —C(=O)—;

a represents —NR$_4$—C(=O)—[C(R$_{5b}$)$_2$]$_r$— or —NR$_4$—C(R$_{5b}$)$_2$—C(=O)— or —C(=O)—NR$_4$—C(R$_{5b}$)$_2$—;

b represents

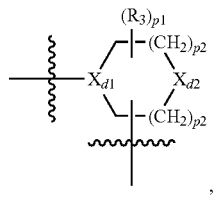

wherein said b ring may contain extra bonds to form a bridged ring system selected from 2,5-diazabicyclo[2.2.2]octanyl, 3,8-diazabicyclo[3.2.1]octanyl, 3,6-diazabicyclo[3.1.1]heptanyl, 3,9-diazabicyclo[3.3.1]nonyl;

$X_{d1}$ represents CH or N;

$X_{d2}$ represents CH$_2$ or NH;

provided that at least one of $X_{d1}$ and $X_{d2}$ represents nitrogen;

c represents a bond, —[C(R$_{5a}$)$_2$]$_m$—, —C(=O)—, —O—, —NR$_{5a}$—, —SO$_2$—, or —SO—, ring

represents phenyl or pyridyl;

R$_1$ represents hydrogen, C$_{1-4}$alkyl, C$_{2-4}$alkenyl, C$_{2-4}$alkynyl, cyanoC$_{1-4}$alkyl, —C(=O)—C$_{1-4}$alkyl, —C(=O)-haloC$_{1-4}$alkyl, hydroxyC$_{1-4}$alkyl, haloC$_{1-4}$alkyl, C$_{1-4}$alkyloxyC$_{1-4}$alkyl, haloC$_{1-4}$alkyloxyC$_{1-4}$alkyl, —C(=O)NR$_7$R$_8$, —SO$_2$—NR$_7$R$_8$, —SO$_2$—R$_9$, R$_{11}$, C$_{1-4}$alkyl substituted with R$_{11}$, —C(=O)—R$_{11}$, or —C(=O)—C$_{1-4}$alkyl-R$_{11}$;

each R$_2$ independently represents hydrogen, C$_{1-4}$alkyl, C$_{1-4}$alkyl substituted with C$_{3-6}$cycloalkyl, hydroxy C$_{1-4}$alkyl, C$_{1-4}$alkyloxyC$_{1-4}$alkyl, carboxyl, —C(=O)—O—C$_{1-4}$alkyl wherein C$_{1-4}$alkyl is optionally substituted with C$_{1-4}$alkyloxy, —C(=O)—NH$_2$, —C(=O)—NH(C$_{1-4}$alkyl) wherein C$_{1-4}$alkyl is optionally substituted with C$_{1-4}$alkyloxy, or —C(=O)—N(C$_{1-4}$alkyl)$_2$ wherein each C$_{1-4}$alkyl is optionally substituted with C$_{1-4}$alkyloxy;

or R$_1$ and one R$_2$ are taken together to form C$_{1-4}$alkanediyl or C$_{2-4}$alkenediyl, each of said C$_{1-4}$alkanediyl and C$_{2-4}$alkenediyl optionally being substituted with 1 to 4 substituents each independently selected from hydroxyl, oxo, halo, cyano, N$_3$, hydroxyC$_{1-4}$alkyl, —NR$_7$R$_8$, —SO$_2$—NR$_7$R$_8$, —NH—SO$_2$—NR$_7$R$_8$, —C(=O)—NR$_7$R$_8$, or —NH—C(=O)—NR$_7$R$_8$;

or R$_1$ and R$_{12}$ are taken together to form C$_{1-4}$alkanediyl or C$_{2-4}$alkenediyl, each of said C$_{1-4}$alkanediyl and C$_{2-4}$alkenediyl optionally being substituted with 1 to 4 substituents each independently selected from hydroxyl, oxo, halo, cyano, N$_3$, hydroxyC$_{1-4}$alkyl, —NR$_7$R$_8$, —SO$_2$—NR$_7$R$_8$, —NH—SO$_2$—NR$_7$R$_8$, —C(=O)—NR$_7$R$_8$, or —NH—C(=O)—NR$_7$R$_8$;

each R$_3$ independently represents hydrogen; oxo; hydroxyl; carboxyl; —NR$_{3a}$R$_{3b}$; —C(=O)—NR$_{3a}$R$_{3b}$; hydroxyC$_{1-4}$alkyl; haloC$_{1-4}$alkyl; —(C=O)—C$_{1-4}$alkyl; —C(=O)—O—C$_{1-4}$alkyl wherein said C$_{1-4}$alkyl may optionally be substituted with phenyl; C$_{1-4}$alkyl optionally substituted with cyano, carboxyl, C$_{1-4}$alkyloxy, —C(=O)—O—C$_{1-4}$alkyl, —O—C(=O)—C$_{1-4}$alkyl, —NR$_{3e}$R$_{3f}$, —C(=O)—NR$_{3e}$R$_{3f}$, —SO$_2$—NR$_{3e}$R$_{3f}$, Q, —C(=O)-Q, or —SO$_2$-Q; hydroxyC$_{1-4}$alkyloxyC$_{1-4}$alkyl; C$_{1-4}$alkyloxyhydroxyC$_{1-4}$alkyl; hydroxyC$_{1-4}$alkyloxyhydroxyC$_{1-4}$alkyl; or C$_{1-4}$alkyloxyC$_{1-4}$alkyl optionally substituted with cyano, carboxyl, C$_{1-4}$alkyloxy, —C(=O)—O—C$_{1-4}$alkyl, —O—C(=O)—C$_{1-4}$alkyl, —NR$_{3e}$R$_{3f}$, —C(=O)—NR$_{3e}$R$_{3f}$, —SO$_2$—NR$_{3e}$R$_{3f}$, R$_{10}$, —C(=O)—R$_{10}$, or —SO$_2$—R$_{10}$;

or two R$_3$ substituents attached to the same carbon atom are taken together to form C$_{2-5}$alkanediyl or —(CH$_2$)$_p$—O—(CH$_2$)$_p$—;

each R$_{3a}$ and R$_{3b}$ independently represent hydrogen; —(C=O)—C$_{1-4}$alkyl; —SO$_2$—NR$_{3c}$R$_{3d}$; or C$_{1-4}$alkyl optionally substituted with C$_{1-4}$alkyloxy; or R$_{3a}$ and R$_{3b}$ are taken together with the nitrogen to which they are attached to form a 4 to 7 membered saturated monocyclic heterocyclic ring which optionally contains 1 or 2 further heteroatoms selected from N, O or SO$_2$, said heterocyclic ring being optionally substituted with 1 to 4 substituents each independently selected from C$_{1-4}$alkyl, halo, hydroxyl, or haloC$_{1-4}$alkyl;

each $R_{3c}$ and $R_{3d}$ independently represent hydrogen, $C_{1-4}$alkyl or —(C=O)—$C_{1-4}$alkyl; or $R_{3c}$ and $R_{3d}$ are taken together with the nitrogen to which they are attached to form a 4 to 7 membered saturated monocyclic heterocyclic ring which optionally contains 1 or 2 further heteroatoms selected from N, O or $SO_2$, said heterocyclic ring being optionally substituted with 1 to 4 substituents each independently selected from $C_{1-4}$alkyl, halo, hydroxyl, or halo$C_{1-4}$alkyl;

each $R_{3e}$ and $R_{3f}$ independently represent hydrogen, $C_{1-4}$alkyl optionally substituted with $C_{1-4}$alkyloxy, —(C=O)—$C_{1-4}$alkyl, or —$SO_2$—$NR_{3c}R_{3d}$;

$R_4$ represents hydrogen, $C_{1-4}$alkyl or $C_{1-4}$alkyloxy$C_{1-4}$alkyl;

each $R_{5a}$ independently represents hydrogen or $C_{1-4}$alkyl; or two $R_{5a}$ substituents attached to the same carbon atom are taken together to form $C_{2-5}$alkanediyl or —$(CH_2)_p$—O—$(CH_2)_p$—;

$R_{5a'}$ represents hydrogen or $C_{1-4}$alkyl;

each $R_{5b}$ independently represents hydrogen; $C_{1-4}$alkyl; $C_{1-4}$alkyl substituted with $NR_{5b1}R_{5b2}$; $C_{1-4}$alkyloxy$C_{1-4}$alkyl; hydroxy$C_{1-4}$alkyl; hydroxyl; $C_{3-6}$cycloalkyl; or phenyl optionally substituted with $C_{1-4}$alkyl, halo, hydroxyl or $C_{1-4}$alkyloxy; or two $R_{5b}$ substituents attached to the same carbon atom are taken together to form $C_{2-5}$alkanediyl or —$(CH_2)_p$—O—$(CH_2)_p$—;

$R_{5b1}$ and $R_{5b2}$ independently represent hydrogen, $C_{1-4}$alkyl optionally substituted with $C_{1-4}$alkyloxy, —(C=O)—$C_{1-4}$alkyl, or —$SO_2$—$NR_{5b3}R_{5b4}$;

$R_{5b3}$ and $R_{5b4}$ independently represent hydrogen, $C_{1-4}$alkyl or —(C=O)—$C_{1-4}$alkyl; or $R_{5b3}$ and $R_{5b4}$ are taken together with the nitrogen to which they are attached to form a 4 to 7 membered saturated monocyclic heterocyclic ring which optionally contains 1 or 2 further heteroatoms selected from N, O or $SO_2$, said heterocyclic ring being optionally substituted with 1 to 4 substituents each independently selected from $C_{1-4}$alkyl, halo, hydroxyl, or halo$C_{1-4}$alkyl;

each $R_6$ independently represents hydrogen, halo, hydroxyl, carboxyl, cyano, $C_{1-4}$alkyl, hydroxy$C_{1-4}$alkyl, halo$C_{1-4}$alkyl, $C_{2-4}$alkenyl, $C_{2-4}$alkynyl, —$NR_{6a}R_{6b}$, or —C(=O)$NR_{6a}R_{6b}$;

each $R_{6a}$ and $R_{6b}$ independently represent hydrogen or $C_{1-4}$alkyl;

each $R_7$ and $R_8$ independently represent hydrogen, $C_{1-4}$alkyl, halo$C_{1-4}$alkyl, or $C_{3-6}$cycloalkyl; or $R_7$ and $R_8$ are taken together with the nitrogen to which they are attached to form a 4 to 7 membered saturated monocyclic heterocyclic ring which optionally contains 1 further heteroatom selected from N, O or $SO_2$, said heterocyclic ring being optionally substituted with 1 to 4 substituents each independently selected from $C_{1-4}$alkyl, halo, hydroxyl, or halo$C_{1-4}$alkyl;

$R_9$ represents $C_{1-4}$alkyl, halo$C_{1-4}$alkyl, or $C_{3-6}$cycloalkyl;

each $R_{10}$ independently represents a 4 to 7 membered saturated monocyclic heterocyclic ring containing up to 2 heteroatoms selected from N, O or $SO_2$, said heterocyclic ring being optionally substituted with 1 to 4 substituents each independently selected from $C_{1-4}$alkyl, halo, hydroxyl or halo$C_{1-4}$alkyl;

each $R_{11}$ independently represents $C_{3-6}$cycloalkyl, phenyl, or a 4 to 7 membered monocyclic heterocyclic ring containing up to 3 heteroatoms selected from N, O or $SO_2$, said heterocyclic ring being optionally substituted with 1 to 4 substituents each independently selected from $C_{1-4}$alkyl, halo, hydroxyl, or halo$C_{1-4}$alkyl;

each $R_{12}$ independently represents hydrogen or $C_{1-4}$alkyl;

Q represents a 4 to 7 membered saturated monocyclic heterocyclic ring containing up to 3 heteroatoms selected from N, O or $SO_2$, said heterocyclic ring being optionally substituted with 1 to 4 substituents each independently selected from $C_{1-4}$alkyl, halo, hydroxyl or halo$C_{1-4}$alkyl;

n represents an integer of value 1 or 2;

m represents an integer of value 1 or 2;

p represents an integer of value 1 or 2;

p1 represents an integer of value 1 or 2;

each p2 independently represents an integer of value 0, 1 or 2;

r represents an integer of value 0, 1 or 2;

each p3 independently represents an integer of value 0 or 1;

each s independently represents an integer of value 0, 1 or 2;

and the pharmaceutically acceptable addition salts, and the solvates thereof.

The present invention also concerns methods for the preparation of compounds of the present invention and pharmaceutical compositions comprising them.

The compounds of the present invention were found to have EF2K inhibitory activity and optionally also have Vps34 inhibitory activity. Therefore the compounds of the present invention may be useful in the treatment or prevention, in particular in the treatment, of diseases such as cancer, depression, neuroplasticity (synaptic plasticity and non-synaptic plasticity), and memory and learning disorders. In particular, the compounds according to the present invention and the pharmaceutical compositions thereof may be useful in the treatment of a haematological malignancy or solid tumour. In a specific embodiment said solid tumour is selected from the group consisting of glioblastoma, medulloblastoma, prostate cancer, breast cancer, ovarian cancer and colorectal cancer, and the like.

In view of the aforementioned pharmacology of the compounds of Formula (I) and pharmaceutically acceptable addition salts, and solvates thereof, it follows that they may be suitable for use as a medicament.

In particular the compounds of Formula (I) and pharmaceutically acceptable addition salts, and solvates thereof, may be suitable in the treatment or prevention, in particular in the treatment, of cancer.

The present invention also concerns the use of compounds of Formula (I) and pharmaceutically acceptable addition salts, and solvates thereof, for the manufacture of a medicament for the treatment or prevention, in particular treatment, of diseases such as cancer, depression, neuroplasticity (synaptic plasticity and non-synaptic plasticity), and memory and learning disorders.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

Combinations of substituents and/or variables are permissible only if such combinations result in chemically stable compounds. "Stable compound" is meant to indicate a compound that is sufficiently robust to survive isolation to a useful degree of purity from a reaction mixture, and formulation into a therapeutic agent.

When any variable occurs more than one time in any constituent or in any Formula (e.g. Formula (I)), its definition in each occurrence is independent of its definition at every other occurrence.

Whenever a radical or group is defined as "optionally substituted" in the present invention, it is meant that said radical or group is unsubstituted or is substituted.

Lines drawn from substituents into ring systems indicate that the bond may be attached to any of the suitable ring atoms.

Whenever the term "substituted with 1 to 4 substituents" is used in the present invention, it is meant, to indicate that from 1 to 4 hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

Whenever the term "substituted with" without an indication of the number of substituents is used in the present invention, it is meant, unless otherwise is indicated or is clear from the context, to indicate that one 1 hydrogen, on the atom or radical indicated in the expression using "substituted" is replaced with a substituent from the indicated group, provided that the substitution results in a chemically stable compound, i.e. a compound that is sufficiently robust to survive isolation to a useful degree of purity from a reaction mixture, and formulation into a therapeutic agent. For example "$C_{1-4}$alkyl substituted with cyano" means a $C_{1-4}$alkyl group substituted with one cyano. "$C_{1-4}$alkyl optionally substituted with cyano" means unsubstituted $C_{1-4}$alkyl or $C_{1-4}$alkyl substituted with one cyano.

The prefix "$C_{x-y}$" (where x and y are integers) as used herein refers to the number of carbon atoms in a given group. Thus, a $C_{1-4}$alkyl group contains from 1 to 4 carbon atoms, a $C_{3-6}$cycloalkyl group contains from 3 to 6 carbon atoms, a $C_{1-4}$alkyloxy group contains from 1 to 4 carbon atoms, and so on.

The term "halo" as a group or part of a group is generic for fluoro, chloro, bromo, iodo unless otherwise is indicated or is clear from the context.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear or branched alkyl groups with between 1 and 4 carbon atoms, and thus includes methyl, ethyl, n-propyl, i-propyl, 2-methyl-ethyl, butyl and its isomers (e.g. n-butyl, isobutyl and tert-butyl), and the like.

The term "$C_{1-4}$alkyloxy" as a group or part of a group refers to a radical having the Formula —$OR^c$ wherein $R^c$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The term "$C_{3-6}$cycloalkyl" alone or in combination, refers to a cyclic saturated hydrocarbon radical having from 3 to 6 carbon atoms. Non-limiting examples of suitable $C_{3-6}$cycloalkyl include cyclopropyl, cyclobutyl, cyclopentyl and cyclohexyl.

The term 'hydroxy$C_{1-4}$alkyl' as used herein as a group or part of a group refers to a $C_{1-4}$alkyl group as defined herein wherein one or more than one hydrogen atom is replaced with a hydroxyl group. The term 'hydroxy$C_{1-4}$alkyl' therefore includes monohydroxy$C_{1-4}$alkyl and also polyhydroxy$C_{1-4}$alkyl. There may be one, two, three or more hydrogen atoms replaced with a hydroxyl group, so the hydroxy$C_{1-4}$alkyl may have one, two, three or more hydroxyl groups. Examples of such groups include hydroxymethyl, hydroxyethyl, hydroxypropyl and the like.

In a particular embodiment 'hydroxy$C_{1-4}$alkyl' is limited to monohydroxy$C_{1-4}$alkyl.

The term 'hydroxy$C_{1-4}$alkyloxy' as used herein as a group or part of a group refers to a hydroxy$C_{1-4}$alkyl-O— group wherein "hydroxy$C_{1-4}$alkyl" is as defined before.

The term 'hydroxy$C_{1-4}$alkyloxy$C_{1-4}$alkyl' as used herein as a group or part of a group refers to a hydroxy$C_{1-4}$alkyl-O—$C_{1-4}$alkyl- group wherein "hydroxy$C_{1-4}$alkyl" and "$C_{1-4}$alkyl" are as defined before.

The term '$C_{1-4}$alkyloxyhydroxy$C_{1-4}$alkyl' as used herein as a group or part of a group refers to a $C_{1-4}$alkyl-O-hydroxy$C_{1-4}$alkyl- group wherein "hydroxy$C_{1-4}$alkyl" and "$C_{1-4}$alkyl" are as defined before.

The term 'hydroxy$C_{1-4}$alkyloxyhydroxy$C_{1-4}$alkyl' as used herein as a group or part of a group refers to a hydroxy$C_{1-4}$alkyl-O-hydroxy$C_{1-4}$alkyl- group wherein "hydroxy$C_{1-4}$alkyl" is as defined before.

The term 'halo$C_{1-4}$alkyl' as used herein as a group or part of a group refers to a $C_{1-4}$alkyl group as defined herein wherein one or more than one hydrogen atom is replaced with a halogen. The term 'halo$C_{1-4}$alkyl' therefore includes monohalo$C_{1-4}$alkyl and also polyhalo$C_{1-4}$alkyl. There may be one, two, three or more hydrogen atoms replaced with a halogen, so the halo$C_{1-4}$alkyl may have one, two, three or more halogens. Examples of such groups include fluoroethyl, fluoromethyl, trifluoromethyl or trifluoroethyl and the like.

The term "cyano$C_{1-4}$alkyl" as used herein refers to a $C_{1-4}$alkyl group as defined herein which is substituted with one cyano group.

The term '$C_{1-4}$alkoxy$C_{1-4}$alkyl' as used herein as a group or part of a group refers to a $C_{1-4}$alkyl-O—$C_{1-4}$alkyl group wherein $C_{1-4}$alkyl is as defined herein. Examples of such groups include methoxyethyl, ethoxyethyl, propoxymethyl, butoxypropyl, and the like.

The term 'halo$C_{1-4}$alkyloxy' as used herein as a group or part of a group refers to a —O—$C_{1-4}$alkyl group as defined herein wherein one or more than one hydrogen atom is replaced with a halogen. The term 'halo$C_{1-4}$alkyloxy' therefore include monohalo$C_{1-4}$alkyloxy and also polyhalo $C_{1-4}$alkyloxy. There may be one, two, three or more hydrogen atoms replaced with a halogen, so the halo$C_{1-4}$alkyloxy may have one, two, three or more halogens. Examples of such groups include 1-fluoroethyloxy, 2-fluoroethyloxy, difluoromethoxy or trifluoromethoxy and the like.

The term 'halo$C_{1-4}$alkyloxy$C_{1-4}$alkyl' as used herein as a group or part of a group means $C_{1-4}$alkyl substituted with one halo$C_{1-4}$alkyloxy. The term 'halo$C_{1-4}$alkyloxy $C_{1-4}$alkyl' therefore refers to a halo$C_{1-4}$alkyloxy-$C_{1-4}$alkyl-group wherein "haloC$_{1-4}$alkyloxy" and "C$_{1-4}$alkyl" are as defined above. Examples of such groups include 1-fluoro-ethyloxymethyl, 2-fluoroethyloxymethyl, 2-(2,2,2-trifluoroethoxy)-ethyl and the like.

The term "C$_{2-4}$alkenyl" as used herein as a group or part of a group refers to a linear or branched hydrocarbon group containing from 2 to 4 carbon atoms and containing a carbon carbon double bond such as, but not limited to, ethenyl, propenyl, butenyl, and the like.

The term "C$_{2-4}$alkynyl" as used herein as a group or part of a group refers to a linear or branched hydrocarbon group having from 2 to 4 carbon atoms and containing a carbon carbon triple bond.

Examples of 4 to 7 membered saturated monocyclic heterocyclic rings containing up to 2 heteroatoms selected from N, O or SO$_2$ (e.g. in the definition of R$_{10}$), include, but are not limited to, morpholinyl, piperidinyl, tetrahydropyranyl, tetrahydrofuranyl, and the like.

4 to 7 membered monocyclic heterocyclic rings containing up to 3 heteroatoms selected from N, O or SO$_2$ (e.g. in the definition of R$_{11}$), include both aromatic and non-aromatic ring systems. This includes unsaturated, partially saturated and saturated heterocyclic ring systems. Examples include, but are not limited to, pyridinyl, pyrimidinyl, morpholinyl, piperidinyl, tetrahydropyranyl, tetrahydrofuranyl, and the like.

The term "C$_{1-4}$alkanediyl" as a group or part of a group defines bivalent straight or branched chained saturated hydrocarbon radicals having from 1 to 4 carbon atoms such as, for example, methylene or methanediyl, ethan-1,2-diyl, ethan-1,1-diyl or ethylidene, propan-1,3-diyl, propan-1,2-diyl, butan-1,4-diyl, and the like.

The term "C$_{2-5}$alkanediyl" as a group or part of a group defines bivalent straight or branched chained saturated hydrocarbon radicals having from 2 to 5 carbon atoms such as, for example, ethan-1,2-diyl, ethan-1,1-diyl or ethylidene, propan-1,3-diyl, propan-1,2-diyl, butan-1,4-diyl, pentan-1,5-diyl, pentan-1,1-diyl, 2-methylbutan-1,4-diyl, and the like.

The term "C$_{2-4}$alkenediyl" as a group or part of a group defines straight or branched chain bivalent hydrocarbon radicals having from 2 to 4 carbon atoms and having a double bond such as 1,2-ethenediyl, 1,3-propenediyl, 1,4-butenediyl, and the like.

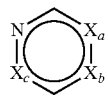

is an alternative representation for

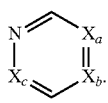

The bonds via which e.g. ring b is attached to the remainder of the molecule are indicated as:

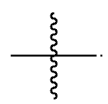

Whenever ring b is substituted with one or two R$_3$ substituents, those R$_3$ substituents may replace any hydrogen atom bound to a carbon or nitrogen atom in ring b, including atoms of the bridge, including NH and CH groups in the definition of X$_{d2}$, and including CH groups in the definition of X$_{d1}$. When two R$_3$ substituents are present, these may be present on the same or different atoms. For instance when X$_{d2}$ represents NH, then the R$_3$ substituent may be present on said nitrogen atom whenever possible. In said case, X$_{d2}$ represents NR$_3$. Or for instance, when X$_{d1}$ or X$_{d2}$ represent a carbon atom, then the R$_3$ substituent may be present on said carbon atom. In said case, X$_{d1}$ may represent CR$_3$ and X$_{d2}$ may represent CHR$_3$ or C(R$_3$)$_2$. Or for instance, when p2 is other than 0, the R$_3$ substituent may be present on any of the carbon atom represented by (CH$_2$)$_{p2}$.

Unless otherwise is indicated or is clear from the context, ring b can be attached to variable 'a' via replacement of a hydrogen atom on any carbon or nitrogen atom in ring b, including carbon and nitrogen atoms in the definition of X$_{d2}$.

In a particular embodiment, in the 'b substituent', the linker with the 'a substituent' is present on X$_{d2}$ or is present on a carbon atom in the alpha position of X$_{d2}$.

In a particular embodiment, in the 'b substituent', the linker with the 'a substituent' is present on X$_{d2}$.

In the present invention, the b ring is linked to the remainder of the molecule as follows

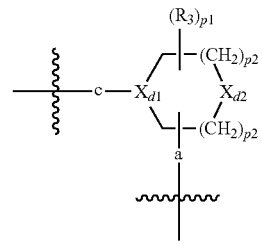

In the present invention, the a linker (-a-) is linked to the remainder of the molecule as depicted below:
—X$_1$—NR$_4$—C(=O)—[C(R$_{5b}$)$_2$]$_r$-b-;  —X$_1$—NR$_4$—C(R$_{5b}$)$_2$—C(=O)-b-;  —X$_1$—C(=O)—NR$_4$—C(R$_{5b}$)$_2$-b-.

In the present invention, X$_1$ being (CHR$_{12}$)$_s$—NR$_1$—X$_e$—C$_{1-4}$alkanediyl-(SO$_2$)$_{p3}$—  or  —(CH$_2$)$_s$—O—X$_e$—C$_{1-4}$alkanediyl-(SO$_2$)$_{p3}$— is attached to the remainder of the molecule as follows:

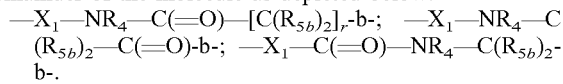

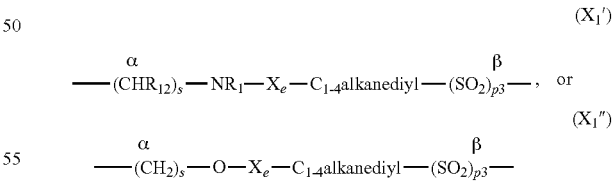

is attached with the carbon atom, the nitrogen atom (when s is 0 in Formula (X$_1$')) or the oxygen atom (when s is 0 in Formula (X$_1$'')) in position α to the ring containing X$_a$, X$_b$ and X$_c$, and is attached with the group in position β ((SO$_2$)$_{p3}$ or C$_{1-4}$alkanediyl (when p3 is 0)) to variable a. In both X$_1$ Formulas C$_{1-4}$alkanediyl is optionally substituted according to the scope.

For example when —X$_1$— represents (CHR$_{12}$)$_s$—NR$_1$—X$_e$—C$_{1-4}$alkanediyl-(SO$_2$)$_{p3}$—, a compound of Formula (I') is formed:

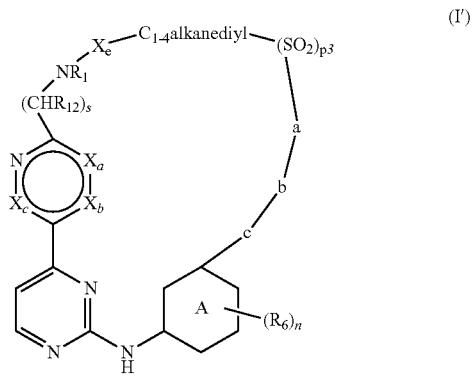
(I')

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compounds of the invention" as used herein, is meant to include the compounds of Formula (I) and pharmaceutically acceptable addition salts, and solvates thereof.

As used herein, any chemical Formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Whenever one of the ring systems, is substituted with one or more substituents, those substituents may replace any hydrogen atom bound to a carbon or nitrogen atom of the ring system.

Hereinbefore and hereinafter, the term "compound of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture. Atropisomers (or atropoisomers) are stereoisomers which have a particular spatial configuration, resulting from a restricted rotation about a single bond, due to large steric hindrance. For the compounds of the present invention this may be caused by the linker (—$X_1$-a-b-c-) of the macrocycle. All atropisomeric forms of the compounds of Formula (I) are intended to be included within the scope of the present invention. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds of Formula (I) may also exist in their tautomeric form. Such forms in so far as they may exist, are intended to be included within the scope of the present invention.

It follows that a single compound may exist in both stereoisomeric and tautomeric form.

For therapeutic use, salts of the compounds of Formula (I) and solvates thereof, are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove or hereinafter are meant to comprise the therapeutically active non-toxic acid and base addition salt forms which the compounds of Formula (I) and solvates thereof, are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as pharmaceutically acceptable addition salts thereof. Examples of such forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I) and pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, an element, in particular when mentioned in relation to a compound of Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^2$H, $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^2$H, $^3$H, and $^{11}$C and $^{18}$F. More preferably, the radioactive isotope is $^2$H. In particular, deuterated compounds are intended to be included within the scope of the present invention As used in the specification and the appended claims, the singular forms "a", "an" and "the" also include plural referents unless the context clearly dictates otherwise. For example, "a compound" means 1 compound or more than 1 compound.

In an embodiment, the present invention concerns novel compounds of Formula (I), tautomers and stereoisomeric forms thereof, wherein $X_a$, $X_b$ and $X_c$ each independently represent CH or N;
—$X_1$— represents —(CHR$_{12}$)$_s$—NR$_1$—$X_e$—C$_{1-4}$alkanediyl-(SO$_2$)$_{p3}$— or —(CH$_2$)$_s$—O—$X_e$—C$_{1-4}$alkanediyl-(SO$_2$)$_{p3}$—; wherein each of said C$_{1-4}$alkanediyl moieties are optionally substituted with hydroxyl or hydroxyC$_{1-4}$alkyl;
—$X_e$— represents —C(R$_2$)$_2$— or —C(=O)—;
a represents —NR$_4$—C(=O)—[C(R$_{5b}$)$_2$]$_r$— or —NR$_4$—C(R$_{5b}$)$_2$—C(=O)—;
b represents

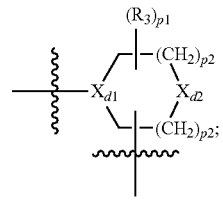

$X_{d1}$ represents CH or N;
$X_{d2}$ represents CH$_2$ or NH;
provided that at least one of $X_{d1}$ and $X_{d2}$ represents nitrogen;
c represents a bond, [C(R$_{5a}$)$_2$]$_m$—, —C(=O)—, —SO$_2$—, or —SO—;
ring

represents phenyl or pyridyl;
R$_1$ represents hydrogen, C$_{1-4}$alkyl, C$_{2-4}$alkenyl, C$_{2-4}$alkynyl, cyanoC$_{1-4}$alkyl, —C(=O)—C$_{1-4}$alkyl, —C(=O)-haloC$_{1-4}$alkyl, hydroxyC$_{1-4}$alkyl, haloC$_{1-4}$alkyl, C$_{1-4}$alkyloxyC$_{1-4}$alkyl, haloC$_{1-4}$alkyloxyC$_{1-4}$alkyl, —C(=O)NR$_7$R$_8$, —SO$_2$—NR$_7$R$_8$, —SO$_2$—R$_9$, R$_{11}$, C$_{1-4}$alkyl substituted with R$_{11}$, —C(=O)—R$_{11}$, or —C(=O)—C$_{1-4}$alkyl-R$_{11}$;
R$_2$ is hydrogen;
or R$_1$ and one R$_2$ are taken together to form C$_{1-4}$alkanediyl or C$_{2-4}$alkenediyl, each of said C$_{1-4}$alkanediyl and C$_{2-4}$alkenediyl optionally being substituted with 1 to 4 hydroxyl substituents;
or R$_1$ and R$_{12}$ are taken together to form C$_{1-4}$alkanediyl or C$_{2-4}$alkenediyl, each of said C$_{1-4}$alkanediyl and C$_{2-4}$alkenediyl optionally being substituted with 1 to 4 hydroxyl substituents;
each R$_3$ independently represents hydrogen; oxo; hydroxyl; carboxyl; —NR$_{3a}$R$_{3b}$; —C(=O)—NR$_{3a}$R$_{3b}$; hydroxyC$_{1-4}$alkyl; haloC$_{1-4}$alkyl; —(C=O)—C$_{1-4}$alkyl; —C(=O)—O—C$_{1-4}$alkyl wherein said C$_{1-4}$alkyl may optionally be substituted with phenyl; C$_{1-4}$alkyl optionally substituted with cyano, carboxyl, C$_{1-4}$alkyloxy, —C(=O)—O—C$_{1-4}$alkyl, —O—C(=O)—C$_{1-4}$alkyl, —NR$_{3e}$R$_{3f}$, —C(=O)—NR$_{3e}$R$_{3f}$, or —SO$_2$—NR$_{3e}$R$_{3f}$; hydroxyC$_{1-4}$alkyloxyC$_{1-4}$alkyl; C$_{1-4}$alkyloxyhydroxyC$_{1-4}$alkyl; hydroxyC$_{1-4}$alkyloxyhydroxyC$_{1-4}$alkyl; or C$_{1-4}$alkyloxyC$_{1-4}$alkyl optionally substituted with cyano, carboxyl, C$_{1-4}$alkyloxy, —C(=O)—O—C$_{1-4}$alkyl, —O—C(=O)—C$_{1-4}$alkyl, —NR$_{3e}$R$_{3f}$, —C(=O)—NR$_{3e}$R$_{3f}$, —SO$_2$—NR$_{3e}$R$_{3f}$, R$_{10}$, —C(=O)—R$_{10}$, or —SO$_2$—R$_{10}$;

each $R_{3a}$ and $R_{3b}$ independently represent hydrogen; —(C=O)—$C_{1-4}$alkyl; or $C_{1-4}$alkyl optionally substituted with $C_{1-4}$alkyloxy;

each $R_{3e}$ and $R_{3f}$ independently represent hydrogen, $C_{1-4}$alkyl optionally substituted with $C_{1-4}$alkyloxy, or —(C=O)—$C_{1-4}$alkyl;

$R_4$ represents hydrogen, $C_{1-4}$alkyl or $C_{1-4}$alkyloxy $C_{1-4}$alkyl;

each $R_{5a}$ independently represents hydrogen or $C_{1-4}$alkyl;

each $R_{5b}$ independently represents hydrogen; $C_{1-4}$alkyl; $C_{1-4}$alkyloxy$C_{1-4}$alkyl; hydroxy$C_{1-4}$alkyl; hydroxyl; $C_{3-6}$cycloalkyl; or phenyl optionally substituted with $C_{1-4}$alkyl, halo, hydroxyl or $C_{1-4}$alkyloxy;

each $R_6$ independently represents hydrogen, halo, hydroxyl, carboxyl, cyano, $C_{1-4}$alkyl, $C_{1-4}$alkyloxy $C_{1-4}$alkyl, hydroxy$C_{1-4}$alkyl, halo$C_{1-4}$alkyl, $C_{2-4}$alkenyl, $C_{2-4}$alkynyl, —$NR_{6a}R_{6b}$, or —C(=O)$NR_{6a}R_{6b}$;

each $R_{6a}$ and $R_{6b}$ independently represent hydrogen or $C_{1-4}$alkyl;

each $R_7$ and $R_8$ independently represent hydrogen, $C_{1-4}$alkyl, halo$C_{1-4}$alkyl, or $C_{3-6}$cycloalkyl; or $R_7$ and $R_8$ are taken together with the nitrogen to which they are attached to form a 4 to 7 membered saturated monocyclic heterocyclic ring which optionally contains 1 further heteroatom selected from N, O or $SO_2$, said heterocyclic ring being optionally substituted with 1 to 4 substituents each independently selected from $C_{1-4}$alkyl, halo, hydroxyl, or halo$C_{1-4}$alkyl;

$R_9$ represents $C_{1-4}$alkyl, halo$C_{1-4}$alkyl, or $C_{3-6}$cycloalkyl;

each $R_{10}$ independently represents a 4 to 7 membered saturated monocyclic heterocyclic ring containing up to 2 heteroatoms selected from N or O, said heterocyclic ring being optionally substituted with 1 to 4 substituents each independently selected from $C_{1-4}$alkyl, halo, hydroxyl or halo$C_{1-4}$alkyl;

each $R_{11}$ independently represents $C_{3-6}$cycloalkyl, phenyl, or a 4 to 7 membered monocyclic heterocyclic ring containing up to 3 heteroatoms selected from N or O, said heterocyclic ring being optionally substituted with 1 to 4 substituents each independently selected from $C_{1-4}$alkyl, halo, hydroxyl, or halo$C_{1-4}$alkyl;

each $R_{12}$ independently represents hydrogen or $C_{1-4}$alkyl; in particular $R_{12}$ represents hydrogen;

n represents an integer of value 1 or 2;
m represents an integer of value 1 or 2;
p1 represents an integer of value 1 or 2;
each p2 independently represents an integer of value 0, 1 or 2;
r represents an integer of value 0, 1 or 2;
each p3 independently represents an integer of value 0 or 1;
each s independently represents an integer of value 0, 1 or 2;
and the pharmaceutically acceptable addition salts, and the solvates thereof.

In an embodiment, the present invention concerns novel compounds of Formula (I), tautomers and stereoisomeric forms thereof, wherein $X_a$, $X_b$ and $X_c$ each independently represent CH or N;
—$X_1$— represents (CHR$_{12}$)$_s$—NR$_1$—$X_e$—$C_{1-4}$alkanediyl-(SO$_2$)$_{p3}$— or (CH$_2$)$_s$—O—$X_e$—$C_{1-4}$alkanediyl-(SO$_2$)$_{p3}$—; wherein each of said $C_{1-4}$alkanediyl moieties are optionally substituted with hydroxyl or hydroxy$C_{1-4}$alkyl;

—$X_e$— represents C(R$_2$)$_2$— or —C(=O)—;
a represents —NR$_4$—C(=O)[C(R$_{5b}$)$_2$]$_r$— or —NR$_4$—C(R$_{5b}$)$_2$—C(=O)—;

b represents

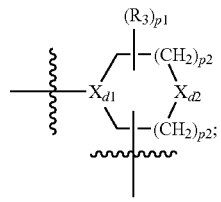

$X_{d1}$ represents CH or N; $X_{d2}$ represents NH;
c represents a bond, —[C(R$_{5b}$)$_2$]$_m$—, —C(=O)—, —SO$_2$—, or —SO—;

ring

represents phenyl or pyridyl;

$R_1$ represents hydrogen, $C_{1-4}$alkyl, $C_{2-4}$alkenyl, $C_{2-4}$alkynyl, cyano$C_{1-4}$alkyl, —C(=O)—$C_{1-4}$alkyl, —C(=O)-halo$C_{1-4}$alkyl, hydroxy$C_{1-4}$alkyl, halo$C_{1-4}$alkyl, $C_{1-4}$alkyloxy$C_{1-4}$alkyl, halo$C_{1-4}$alkyloxy$C_{1-4}$alkyl, —C(=O)NR$_7$R$_8$, —SO$_2$—NR$_7$R$_8$, —SO$_2$—R$_9$, R$_{11}$, $C_{1-4}$alkyl substituted with R$_{11}$, —C(=O)—R$_{11}$, or —C(=O)—$C_{1-4}$alkyl-R$_{11}$;

$R_2$ is hydrogen;
or $R_1$ and one $R_2$ are taken together to form $C_{1-4}$alkanediyl or $C_{2-4}$alkenediyl, each of said $C_{1-4}$alkanediyl and $C_{2-4}$alkenediyl optionally being substituted with 1 to 4 hydroxyl substituents;

each $R_3$ independently represents hydrogen; oxo; hydroxyl; carboxyl; —NR$_{3a}$R$_{3b}$; —C(=O)—NR$_{3a}$R$_{3b}$; hydroxy$C_{1-4}$alkyl; halo$C_{1-4}$alkyl; —(C=O)—$C_{1-4}$alkyl; —C(=O)—O—$C_{1-4}$alkyl wherein said $C_{1-4}$alkyl may optionally be substituted with phenyl; $C_{1-4}$alkyl optionally substituted with cyano, carboxyl, $C_{1-4}$alkyloxy, —C(=O)—O—$C_{1-4}$alkyl, —O—C(=O)—$C_{1-4}$alkyl, —NR$_{3e}$R$_{3f}$, —C(=O)—NR$_{3e}$R$_{3f}$ or —SO$_2$—NR$_{3e}$R$_{3f}$;
hydroxy$C_{1-4}$alkyloxy$C_{1-4}$alkyl; $C_{1-4}$alkyloxyhydroxy$C_{1-4}$alkyl;
hydroxy$C_{1-4}$alkyloxyhydroxy$C_{1-4}$alkyl; or
$C_{1-4}$alkyloxy$C_{1-4}$alkyl optionally substituted with cyano, carboxyl, $C_{1-4}$alkyloxy, —C(=O)—O—$C_{1-4}$alkyl, —O—C(=O)—$C_{1-4}$alkyl, —NR$_{3e}$R$_{3f}$, —C(=O)—NR$_{3e}$R$_{3f}$, —SO$_2$—NR$_{3e}$R$_{3f}$, R$_{10}$, —C(=O)—R$_{10}$, or —SO$_2$—R$_{10}$;

each $R_{3a}$ and $R_{3b}$ independently represent hydrogen;
each $R_{3e}$ and $R_{3f}$ independently represent hydrogen, $C_{1-4}$alkyl optionally substituted with $C_{1-4}$alkyloxy, or —(C=O)—$C_{1-4}$alkyl;

$R_4$ represents hydrogen, $C_{1-4}$alkyl or $C_{1-4}$alkyloxy $C_{1-4}$alkyl;

each $R_{5a}$ independently represents hydrogen;

each $R_{5b}$ independently represents hydrogen; $C_{1-4}$alkyl; $C_{1-4}$alkyloxy$C_{1-4}$alkyl; hydroxy$C_{1-4}$alkyl; hydroxyl; $C_{3-6}$cycloalkyl; or phenyl optionally substituted with $C_{1-4}$alkyl, halo, hydroxyl or $C_{1-4}$alkyloxy;

each $R_6$ independently represents hydrogen, halo, hydroxyl, carboxyl, cyano, $C_{1-4}$alkyl, $C_{1-4}$alkyloxy C$_{1-4}$alkyl, hydroxyC$_{1-4}$alkyl, haloC$_{1-4}$alkyl, C$_{2-4}$alkenyl, C$_{2-4}$alkynyl, —NR$_{6a}$R$_{6b}$, or —C(=O)NR$_{6a}$R$_{6b}$;

each R$_{6a}$ and R$_{6b}$ independently represent hydrogen or C$_{1-4}$alkyl;

each R$_7$ and R$_8$ independently represent hydrogen; or

R$_7$ and R$_8$ are taken together with the nitrogen to which they are attached to form a 4 to 7 membered saturated monocyclic heterocyclic ring which optionally contains 1 further heteroatom selected from N, O or SO$_2$, said heterocyclic ring being optionally substituted with 1 to 4 substituents each independently selected from C$_{1-4}$alkyl, halo, hydroxyl, or haloC$_{1-4}$alkyl;

R$_9$ represents C$_{1-4}$alkyl or haloC$_{1-4}$alkyl;

each R$_{10}$ independently represents a 4 to 7 membered saturated monocyclic heterocyclic ring containing up to 2 heteroatoms selected from N or O, said heterocyclic ring being optionally substituted with 1 to 4 substituents each independently selected from C$_{1-4}$alkyl, halo, hydroxyl or haloC$_{1-4}$alkyl; each R$_{11}$ independently represents C$_{3-6}$cycloalkyl, phenyl, or a 4 to 7 membered monocyclic heterocyclic ring containing up to 3 heteroatoms selected from N or O, said heterocyclic ring being optionally substituted with 1 to 4 substituents each independently selected from C$_{1-4}$alkyl, halo, hydroxyl, or haloC$_{1-4}$alkyl;

each R$_{12}$ independently represents hydrogen;

n represents an integer of value 1 or 2;

m represents an integer of value 1 or 2;

p1 represents an integer of value 1 or 2;

each p2 independently represents an integer of value 0, 1 or 2;

r represents an integer of value 1;

each p3 independently represents an integer of value 0 or 1;

each s independently represents an integer of value 0, 1 or 2;

and the pharmaceutically acceptable addition salts, and the solvates thereof.

In an embodiment, the present invention concerns novel compounds of Formula (I), tautomers and stereoisomeric forms thereof, wherein X$_a$ is CH or N;

X$_b$ and X$_c$ represent CH;

—X$_1$— represents (CHR$_{12}$)$_s$—NR$_1$—X$_e$—C$_{1-4}$alkanediyl-(SO$_2$)$_{p3}$— or —(CH$_2$)$_s$—O—X$_e$—C$_{1-4}$alkanediyl-(SO$_2$)$_{p3}$—; wherein each of said C$_{1-4}$alkanediyl moieties are optionally substituted with hydroxyl;

—X$_e$— represents C(R$_2$)$_2$— or —C(=O)—;

a represents —NR$_4$—C(=O)—[C(R$_{5b}$)$_2$]$_r$— or —NR$_4$—C(R$_{5b}$)$_2$—C(=O)—;

b represents

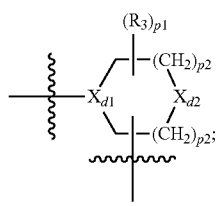

X$_{d1}$ represents CH or N;

X$_{d2}$ represents CH$_2$ or NH;

provided that at least one of X$_{d1}$ and X$_{d2}$ represents nitrogen;

c represents a bond, —[C(R$_{5a}$)$_2$]$_m$—, —C(=O)—, or —SO$_2$—;

ring

represents phenyl or pyridyl;

R$_1$ represents hydrogen, C$_{1-4}$alkyl, C$_{2-4}$alkenyl, C$_{2-4}$alkynyl, cyanoC$_{1-4}$alkyl, —C(=O)-haloC$_{1-4}$alkyl, C$_{1-4}$alkyloxyC$_{1-4}$alkyl, haloC$_{1-4}$alkyloxyC$_{1-4}$alkyl, —SO$_2$—NR$_7$R$_8$, —SO$_2$—R$_9$, C$_{1-4}$alkyl substituted with R$_{11}$, or —C(=O)—R$_{11}$;

each R$_2$ independently represents hydrogen;

or R$_1$ and one R$_2$ are taken together to form C$_{1-4}$alkanediyl optionally being substituted with 1 hydroxyl substituent;

each R$_3$ independently represents hydrogen; oxo; hydroxyl; —C(=O)—NR$_{3a}$R$_{3b}$;

hydroxyC$_{1-4}$alkyl; haloC$_{1-4}$alkyl; —C(=O)—O—C$_{1-4}$alkyl wherein said C$_{1-4}$alkyl may optionally be substituted with phenyl; C$_{1-4}$alkyl optionally substituted with —O—C(=O)—C$_{1-4}$alkyl; hydroxyC$_{1-4}$alkyloxyC$_{1-4}$alkyl; or C$_{1-4}$alkyloxyC$_{1-4}$alkyl optionally substituted with cyano, C$_{1-4}$alkyloxy, —NR$_{3e}$R$_{3f}$ or R$_{10}$;

R$_{3a}$ and R$_{3b}$ represent hydrogen;

R$_{3e}$ and R$_{3f}$ represent C$_{1-4}$alkyl;

R$_4$ represents hydrogen, C$_{1-4}$alkyl or C$_{1-4}$alkyloxyC$_{1-4}$alkyl; R$_{5a}$ represents hydrogen;

each R$_{5b}$ independently represents hydrogen; C$_{1-4}$alkyl; C$_{1-4}$alkyloxyC$_{1-4}$alkyl;

hydroxyC$_{1-4}$alkyl; or phenyl;

each R$_6$ independently represents hydrogen, halo, hydroxyl, carboxyl, cyano, C$_{1-4}$alkyl, or —C(=O) NR$_{6a}$R$_{6b}$;

each R$_{6a}$ and R$_{6b}$ independently represent hydrogen or C$_{1-4}$alkyl;

R$_7$ and R$_8$ represent hydrogen;

R$_9$ represents C$_{1-4}$alkyl;

each R$_{10}$ independently represents a 4 to 7 membered saturated monocyclic heterocyclic ring containing up to 2 heteroatoms selected from N or O, said heterocyclic ring being optionally substituted with 1 C$_{1-4}$alkyl substituent;

each R$_{11}$ independently represents C$_{3-6}$cycloalkyl, or a 4 to 7 membered monocyclic heterocyclic ring containing up to 3 oxygen atoms;

each R$_{12}$ independently represents hydrogen;

n represents an integer of value 1;

m represents an integer of value 1 or 2;

p1 represents an integer of value 1;

each p2 independently represents an integer of value 1 or 2;

r represents an integer of value 0 or 1;

each p3 independently represents an integer of value 0;

each s independently represents an integer of value 0 or 1;

and the pharmaceutically acceptable addition salts, and the solvates thereof.

Another embodiment of the present invention relates to those compounds of Formula (I) and the pharmaceutically acceptable addition salts, and the solvates thereof, or any subgroup thereof as mentioned in any of the other embodiments wherein one or more of the following restrictions apply:
(i) $X_a$ is CH or N; $X_b$ and $X_c$ represent CH;
(ii) —$X_1$— represents —(CHR$_{12}$)$_s$—NR$_1$—X$_e$—C$_{1-4}$alkanediyl-(SO$_2$)$_{p3}$— or —(CH$_2$)$_s$—O—X$_e$—C$_{1-4}$alkanediyl-(SO$_2$)$_{p3}$—; wherein each of said C$_{1-4}$alkanediyl moieties are optionally substituted with hydroxyl;
(iii) a represents NR$_4$—C(=O)[C(R$_{5b}$)$_2$]$_r$— or —NR$_4$—C(R$_{5b}$)$_2$—C(=O)—;
(iv) b represents

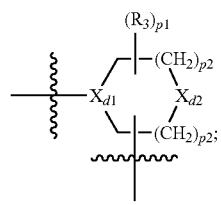

(v) c represents a bond, [C(R$_{5a}$)$_2$]$_m$—, —C(=O)—, or —SO$_2$—;
(vi) R$_1$ represents hydrogen, C$_{1-4}$alkyl, C$_{2-4}$alkenyl, C$_{2-4}$alkynyl, cyanoC$_{1-4}$alkyl, —C(=O)-haloC$_{1-4}$alkyl, C$_{1-4}$alkyloxyC$_{1-4}$alkyl, haloC$_{1-4}$alkyloxyC$_{1-4}$alkyl, —SO$_2$—NR$_7$R$_8$, —SO$_2$—R$_9$, C$_{1-4}$alkyl substituted with R$_{11}$, or —C(=O)—R$_{11}$;
each R$_2$ independently represents hydrogen; or
R$_1$ and one R$_2$ are taken together to form C$_{1-4}$alkanediyl optionally being substituted with 1 hydroxyl substituent;
(vii) each R$_3$ independently represents hydrogen; oxo; hydroxyl; —C(=O)—NR$_{3a}$R$_{3b}$; hydroxyC$_{1-4}$alkyl; haloC$_{1-4}$alkyl; —C(=O)—O—C$_{1-4}$alkyl wherein said C$_{1-4}$alkyl may optionally be substituted with phenyl; C$_{1-4}$alkyl optionally substituted with —O—C(=O)—C$_{1-4}$alkyl; hydroxyC$_{1-4}$alkyloxyC$_{1-4}$alkyl; or C$_{1-4}$alkyloxyC$_{1-4}$alkyl optionally substituted with cyano, C$_{1-4}$alkyloxy, —NR$_{3e}$R$_{3f}$, or R$_{10}$;
(viii) R$_{3a}$ and R$_{3b}$ represent hydrogen;
(ix) R$_{3e}$ and R$_{3f}$ represent C$_{1-4}$alkyl;
(x) R$_4$ represents hydrogen, C$_{1-4}$alkyl or C$_{1-4}$alkyloxyC$_{1-4}$alkyl;
(xi) R$_{5a}$ represents hydrogen;
(xii) each R$_{5b}$ independently represents hydrogen; C$_{1-4}$alkyl; C$_{1-4}$alkyloxyC$_{1-4}$alkyl; hydroxyC$_{1-4}$alkyl; or phenyl;
(xiii) each R$_6$ independently represents hydrogen, halo, hydroxyl, carboxyl, cyano, C$_{1-4}$alkyl, or —C(=O)NR$_{6a}$R$_{6b}$;
(xiv) each R$_{6a}$ and R$_{6b}$ independently represent hydrogen or C$_{1-4}$alkyl;
(xv) R$_7$ and R$_8$ represent hydrogen;
(xvi) R$_9$ represents C$_{1-4}$alkyl;
(xvii) each R$_{10}$ independently represents a 4 to 7 membered saturated monocyclic heterocyclic ring containing up to 2 heteroatoms selected from N or O, said heterocyclic ring being optionally substituted with 1 C$_{1-4}$alkyl substituent;
(xviii) each R$_{11}$ independently represents C$_{3-6}$cycloalkyl, or a 4 to 7 membered monocyclic heterocyclic ring containing up to 3 oxygen atoms;
(xix) each R$_{12}$ independently represents hydrogen;
(xx) n represents an integer of value 1;
(xxi) p1 represents an integer of value 1;
(xxii) each p2 independently represents an integer of value 1 or 2;

(xxiii) r represents an integer of value 0 or 1;
(xxiv) each p3 independently represents an integer of value 0;
(xxv) each s independently represents an integer of value 0 or 1.

Another embodiment of the present invention relates to those compounds of Formula (I) and the pharmaceutically acceptable addition salts, and the solvates thereof, or any subgroup thereof as mentioned in any of the other embodiments wherein one or more of the following restrictions apply:
(i) $X_a$, $X_b$ and $X_c$ represent CH;
(ii) —$X_1$— represents —(CHR$_{12}$)$_s$—NR$_1$—X$_c$—C$_{1-4}$alkanediyl-;
(iii) —X$_c$— represents —C(R$_2$)$_2$—;
(iv) a represents —NR$_4$—C(=O)—[C(R$_{5b}$)$_2$]$_r$ or —NR$_4$—C(R$_{5b}$)$_2$—C(=O)—; in particular a represents —NR$_4$—C(=O)—[C(R$_{5b}$)$_2$]$_r$—;
(v) b represents

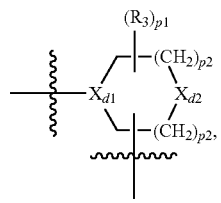

provided that the linker with the 'a substituent' is present on $X_{d2}$ or is present on a carbon atom in the alpha position of $X_{d2}$;
(vi) c represents CH$_2$ or a bond; in particular c represents CH$_2$; in particular c represents a bond;
(vii) r is 1.

In an embodiment, the present invention concerns novel compounds of Formula (I), tautomers and stereoisomeric forms thereof, wherein
$X_a$ is CH or N;
$X_b$ and $X_c$ represent CH;
—$X_1$— represents —(CHR$_{12}$)$_s$—NR$_1$—X$_e$—C$_{1-4}$alkanediyl- or —(CH$_2$)$_s$—O—X—C$_{1-4}$alkanediyl-; wherein each of said C$_{1-4}$alkanediyl moieties are optionally substituted with hydroxyl; —X$_e$— represents —C(R$_2$)$_2$— or —C(=O)—;
a represents —NR$_4$—C(=O)—[C(R$_{5b}$)$_2$]$_r$ or —NR$_4$—C(R$_{5b}$)$_2$—C(=O)—;
b represents

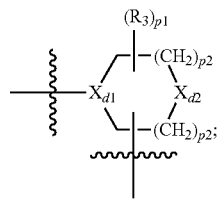

$X_{d1}$ represents CH or N;
$X_{d2}$ represents CH$_2$ or NH;
provided that at least one of $X_{d1}$ and $X_{d2}$ represents nitrogen;

c represents a bond, $-[C(R_{5a})_2]_m-$, $-C(=O)-$, or $-SO_2-$;
ring

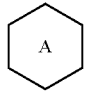

represents phenyl or pyridyl;

$R_1$ represents hydrogen, $C_{1-4}$alkyl, $C_{2-4}$alkenyl, 1-propyn-3-yl, 2-cyanoethyl, $-C(=O)-CF_3$, methyloxyethyl, trifluoromethyloxyC$_{1-4}$alkyl, $-SO_2-NR_7R_8$, $-SO_2-R_9$, $C_{1-4}$alkyl substituted with $R_{11}$, or $-C(=O)-R_{11}$;

each $R_2$ independently represents hydrogen;

or $R_1$ and one $R_2$ are taken together to form $C_{1-4}$alkanediyl optionally being substituted with 1 hydroxyl substituent;

each $R_3$ independently represents hydrogen; oxo; hydroxyl; $-C(=O)-NR_{3a}R_{3b}$; hydroxyC$_{1-4}$alkyl; $CF_3$; $-C(=O)-O$-methyl wherein said methyl may optionally be substituted with phenyl; methyl optionally substituted with $-O-C(=O)$-methyl; hydroxyethyloxymethyl; $C_{1-4}$alkyloxymethyl optionally substituted with cyano, methyloxy, $-NR_{3e}R_{3f}$, or $R_{10}$;

$R_{3a}$ and $R_{3b}$ represent hydrogen;

$R_{3e}$ and $R_{3f}$ represent methyl;

$R_4$ represents hydrogen, methyl, isopropyl or methoxyethyl;

$R_{5a}$ represents hydrogen;

each $R_{5b}$ independently represents hydrogen; methyl; methyloxymethyl; hydroxymethyl; or phenyl;

each $R_6$ independently represents hydrogen, chloro, fluoro, hydroxyl, carboxyl, cyano, methyl, or $-C(=O)NR_{6a}R_{6b}$;

each $R_{6a}$ and $R_{6b}$ independently represent hydrogen or methyl;

$R_7$ and $R_8$ represent hydrogen;

$R_9$ represents methyl;

each $R_{10}$ independently represents a 6 membered saturated monocyclic heterocyclic ring containing 2 heteroatoms selected from N or O, said heterocyclic ring being optionally substituted with 1 methyl substituent;

each $R_{11}$ independently represents $C_{3-6}$cyclopropyl, or a 5 to 6 membered monocyclic heterocyclic ring containing 1 oxygen atom;

each $R_{12}$ independently represents hydrogen;

n represents an integer of value 1;

m represents an integer of value 1 or 2;

p1 represents an integer of value 1;

each p2 independently represents an integer of value 1 or 2;

r represents an integer of value 0 or 1;

each p3 independently represents an integer of value 0;

each s independently represents an integer of value 0 or 1;

and the pharmaceutically acceptable addition salts, and the solvates thereof.

In an embodiment, the present invention relates to those compounds of Formula (I) and the pharmaceutically acceptable addition salts, and the solvates thereof, or any subgroup thereof as mentioned in any of the other embodiments, wherein b represents

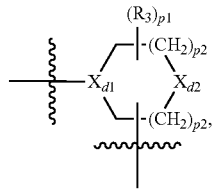

in particular wherein b represents

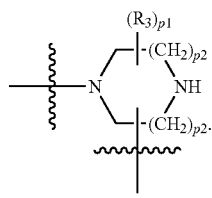

In an embodiment, the present invention relates to those compounds of Formula (I) and the pharmaceutically acceptable addition salts, and the solvates thereof, or any subgroup thereof as mentioned in any of the other embodiments, wherein b represents

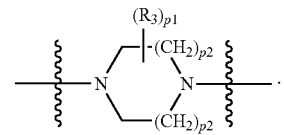

In an embodiment, the present invention relates to those compounds of Formula (I) and the pharmaceutically acceptable addition salts, and the solvates thereof, or any subgroup thereof as mentioned in any of the other embodiments, wherein
  r is 1;
  $-X_1-$ represents $-(CHR_{12})-NR_1-X_e-C_{1-4}$alkanediyl- wherein $C_{1-4}$alkanediyl is optionally substituted with hydroxyl or hydroxyC$_{1-4}$alkyl; or $-X_1-$ represents $-NR_1-X_e-C_{2-4}$alkanediyl- wherein $C_{2-4}$alkanediyl is optionally substituted with hydroxyl or hydroxyC$_{1-4}$alkyl;
  m is 1;
  $R_6$ is other than $C_{1-4}$alkyl;
  $R_3$ is other than hydroxyC$_{1-4}$alkyloxyC$_{1-4}$alkyl; and
  b represents

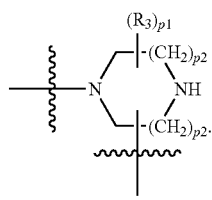

In an embodiment, the present invention relates to those compounds of Formula (I) and the pharmaceutically acceptable addition salts, and the solvates thereof, or any subgroup thereof as mentioned in any of the other embodiments, wherein r is 1;

—X$_1$— represents —(CHR$_{12}$)—NR$_1$—X$_e$—C$_{1-4}$alkanediyl- wherein C$_{1-4}$alkanediyl is optionally substituted with hydroxyl or hydroxyC$_{1-4}$alkyl; or —X$_1$— represents —NR$_1$—X$_e$—C$_{2-4}$alkanediyl- wherein C$_{2-4}$alkanediyl is optionally substituted with hydroxyl or hydroxyC$_{1-4}$alkyl;

m is 1;

R$_6$ is other than C$_{1-4}$alkyl;

R$_3$ is other than hydroxyC$_{1-4}$alkyloxyC$_{1-4}$alkyl; and b represents

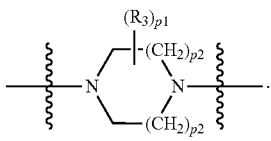

In an embodiment, the present invention relates to those compounds of Formula (I) and the pharmaceutically acceptable addition salts, and the solvates thereof, or any subgroup thereof as mentioned in any of the other embodiments, wherein r is 1;

—X$_1$— represents —(CHR$_{12}$)—NR$_1$—X$_e$—C$_{1-4}$alkanediyl- wherein C$_{1-4}$alkanediyl is optionally substituted with hydroxyl or hydroxyC$_{1-4}$alkyl; or —X$_{1-4}$— represents —NR$_1$—X$_e$—C$_{2-4}$alkanediyl- wherein C$_{2-4}$alkanediyl is optionally substituted with hydroxyl or hydroxyC$_{1-4}$alkyl;

c is CH$_2$;

R$_6$ is other than C$_{1-4}$alkyl;

R$_3$ is other than hydroxyC$_{1-4}$alkyloxyC$_{1-4}$alkyl; and b represents

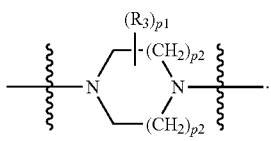

In an embodiment, the present invention relates to those compounds of Formula (I) and the pharmaceutically acceptable addition salts, and the solvates thereof, or any subgroup thereof as mentioned in any of the other embodiments, wherein b represents

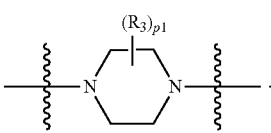

In an embodiment, the present invention relates to those compounds of Formula (I) and the pharmaceutically acceptable addition salts, and the solvates thereof, or any subgroup thereof as mentioned in any of the other embodiments, wherein r is 1, and b represents

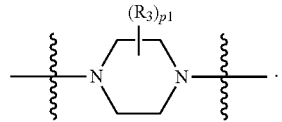

In an embodiment, the present invention relates to those compounds of Formula (I) and the pharmaceutically acceptable addition salts, and the solvates thereof, or any subgroup thereof as mentioned in any of the other embodiments, wherein ring b does not contain extra bonds to form a bridged ring system.

In an embodiment, the present invention relates to those compounds of Formula (I) and the pharmaceutically acceptable addition salts, and the solvates thereof, or any subgroup thereof as mentioned in any of the other embodiments, wherein r is 1 and X$_{d2}$ is NH.

In an embodiment, the present invention relates to those compounds of Formula (I) and the pharmaceutically acceptable addition salts, and the solvates thereof, or any subgroup thereof as mentioned in any of the other embodiments, wherein X$_a$, X$_b$ and X$_c$ represent CH; r is 1; and X$_{d2}$ is NH.

In an embodiment, the present invention relates to those compounds of Formula (I) and the pharmaceutically acceptable addition salts, and the solvates thereof, or any subgroup thereof as mentioned in any of the other embodiments, wherein r is 1, X$_{d1}$ is N, and X$_{d2}$ is NH.

In an embodiment, the present invention relates to those compounds of Formula (I) and the pharmaceutically acceptable addition salts, and the solvates thereof, or any subgroup thereof as mentioned in any of the other embodiments, wherein X$_{d1}$ is N, and X$_{d2}$ is NH; and c represents a bond, —[C(R$_{5a}$)$_2$]$_m$—, —C(=O)—, —SO$_2$—, or —SO—.

In an embodiment, the present invention relates to those compounds of Formula (I) and the pharmaceutically acceptable addition salts, and the solvates thereof, or any subgroup thereof as mentioned in any of the other embodiments, wherein X$_{d1}$ is CH, and X$_{d2}$ is NH; and c represents —O—.

In an embodiment, the present invention relates to those compounds of Formula (I) and the pharmaceutically acceptable addition salts, and the solvates thereof, or any subgroup thereof as mentioned in any of the other embodiments, wherein when X$_{d1}$ is N, then c represents a bond, —[C(R$_{5a}$)$_2$]$_m$—, —C(=O)—, —SO$_2$—, or —SO—; in particular when X$_{d1}$ is N, then c represents a bond, —[C(R$_{5a}$)$_2$]$_m$—, or —C(=O)—; more in particular when X$_{d1}$ is N, then c represents —[C(R$_{5a}$)$_2$]$_m$—; even more in particular when X$_{d1}$ is N, then c represents —CH$_2$—.

In an embodiment, the present invention relates to those compounds of Formula (I) and the pharmaceutically acceptable addition salts, and the solvates thereof, or any subgroup thereof as mentioned in any of the other embodiments, wherein when b represents

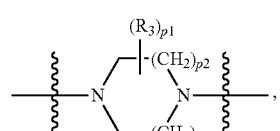

then c is other than —O— or —NR$_{5a'}$—.

In an embodiment, the present invention relates to those compounds of Formula (I) and the pharmaceutically acceptable addition salts, and the solvates thereof, or any subgroup thereof as mentioned in any of the other embodiments, wherein when b represents

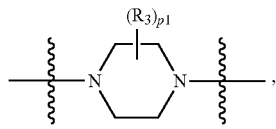

then c is other than —O— or —NR$_{5a}$—.

In an embodiment, the present invention relates to those compounds of Formula (I) and the pharmaceutically acceptable addition salts, and the solvates thereof, or any subgroup thereof as mentioned in any of the other embodiments, wherein c represents a bond or —[C(R$_{5a}$)$_2$]$_m$— when X$_{d1}$ represents CH or N; or c may also represent —O— or —NR$_{5a}$— when X$_{d1}$ represents CH.

In an embodiment, the present invention relates to those compounds of Formula (I) and the pharmaceutically acceptable addition salts, and the solvates thereof, or any subgroup thereof as mentioned in any of the other embodiments, wherein c represents a bond, —[C(R$_{5a}$)$_2$]$_m$—, —C(=O)—, —SO$_2$—, or —SO— when X$_{d1}$ represents CH or N; or c may also represent —O— or —NR$_{5a}$— when X$_{d1}$ represents CH.

In an embodiment, the present invention relates to those compounds of Formula (I) and the pharmaceutically acceptable addition salts, and the solvates thereof, or any subgroup thereof as mentioned in any of the other embodiments, wherein r is 1 or 2; in particular wherein r is 1.

In an embodiment, the present invention relates to those compounds of Formula (I) and the pharmaceutically acceptable addition salts, and the solvates thereof, or any subgroup thereof as mentioned in any of the other embodiments, wherein X$_{d1}$ represents CH and X$_{d2}$ represents NH.

In an embodiment, the present invention relates to those compounds of Formula (I) and the pharmaceutically acceptable addition salts, and the solvates thereof, or any subgroup thereof as mentioned in any of the other embodiments, wherein s is 1.

In an embodiment, the present invention relates to those compounds of Formula (I) and the pharmaceutically acceptable addition salts, and the solvates thereof, or any subgroup thereof as mentioned in any of the other embodiments, wherein p3 is 0.

In an embodiment, the present invention relates to those compounds of Formula (I) and the pharmaceutically acceptable addition salts, and the solvates thereof, or any subgroup thereof as mentioned in any of the other embodiments, wherein s is 0.

In an embodiment, the present invention relates to those compounds of Formula (I) and the pharmaceutically acceptable addition salts, and the solvates thereof, or any subgroup thereof as mentioned in any of the other embodiments, wherein s is 0 or 1.

In an embodiment, the present invention relates to those compounds of Formula (I) and the pharmaceutically acceptable addition salts, and the solvates thereof, or any subgroup thereof as mentioned in any of the other embodiments, wherein s is 0 and p3 is 0.

In an embodiment, the present invention relates to those compounds of Formula (I) and the pharmaceutically acceptable addition salts, and the solvates thereof, or any subgroup thereof as mentioned in any of the other embodiments, wherein s is 1, p3 is 0 and R$_{12}$ is H.

In an embodiment, the present invention relates to those compounds of Formula (I) and the pharmaceutically acceptable addition salts, and the solvates thereof, or any subgroup thereof as mentioned in any of the other embodiments, wherein m is 1.

In an embodiment, the present invention relates to those compounds of Formula (I) and the pharmaceutically acceptable addition salts, and the solvates thereof, or any subgroup thereof as mentioned in any of the other embodiments, wherein p2 is 1.

In an embodiment, the present invention relates to those compounds of Formula (I) and the pharmaceutically acceptable addition salts, and the solvates thereof, or any subgroup thereof as mentioned in any of the other embodiments, wherein X$_a$ is CH.

In an embodiment, the present invention relates to those compounds of Formula (I) and the pharmaceutically acceptable addition salts, and the solvates thereof, or any subgroup thereof as mentioned in any of the other embodiments, wherein X$_a$, X$_b$ and X$_c$ represent CH.

In an embodiment, the present invention relates to those compounds of Formula (I) and the pharmaceutically acceptable addition salts, and the solvates thereof, or any subgroup thereof as mentioned in any of the other embodiments, wherein ring A is phenyl.

In an embodiment, the present invention relates to those compounds of Formula (I) and the pharmaceutically acceptable addition salts, and the solvates thereof, or any subgroup thereof as mentioned in any of the other embodiments, wherein ring A is pyridyl.

In an embodiment, the present invention relates to those compounds of Formula (I) and the pharmaceutically acceptable addition salts, and the solvates thereof, or any subgroup thereof as mentioned in any of the other embodiments, wherein R$_1$ represents C$_{1-4}$alkyl, C$_{2-4}$alkenyl, C$_{2-4}$alkynyl, —C(=O)—C$_{1-4}$alkyl, —C(=O)-haloC$_{1-4}$alkyl, hydroxyC$_{1-4}$alkyl, haloC$_{1-4}$alkyl, C$_{1-4}$alkyloxyC$_{1-4}$alkyl, haloC$_{1-4}$alkyloxyC$_{1-4}$alkyl, —C(=O)NR$_7$R$_8$, —SO$_2$—R$_9$, R$_{11}$, C$_{1-4}$alkyl substituted with R$_{11}$, —C(=O)—R$_1$, or —C(=O)—C$_{1-4}$alkyl-R$_{11}$.

In an embodiment, the present invention relates to those compounds of Formula (I) and the pharmaceutically acceptable addition salts, and the solvates thereof, or any subgroup thereof as mentioned in any of the other embodiments, wherein R$_1$ represents C$_{1-4}$alkyl, C$_{2-4}$alkenyl, C$_{2-4}$alkynyl, or C$_{1-4}$alkyloxyC$_{1-4}$alkyl; in particular R$_1$ represents C$_{1-4}$alkyl, C$_{2-4}$alkenyl, or C$_{1-4}$alkyloxyC$_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein R$_1$ represents C$_{1-4}$alkyl, C$_{2-4}$alkenyl, C$_{2-4}$alkynyl, —C(=O)—C$_{1-4}$alkyl, —C(=O)-haloC$_{1-4}$alkyl, hydroxyC$_{1-4}$alkyl, haloC$_{1-4}$alkyl, C$_{1-4}$alkyloxyC$_{1-4}$alkyl, haloC$_{1-4}$alkyloxyC$_{1-4}$alkyl, —C(=O)NR$_7$R$_8$, —SO$_2$—R$_9$, R$_{11}$, C$_{1-4}$alkyl substituted with R$_{11}$, —C(=O)—R$_{11}$, or —C(=O)—C$_{1-4}$alkyl-R$_{11}$; or R$_1$ is taken together with one R$_2$ or R$_{12}$.

In an embodiment, the present invention relates to those compounds of Formula (I) and the pharmaceutically acceptable addition salts, and the solvates thereof, or any subgroup thereof as mentioned in any of the other embodiments, wherein R$_1$ represents C$_{1-4}$alkyl, C$_{2-4}$alkenyl, C$_{2-4}$alkynyl, —C(=O)—C$_{1-4}$alkyl, —C(=O)-haloC$_{1-4}$alkyl, hydroxyC$_{1-4}$alkyl, haloC$_{1-4}$alkyl, C$_{1-4}$alkyloxyC$_{1-4}$alkyl, haloC$_{1-4}$alkyloxyC$_{1-4}$alkyl, —C(=O)NR$_7$R$_8$, —SO$_2$—R$_9$, $R_{11}$, $C_{1-4}$alkyl substituted with $R_{11}$, —C(=O)—$R_1$, or —C(=O)—$C_{1-4}$alkyl-$R_{11}$; or $R_1$ is taken together with one $R_2$.

In an embodiment, the present invention relates to those compounds of Formula (I) and the pharmaceutically acceptable addition salts, and the solvates thereof, or any subgroup thereof as mentioned in any of the other embodiments, wherein when $R_1$ and $R_2$ are taken together, they form $C_{3-4}$alkanediyl or $C_{3-4}$alkenediyl, each of said $C_{3-4}$alkanediyl and $C_{3-4}$alkenediyl optionally being substituted with 1 to 4 substituents each independently selected from hydroxyl, oxo, halo, cyano, $N_3$, hydroxy$C_{1-4}$alkyl, —$NR_7R_8$, —$SO_2$—$NR_7R_8$, —NH—$SO_2$—$NR_7R_8$, —C(=O)—$NR_7R_8$, or —NH—C(=O)—$NR_7R_8$.

In an embodiment, the present invention relates to those compounds of Formula (I) and the pharmaceutically acceptable addition salts, and the solvates thereof, or any subgroup thereof as mentioned in any of the other embodiments, wherein when $R_1$ and $R_{12}$ are taken together, they form $C_{3-4}$alkanediyl or $C_{3-4}$alkenediyl, each of said $C_{3-4}$alkanediyl and $C_{3-4}$alkenediyl optionally being substituted with 1 to 4 substituents each independently selected from hydroxyl, oxo, halo, cyano, $N_3$, hydroxy$C_{1-4}$alkyl, —$NR_7R_8$, —$SO_2$—$NR_7R_8$, —NH—$SO_2$—$NR_7R_8$, —C(=O)—$NR_7R_8$, or —NH—C(=O)—$NR_7R_8$.

In an embodiment, the present invention relates to those compounds of Formula (I) and the pharmaceutically acceptable addition salts, and the solvates thereof, or any subgroup thereof as mentioned in any of the other embodiments, wherein $R_1$ represents hydrogen, $C_{1-4}$alkyl, $C_{2-4}$alkenyl, $C_{2-4}$alkynyl, cyano$C_{1-4}$alkyl, —C(=O)—$C_{1-4}$alkyl, —C(=O)-halo$C_{1-4}$alkyl, hydroxy$C_{1-4}$alkyl, halo$C_{1-4}$alkyl, $C_{1-4}$alkyloxy$C_{1-4}$alkyl, halo$C_{1-4}$alkyloxy$C_{1-4}$alkyl, —C(=O)$NR_7R_8$, —$SO_2$—$NR_7R_8$, —$SO_2$—$R_9$, $R_{11}$, $C_{1-4}$alkyl substituted with $R_{11}$, —C(=O)—$R_{11}$, or —C(=O)—$C_{1-4}$alkyl-$R_{11}$; $R_2$ is hydrogen; or $R_1$ and one $R_2$ are taken together to form $C_{3-4}$alkanediyl or $C_{3-4}$alkenediyl, each of said $C_{3-4}$alkanediyl and $C_{3-4}$alkenediyl optionally being substituted with 1 to 4 hydroxyl substituents.

In an embodiment, the present invention relates to those compounds of Formula (I) and the pharmaceutically acceptable addition salts, and the solvates thereof, or any subgroup thereof as mentioned in any of the other embodiments, wherein $R_1$ is other than hydrogen.

In an embodiment, the present invention relates to those compounds of Formula (I) and the pharmaceutically acceptable addition salts, and the solvates thereof, or any subgroup thereof as mentioned in any of the other embodiments, wherein $R_2$ represents hydrogen.

In an embodiment, the present invention relates to those compounds of Formula (I) and the pharmaceutically acceptable addition salts, and the solvates thereof, or any subgroup thereof as mentioned in any of the other embodiments, wherein $R_2$ represents hydrogen: or $R_1$ and $R_2$ are taken together.

In an embodiment, the present invention relates to those compounds of Formula (I) and the pharmaceutically acceptable addition salts, and the solvates thereof, or any subgroup thereof as mentioned in any of the other embodiments, wherein $R_1$ and one $R_2$ are taken together to form $C_{1-4}$alkanediyl optionally being substituted with 1 hydroxyl substituent; and wherein the other $R_2$ variables are hydrogen.

In an embodiment, the present invention relates to those compounds of Formula (I) and the pharmaceutically acceptable addition salts, and the solvates thereof, or any subgroup thereof as mentioned in any of the other embodiments, wherein each $R_{10}$ independently represents a 6 membered saturated monocyclic heterocyclic ring containing up to 2 heteroatoms selected from N or O, said heterocyclic ring being optionally substituted with 1 $C_{1-4}$alkyl substituent.

In an embodiment, the present invention relates to those compounds of Formula (I) and the pharmaceutically acceptable addition salts, and the solvates thereof, or any subgroup thereof as mentioned in any of the other embodiments, wherein each $R_{10}$ independently represents morpholinyl or piperazinyl optionally substituted with 1 $C_{1-4}$alkyl substituent.

In an embodiment, the present invention relates to those compounds of Formula (I) and the pharmaceutically acceptable addition salts, and the solvates thereof, or any subgroup thereof as mentioned in any of the other embodiments, wherein each $R_{10}$ independently represents 4-morpholinyl, 1-piperazinyl or 4-methyl-1-piperazinyl.

In an embodiment, the present invention relates to those compounds of Formula (I) and the pharmaceutically acceptable addition salts, and the solvates thereof, or any subgroup thereof as mentioned in any of the other embodiments, wherein each $R_{11}$ independently represents $C_{3-4}$cycloalkyl, or a 4 to 7 membered monocyclic heterocyclic ring containing one oxygen atom.

In an embodiment, the present invention relates to those compounds of Formula (I) and the pharmaceutically acceptable addition salts, and the solvates thereof, or any subgroup thereof as mentioned in any of the other embodiments, wherein each $R_{11}$ independently represents $C_{3-4}$cycloalkyl, or a 4 to 7 membered monocyclic heterocyclic ring containing one oxygen atom.

In an embodiment, the present invention relates to those compounds of Formula (I) and the pharmaceutically acceptable addition salts, and the solvates thereof, or any subgroup thereof as mentioned in any of the other embodiments, wherein each $R_{11}$ independently represents $C_{3-4}$cycloalkyl, tetrahydropyranyl or tetrahydrofuranyl.

In an embodiment, the present invention relates to those compounds of Formula (I) and the pharmaceutically acceptable addition salts, and the solvates thereof, or any subgroup thereof as mentioned in any of the other embodiments, wherein c represents a bond, —C(=O)—, —O—, —$NR_{5a}$—, —$SO_2$—, or —SO—; in particular a bond, —C(=O)—, or —$SO_2$—.

In an embodiment, the present invention relates to those compounds of Formula (I) and the pharmaceutically acceptable addition salts, and the solvates thereof, or any subgroup thereof as mentioned in any of the other embodiments, wherein c represents a bond, —[C($R_{5a}$)$_2$]$_m$—, —C(=O)—, or —$SO_2$—.

In an embodiment, the present invention relates to those compounds of Formula (I) and the pharmaceutically acceptable addition salts, and the solvates thereof, or any subgroup thereof as mentioned in any of the other embodiments, wherein CH$R_{12}$ is CH$_2$.

In an embodiment, the present invention relates to those compounds of Formula (I) and the pharmaceutically acceptable addition salts, and the solvates thereof, or any subgroup thereof as mentioned in any of the other embodiments, wherein $R_{12}$ is H.

In an embodiment, the present invention relates to those compounds of Formula (I) and the pharmaceutically acceptable addition salts, and the solvates thereof, or any subgroup thereof as mentioned in any of the other embodiments, wherein c represents CH$_2$.

In an embodiment, the present invention relates to those compounds of Formula (I) and the pharmaceutically acceptable addition salts, and the solvates thereof, or any subgroup thereof as mentioned in any of the other embodiments, wherein c represents —[C(R$_{5a}$)$_2$]$_m$—.

In an embodiment, the present invention relates to those compounds of Formula (I) and the pharmaceutically acceptable addition salts, and the solvates thereof, or any subgroup thereof as mentioned in any of the other embodiments, wherein a represents —NR$_4$—C(R$_{5a}$)$_2$—C(=O)—.

In an embodiment, the present invention relates to those compounds of Formula (I) and the pharmaceutically acceptable addition salts, and the solvates thereof, or any subgroup thereof as mentioned in any of the other embodiments, wherein a represents —NR$_4$—C(=O)—[C(R$_{5b}$)$_2$]$_r$—.

In an embodiment, the present invention relates to those compounds of Formula (I) and the pharmaceutically acceptable addition salts, and the solvates thereof, or any subgroup thereof as mentioned in any of the other embodiments, wherein a represents —NR$_4$—C(=O)—[C(R$_{5b}$)$_2$]$_r$—; and r is 1.

In an embodiment, the present invention relates to those compounds of Formula (I) and the pharmaceutically acceptable addition salts, and the solvates thereof, or any subgroup thereof as mentioned in any of the other embodiments, wherein a represents —C(=O)—NR$_4$—C(R$_{5b}$)$_2$—.

In an embodiment, the present invention relates to those compounds of Formula (I) and the pharmaceutically acceptable addition salts, and the solvates thereof, or any subgroup thereof as mentioned in any of the other embodiments, wherein in the 'b substituent', the linker with the 'a substituent' is present on X$_{d2}$ or is present on a carbon atom in the alpha position of X$_{d2}$.

In an embodiment, the present invention relates to those compounds of Formula (I) and the pharmaceutically acceptable addition salts, and the solvates thereof, or any subgroup thereof as mentioned in any of the other embodiments, wherein in the 'b substituent', the linker with the 'a substituent' is present on X$_{d2}$.

In an embodiment, the present invention relates to those compounds of Formula (I) and the pharmaceutically acceptable addition salts, and the solvates thereof, or any subgroup thereof as mentioned in any of the other embodiments, wherein in the 'b substituent', the linker with the 'a substituent' is present on X$_{d2}$; and wherein p1 is 1.

In an embodiment, the present invention relates to those compounds of Formula (I) and the pharmaceutically acceptable addition salts, and the solvates thereof, or any subgroup thereof as mentioned in any of the other embodiments, wherein —X$_1$— represents —(CHR$_{12}$)—NR$_1$—X—C$_{1-4}$alkanediyl- wherein C$_{1-4}$alkanediyl is optionally substituted with hydroxyl or hydroxyC$_{1-4}$alkyl; or —X$_1$— represents —NR$_1$—X—C$_{2-4}$alkanediyl- wherein C$_{2-4}$alkanediyl is optionally substituted with hydroxyl or hydroxyC$_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein —X$_1$— represents —(CHR$_{12}$)—NR$_1$—X—C$_{1-4}$alkanediyl-; or —X$_1$— represents —NR$_1$—X$_e$—C$_{2-4}$alkanediyl-.

In an embodiment, the present invention relates to those compounds of Formula (I) and the pharmaceutically acceptable addition salts, and the solvates thereof, or any subgroup thereof as mentioned in any of the other embodiments, wherein R$_3$ is H.

In an embodiment, the present invention relates to those compounds of Formula (I) and the pharmaceutically acceptable addition salts, and the solvates thereof, or any subgroup thereof as mentioned in any of the other embodiments, wherein R$_6$ is H.

In an embodiment, the present invention relates to those compounds of Formula (I) and the pharmaceutically acceptable addition salts, and the solvates thereof, or any subgroup thereof as mentioned in any of the other embodiments, wherein —X$_1$— represents —CH$_2$—NR$_1$—CH$_2$—C$_{1-4}$alkanediyl-, —NR$_1$—CH$_2$—C$_{2-4}$alkanediyl-, or —X$_1$— represents one of the following groups wherein —(CH$_2$)$_2$— is attached to 'variable a':

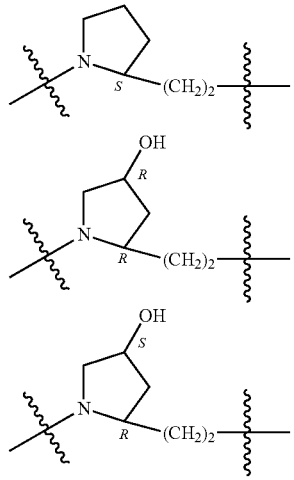

R$_1$ represents C$_{1-4}$alkyl, C$_{2-4}$alkenyl, or C$_{1-4}$alkyloxy C$_{1-4}$alkyl;
a represents —NR$_4$—C(=O—CH$_2$—;
b represents

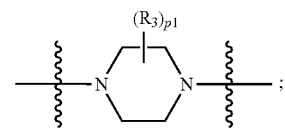

each R$_3$ independently represents hydrogen; C$_{1-4}$alkyloxyC$_{1-4}$alkyl optionally substituted with cyano; or hydroxyC$_{1-4}$alkyloxyC$_{1-4}$alkyl; in particular R$_3$ is hydrogen;
c is CH$_2$.

In an embodiment, the present invention relates to those compounds of Formula (I) and the pharmaceutically acceptable addition salts, and the solvates thereof, or any subgroup thereof as mentioned in any of the other embodiments, wherein
X$_a$, X$_b$ and X$_c$ are CH;
—X$_1$— represents —CH$_2$—NR$_1$—CH$_2$—C$_{1-4}$alkanediyl-, —NR$_1$—CH$_2$—C$_{2-4}$alkanediyl-, or —X$_1$— represents one of the following groups wherein —(CH$_2$)$_2$— is attached to 'variable a':

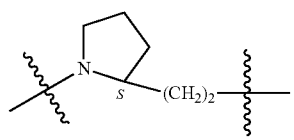

-continued

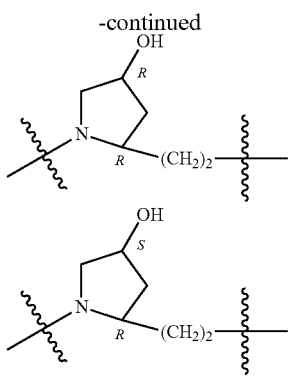

R₁ represents C₁₋₄alkyl, C₂₋₄alkenyl, C₂₋₄alkynyl, C₁₋₄alkyloxyC₁₋₄alkyl; in particular R₁ represents C₁₋₄alkyl, C₂₋₄alkenyl, or C₁₋₄alkyloxyC₁₋₄alkyl;
a represents —NR₄—C(=O)—CH₂—;
b represents

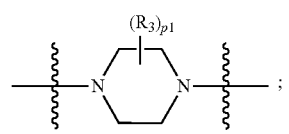

p1 is 1;
R₃ represents hydrogen; C₁₋₄alkyloxyC₁₋₄alkyl optionally substituted with cyano; or hydroxyC₁₋₄alkyloxy C₁₋₄alkyl; in particular R₃ is hydrogen;
c is CH₂; and
R₆ represents H.

In an embodiment, the present invention relates to those compounds of Formula (I) and the pharmaceutically acceptable addition salts, and the solvates thereof, or any subgroup thereof as mentioned in any of the other embodiments, wherein
—X₁— represents —CH₂—NR₁—CH₂—C₁₋₄alkanediyl-, —NR₁—CH₂—C₂₋₄alkanediyl-, or —X₁— represents one of the following groups wherein —(CH₂)₂— is attached to 'variable a':

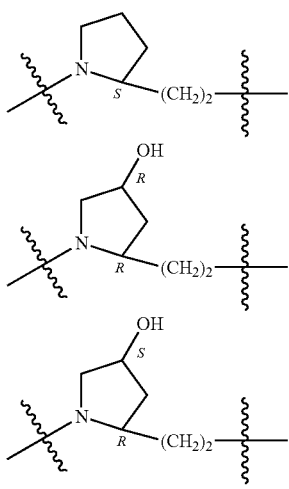

R₁ represents C₁₋₄alkyl, C₂₋₄alkenyl, C₂₋₄alkynyl, C₁₋₄alkyloxyC₁₋₄alkyl; in particular R₁ represents C₁₋₄alkyl, C₂₋₄alkenyl, or C₁₋₄alkyloxyC₁₋₄alkyl;

a represents —NR₄—C(=O)—[C(R₅ᵦ)₂]ᵣ— or —NR₄—C(R₅ᵦ)₂—C(=O)—; in particular a represents —NR₄—C(=O)—[C(R₅ᵦ)₂]ᵣ—; more in particular a represents —NR₄—C(=O)—CH₂—.

Another embodiment of the present invention relates to those compounds of Formula (I) and the pharmaceutically acceptable addition salts, and the solvates thereof, or any subgroup thereof as mentioned in any of the other embodiments wherein one or more of the following restrictions apply:
(i) Xₐ, Xᵦ and X_c are CH;
(ii) —X₁— represents —CH₂—NR₁—CH₂—C₁₋₄alkanediyl-, —NR₁—CH₂—C₂₋₄alkanediyl-, or —X₁— represents one of the following groups wherein —(CH₂)₂— is attached to 'variable a':

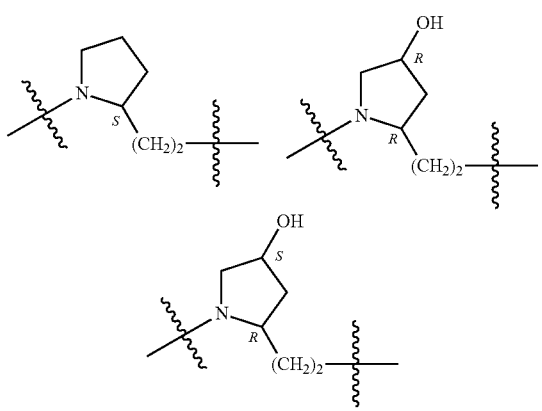

(iii) R₁ represents C₁₋₄alkyl, C₂₋₄alkenyl, C₂₋₄alkynyl, C₁₋₄alkyloxyC₁₋₄alkyl; in particular R₁ represents C₁₋₄alkyl, C₂₋₄alkenyl, or C₁₋₄alkyloxyC₁₋₄alkyl;
(iv) a represents —NR₄—C(=O)—CH₂—;
(v) b represents

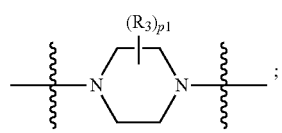

(vi) p1 is 1
(vii) R₃ represents hydrogen; C₁₋₄alkyloxyC₁₋₄alkyl optionally substituted with cyano; or hydroxyC₁₋₄alkyloxyC₁₋₄alkyl; in particular R₃ is hydrogen;
(viii) R₆ represents H;
(ix) r represents 1;
(x) c is CH₂.

In an embodiment, the present invention relates to those compounds of Formula (I) and the pharmaceutically acceptable addition salts, and the solvates thereof, or any subgroup thereof as mentioned in any of the other embodiments, wherein —X₁— represents —CH₂—NR₁—CH₂—C₁₋₄alkanediyl- or —NR₁—CH₂—C₁₋₄alkanediyl-.

In an embodiment, the present invention relates to those compounds of Formula (I) and the pharmaceutically acceptable addition salts, and the solvates thereof, or any subgroup thereof as mentioned in any of the other embodiments, wherein —X₁— represents one of the following groups wherein —(CH₂)₂— is attached to 'variable a':

a represents —NR$_4$—C(=O)—[C(R$_{5b}$)$_2$]$_r$— or —NR$_4$—C(R$_{5b}$)$_2$—C(=O)—; in particular a represents —NR$_4$—C(=O)—[C(R$_{5b}$)$_2$]$_r$—; more in particular a represents —NR$_4$—C(=O)—CH$_2$—.

In an embodiment, the present invention relates to those compounds of Formula (I) and the pharmaceutically acceptable addition salts, and the solvates thereof, or any subgroup thereof as mentioned in any of the other embodiments, wherein —X$_1$— represents one of the following groups wherein C$_{1-4}$alkanediyl is attached to 'variable a':

In an embodiment, the present invention relates to those compounds of Formula (I) and the pharmaceutically acceptable addition salts, and the solvates thereof, or any subgroup thereof as mentioned in any of the other embodiments, wherein if R$_1$ is taken together with R$_2$, then —X$_1$— represents one of the following groups wherein C$_{1-4}$alkanediyl is attached to 'variable a':

In an embodiment, the present invention relates to those compounds of Formula (I) and the pharmaceutically acceptable addition salts, and the solvates thereof, or any subgroup thereof as mentioned in any of the other embodiments, wherein if R$_1$ is taken together with one R$_2$, the bond towards the second R$_2$ substituent is oriented as shown hereunder:

In an embodiment, the present invention relates to those compounds of Formula (I) and the pharmaceutically acceptable addition salts, and the solvates thereof, or any subgroup thereof as mentioned in any of the other embodiments, wherein X$_a$, X$_b$ and X$_c$ are CH;
ring A represents phenyl;
R$_6$ is hydrogen;
n is 1;
c represents —[C(R$_{5a}$)$_2$]$_m$—;
m is 1;
R$_{5a}$ is hydrogen;
b represents a represents —NR$_4$—C(=O)—[C(R$_{5b}$)$_2$]$_r$—;
R$_4$ represents hydrogen;
r represents 1;
R$_{5b}$ represents hydrogen;
—X$_1$— represents —CH$_2$—NR$_1$—(CH$_2$)$_2$—;

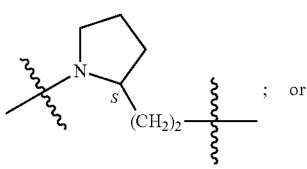 ; or

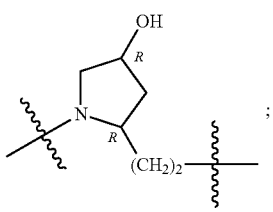 ;

$R_1$ represents $C_{1-4}$alkyl, $C_{2-4}$alkenyl, $C_{1-4}$alkyloxy $C_{1-4}$alkyl, or $C_{1-4}$alkyl substituted with $R_{11}$;

$R_{11}$ is $C_{3-6}$cycloalkyl; or a 4 to 7 membered monocyclic heterocyclic ring containing up to 3 heteroatoms selected from N or O, said heterocyclic ring being optionally substituted with 1 or 2 substituents each independently selected from $C_{1-4}$alkyl, halo, hydroxyl, or halo$C_{1-4}$alkyl; in particular $R_{11}$ is cyclopropyl or tetrahydrofuranyl.

In an embodiment, the present invention relates to those compounds of Formula (I) and the pharmaceutically acceptable addition salts, and the solvates thereof, or any subgroup thereof as mentioned in any of the other embodiments, wherein a represents —NR$_4$—C(=O)—[C(R$_{5b}$)$_2$]$_r$—;

—X$_1$— represents —CH$_2$—NR$_1$—(CH$_2$)$_2$—;

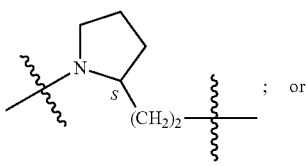 ; or

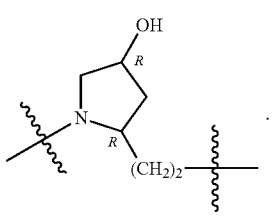 .

It will be clear for the skilled person that in the above embodiments wherein

—X$_1$— represents e.g. —CH$_2$—NR$_1$—(CH$_2$)$_2$—;

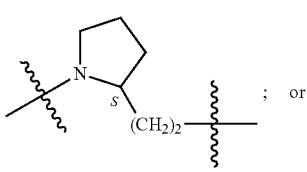 ; or

-continued

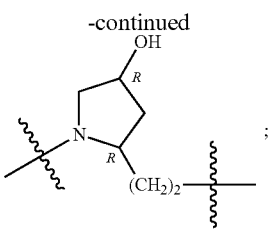 ;

the —(CH$_2$)$_2$— group is attached to 'variable a'.

In an embodiment, the present invention relates to those compounds of Formula (I) and the pharmaceutically acceptable addition salts, and the solvates thereof, or any subgroup thereof as mentioned in any of the other embodiments, wherein $X_{d1}$ and $X_{d2}$ are N;

the linker with the 'a substituent' is present on $X_{d2}$ or is present on a carbon atom in the alpha position of $X_{d2}$;

—X$_1$— represents —NH—X$_e$—C$_{2-4}$alkanediyl- in which case a represents —NR$_4$—C(=O)—CH$_2$— or —NR$_4$—CH$_2$—C(=O)—; or —X$_1$— represents —N(CH$_3$)—X$_e$—C$_{2-4}$alkanediyl- in which case a represents —NR$_4$—CH$_2$—C(=O)—; or —X$_1$— represents one of the following groups wherein —(CH$_2$)$_2$— is attached to 'variable a':

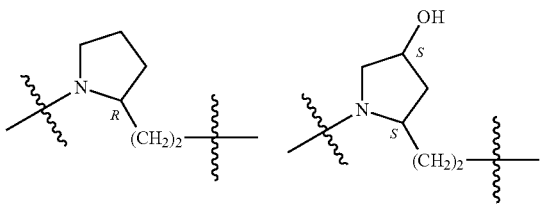

in which case a represents —NR$_4$—C(=O)—CH$_2$;

c is CH$_2$; and each R$_6$ independently represents hydrogen, halo, or —C(=O)NH$_2$.

In an embodiment, the present invention relates to those compounds of Formula (I) and the pharmaceutically acceptable addition salts, and the solvates thereof, or any subgroup thereof as mentioned in any of the other embodiments, wherein $X_{d1}$ and $X_{d2}$ are N;

the linker with the 'a substituent' is present on $X_{d2}$ or is present on a carbon atom in the alpha position of $X_{d2}$;

—X$_1$— represents —NH—X$_e$—C$_{2-4}$alkanediyl- in which case a represents —NR$_4$—C(=O)—CH$_2$— or —NR$_4$—CH$_2$—C(=O)—; or —X$_1$— represents —N(CH$_3$)—X$_e$—C$_{2-4}$alkanediyl- in which case a represents —NR$_4$—CH$_2$—C(=O)—; or —X$_1$— represents one of the following groups wherein —(CH$_2$)$_2$— is attached to 'variable a':

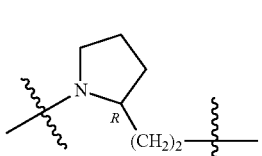 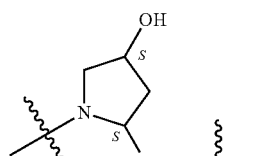

in which case a represents —NR$_4$—C(=O)—CH$_2$;

R$_3$ is hydrogen;

c is CH$_2$; and each R$_6$ independently represents hydrogen, halo, or —C(=O)NH$_2$.

In an embodiment, the present invention relates to those compounds of Formula (I) and the pharmaceutically acceptable addition salts, and the solvates thereof, or any subgroup thereof as mentioned in any of the other embodiments, wherein if $R_1$ is taken together with one $R_2$, the bond towards the second $R_2$ substituent is oriented as shown hereunder:

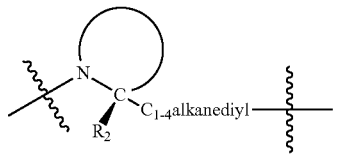

In an embodiment, the present invention relates to those compounds of Formula (I) and the pharmaceutically acceptable addition salts, and the solvates thereof, or any subgroup thereof as mentioned in any of the other embodiments, wherein $R_1$ is always taken together with one $R_2$.

In an embodiment, the present invention relates to those compounds of Formula (I) and the pharmaceutically acceptable addition salts, and the solvates thereof, or any subgroup thereof as mentioned in any of the other embodiments, wherein $R_1$ is always taken together with one $R_2$, and the bond towards the second $R_2$ substituent is oriented as shown hereunder:

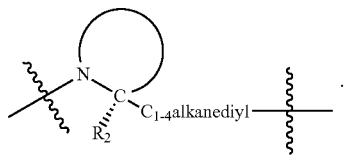

In an embodiment, the present invention relates to those compounds of Formula (I) and the pharmaceutically acceptable addition salts, and the solvates thereof, or any subgroup thereof as mentioned in any of the other embodiments, wherein each $R_3$ independently represents hydrogen; oxo; hydroxyl; carboxyl; $-NR_{3a}R_{3b}$; $-C(=O)-NR_{3a}R_{3b}$; hydroxy$C_{1-4}$alkyl; halo$C_{1-4}$alkyl; $-(C=O)-C_{1-4}$alkyl; $-C(=O)-O-C_{1-4}$alkyl wherein said $C_{1-4}$alkyl may optionally be substituted with phenyl; $C_{1-4}$alkyl optionally substituted with cyano, carboxyl, $C_{1-4}$alkyloxy, $-C(=O)-O-C_{1-4}$alkyl, $-O-C(=O)-C_{1-4}$alkyl, $-NR_{3e}R_{3f}$, $-C(=O)-NR_{3e}R_{3f}$, or $-SO_2-NR_{3e}R_{3f}$; hydroxy$C_{1-4}$alkyloxy$C_{1-4}$alkyl; $C_{1-4}$alkyloxyhydroxy$C_{1-4}$alkyl; hydroxy$C_{1-4}$alkyloxyhydroxy$C_{1-4}$alkyl; or $C_{1-4}$alkyloxy$C_{1-4}$alkyl optionally substituted with cyano, carboxyl, $C_{1-4}$alkyloxy, $-C(=O)-O-C_{1-4}$alkyl, $-O-C(=O)-C_{1-4}$alkyl, $-NR_{3e}R_{3f}$, $-C(=O)-NR_{3e}R_{3f}$, $-SO_2-NR_{3e}R_{3f}$, $R_{10}$, $-C(=O)-R_{10}$, or $-SO_2-R_{10}$.

In an embodiment, the present invention relates to those compounds of Formula (I) and the pharmaceutically acceptable addition salts, and the solvates thereof, or any subgroup thereof as mentioned in any of the other embodiments, wherein a represents $-NR_4-C(=O)-[C(R_{5b})_2]_r-$; and
c represents a bond, $-[C(R_{5a})_2]_m-$, $-O-$ or $-NR_{5a'}-$.

In an embodiment, the present invention relates to those compounds of Formula (I) and the pharmaceutically acceptable addition salts, and the solvates thereof, or any subgroup thereof as mentioned in any of the other embodiments, wherein a represents $-NR_4-C(=O)-[C(R_{5b})_2]_r-$; r is 1; and
c represents a bond, $-[C(R_{5a})_2]_m-$, $-O-$ or $-NR_{5a'}-$.

In an embodiment, the present invention relates to those compounds of Formula (I) and the pharmaceutically acceptable addition salts, and the solvates thereof, or any subgroup thereof as mentioned in any of the other embodiments, wherein a represents $-NR_4-C(=O)-[C(R_{5b})_2]_r-$; r is 1; and c represents $-[C(R_{5a})_2]_m-$.

In an embodiment, the present invention relates to those compounds of Formula (I) and the pharmaceutically acceptable addition salts, and the solvates thereof, or any subgroup thereof as mentioned in any of the other embodiments, wherein a represents $-NR_4-C(=O)-[C(R_{5b})_2]_r-$; r is 1; and c represents $-CH_2-$.

In an embodiment, the present invention relates to those compounds of Formula (I) and the pharmaceutically acceptable addition salts, and the solvates thereof, or any subgroup thereof as mentioned in any of the other embodiments, wherein two $R_{5b}$ substituents attached to the same carbon atom are taken together to form $C_{2-5}$alkanediyl or $-(CH_2)_p-O-(CH_2)_p-$, in particular $C_{2-5}$alkanediyl.

In an embodiment, the present invention relates to those compounds of Formula (I) and the pharmaceutically acceptable addition salts, and the solvates thereof, or any subgroup thereof as mentioned in any of the other embodiments, wherein a represents $-NR_4-C(=O)-[C(R_{5b})_2]_r-$; and wherein two $R_{5b}$ substituents attached to the same carbon atom are taken together to form $C_{2-5}$alkanediyl or $-(CH_2)_p-O-(CH_2)_p-$, in particular $C_{2-5}$alkanediyl.

In an embodiment, the present invention relates to those compounds of Formula (I) and the pharmaceutically acceptable addition salts, and the solvates thereof, or any subgroup thereof as mentioned in any of the other embodiments, wherein a represents $-NR_4-C(=O)-[C(R_{5b})_2]_r-$; r is 1; and wherein the two $R_{5b}$ substituents attached to the same carbon atom are taken together to form $C_{2-5}$alkanediyl or $-(CH_2)_p-O-(CH_2)_p-$, in particular $C_{2-5}$alkanediyl.

In an embodiment, the present invention relates to those compounds of Formula (I) and the pharmaceutically acceptable addition salts, and the solvates thereof, or any subgroup thereof as mentioned in any of the other embodiments, wherein a represents $-NR_4-C(=O)-[C(R_{5b})_2]_r-$; r is 1; wherein the two $R_{5b}$ substituents attached to the same carbon atom are taken together to form $C_{2-5}$alkanediyl or $-(CH_2)_p-O-(CH_2)_p-$, in particular $C_{2-5}$alkanediyl; and c represents $-CH_2-$.

In an embodiment, the present invention relates to those compounds of Formula (I) and the pharmaceutically acceptable addition salts, and the solvates thereof, or any subgroup thereof as mentioned in any of the other embodiments, wherein $-X_1-$ represents $-NR_1-X_e-C_{1-4}$alkanediyl- wherein said $C_{1-4}$alkanediyl moiety is optionally substituted with hydroxyl or hydroxy$C_{1-4}$alkyl;
$-X_e-$ represents $-C(R_2)_2-$; and
$R_1$ is taken together with $R_2$ to form $C_{1-4}$alkanediyl or $C_{2-4}$alkenediyl, each of said $C_{1-4}$alkanediyl and $C_{2-4}$alkenediyl optionally being substituted with 1 to 4 substituents each independently selected from hydroxyl, oxo, halo, cyano, $N_3$, hydroxy$C_{1-4}$alkyl, —NR$_7$R$_8$, —SO$_2$—NR$_7$R$_8$, —NH—SO$_2$—NR$_7$R$_8$, —C(=O)—NR$_7$R$_8$, or —NH—C(=O)—NR$_7$R$_8$.

In an embodiment, the present invention relates to those compounds of Formula (I) and the pharmaceutically acceptable addition salts, and the solvates thereof, or any subgroup thereof as mentioned in any of the other embodiments, wherein —X$_1$— represents —NR$_1$—X$_e$—C$_{1-4}$alkanediyl- wherein said C$_{1-4}$alkanediyl moiety is optionally substituted with hydroxyl or hydroxyC$_{1-4}$alkyl;

—X$_e$— represents —C(R$_2$)$_2$—; and

R$_1$ is taken together with R$_2$ to form C$_{1-4}$alkanediyl substituted with 1 hydroxyl substituent.

In an embodiment, the present invention relates to those compounds of Formula (I) and the pharmaceutically acceptable addition salts, and the solvates thereof, or any subgroup thereof as mentioned in any of the other embodiments, wherein —X$_1$— represents

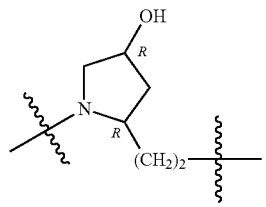

wherein —(CH$_2$)$_2$— is attached to 'variable a'.

In an embodiment, the present invention relates to those compounds of Formula (I) and the pharmaceutically acceptable addition salts, and the solvates thereof, or any subgroup thereof as mentioned in any of the other embodiments, wherein —X$_1$— represents one of the following groups wherein —(CH$_2$)$_2$— is attached to 'variable a':

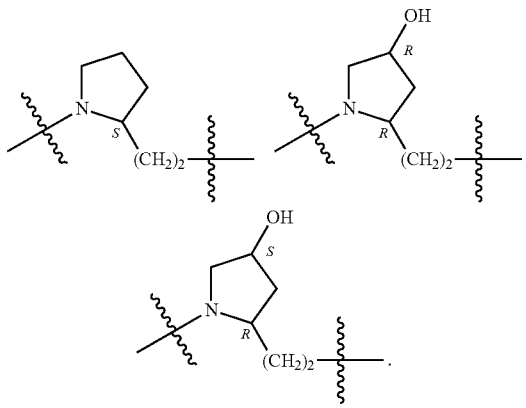

In an embodiment, the present invention relates to those compounds of Formula (I) and the pharmaceutically acceptable addition salts, and the solvates thereof, or any subgroup thereof as mentioned in any of the other embodiments, wherein a represents —NR$_4$—C(=O)—[C(R$_{5b}$)$_2$]$_r$—; r is 1; wherein the two R$_{5b}$ substituents attached to the same carbon atom are taken together to form C$_{2-5}$alkanediyl;

c represents —CH$_2$—;

—X$_1$— represents —NR$_1$—X$_e$—C$_{1-4}$alkanediyl- wherein said C$_{1-4}$alkanediyl moiety is optionally substituted with hydroxyl or hydroxyC$_{1-4}$alkyl;

—X$_e$— represents —C(R$_2$)$_2$—; and

R$_1$ is taken together with R$_2$ to form C$_{1-4}$alkanediyl substituted with 1 hydroxyl substituent.

In an embodiment, the present invention relates to those compounds of Formula (I) and the pharmaceutically acceptable addition salts, and the solvates thereof, or any subgroup thereof as mentioned in any of the other embodiments, wherein a represents —NR$_4$—C(=O)—[C(R$_{5b}$)$_2$]$_r$—; r is 1; wherein the two R$_{5b}$ substituents attached to the same carbon atom are taken together to form C$_{2-5}$alkanediyl;

c represents —CH$_2$—;

—X$_1$— represents —NR$_1$—X$_e$—C$_{1-4}$alkanediyl- wherein said C$_{1-4}$alkanediyl moiety is optionally substituted with hydroxyl or hydroxyC$_{1-4}$alkyl;

—X$_e$— represents —C(R$_2$)$_2$—; and

R$_1$ is taken together with R$_2$ to form C$_{1-4}$alkanediyl or C$_{2-4}$alkenediyl, each of said C$_{1-4}$alkanediyl and C$_{2-4}$alkenediyl optionally being substituted with 1 to 4 substituents each independently selected from hydroxyl, oxo, halo, cyano, N$_3$, hydroxyC$_{1-4}$alkyl, —NR$_7$R$_8$, —SO$_2$—NR$_7$R$_8$, —NH—SO$_2$—NR$_7$R$_8$, —C(=O)—NR$_7$R$_8$, or —NH—C(=O)—NR$_7$R$_8$.

In an embodiment, the present invention relates to those compounds of Formula (I) and the pharmaceutically acceptable addition salts, and the solvates thereof, or any subgroup thereof as mentioned in any of the other embodiments, wherein a represents —NR$_4$—C(=O)—[C(R$_{5b}$)$_2$]$_r$—; r is 1; wherein the two R$_{5b}$ substituents attached to the same carbon atom are taken together to form C$_{2-5}$alkanediyl;

c represents —C$_2$—; and

—X$_1$— represents

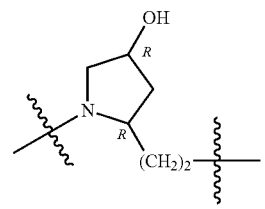

wherein —(CH$_2$)$_2$— is attached to 'variable a'.

In an embodiment, the present invention relates to those compounds of Formula (I) and the pharmaceutically acceptable addition salts, and the solvates thereof, or any subgroup thereof as mentioned in any of the other embodiments, wherein a represents —NR$_4$—C(=O)—[C(R$_{5b}$)$_2$]$_r$—; r is 1; wherein the two R$_b$ substituents attached to the same carbon atom are taken together to form C$_{2-5}$alkanediyl;

c represents —CH$_2$—; and

—X$_1$— represents one of the following groups wherein —(CH$_2$)$_2$— is attached to 'variable a':

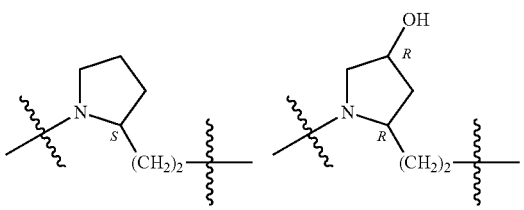

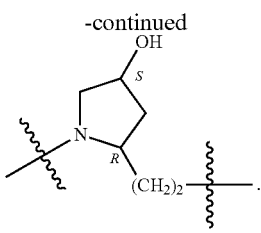

In an embodiment, the present invention relates to a subgroup of Formula (I) as defined in the general reaction schemes.

In an embodiment the compound of Formula (I) is selected from the group consisting of compounds 43, 96, 37, 88, 45, 62, 38, 91, 42, 1, 102 and 105, tautomers and stereoisomeric forms thereof,
and the pharmaceutically acceptable addition salts, and the solvates thereof.

In an embodiment the compound of Formula (I) is selected from the group consisting of compounds 70, 56, 71, 59, 48, 61, 89, 15, 112, 134, 3, 5, 83, 25, 86, 137 and 54, tautomers and stereoisomeric forms thereof,
and the pharmaceutically acceptable addition salts, and the solvates thereof.

In an embodiment the compound of Formula (I) is selected from the group consisting of compounds 88, 91, 45, 35, 37, 42, 38, 40 and 43,
tautomers and stereoisomeric forms thereof,
and the pharmaceutically acceptable addition salts, and the solvates thereof.

In an embodiment the compound of Formula (I) is selected from the group consisting of any of the exemplified compounds,
tautomers and stereoisomeric forms thereof,
and the free bases, the pharmaceutically acceptable addition salts, and the solvates thereof.

All possible combinations of the above-indicated embodiments are considered to be embraced within the scope of this invention.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry. Additionally, compounds of the present invention may also be prepared by analogous reaction protocols as described in the general schemes below combined with methods described in WO2009112439. Starting materials may also be prepared by methods as described in the literature for example by the procedures described in WO 2011008788, WO 2004105765, WO 2005058318, WO 2005058913, WO2006061415, WO2006061417, WO2009016132, WO2008155421 and WO 2007003525; or Burger et al., Medicinal Chemistry Letters (2011), 2(1), 34-38.

The skilled person will realize that in the reactions described in the Schemes, it may be necessary to protect reactive functional groups, for example hydroxy, amino (for example $NHR_4$ in an intermediate of Formula (V-a) wherein $R_1$ and $R_4$ are different), or carboxy groups, where these are desired in the final product, to avoid their unwanted participation in the reactions. Conventional protecting groups can be used in accordance with standard practice. This is illustrated in the specific examples. The protecting groups may be removed at a convenient subsequent stage using methods known from the art.

The skilled person will realize that in the reactions described in the Schemes, it may be advisable or necessary to perform the reaction under an inert atmosphere, such as for example under $N_2$-gas atmosphere, for example when NaH is used in the reaction.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of Formula (I).

The skilled person will realize that intermediates and final compounds shown in the schemes below may be further functionalized according to methods well-known by the person skilled in the art. Examples are shown in the specific experimental part.

The skilled person will realize that more Compounds of Formula (I) can be prepared by using similar synthetic protocols as described in the Schemes below. For example, in Scheme 1, an intermediate of Formula (III) can be replaced by an intermediate of Formula (LXVI). Or an intermediate of Formula (V-a) can typically be replaced by an intermediate of Formula —$NHR_1$—X—$C_{1-4}$alkanediyl-$(SO_2)_{p3}$—$NHR_4$—.

In case one of the starting materials is available as a salt form, the skilled person will realize that it may be necessary to first treat the salt with a base, such as for example DIPEA.

Although not shown in the general schemes, the rings in the position of ring b, may also contain extra bonds to form a bridged ring according to the scope.

In the schemes below, the $C_{1-4}$alkanediyl moiety in the intermediates and the final compounds, such as for example the $C_{1-4}$alkanediyl moiety in Formula (V-a), (VI), (VII) and (I-a) of scheme 1, is optionally substituted as defined in the scope.

All variables are defined as mentioned hereabove unless otherwise is indicated or is clear from the context.

In general, compounds of Formula (I-a) can be prepared according to Scheme 1:

Scheme 1
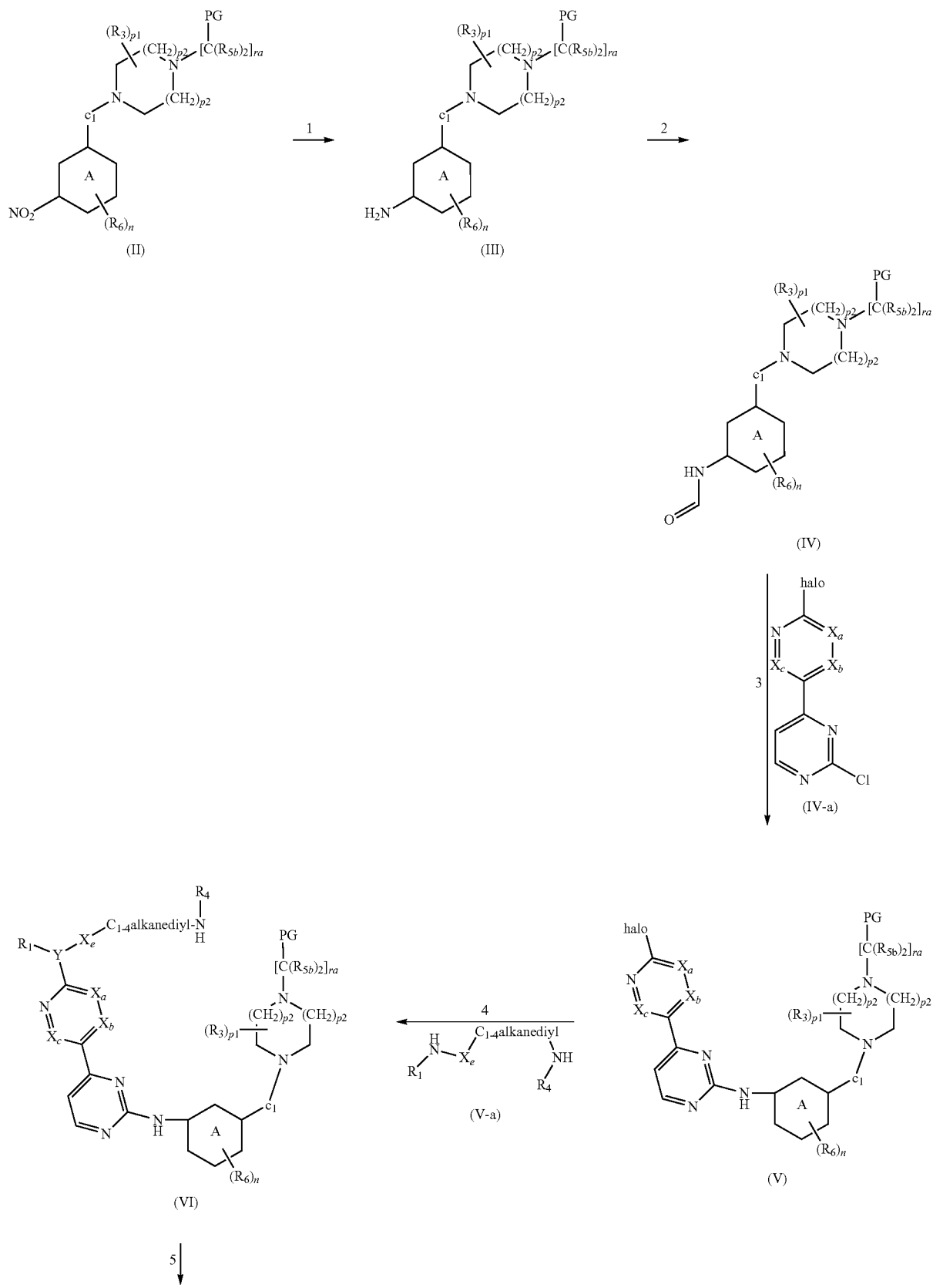

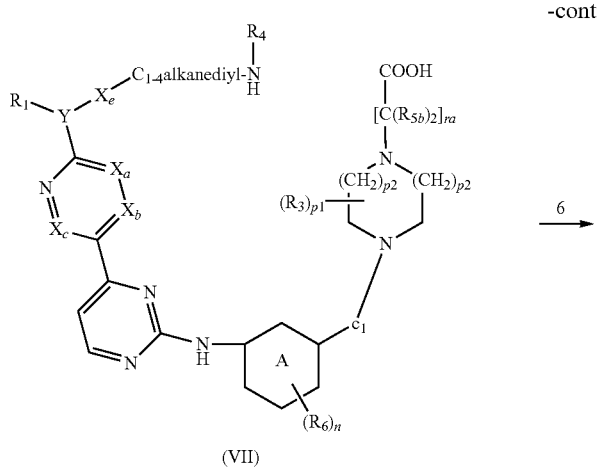

(VII)

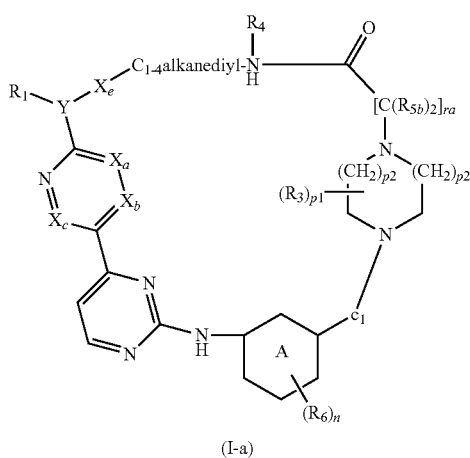

(I-a)

In scheme 1, 'halo' is defined as Br, Cl or F; 'PG' is defined as a protecting group such as for example tert-butoxycarbonyl, methoxycarbonyl or ethoxycarbonyl; '$c_1$' is defined as a bond, —[C($R_{5a}$)$_2$]$_m$—, —C(=O)—, —SO$_2$—, or —SO—; and 'ra' is defined as 1 or 2.

All other variables in Scheme 1 are defined according to the scope of the present invention.

In Scheme 1, the following reaction conditions apply:

1: The reduction of the nitro group in an intermediate of Formula (II) was performed
   a) under hydrogenation conditions: H$_2$-gas atmosphere in the presence of a catalyst such as for example Raney Ni, Pd/C (for example 5 wt % or 10 wt %) or Pt/C (for example 5 wt %) in a suitable solvent such as for example methanol (MeOH), ethanol (EtOH) or tetrahydrofuran (THF); or
   b) in the presence of Fe and NH$_4$Cl in a suitable mixture of solvents such as for example THF/H$_2$O/MeOH;

2: in the presence of phenyl formate, and a suitable solvent such as for example dichloromethane (DCM);

3: in the presence of a base such as for example NaH, and a suitable solvent such as for example N,N-dimethyl formamide (DMF);

4: optionally in the presence of a suitable base, such as for example Na$_2$CO$_3$, optionally in the presence of a suitable solvent such as for example N,N-dimethylacetamide (DMA) or 1-methyl-2-pyrrolidinone (NMP) or mixture of solvents such as for example DMA/DMSO ("DMSO" means dimethyl sulfoxide);

5: in the presence of an acid such as for example trifluoroacetic acid (TFA) in a solvent such as for example DCM; or
alternatively in the presence of an acid such as for example HCl in a solvent such as for example 1,4-dioxane optionally in the presence of water; or
alternatively first in the presence of a base such as for example NaOH, and subsequently in the presence of an acid such as for example HCl, in the presence of a suitable solvent such as for example THF;

6: in the presence of a coupling agent such as for example diethyl cyanophosphonate, (1H-benzotriazol-1-yloxy)(tripyrrolidin-1-yl)phosphonium hexafluorophosphate (PyBOP), 1-[bis(dimethylamino)methylene]-1H-benzotriazol-1-ium 3-oxide hexafluorophosphate (HBTU) or 1-[bis(dimethylamino)methylene]-1H-[1,2,3]triazolo[4,5-b]pyridin-1-ium 3-oxide hexafluorophosphate (HATU) in the presence of a base such as for example triethylamine (Et$_3$N) or N,N-diisopropylethylamine (DIPEA), in a suitable solvent such as for example DMF.

The compounds of Formula (I) may also be converted into each other via art-known reactions or functional group transformations.

For instance, a compound of Formula (I), in particular a compound of Formula (I-a), wherein $R^6$ represents aminocarbonyl can be converted to a compound wherein $R^6$ represents carboxyl, by reaction with a suitable acid such as for example HCl. During this reaction, ring-opening of the macrocycle may occur. In this case, it is necessary to react the outcome of the reaction with a coupling agent such as for example diethyl cyanophosphonate, in the presence of a base such as for example triethylamine (Et$_3$N), in a suitable solvent such as for example DMF, to close the macrocylic ring.

Intermediates of Formula (II) and (II-a) can be prepared according to Scheme 1a.

Scheme 1a

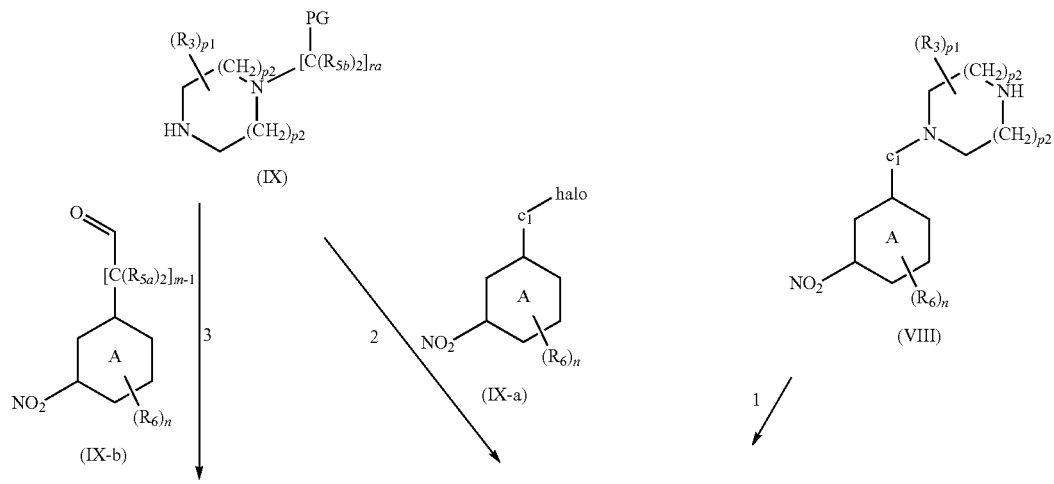

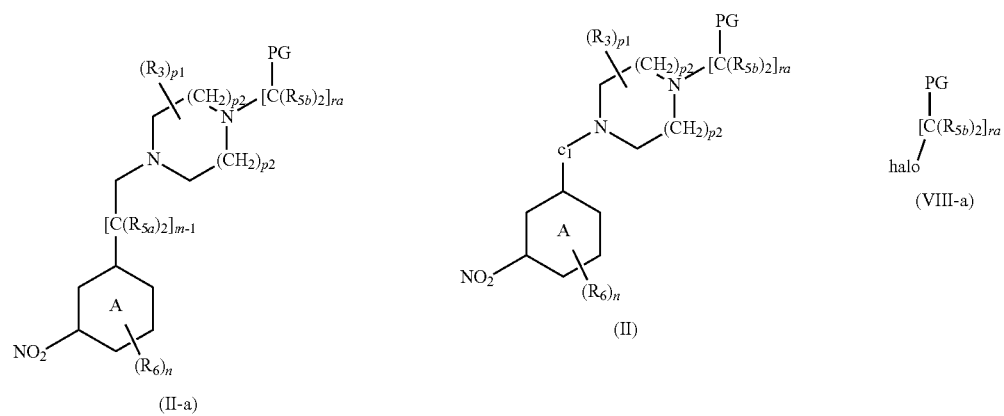

In scheme 1a, 'halo' is defined as Br, Cl or F; 'PG' is defined as a protecting group such as for example tert-butoxycarbonyl, methoxycarbonyl or ethoxycarbonyl; '$c_1$' is defined as a bond, $-[C(R_{5a})_2]_m-$, $-C(=O)-$, $-SO_2-$, or $-SO-$; 'ra' is defined as 1 or 2; and all other variables are defined according to the scope of the present invention.

In Scheme 1a, the following reaction conditions apply:
1: in the presence of a base such as for example NaH, $Et_3N$ or DIPEA, in a suitable solvent such as for example DMF;
2: in the presence of a base such as for example $K_2CO_3$, $Et_3N$ or DIPEA, in a suitable solvent such as $CH_3CN$, DCM or N,N-dimethylacetamide (DMA);
3: in the presence of a suitable reducing agent such as sodium triacetoxyborohydride, in suitable solvent or mixtures of solvents such as acetic acid or DCM.

An intermediate of Formula (IX) is commercially available or can be prepared by standard means obvious to those skilled in the art. Examples are shown in the specific experimental part.

In general, compounds of Formula (I-b) can be prepared according to Scheme 2:

Scheme 2
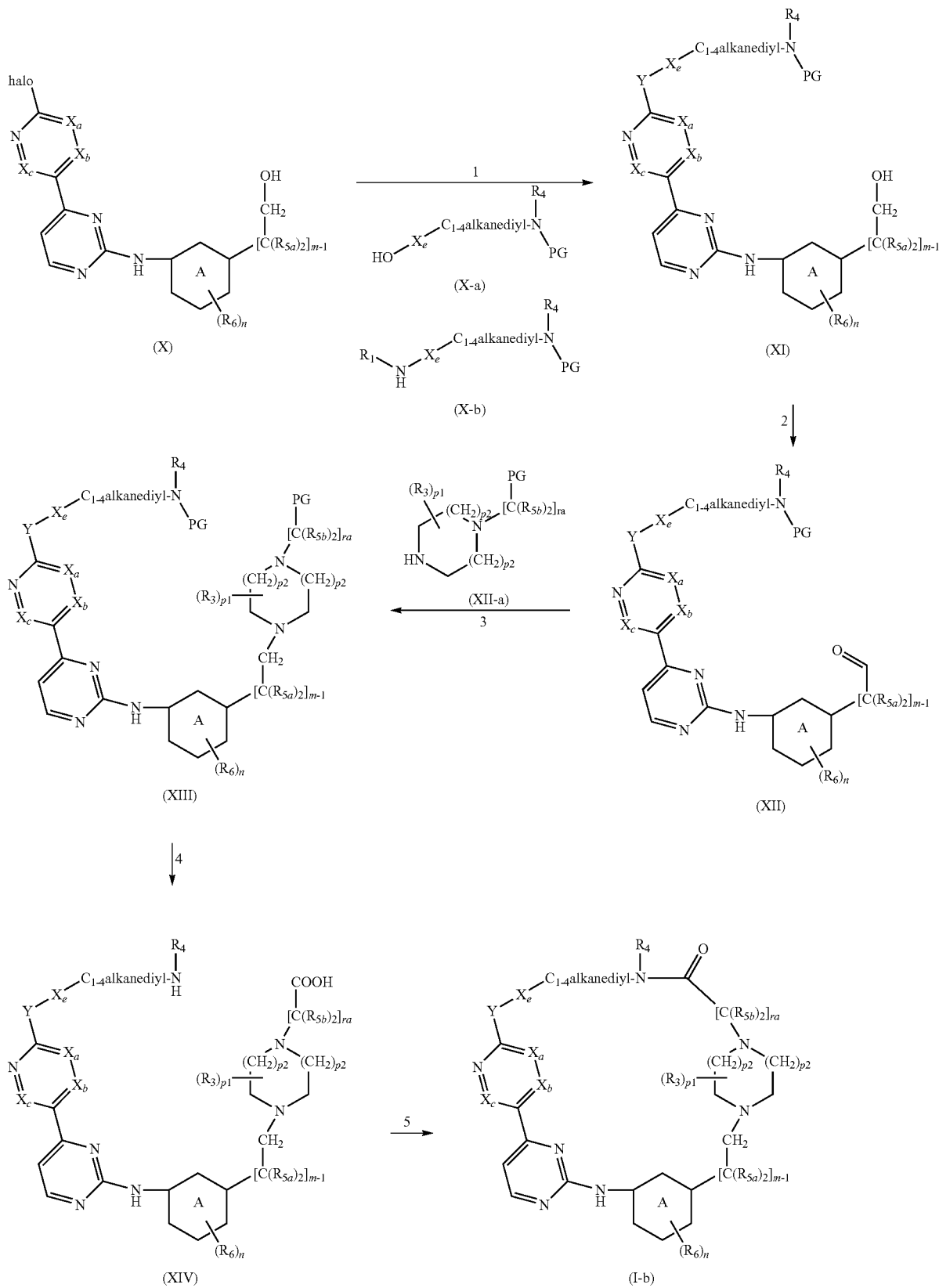

In scheme 2, Y is defined as O (in case the intermediate of Formula (X-a) was used in step 1) or Y is defined as NR₁ (in case the intermediate of Formula (X-b) was used in step 1); 'PG' and 'halo' are as defined before in the general reaction schemes; 'ra' is defined as 1 or 2; and all other variables are defined according to the scope of the present invention.

In Scheme 2, the following reaction conditions apply:
1a (Y is defined as O): in a suitable solvent such as for example 2-methyl-2-propanol or NMP, in the presence of a base such as for example potassium tert-butoxide;
1b (Y is defined as NR₁): optionally in the presence of a suitable base, such as for example Na₂CO₃, optionally in the presence of a suitable solvent such as for example N,N-dimethylacetamide (DMA) or 1-methyl-2-pyrrolidinone (NMP) or mixture of solvents such as for example DMA/DMSO ("DMSO" means dimethyl sulfoxide);
2: in the presence of an oxidizing agent such as for example MnO₂, in the presence of a suitable solvent such as for example DCM;
3: in the presence of a reducing agent such as for example sodium triacetoxyborohydride (NaBH(OAc)₃), and in the presence of a suitable solvent such as for example 1,2-dichloroethane (DCE);
4: in the presence of an acid such as for example trifluoroacetic acid (TFA) in a solvent such as for example DCM; or alternatively in the presence of an acid such as for example HCl in a solvent such as for example 1,4-dioxane optionally in the presence of water; or alternatively first in the presence of a base such as for example NaOH, and subsequently in the presence of an acid such as for example HCl, in the presence of a suitable solvent such as for example THF;
5: in the presence of a coupling agent such as for example diethyl cyanophosphonate, (1H-benzotriazol-1-yloxy)(tripyrrolidin-1-yl)phosphonium hexafluorophosphate (PyBOP), 1-[bis(dimethylamino)methylene]-1H-benzotriazol-1-ium 3-oxide hexafluorophosphate (HBTU) or 1-[bis(dimethylamino)methylene]-1H-[1,2,3]triazolo[4,5-b]pyridin-1-ium 3-oxide hexafluorophosphate (HATU) in the presence of a base such as for example triethylamine (Et₃N) or diisopropylethylamine (DIPEA), in a suitable solvent such as for example DMF.

In case 'ra' is 0 in an intermediate of Formula (XIII), hereby named an intermediate of Formula (XIII-a), a compound of Formula (I-b1) can be obtained as shown in Scheme 2a:

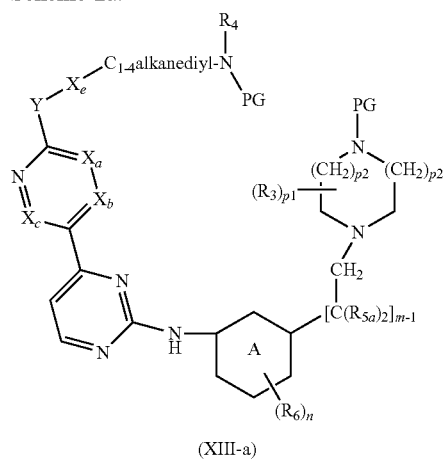

(XIII-a)

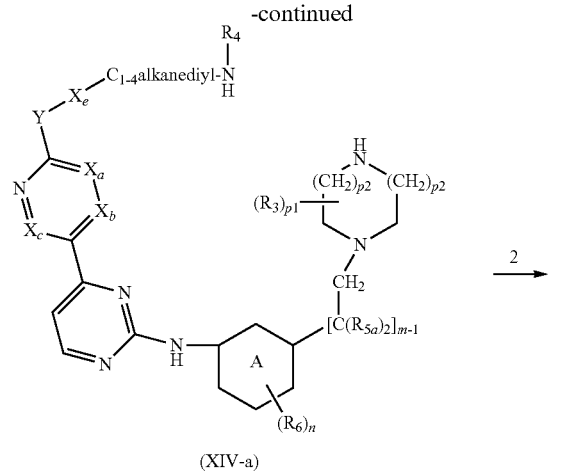

(XIV-a)

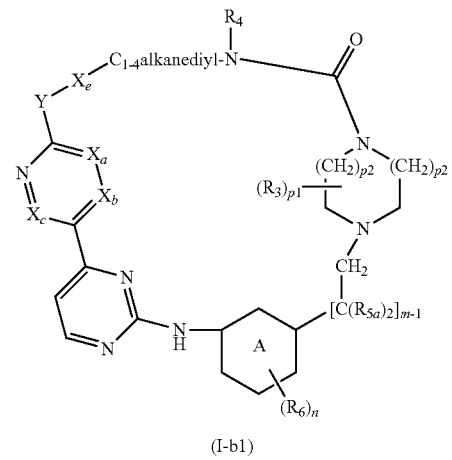

(I-b1)

In scheme 2a the following conditions apply:
1: in the presence of an acid such as for example trifluoroacetic acid (TFA) in a solvent such as for example DCM; or alternatively in the presence of an acid such as for example HCl in a solvent such as for example 1,4-dioxane optionally in the presence of water; or alternatively first in the presence of a base such as for example NaOH, and subsequently in the presence of an acid such as for example HCl, in the presence of a suitable solvent such as for example THF;

2: in the presence of a carbonyl source such as for example 4-nitrophenyl chloroformate in the presence of a base such as for example triethylamine (Et₃N) or diisopropylethylamine (DIPEA), in a suitable solvent such as for example DMF or 1,4-dioxane.

In general, compounds of Formula (I-c) can be prepared according to Scheme 3a:

Scheme 3a

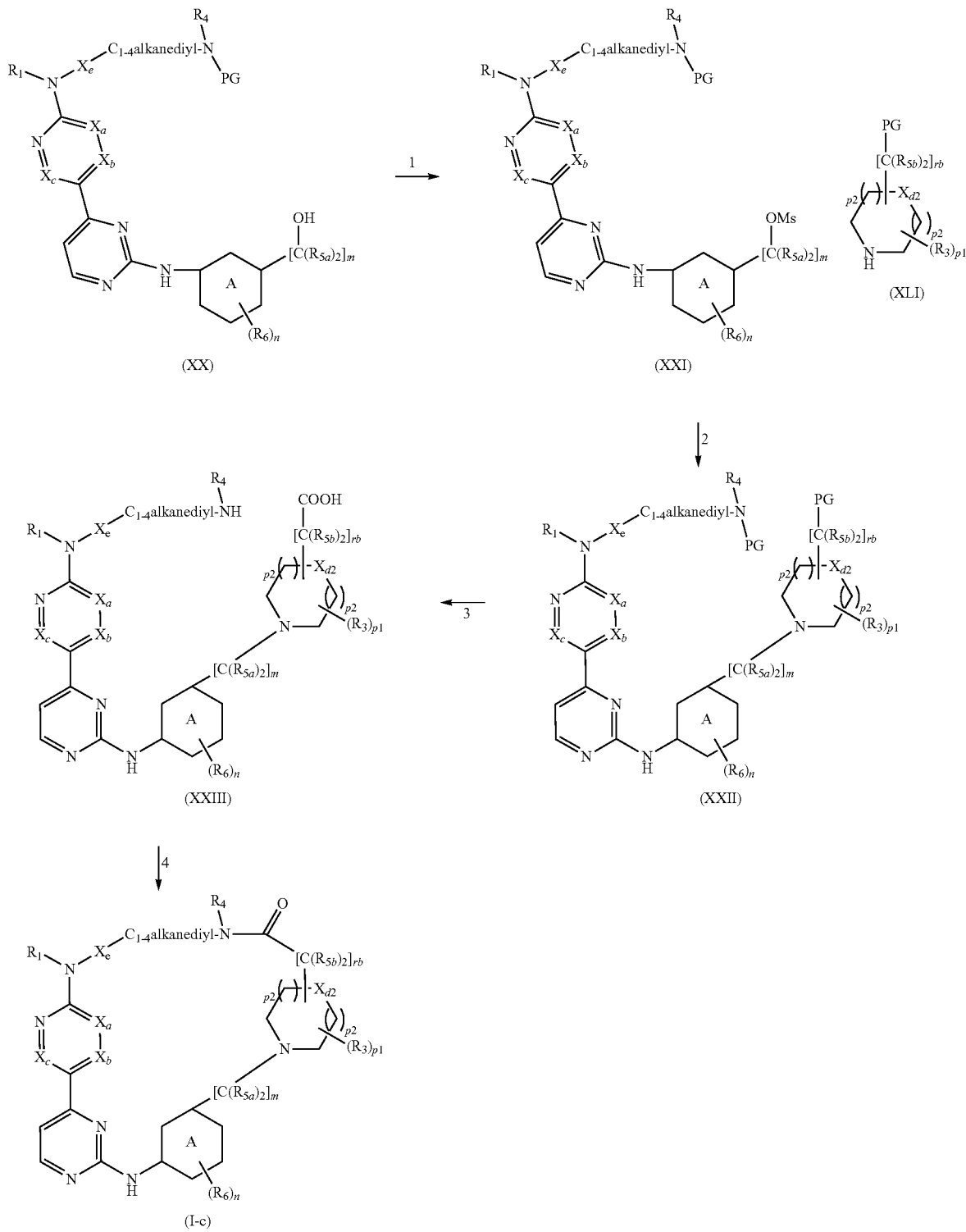

In scheme 3a, 'Ms' means mesyl(methanesulfonyl); 'rb' represents an integer of value 1 or 2 in case $[C(R_{5b})_2]_{rb}$ is attached to the ring via $X_{d2}$ and $X_{d2}$ represents N, or 'rb' represents an integer of value 0, 1 or 2 in case $[C(R_{5b})_2]_{rb}$ is attached to ring via a carbon atom; all other variables are defined according to the scope of the present invention.

In Scheme 3, the following reaction conditions apply:
1: in the presence of methanesulfonyl chloride, in the presence of a base such as for example DIPEA, in the presence of a suitable solvent such as for example DCM;
2: coupling reaction between an intermediate of Formula (XXI) and an intermediate of Formula (XLI), in the presence of a suitable base such as for example K₂CO₃, in the presence of a suitable solvent such as for example DMF;
3: in the presence of an acid such as for example trifluoroacetic acid (TFA) in a solvent such as for example DCM; or
alternatively in the presence of an acid such as for example HCl in a solvent such as for example 1,4-dioxane optionally in the presence of water; or
alternatively first in the presence of a base such as for example NaOH, and subsequently in the presence of an acid such as for example HCl, in the presence of a suitable solvent such as for example THF;
4: in the presence of a coupling agent such as for example diethyl cyanophosphonate, (1H-benzotriazol-1-yloxy) (tripyrrolidin-1-yl)phosphonium hexafluorophosphate (PyBOP), 1-[bis(dimethylamino)methylene]-1H-benzotriazol-1-ium 3-oxide hexafluorophosphate (HBTU) or 1-[bis(dimethylamino)methylene]-1H-[1,2,3]triazolo[4,5-b]pyridin-1-ium 3-oxide hexafluorophosphate (HATU) in the presence of a base such as for example triethylamine (Et₃N) or diisopropylethylamine (DIPEA), in a suitable solvent such as for example DMF.

An intermediate of Formula (XLI) is commercially available or can be prepared by standard means obvious to those skilled in the art. Examples are shown in the specific experimental part. The skilled person will also realize that obvious deviations from Scheme 3a are possible, such as illustrated in Example A15.

In general, an intermediate of Formula (XX-a), a subgroup of (XX), may be prepared according to Scheme 3b:

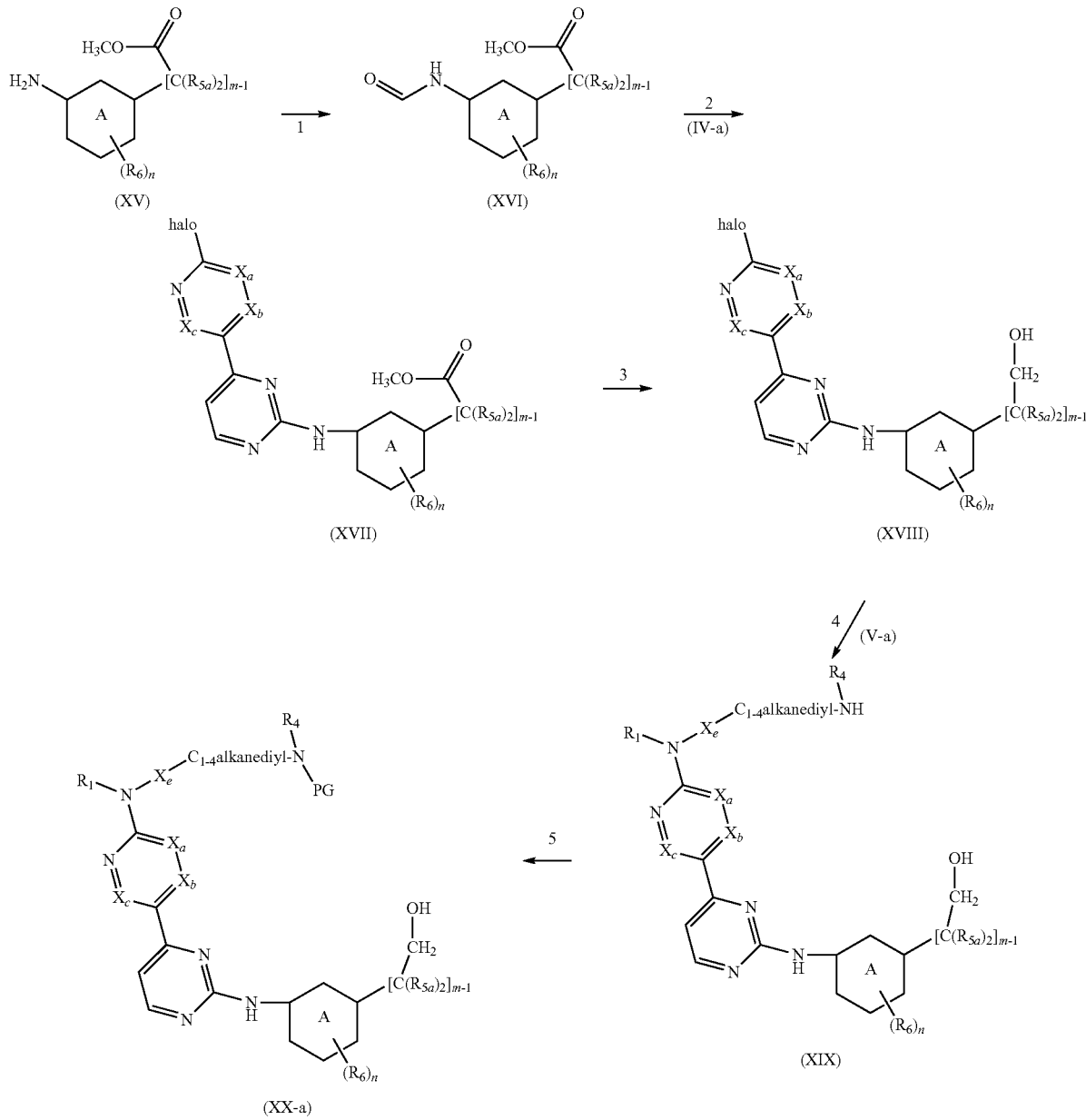

In scheme 3b, 'halo' and 'PG' are as defined before in the general reaction schemes; and all other variables are defined according to the scope of the present invention.

In Scheme 3b, the following reaction conditions apply:
1: in the presence of phenyl formate, and a suitable solvent such as for example dichloromethane (DCM);
2: coupling reaction between an intermediate of Formula (XVI) and an intermediate of Formula (IV-a) (see Scheme 1), in the presence of a base such as for example NaH, and a suitable solvent such as for example N,N-dimethyl formamide (DMF);
3: in the presence of a reducing agent such as for example $NaBH_4$, in the presence of a suitable solvent such as for example TH or a mixture of solvents such as for example MeOH/THF; or $LiAlH_4$ in the presence of a suitable solvent such as for example THF;
4: coupling reaction between an intermediate of Formula (XVIII) and an intermediate of Formula (V-a) (see Scheme 1), optionally in the presence of a suitable base, such as for example $Na_2CO_3$, optionally in the presence of a suitable solvent such as for example N,N-dimethyl-acetamide (DMA) or 1-methyl-2-pyrrolidinone (NMP) or mixture of solvents such as for example DMA/DMSO ("DMSO" means dimethyl sulfoxide);
5: introduction of a protecting group, by using for example di-tert-butyl dicarbonate, in the presence of a suitable mixture of solvents such as for example DCM/MeOH.

In general, an intermediate of Formula (XX) may be prepared according to Scheme 3c:

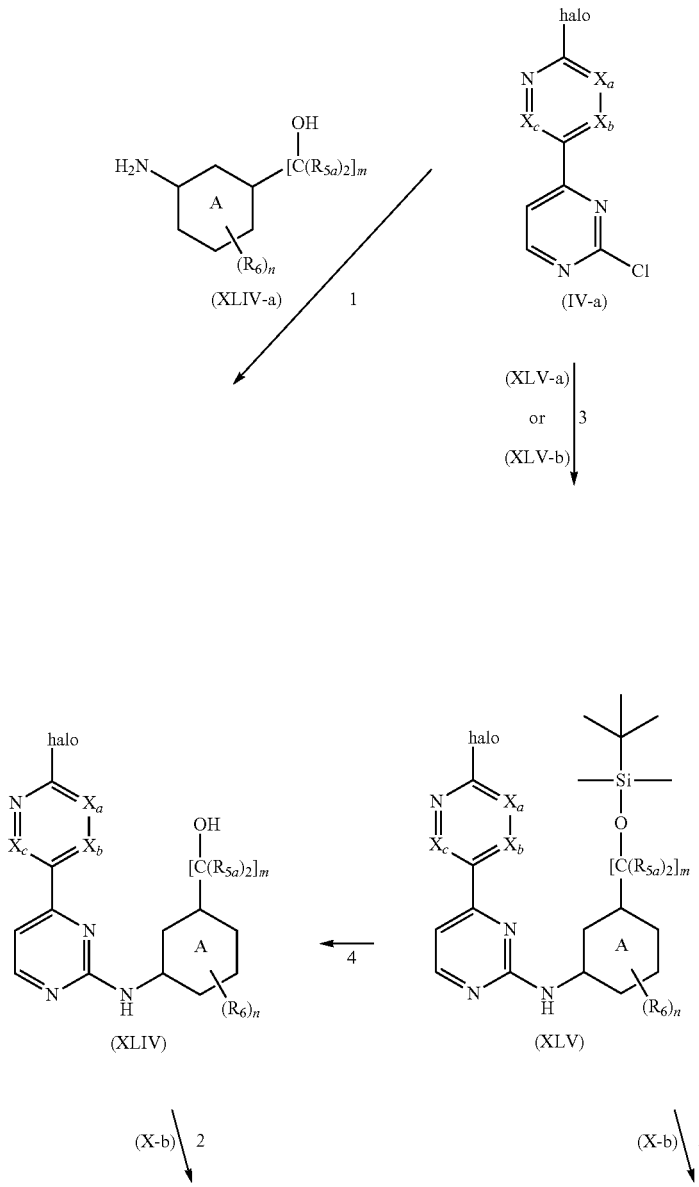

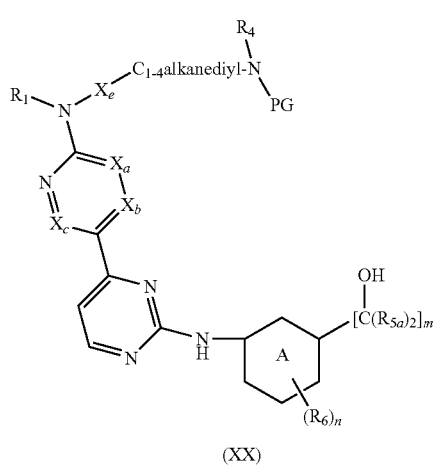

(XX)

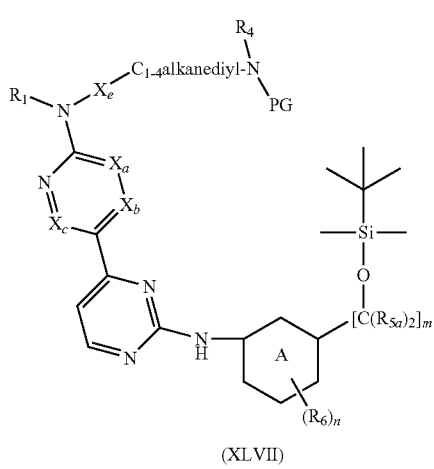

(XLVII)

In scheme 3c, 'PG' is as defined before; and all other variables are defined according to the scope of the present invention.

In Scheme 3c, the following reaction conditions apply:
1: coupling reaction between an intermediate of Formula (IV-a) and an intermediate of Formula (XLIV-a), in a suitable solvent such as for example n-butanol;
2: in a suitable solvent such as for example 2-methyl-2-propanol or NMP, optionally in the presence of a base such as for example $K_2CO_3$;
3: coupling reaction between an intermediate of Formula (IV-a) and an intermediate of Formula (XLV-a), in a suitable solvent such as for example n-butanol; or coupling reaction between an intermediate of Formula (IV-a) and an intermediate of Formula (XLV-b) in the presence of a base such as for example NaH, and a suitable solvent such as for example N,N-dimethyl formamide (DMF);

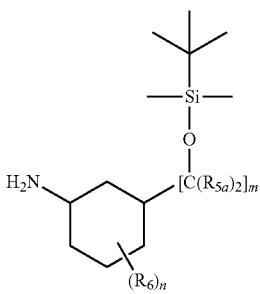

(XLV-a)

-continued

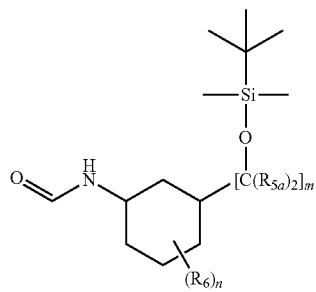

(XLV-b)

4: in the presence of a deprotecting agent such as for example tetrabutylammonium fluoride (TBAF) in THF; or alternatively in the presence of an acid such as for example HCl in $H_2O$; or alternatively in the presence of $CH_3COOH$ optionally in the presence of water;
5: in a suitable solvent such as for example 2-methyl-2-propanol or NMP, optionally in the presence of a base such as for example $K_2CO_3$;
6: in the presence of a deprotecting agent such as for example TBAF in THF; or
alternatively in the presence of an acid such as for example HCl in $H_2O$; or
alternatively in the presence of $CH_3COOH$ optionally in the presence of water.

The skilled person will realize that an intermediate of Formula (X-b) in Scheme 3c can be replaced by an intermediate of Formula —$NHR_1$—$X_e$—$C_{1-4}$alkanediyl-$(SO_2)_{p3}$—$N(PG)R_4$—.

In general, compounds of Formula (I-d) can be prepared according to Scheme 4:

Scheme 4
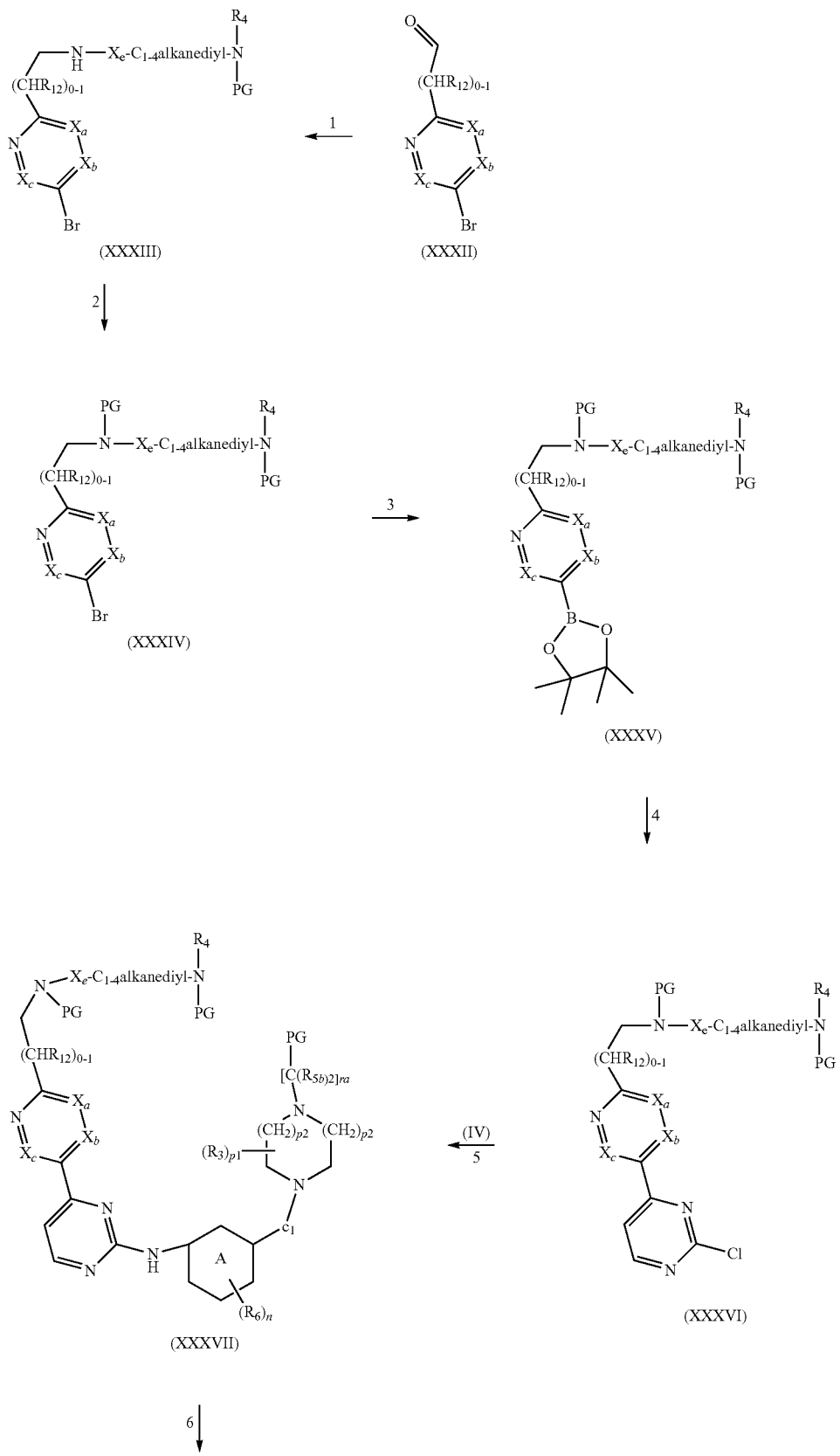

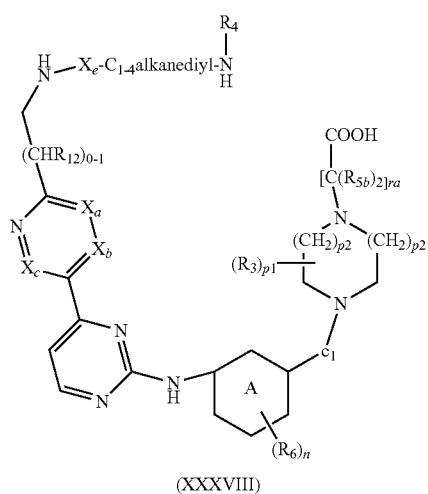

(XXXVIII)

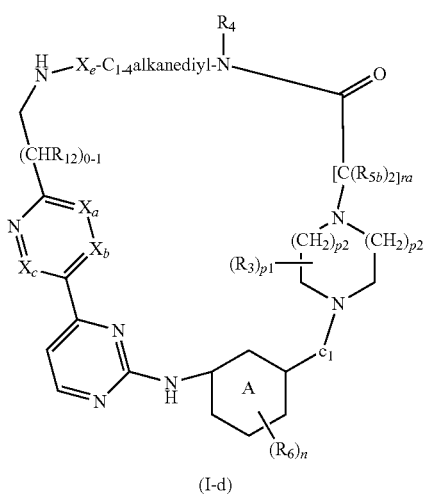

(I-d)

In scheme 4, 'PG' is as defined before; 'ra' is defined as 1 or 2; and all other variables are defined according to the scope of the present invention.

In Scheme 4, the following reaction conditions apply:
1: in the presence of a reducing agent such as for example sodium triacetoxyborohydride (NaBH(OAc)$_3$), in the presence of a suitable solvent such as for example DCM (anhydrous);
2: in the presence of di-tert-butyl dicarbonate, in the presence of a suitable solvent such as for example DCM;
3: in the presence of bis(pinacolato)diboron, in the presence of a suitable base such as for example potassium acetate, in the presence of a suitable catalyst such as for example [1,1'-bis(diphenylphosphino-κP)ferrocene]dichloropalladium-dichloromethane (1:1) (PdCl$_2$(dppf)-DCM), in the presence of a suitable solvent such as for example 1,4-dioxane;
4: coupling reaction between an intermediate of Formula (XXXV) and 2,4-dichloropyrimidine, in the presence of a suitable catalyst such as for example (PdCl$_2$(dppf)-DCM), in the presence of a suitable base such as for example Na$_2$CO$_3$, in the presence of a suitable solvent such as for example 1,4-dioxane;
5: coupling reaction between an intermediate of Formula (XXXVI) and an intermediate of Formula (IV), in the presence of a base such as for example NaH, in the presence of a suitable solvent such as for example N,N-dimethylacetamide (DMA);
6: in the presence of an acid such as for example trifluoroacetic acid (TFA) in a solvent such as for example DCM; or alternatively in the presence of an acid such as for example HCl in a solvent such as for example 1,4-dioxane optionally in the presence of water; or alternatively first in the presence of a base such as for example NaOH, and subsequently in the presence of an acid such as for example HCl, in the presence of a suitable solvent such as for example THF;
7: in the presence of a coupling agent such as for example diethyl cyanophosphonate (1H-benzotriazol-1-yloxy)(tripyrrolidin-1-yl)phosphonium hexafluorophosphate (PyBOP), 1-[bis(dimethylamino)methylene]-1H-benzotriazol-1-ium 3-oxide hexafluorophosphate (HBTU) or 1-[bis(dimethylamino)methylene]-1H-[1,2,3]triazolo[4,5-b]pyridin-1-ium 3-oxide hexafluorophosphate (HATU) in the presence of a base such as for example triethylamine (Et$_3$N) or diisopropylethylamine (DIPEA), in a suitable solvent such as for example DMF.

In general, compounds of Formula (I-d) can be converted to compounds of Formula (I-d-2) as shown in Scheme 5:

Scheme 5

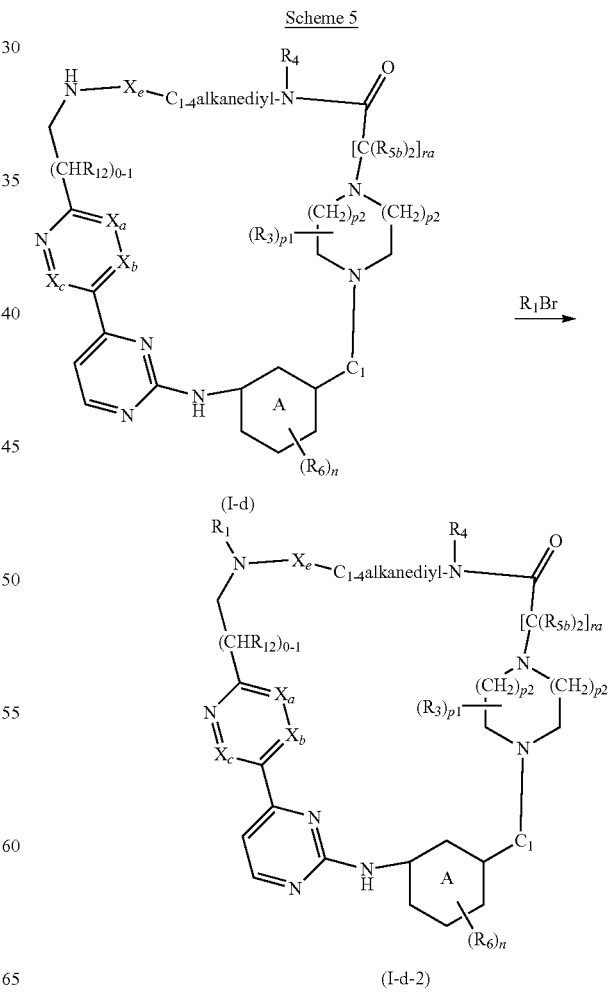

In Scheme 5, a compound of Formula (I-d) is reacted with an intermediate of Formula $R_1$—Br, to result in a compound of Formula (I-d-2). This reaction typically is performed in the presence of a suitable base such as for example DIPEA, in the presence of a suitable solvent such as for example DMF.

Analogous functionalization reactions can be performed by replacing $R_1Br$, for example, with alkylsulfonyl chlorides, acid chlorides or sulfamides. Other functional groups can also be introduced via reductive amination. All these reactions can be performed under standard reaction conditions well-known by the skilled person.

In general, a compound of Formula (I-f) can be prepared according to Scheme 6:

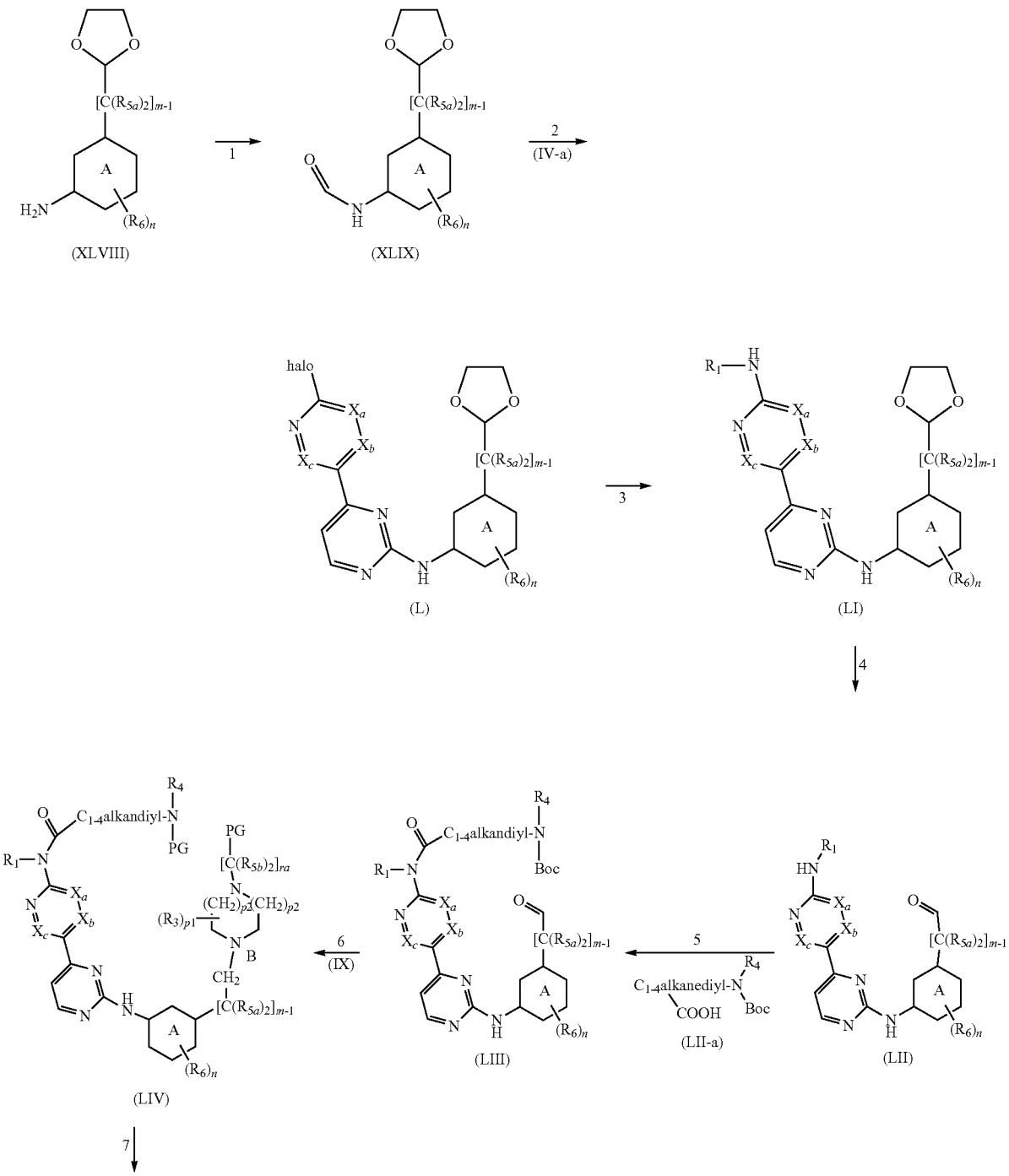

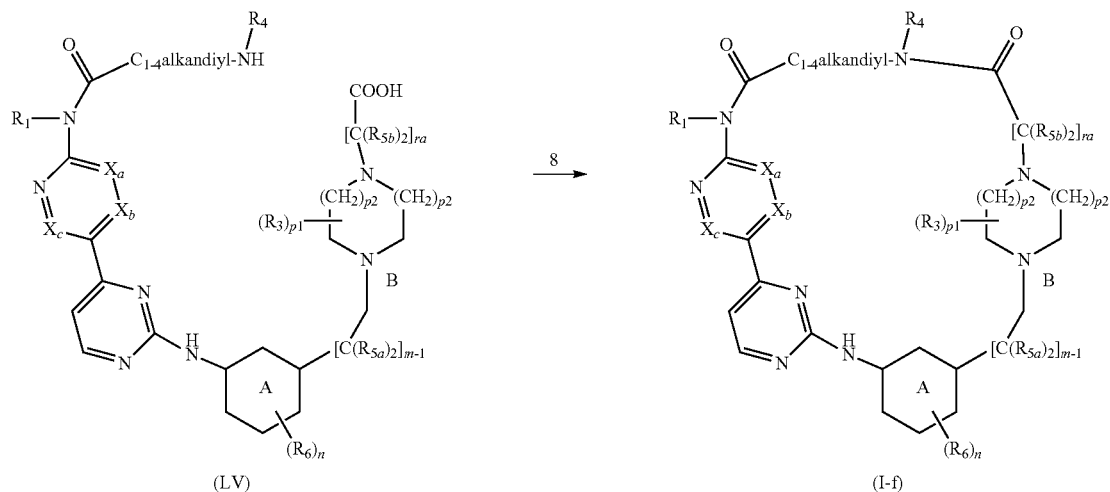

In scheme 6, 'PG' and 'halo' are as defined before in the general reaction schemes; 'ra' is defined as 1 or 2; and all other variables are defined according to the scope of the present invention.

In Scheme 6, the following reaction conditions apply:
1: in the presence of phenylformate, in a suitable solvent such as for example DCM;
2: coupling reaction between an intermediate of Formula (XLIX) and an intermediate of Formula (IV-a), in the presence of a base such as for example NaH, and a suitable solvent such as for example N,N-dimethyl formamide (DMF);
3: in the presence of $NH_2R_1$ (e.g. $NH_3$ in case $R_1$ represents H), in a suitable solvent such as for example THF;
4: in the presence of a ketone such as acetone, an acid such as p-toluenesulfonic acid and in the presence of $H_2O$;
5: coupling reaction between an intermediate of Formula (LII-a) and an intermediate of Formula (LII), in the presence of a coupling agent such as for example diethyl cyanophosphonate, (1H-benzotriazol-1-yloxy)(tripyrrolidin-1-yl)phosphonium hexafluorophosphate (PyBOP), 1-[bis(dimethylamino)methylene]-1H-benzotriazol-1-ium 3-oxide hexafluorophosphate (HBTU) or 1-[bis(dimethylamino)methylene]-1H-[1,2,3]triazolo[4,5-b]pyridin-1-ium 3-oxide hexafluorophosphate (HATU) in the presence of a base such as for example triethylamine ($Et_3N$) or N,N-diisopropylethylamine (DIPEA), in a suitable solvent such as for example THF or DMF;
6: coupling reaction between an intermediate of Formula (LIII) and an intermediate of Formula (IX), in the presence of a reducing agent such as for example sodium triacetoxyborohydride ($NaBH(OAc)_3$), and in the presence of a suitable solvent such as for example 1,2-dichloroethane (DCE);
7: in the presence of an acid such as for example trifluoroacetic acid (TFA) in a solvent such as for example DCM; or alternatively in the presence of an acid such as for example HCl in a solvent such as for example 1,4-dioxane optionally in the presence of water; or alternatively first in the presence of a base such as for example NaOH, and subsequently in the presence of an acid such as for example HCl, in the presence of a suitable solvent such as for example THF;
8: in the presence of a coupling agent such as for example diethyl cyanophosphonate. (1H-benzotriazol-1-yloxy)(tripyrrolidin-1-yl)phosphonium hexafluorophosphate (PyBOP), 1-[bis(dimethylamino)methylene]-1H-benzotriazol-1-ium 3-oxide hexafluorophosphate (HBTU) or 1-[bis(dimethylamino)methylene]-1H-[1,2,3]triazolo[4,5-b]pyridin-1-ium 3-oxide hexafluorophosphate (HATU) in the presence of a base such as for example triethylamine ($Et_3N$) or N,N-diisopropylethylamine (DIPEA), in a suitable solvent such as for example DMF. In general, a compound of Formula (I-g) can be prepared according to Scheme 7a:

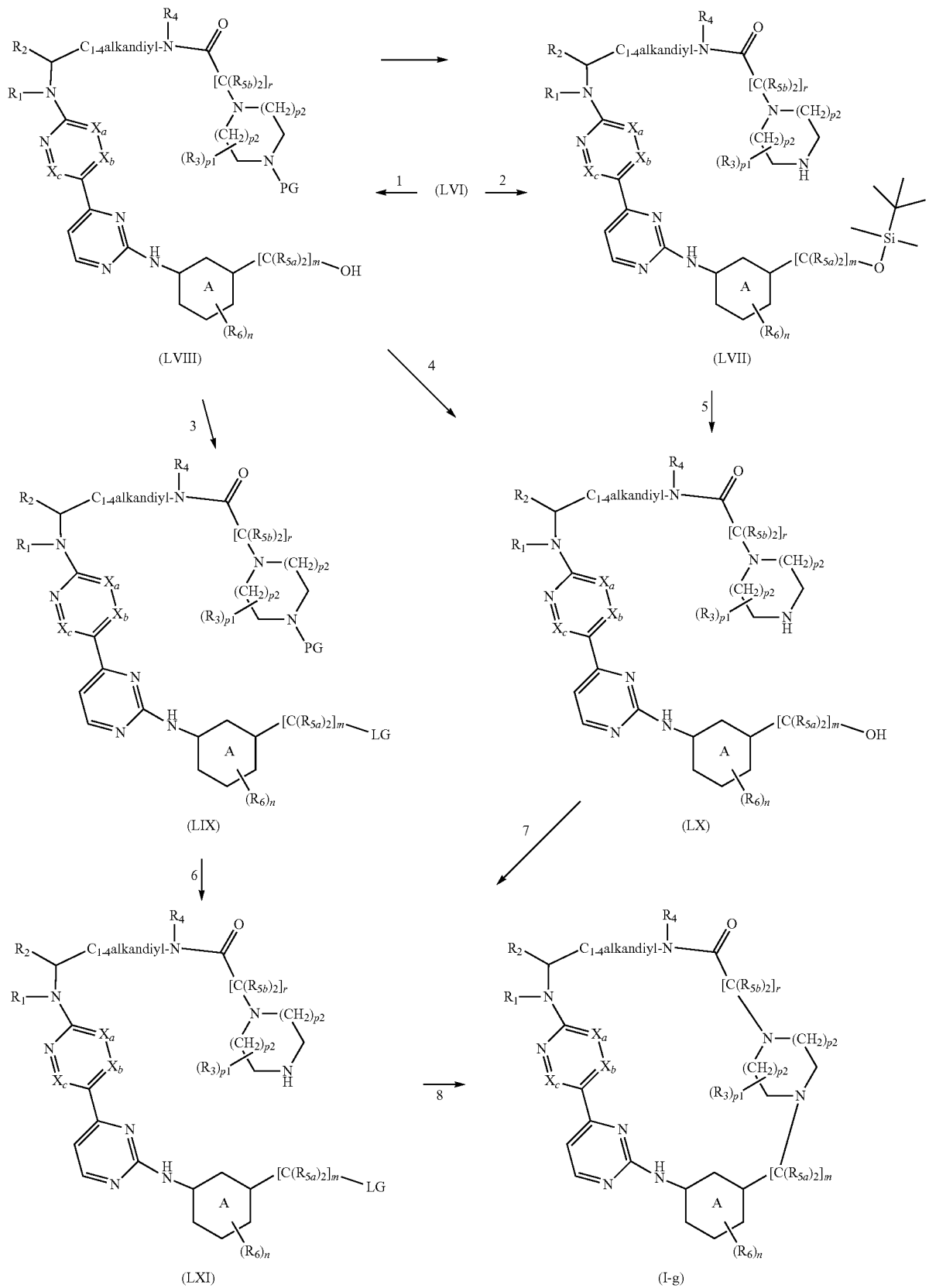

In scheme 7a, 'PG' is as defined before; 'LG' means leaving group such as for example chloro or mesylate; and all other variables are defined according to the scope of the present invention.

The skilled person will realize that protecting groups can be easily converted into each other by using well-known reactions as illustrated in the specific examples.

In Scheme 7a, the following reaction conditions apply:

1: deprotection of the hydroxyl group by addition of an appropriate hydrolyzing agent such as for example tetrabutylammonium fluoride, in the presence of a suitable solvent such as for example THF;

2: deprotection of the piperazinyl moiety in the presence of $H_2$-gas atmosphere and a catalyst such as for example Pd/C (for example 5 wt % or 10 wt %) in a suitable solvent such as for example MeOH;

3: introduction of a leaving group (LG) using sulfonyl chlorides such as for example methanesulfonyl chloride (MsCl) or p-toluenesulfonyl chloride (TsCl) in the presence of a suitable base such as for example DIPEA, in the presence of a suitable solvent such as for example DCM;

4: deprotection of the piperazinyl moiety in the presence of an acid such as for example TFA in a solvent such as for example DCM; or alternatively in the presence of an acid such as for example HCl in a solvent such as for example 1,4-dioxane optionally in the presence of water;

5: in the presence of a deprotecting agent such as for example TBAF in THF; or alternatively in the presence of an acid such as for example HCl in $H_2O$; or alternatively in the presence of $CH_3COOH$ optionally in the presence of water;

6: deprotection of the piperazinyl moiety in the presence of an acid such as for example TFA in a solvent such as for example DCM; or alternatively in the presence of an acid such as for example HCl in a solvent such as for example 1,4-dioxane optionally in the presence of water;

7: introduction of a leaving group (LG) using for example thionyl chloride in the presence of a suitable solvent such as for example 1,2-dichloroethane;

8: in the presence of a suitable base, such as for example $K_2CO_3$, in the presence of a suitable solvent such as for example DMF;

In general, an intermediate of Formula (LVI) can be prepared according to Scheme 7b:

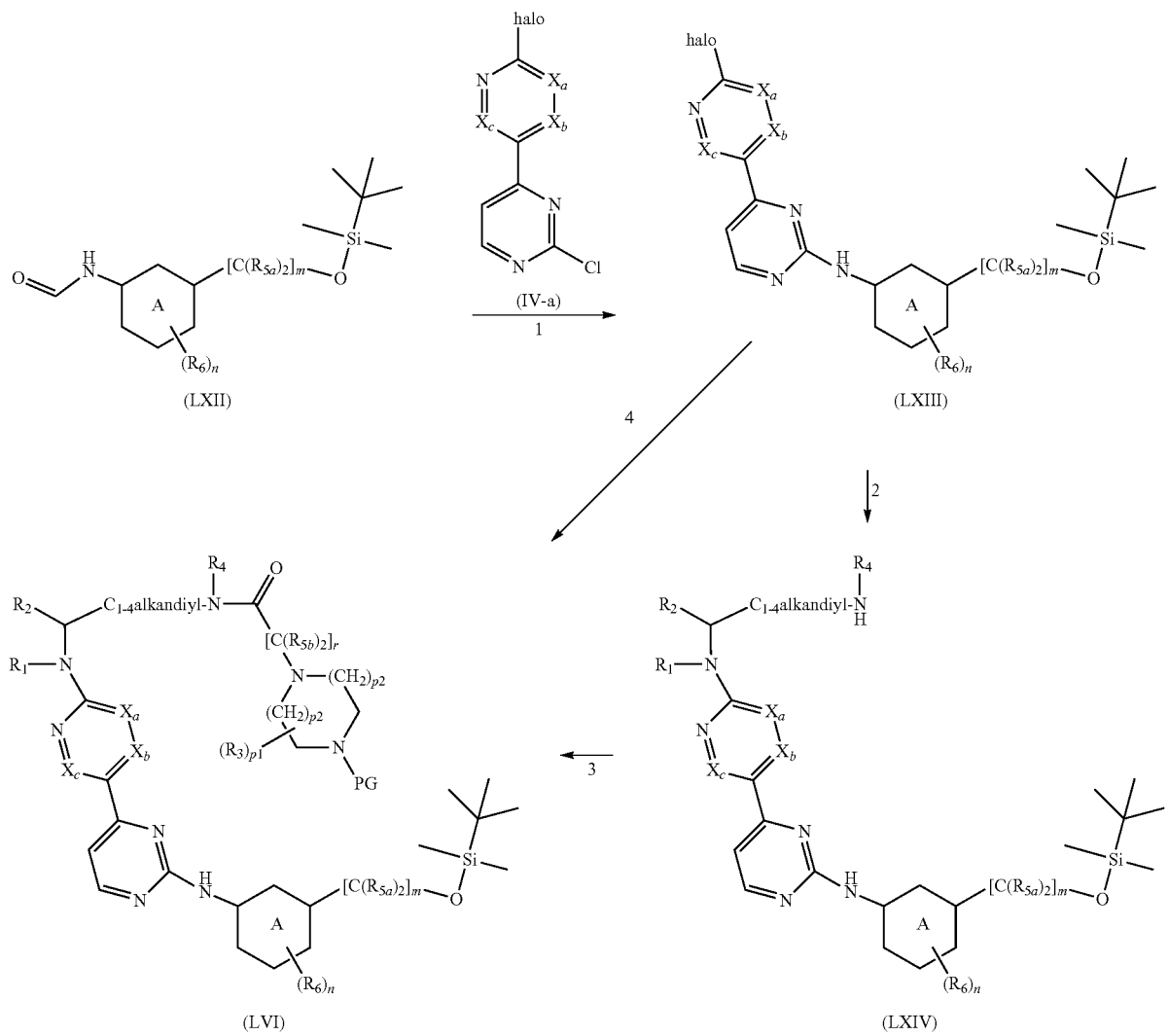

In scheme 7b, 'PG' and 'halo' are as defined before in the general reaction schemes; and all other variables are defined according to the scope of the present invention.

In Scheme 7b, the following reaction conditions apply:
1: in the presence of a base such as for example NaH, and a suitable solvent such as for example N,N-dimethyl formamide (DMF);
2: reaction with an intermediate of Formula (V-a1):

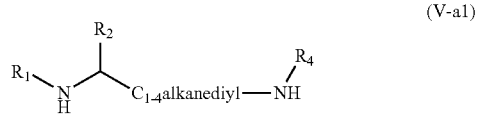
(V-a1)

optionally in the presence of a suitable base, such as for example $Na_2CO_3$, optionally in the presence of a suitable solvent such as for example DMA or NMP, or in a mixture of solvents such as for example DMA/DMSO ("DMSO" means dimethyl sulfoxide);
3: firstly reaction with an intermediate of Formula (LXIV-a) in the presence of a suitable base, such as for example $Et_3N$, in the presence of a suitable solvent such as for example $CH_3CN$; and subsequently addition of (LXIV-b) to the mixture:

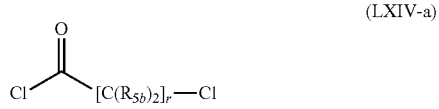
(LXIV-a)

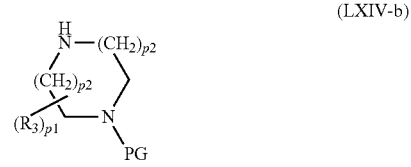
(LXIV-b)

4: reaction with an intermediate of Formula (LXV):

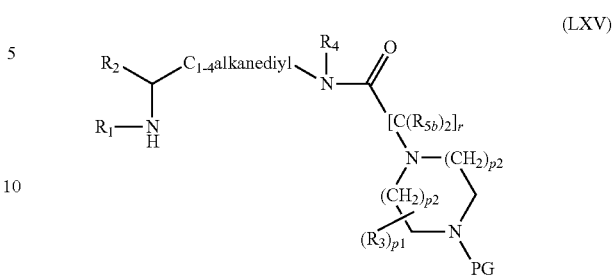
(LXV)

in the presence of a suitable base, such as for example $K_2CO_3$, in the presence of a suitable solvent such as for example DMF.

An intermediate of Formula (LXV) is commercially available or can be prepared by standard means obvious to those skilled in the art or as described in the specific experimental part.

As mentioned before, the skilled person will realize that compounds of Formula (I) may be further functionalized according to methods well-known by the person skilled in the art.

For example, compounds of Formula (I) wherein $R_3$ represents hydroxy$C_{1-4}$alkyl, may be further functionalized to compounds of Formula (I) wherein $R_3$ represents optionally substituted $C_{1-4}$alkyloxy$C_{1-4}$alkyl, according to methods well-known by the person skilled in the art. It may be necessary to protect reactive functional groups to avoid their unwanted participation in the reactions. Conventional protecting groups can be used in accordance with standard practice. For example 2-(trimethylsilyl)ethoxymethyl can be used to protect the amino group between the pyrimidinyl ring and ring A.

For example, in case $R_3$ represents $C_{1-4}$alkyloxy$C_{1-4}$alkyl substituted with an hydroxy group, said hydroxy group may be functionalized to a leaving group (via reaction with for example methanesulfonyl chloride) after which it may be reacted with a functionalized nitrogen atom (—$NR_{3e}R_{3f}$ or $R_{10}$) to obtain other compounds of Formula (I) according to the scope.

In general, a compound of Formula (I-h) can be prepared according to Scheme 8:

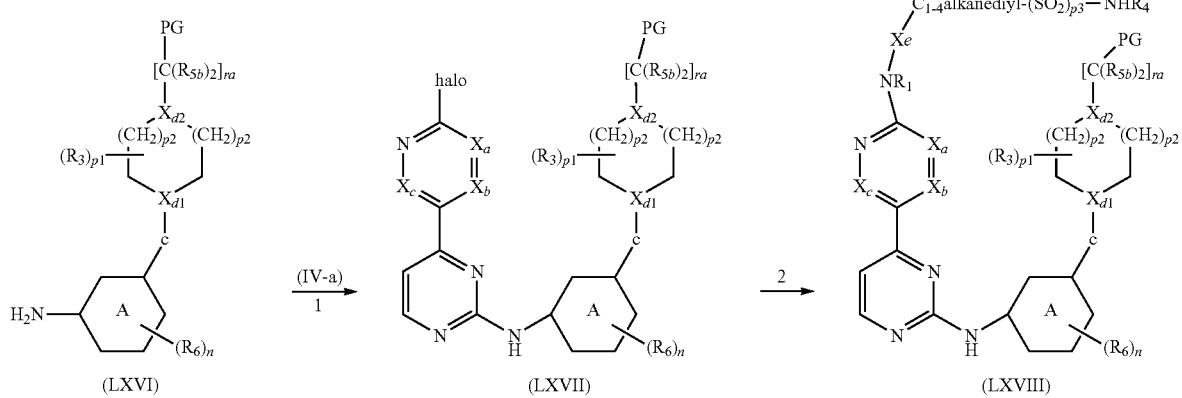

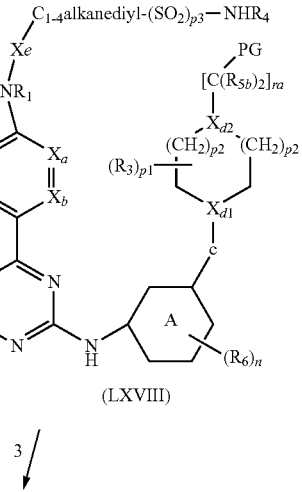

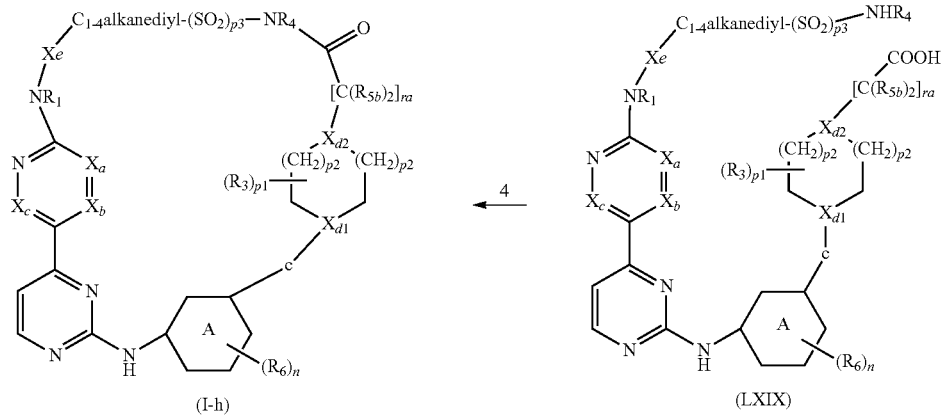

(I-h) (LXIX)

In Scheme 8, 'PG' and 'halo' are as defined before in the general reaction schemes; 'ra' is defined as 1 or 2; and all other variables are defined according to the scope of the present invention.

In Scheme 8, the following reaction conditions apply:
1: An intermediate of Formula (LXVI) can be reacted with an intermediate of Formula (IV-a) in the presence of a suitable acid such as for example p-toluenesulfonic acid monohydrate in a suitable solvent such as, for example, 1,4-dioxane, or a mixture of suitable solvents such as, for example, a mixture of 1,4-dioxane and 2-propanol;
2: An intermediate of Formula (LXVII) can be reacted with an intermediate of Formula —NHR$_1$—X$_c$—C$_{1-4}$alkanediyl-(SO$_2$)$_{p3}$—NHR$_4$— optionally in the presence of a suitable base, such as for example Na$_2$CO$_3$, optionally in the presence of a suitable solvent such as for example N,N-dimethylacetamide (DMA) or 1-methyl-2-pyrrolidinone (NMP) or mixture of solvents such as for example DMA/DMSO ("DMSO" means dimethyl sulfoxide);
3: in the presence of an acid such as for example trifluoroacetic acid (TFA) in a solvent such as for example DCM; or
alternatively in the presence of an acid such as for example HCl in a solvent such as for example 1,4-dioxane optionally in the presence of water; or
alternatively first in the presence of a base such as for example NaOH, and subsequently in the presence of an acid such as for example HCl, in the presence of a suitable solvent such as for example THF;

4: in the presence of a coupling agent such as for example diethyl cyanophosphonate. (1H-benzotriazol-1-yloxy)(tripyrrolidin-1-yl)phosphonium hexafluorophosphate (PyBOP), 1-[bis(dimethylamino)methylene]-1H-benzotriazol-1-ium 3-oxide hexafluorophosphate (HBTU) or 1-[bis(dimethylamino)methylene]-1H-[1,2,3]triazolo[4,5-b]pyridin-1-ium 3-oxide hexafluorophosphate (HATU) in the presence of a base such as for example triethylamine (Et$_3$N) or N,N-diisopropylethylamine (DIPEA), in a suitable solvent such as for example DMF.

An intermediate of Formula (LXVI) is commercially available or can be prepared by standard means obvious to those skilled in the art or as described in the specific experimental part.

In case the Boc group is directly attached to the nitrogen atom in an intermediate of Formula (LXVIII) (this is when r is 0 in the scope), the nitrogen atom can be deprotected, for example under acidic conditions (e.g. HCl in dioxane). Subsequently, the obtained intermediate may be reacted with RG-[C(R$_{5b}$)$_2$]$_{ra}$-Boc wherein RG is a reactive group such as, for example, bromo.

In general, a compound of Formula (I-i) can be prepared according to Scheme 9:

Scheme 9
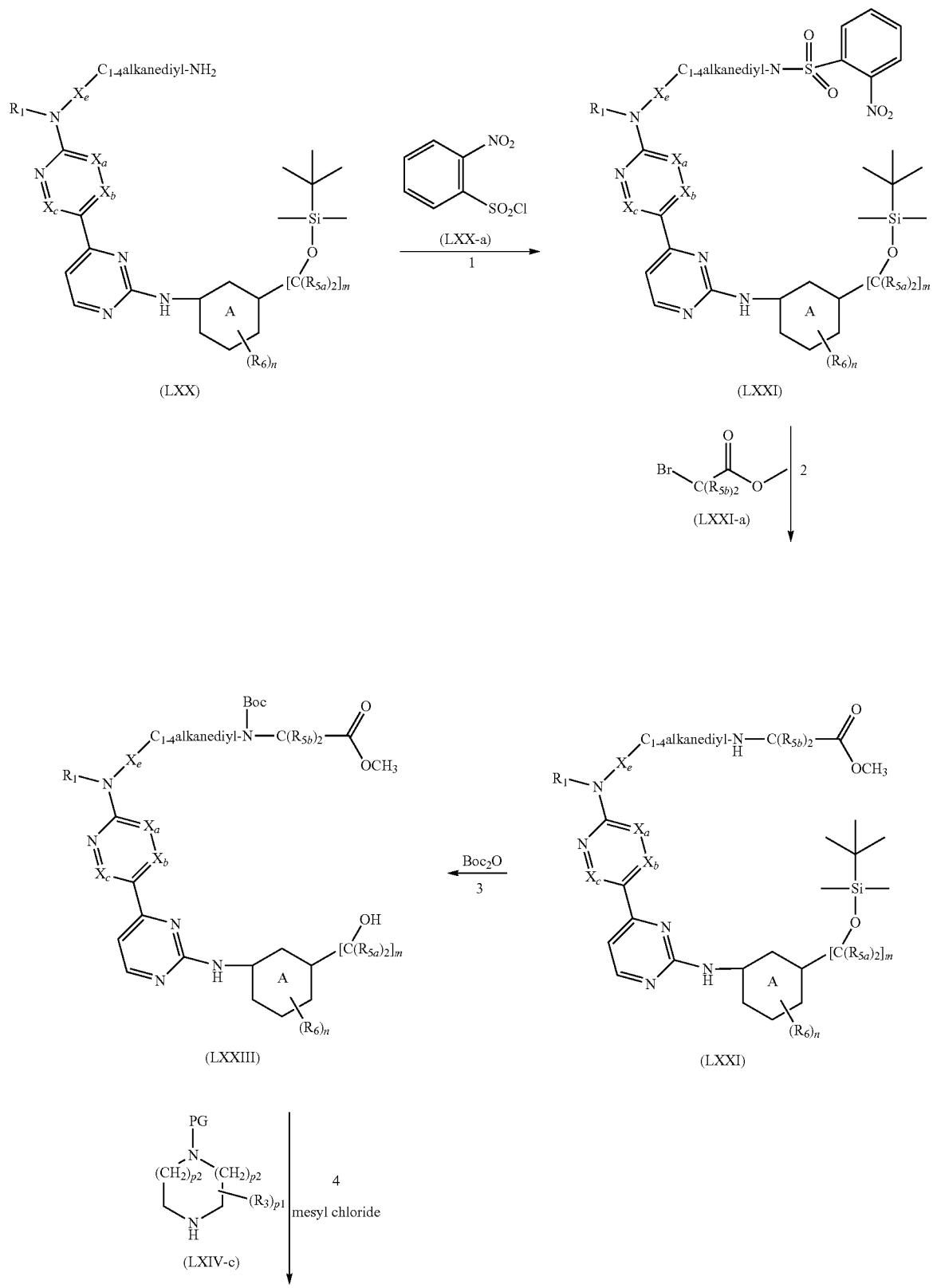

-continued

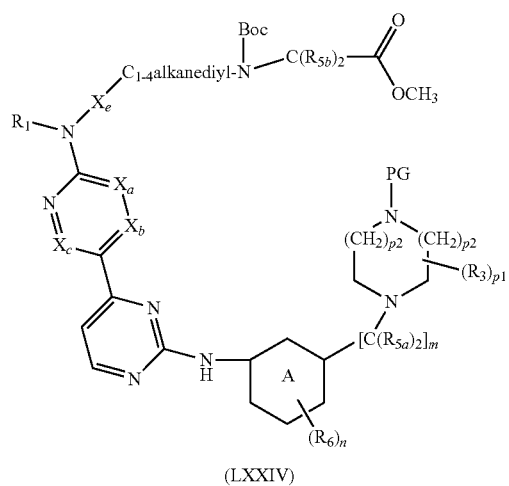

(LXXIV)

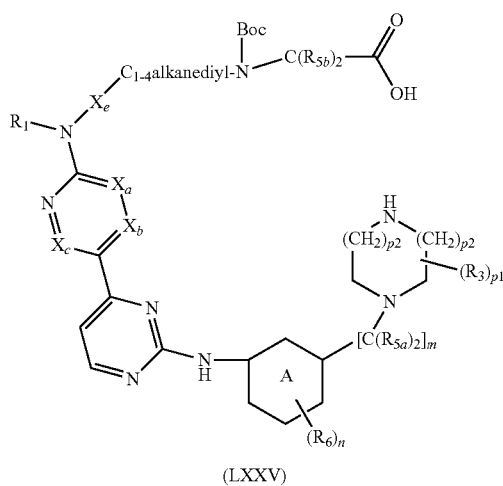

(LXXV)

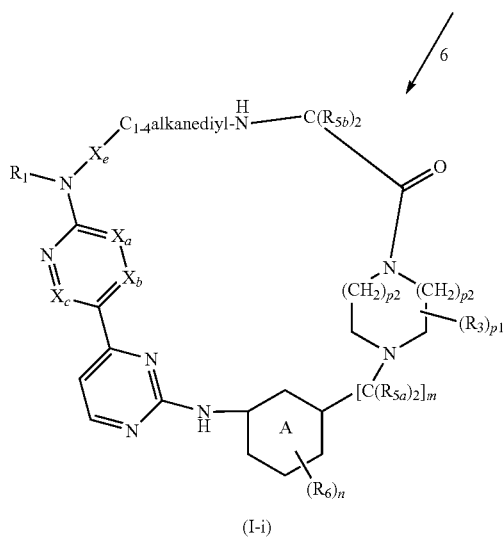

(I-i)

In Scheme 9a, 'PG' is as defined before; 'Boc' is tert-butoxycarbonyl; and all other variables are defined according to the scope of the present invention.

In Scheme 9a, the following reaction conditions apply:
1: in the presence of a suitable base such as for example Et$_3$N or DIPEA, in a suitable solvent such as for example DCM;
2: firstly in the presence of a suitable base such as for example Cs$_2$CO$_3$ in a suitable solvent such as for example DMF; and subsequently in the presence of a deprotecting group such as for example thiophenol;
3: firstly a reaction with tert-butoxycarbonyl anhydride in the presence of a suitable catalyst such as DMAP in a suitable solvent such as for example DCM; and subsequently in the presence of a suitable base such as for example tetrabutylammonium fluoride (TBAF) in a suitable solvent such as for example THF;
4: firstly in the presence of methanesulfonyl chloride, in the presence of a base such as for example DIPEA, in the presence of a suitable solvent such as for example DCM or DMF; and subsequently a coupling reaction with an intermediate of Formula (LXIV-c);
5: in the presence of an acid such as for example trifluoroacetic acid (TFA) in a solvent such as for example DCM; or alternatively in the presence of an acid such as for example HCl in a solvent such as for example 1,4-dioxane optionally in the presence of water; or alternatively first in the presence of a base such as for example NaOH, and subsequently in the presence of an acid such as for example HCl, in the presence of a suitable solvent such as for example THF;
6: in the presence of a coupling agent such as for example diethyl cyanophosphonate, (1H-benzotriazol-1-yloxy)(tripyrrolidin-1-yl)phosphonium hexafluorophosphate (PyBOP), 1-[bis(dimethylamino)methylene]-1H-benzotriazol-1-ium 3-oxide hexafluorophosphate (HBTU) or 1-[bis(dimethylamino)methylene]-1H-[1,2,3]triazolo[4,5-b]pyridin-1-ium 3-oxide hexafluorophosphate (HATU) in the presence of a base such as for example triethylamine (Et$_3$N) or N,N-diisopropylethylamine (DIPEA), in a suitable solvent such as for example DMF.

In scheme 9, an intermediate of Formula (LXXIII) can be replaced by an intermediate of Formula (XX) which can be reacted further according to analogues reaction protocols as described in Scheme 9 to obtain compounds of Formula (I-i2):

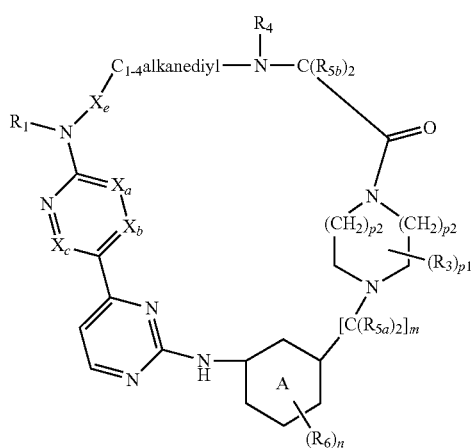

In general, an intermediate of Formula (LXXIX) can be prepared according to Scheme 10:

In Scheme 10, the following reaction conditions apply:
1: in the presence of methanesulfonyl chloride, in the presence of a base such as for example DIPEA, in the presence of a suitable solvent such as for example DCM;
2: coupling reaction between an intermediate of Formula (LXXVI) and an intermediate of Formula (LXIV-c), in the presence of a suitable base such as for example $K_2CO_3$, in the presence of a suitable solvent such as for example DMF;
3: in the presence of an acid such as for example trifluoroacetic acid (TFA) in a solvent such as for example DCM; or alternatively in the presence of an acid such as for example HCl in a solvent such as for example 1,4-dioxane optionally in the presence of water; or alternatively first in the presence of a base such as for example NaOH, and subsequently in the presence of an acid such as for example HCl, in the presence of a suitable solvent such as for example THF;
4: reaction between an intermediate of Formula (LXXVIII) and an intermediate of Formula (LXXVIII-a) in the presence of a suitable base such as for example $Et_3N$ in a suitable solvent such as for example DCM.

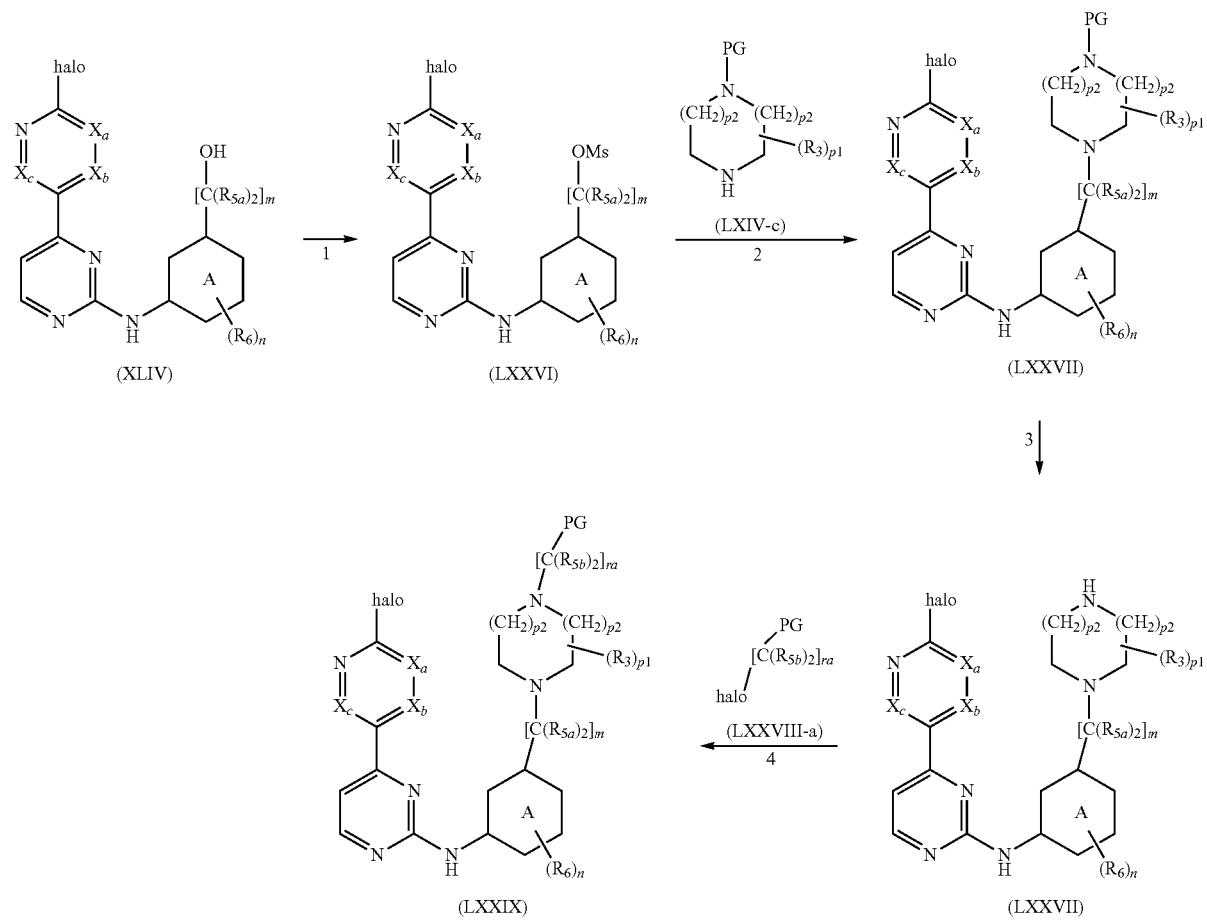

Scheme 10

An intermediate of Formula (LXXIX) subsequently can be further reacted according to similar reaction protocols as described in Scheme 1 steps 4, 5 and 6.

In Scheme 10, 'PG', 'halo' and 'Ms' is as defined before in the general reaction schemes; and all other variables are defined according to the scope of the present invention.

Compounds of Formula (I) wherein $R_1$ and $R_2$, or $R_1$ and $R_{12}$, are taken together to form $C_{1-4}$alkanediyl or $C_{2-4}$alkenediyl, and which are substituted with hydroxyl on said $C_{1-4}$alkanediyl or $C_{2-4}$alkenediyl, may be converted to other compounds of Formula (I) by the following reactions:

hydroxyl to azide ion: in a suitable solvent such as THF, in the presence of a ligand such as triphenylphosphine (PPh$_3$), an azide source such as diphenylphosphoryl azide (DPPA) and in the presence of an azodicarboxylate such as for example diisopropyl azodicarboxylate (DIAD);

azide to NH$_2$: via reduction reaction in the presence of H$_2$-gas atmosphere and a catalyst such as for example Pt/C or Pd/C (for example 5 wt % or 10 wt %) in a suitable solvent such as for example MeOH or THF;

NH$_2$ to NH$_2$—S(=O)$_2$—NH—: via reaction with sulfamide in a suitable solvent such as for example dioxane;

hydroxyl to oxo: Swern oxidation to a ketone using oxalyl chloride, dimethyl sulfoxide (DMSO) and an organic base such as for example Et$_3$N;

hydroxyl to cyano: first conversion of the hydroxyl group to CH$_3$—S(=O)$_2$—O— via reaction with mesylchloride in a suitable solvent such as DCM in the presence of a suitable base such as for example DIPEA; second conversion of CH$_3$—S(=O)$_2$—O— to the cyano group by reaction with e.g. NaCN in a suitable solvent such as for example DMSO;

hydroxyl to fluoro: in a suitable solvent such as THF in the presence of a suitable base (promotor) such as for example 1,8-diazabicyclo[5.4.0]undecene-7 (DBU) in the presence of a fluorinating reagent such as (diethylamino)difluorosulfonium tetrafluoroborate (XtalFluor-E®).

In all these preparations, the reaction products may be isolated from the reaction medium and, if necessary, further purified according to methodologies generally known in the art such as, for example, extraction, crystallization, trituration and chromatography. In particular, stereoisomers can be isolated chromatographically using a chiral stationary phase such as, for example, Chiralpak® AD (amylose 3,5 dimethyl-phenyl carbamate) or Chiralpak® AS, both purchased from Daicel Chemical Industries, Ltd, in Japan, or by Supercritical Fluid Chromatography (SFC).

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

Pharmacology

It has been found that the compounds of the present invention have EF2K inhibitory activity and optionally may also have Vps34 inhibitory activity.

The compounds according to the invention and the pharmaceutical compositions comprising such compounds may be useful for treating or preventing, in particular treating, diseases such as cancer, depression, neuroplasticity (synaptic plasticity and non-synaptic plasticity), and memory and learning disorders.

In particular, the compounds according to the present invention and the pharmaceutical compositions thereof may be useful in the treatment or the prevention, in particular in the treatment, of a haematological malignancy or solid tumour.

In a specific embodiment said solid tumour is selected from the group consisting of glioblastoma, medulloblastoma, prostate cancer, breast cancer, ovarian cancer and colorectal cancer.

In particular, the compounds according to the present invention and the pharmaceutical compositions thereof may be useful in the treatment or the prevention, in particular in the treatment, of brain tumours, in particular glioblastoma and medulloblastoma.

In particular, the compounds according to the present invention and the pharmaceutical compositions thereof may be useful in the treatment or the prevention, in particular in the treatment, of prostate cancer, breast cancer, ovarian cancer and colorectal cancer.

Examples of other cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma), T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma a tumour of the central or peripheral nervous system, for example astrocytoma, neuroblastoma, glioma (such as glioblastoma multiforme) or schwannoma melanoma; seminoma; teratocarcinoma; osteosarcoma; xeroderma pigmentosum; keratoctanthoma thyroid follicular cancer; or Kaposi's sarcoma. In particular, squamous lung cancer, breast cancer, colorectal cancer, glioblastoma, astrocytomas, prostate cancer, small cell lung cancer, melanoma, head and neck cancer, thyroid cancer, uterine cancer, gastric cancer, hepatocellular cancer, cervix cancer, multiple myeloma, bladder cancer, endometrial cancer, urothelial cancer, colon cancer, rhabdomyosarcoma, pituitary gland cancer.

The compounds according to the invention and the pharmaceutical compositions comprising such compounds may also be useful for treating or preventing, in particular treating, diseases such as malaria, rheumatoid arthritis, lupus and HIV.

The compounds of the invention and compositions thereof can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome.

Myeloproliferative diseases include polycythemia vera, essential thrombocythemia and primary myelofibrosis. A further haematological disorder is hypereosinophilic syndrome. T-cell lymphoproliferative diseases include those derived from natural Killer cells.

Thus, in the pharmaceutical compositions, uses or methods of this invention for treating a disease or condition comprising abnormal cell growth, the disease or condition comprising abnormal cell growth in one embodiment is a cancer.

The compounds of the present invention also have therapeutic applications in sensitising tumour cells for radiotherapy and chemotherapy.

Hence the compounds of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases. Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

The invention relates to compounds of Formula (I) and pharmaceutically acceptable addition salts, and solvates thereof, for use as a medicament.

The invention also relates to compounds of Formula (I) and pharmaceutically acceptable addition salts, and solvates thereof, for use in the inhibition of EF2K and optionally also for use in the inhibition of Vps34.

The compounds of the present invention can be "anti-cancer agents", which term also encompasses "anti-tumor cell growth agents" and "anti-neoplastic agents".

The invention also relates to compounds of Formula (I) and pharmaceutically acceptable addition salts, and solvates thereof, for use in the treatment of diseases mentioned above.

The invention also relates to compounds of Formula (I) and pharmaceutically acceptable addition salts, and solvates thereof, for the treatment or prevention, in particular for the treatment, of said diseases.

The invention also relates to compounds of Formula (I) and pharmaceutically acceptable addition salts, and solvates thereof, for the treatment or prevention, in particular in the treatment, of EF2K mediated diseases or conditions.

The invention also relates to compounds of Formula (I) and pharmaceutically acceptable addition salts, and solvates thereof, for the treatment or prevention, in particular in the treatment, of EF2K and optionally Vps34 mediated diseases or conditions.

The invention also relates to the use of compounds of Formula (I) and pharmaceutically acceptable addition salts, and solvates thereof, for the manufacture of a medicament.

The invention also relates to the use of compounds of Formula (I) and pharmaceutically acceptable addition salts, and solvates thereof, for the manufacture of a medicament for the inhibition of EF2K and optionally also for the inhibition of Vps34.

The invention also relates to the use of compounds of Formula (I) and pharmaceutically acceptable addition salts, and solvates thereof, for the manufacture of a medicament for the treatment or prevention, in particular for the treatment, of any one of the disease conditions mentioned hereinbefore.

The invention also relates to the use of compounds of Formula (I) and pharmaceutically acceptable addition salts, and solvates thereof, for the manufacture of a medicament for the treatment of any one of the disease conditions mentioned hereinbefore.

The compounds of Formula (I) and pharmaceutically acceptable addition salts, and solvates thereof, can be administered to mammals, preferably humans for the treatment or prevention of any one of the diseases mentioned hereinbefore.

The compounds of the present invention may also be used in the optimisation of industrial protein production.

In view of the utility of the compounds of Formula (I) and pharmaceutically acceptable addition salts, and solvates thereof, there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I) and pharmaceutically acceptable addition salts, and solvates thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent cancer or cancer-related conditions, may be administered alone or in combination with one or more additional therapeutic agents. Combination therapy includes administration of a single pharmaceutical dosage formulation which contains a compound of Formula (I), a pharmaceutically acceptable addition salt, or a solvate thereof, and one or more additional therapeutic agents, as well as administration of the compound of Formula (I), a pharmaceutically acceptable addition salt, or a solvate thereof, and each additional therapeutic agents in its own separate pharmaceutical dosage formulation. For example, a compound of Formula (I), a pharmaceutically acceptable addition salt, or a solvate thereof, and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound of Formula (I), a pharmaceutically acceptable addition salt, or a solvate thereof.

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds of Formula (I) and pharmaceutically acceptable addition salts, and solvates thereof, or any subgroup or combination thereof may be formulated into various pharmaceutical forms for administration purposes.

As appropriate compositions there may be cited all compositions usually employed for systemically administering drugs.

To prepare the pharmaceutical compositions of this invention, an effective amount of the particular compound as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing a compound of Formula (I), a pharmaceutically acceptable addition salt, or a solvate thereof, may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the compounds of Formula (I) and pharmaceutically acceptable addition salts, and solvates thereof, in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), a pharmaceutically acceptable addition salt, or a solvate thereof, and from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

- platinum coordination compounds for example cisplatin optionally combined with amifostine, carboplatin or oxaliplatin;
- taxane compounds for example paclitaxel, paclitaxel protein bound particles (Abraxane™) or docetaxel;
- topoisomerase I inhibitors such as camptothecin compounds for example irinotecan, SN-38, topotecan, topotecan hcl;
- topoisomerase II inhibitors such as anti-tumour epipodophyllotoxins or podophyllotoxin derivatives for example etoposide, etoposide phosphate or teniposide;
- anti-tumour *vinca* alkaloids for example vinblastine, vincristine or vinorelbine;
- anti-tumour nucleoside derivatives for example 5-fluorouracil, leucovorin, gemcitabine, gemcitabine hcl, capecitabine, cladribine, fludarabine, nelarabine;
- alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;
- anti-tumour anthracycline derivatives for example daunorubicin, doxorubicin optionally in combination with dexrazoxane, doxil, idarubicin, mitoxantrone, epirubicin, epirubicin hcl, valrubicin;
- molecules that target the IGF-1 receptor for example picropodophilin;
- tetracarcin derivatives for example tetrocarcin A;
- glucocorticords for example prednisone;
- antibodies for example trastuzumab (HER$_2$ antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
- estrogen receptor antagonists or selective estrogen receptor modulators or inhibitors of estrogen synthesis for example tamoxifen, fulvestrant, toremifene, droloxifene, faslodex, raloxifene or letrozole;
- aromatase inhibitors such as exemestane, anastrozole, letrozole, testolactone and vorozole;
- differentiating agents such as retinoids, vitamin D or retinoic acid and retinoic acid metabolism blocking agents (RAMBA) for example accutane;
- DNA methyl transferase inhibitors for example azacytidine or decitabine;
- antifolates for example premetrexed disodium;
- antibiotics for example antinomycin D, bleomycin, mitomycin C, dactinomycin, carminomycin, daunomycin, levamisole, plicamycin, mithramycin;
- antimetabolites for example clofarabine, aminopterin, cytosine arabinoside or methotrexate, azacitidine, cytarabine, floxuridine, pentostatin, thioguanine;
- apoptosis inducing agents and antiangiogenic agents such as Bcl-2 inhibitors for example YC 137, BH 312, ABT 737, gossypol, HA 14-1, TW 37 or decanoic acid;
- tubuline-binding agents for example combrestatin, colchicines or nocodazole;
- kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;
- famesyltransferase inhibitors for example tipifarnib;
- histone deacetylase (HDAC) inhibitors for example sodium butyrate, suberoylanilide hydroxamic acid (SAHA), depsipeptide (FR 901228), NVP-LAQ824, R306465, JNJ-26481585, trichostatin A, vorinostat;
- Inhibitors of the ubiquitin-proteasome pathway for example PS-341, MLN 0.41 or bortezomib;
- Yondelis;
- Telomerase inhibitors for example telomestatin;
- Matrix metalloproteinase inhibitors for example batimastat, marimastat, prinostat or metastat;
- Recombinant interleukins for example aldesleukin, denileukin diftitox, interferon alfa 2a, interferon alfa 2b, peginterferon alfa 2b;
- MAPK inhibitors;
- Retinoids for example alitretinoin, bexarotene, tretinoin;
- Arsenic trioxide;
- Asparaginase;
- Steroids for example dromostanolone propionate, megestrol acetate, nandrolone (decanoate, phenpropionate), dexamethasone;
- Gonadotropin releasing hormone agonists or antagonists for example abarelix, goserelin acetate, histrelin acetate, leuprolide acetate;
- Thalidomide, lenalidomide;
- Mercaptopurine, mitotane, pamidronate, pegademase, pegaspargase, rasburicase;
- BH3 mimetics for example ABT-737;
- MEK inhibitors for example PD98059, AZD6244, CI-1040;
- colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin;

a steroidal cytochrome P450 17alpha-hydroxylase-17,20-lyase inhibitor (CYP 17), e.g. abiraterone, abiraterone acetate;

Glycolysis inhibitors, such as 2-deoxyglucose;

mTOR inhibitors such as rapamycins and rapalogs, and mTOR kinase inhibitors;

PI3K inhibitors and dual mTOR/PI3K inhibitors;

autophagy inhibitors, such as chloroquine and hydroxychloroquine;

B-raf inhibitors, e.g. vemurafenib;

androgen receptor antagonist drugs, e.g. enzalutamide or ARN-509.

The present invention further relates to a product containing as first active ingredient a compound according to the invention and as further active ingredient one or more anticancer agents, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m$^2$) of body surface area, for example 50 to 400 mg/m$^2$, particularly for cisplatin in a dosage of about 75 mg/m$^2$ and for carboplatin in about 300 mg/m$^2$ per course of treatment.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

These dosages may be administered for example once, twice or more per course of treatment, which may be repeated for example every 7, 14, 21 or 28 days.

The following examples illustrate the present invention. In case no specific stereochemistry is indicated for a stereocenter of a compound, this means that the compound was obtained as a mixture of the R and the S enantiomers.

When an intermediate is indicated as 'HCl salt' or 'TFA salt', this means that the number of equivalents of HCl or TFA was not determined.

EXAMPLES

Hereinafter, the term "NaH" means sodium hydride (60% in mineral oil); "DCM" means dichloromethane; "q.s." means quantum sufficit; "Int." Means intermediate; "Co." means compound; "DCE" means 1,2-dichloroethane; "DIPE" means diisopropyl ether, "Boc" means tert-butoxycarbonyl; "ACN" means acetonitrile; "BDS" means base deactivated silica"; "NMP" means 1-methyl-2-pyrrolidinone; "DMA" means N,N-dimethylacetamide; "MeOH" means methanol; "LC" means liquid chromatography; "LCMS" means Liquid Chromatography/Mass spectrometry; "HATU" means 1-[bis(dimethylamino)methylene]-1H-[1,2,3]triazolo[4,5-b]pyridin-1-ium 3-oxide hexafluorophosphate; "HPLC" means high-performance liquid chromatography; "BINAP" means [1,1'-binaphthalene]-2,2'-diylbis[diphenylphosphine] (racemic); "TFA" means trifluoroacetic acid; "m.p." means melting point; "N$_2$" means nitrogen; "RP" means reversed phase; "min" means minute(s); "h" means hour(s); "EtOAc" means ethyl acetate; "Et$_3$N" means triethylamine; "PE" means petroleum ether; "EtOH" means ethanol; "THF" means tetrahydrofuran; "Celite" means diatomaceous earth; "DMF" means N,N-dimethyl formamide; "DMSO" means dimethyl sulfoxide; 'iPrOH" means 2-propanol; "iPrNH$_2$" means isopropylamine; "SFC" means Supercritical Fluid Chromatography; "DIPEA" means N,N-diisopropylethylamine; "HBTU" means 1-[bis(dimethylamino)methylene]-1H-benzotriazol-1-ium 3-oxide hexafluorophosphate; "w/v" means weight/volume; "NaBH(OAc)$_3$" means sodium triacetoxyborohydride; "PPh$_3$" means triphenylphosphine; "Et$_2$O" means diethyl ether; "Pd/C" means palladium on carbon; "Pt/C" means platina on carbon; "Pd(OAc)$_2$" means palladium(II) acetate; "Pd$_2$(dba)$_3$" means tris(dibenzylideneacetone)dipalladium; "Et" means ethyl; "Me" means methyl; "PdCl$_2$(dppf)-DCM" means [1,1'-bis(diphenylphosphino-κP)ferrocene]dichloropalladium-dichloromethane (1:1); and "TLC" means thin layer chromatography.

A. Preparation of the Intermediates

Example A1 a) Preparation of Int. 1

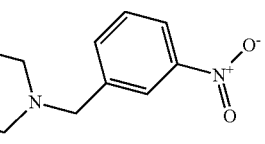

The synthesis protocol was conducted twice on the same quantities of 1-(3-nitrobenzyl)piperazine (20 g; 84.74 mmol).

NaH (60% in mineral oil) (8.7 g; 216.94 mmol) was added portionwise to a stirred solution of 1-(3-Nitrobenzyl)piperazine (40 g; 180.784 mmol) in DMF (190 mL) at room temperature. The reaction mixture was stirred for 20 minutes. Tert-butyl bromoacetate (26.5 mL; 180.784 mmol) was added dropwise at 5° C. The reaction mixture was stirred for 20 minutes. Water and EtOAc were added and the layers were separated. The organic layer was dried (MgSO$_4$), filtered and evaporated to dryness. The solid was purified by preparative LC (Irregular SiOH 20-45 µm 1000 g DAVISIL). Mobile phase (60% Heptane, 3% MeOH, 37% EtOAc). The desired fractions were collected and the solvent was evaporated.

Total yield: 44.5 g of Int. 1 (73%).

b) Preparation of Int. 2

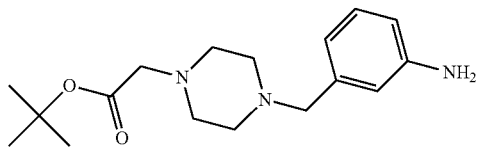 [SMILES: CC(C)(C)OC(=O)CN1CCN(Cc2cccc(N)c2)CC1]

The synthesis protocol was conducted twice on the same quantities of Int. 1 (9 g; 26.833 mmol).

A mixture of Int. 1 (18 g; 53.667 mmol) in MeOH (650 mL) was hydrogenated under H$_2$-gas atmosphere at atmospheric pressure at room temperature in the presence of Raney nickel (19 g; 322.819 mmol) as a catalyst. The catalyst was filtered off on a pad of Celite@ and the filtrate was evaporated. Total yield 15.3 g of Int. 2 (93%).

c) Preparation of Int. 3

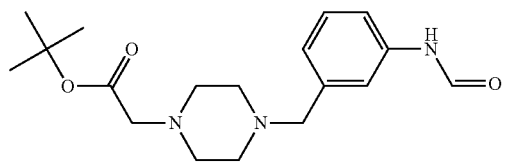 [SMILES: CC(C)(C)OC(=O)CN1CCN(Cc2cccc(NC=O)c2)CC1]

Phenyl formate (12.1 mL, 110.667 mmol) was added to a solution of Int. 2 (16.9 g; 55.334 mmol) in DCM (7 mL) at room temperature. The reaction mixture was stirred overnight at room temperature. Subsequently, the solvent was evaporated to give 30.5 g of a brown oil. This oil was purified by preparative LC (irregular SiOH 15-40 µm 300 g MERCK). Mobile phase (40% Heptane, 10% MeOH, 50% EtOAc). The desired fractions were collected and the solvent was evaporated. Yield: 14.9 g of Int. 3 (81%).

d) Preparation of Int. 4

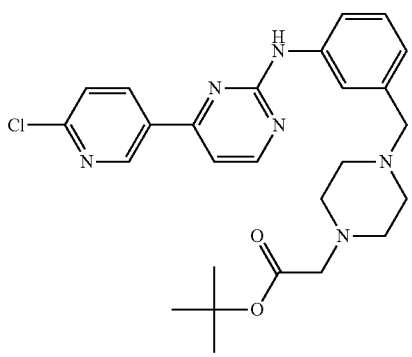 [SMILES: CC(C)(C)OC(=O)CN1CCN(Cc2cccc(Nc3nccc(-c4ccc(Cl)nc4)n3)c2)CC1]

NaH (60% dispersion in mineral oil) (1.327 g, 33.176 mmol) was added to a stirred solution of Int. 3 (3.687 g, 11.059 mmol) in DMF (200 ml) under N$_2$ atmosphere at room temperature, and the mixture was stirred for 20 minutes at room temperature. 2-Chloro-4-(6-chloro-3-pyridinyl)-pyrimidine (WO 2009112439) (2.5 g, 11.059 mmol) was added and the reaction mixture was then stirred for 18 h at room temperature. Subsequently, 5 mL of glacial acetic acid was added and the reaction was quenched by the addition of water. The product was extracted 3 times with EtOAc. The combined organic layer was washed with water and brine, dried with MgSO$_4$, filtered and the filtrate was evaporated. Yield: 7.21 g of Int. 4 (92%).

e) Preparation of Int. 10

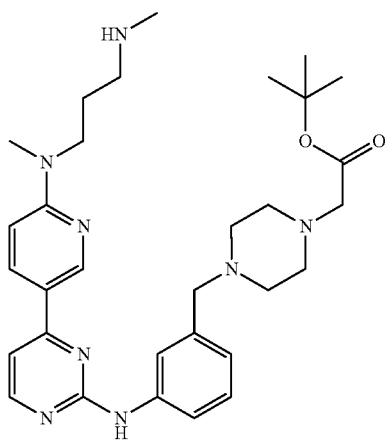 [SMILES: CNCCCN(C)c1ccc(-c2ccnc(Nc3cccc(CN4CCN(CC(=O)OC(C)(C)C)CC4)c3)n2)cn1]

A mixture of Int. 4 (2 g, 2.828 mmol) and and N$^1$,N$^3$-dimethyl-1,3-propanediamine (3.568 mL, 28.281 mmol) was stirred at 125° C. for 1 h. The reaction mixture was cooled, diluted with EtOAc, and washed with a saturated aqueous NaHCO$_3$ solution, then washed with water, dried with MgSO$_4$, filtered and the filtrate was evaporated. The residue was dissolved in DCM and purified by chromatography over a SiO$_2$ column, type Grace Reveleris SRC, 80 g, Si 40, on a Armen Spot II Ultimate purification system using DCM and MeOH as eluents in a gradient starting from 100% DCM and ending with 5% MeOH and 95% DCM. The fractions containing the product were combined and the solvent was evaporated. Yield: 1.63 g of Int. 10 (99.7%).

f) Preparation of Int. 11

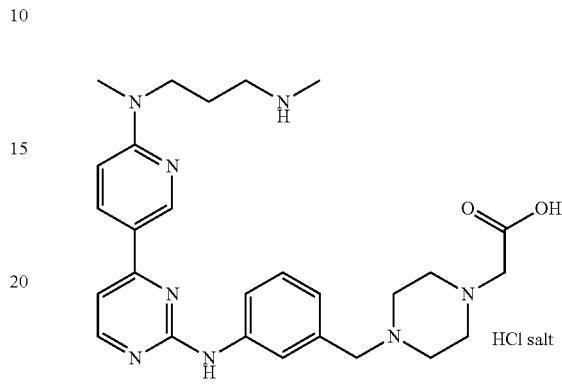

HCl (4 M in dioxane) (5.4 mL, 21.62 mmol) was added to a stirred solution of Int. 10 (1.25 g, 2.162 mmol) in 1,4-dioxane (80 ml) at room temperature. The reaction mixture was stirred at 60° C. for 2 h. A yellow precipitate was formed. The solvent was evaporated yielding 1.8 g of Int. 11.

f-2) Preparation of Int. 59

Int. 4 was reacted with N$^1$,N$^4$-dimethyl-1,4-butanediamine according to analogous synthesis protocols as described successively for Int. 10 (A1.e) and Int. 11 (A1.f), to obtain Int. 59, which was used for the synthesis of compound 20:

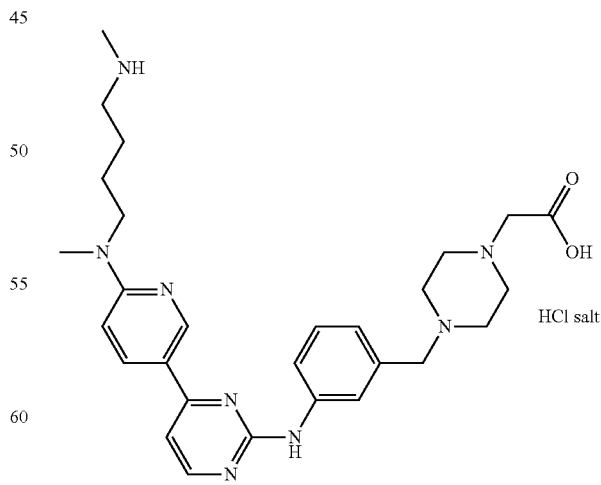

The intermediates in the table below were prepared according to an analogous reaction protocol as used for Int. 59:

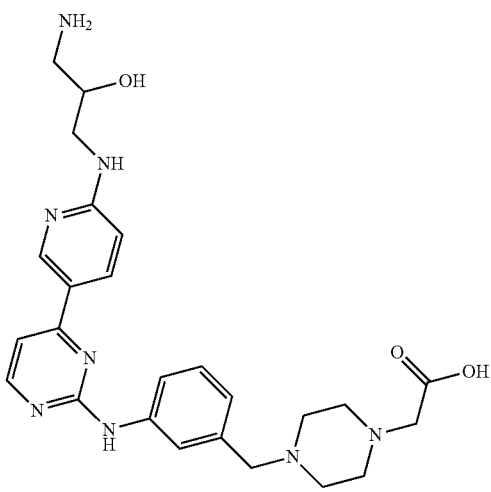
Int. 62
HCl salt
(from Int. 4 and 1,3-diamino-2-
hydroxopropane; used for Co. 23)
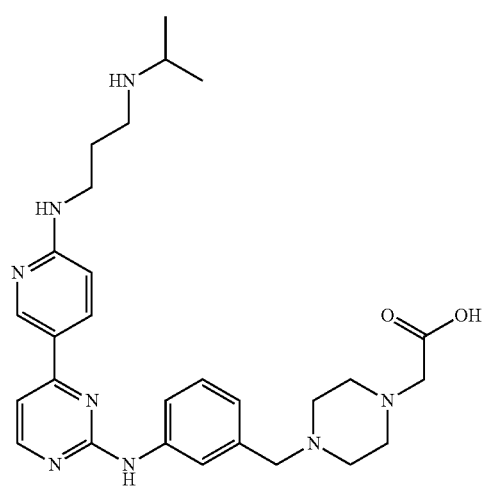
Int. 61
HCl salt
(from Int. 4 and N-isopropyl-1,3-
propanediamine; used for Co. 22)
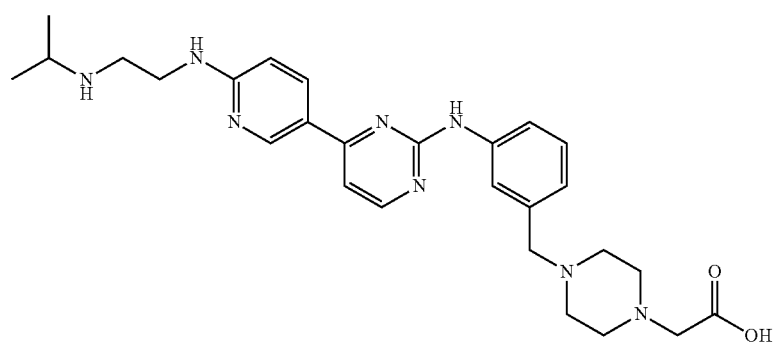
Int. 60
HCl salt
(from Int. 4 and N-isopropyl-1,2-diaminoethane; used for Co. 21)

Example A2 a) Preparation of Int. 5

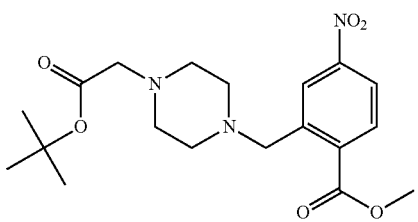 [SMILES: COC(=O)c1ccc([N+](=O)[O-])cc1CN1CCN(CC(=O)OC(C)(C)C)CC1]

A solution of 2-bromomethyl-4-nitrobenzoic acid methyl ester (110 g, 401 mmol), piperazine-1-acetic acid tert-butyl ester (81 g, 405 mmol) and $K_2CO_3$ (q.s.) in ACN (1000 ml) was stirred for 6 h at 50° C. The precipitate was filtered off and the solvent was removed. The residue was purified by column chromatography over silica gel (gradient eluent: PE/EtOAc from 10/1 to 1/1). The desired fractions were collected and the solvent was evaporated. Yield: 130 g of Int. 5 (93%).

b) Preparation of Int. 6

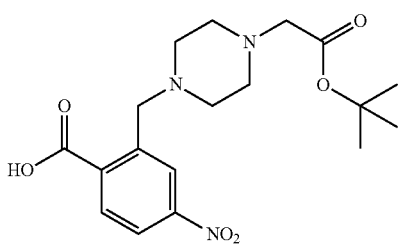 [SMILES: CC(C)(C)OC(=O)CN1CCN(Cc2cc([N+](=O)[O-])ccc2C(=O)O)CC1]

A solution of Int. 5 (91 g, 231.3 mmol) and LiOH (1 mol/L in water; 693.9 mL, 693.9 mmol) in THF (700 mL) was stirred for 3 h at room temperature. The pH of the reaction was adjusted to to pH 4-5 by addition of 2 N HCl. The organic solvent was evaporated under reduced pressure. The mixture was cooled to room temperature, and filtered to give 70 g of nt. 6 (80%).

c) Preparation of Int. 7

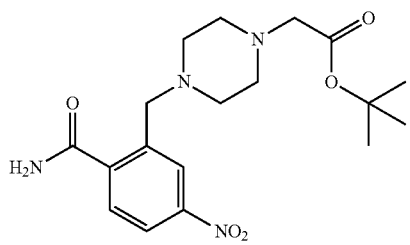

A solution of Int. 6 (33 g, 87 mmol), ammonium hydrochloride (6.52 g, 121.8 mmol), 1-hydroxy-1H-benzotriazole hydrate (14.11 g, 104.4 mmol), 3-ethyl-1-(3-dimethylaminopropyl)carbodiimide. HCl (20.01 g, 104.4 mmol) and $Et_3N$ (35.21 g, 348 mmol) in DMF (250 ml) was stirred overnight at room temperature. The mixture was evaporated in vacuo, water was added to the residue and this aqueous mixture was extracted with DCM. The organic phase was washed by water, brine, dried over $Na_2SO_4$ and filtered. The solvent was evaporated and the crude product was purified by column chromatography over silica gel (eluent: EtOAc). The desired fractions were collected and the solvent was evaporated. Yield: 18.8 g of Int. 7 (57%).

The intermediates in the table below were prepared according to an analogous reaction protocol as used for Int. 7:

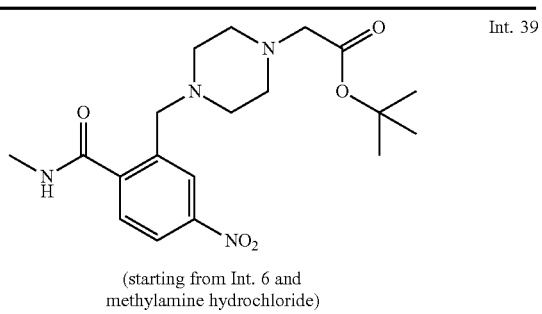

Int. 39
(starting from Int. 6 and methylamine hydrochloride)

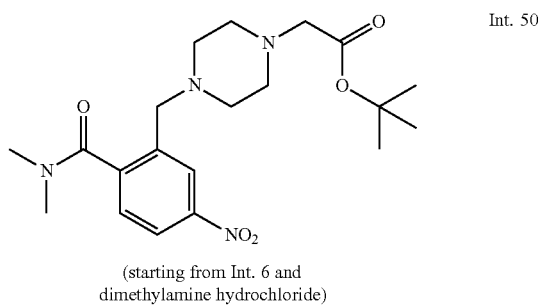

Int. 50
(starting from Int. 6 and dimethylamine hydrochloride)

d) Preparation of Int. 8

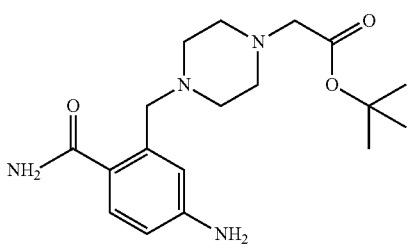 [SMILES: CC(C)(C)OC(=O)CN1CCN(Cc2cc(N)ccc2C(N)=O)CC1]

Pt/C (5%) (1 g, 5.1 mmol) was added as a catalyst to a solution of Int. 7 (18.8 g, 49.7 mmol) in EtOH (350 ml) and the resulting suspension was hydrogenated under a hydrogen atmosphere for 15 h at 40° C. The catalyst was removed by filtration and the filtrate was evaporated under reduced pressure. Yield: 16.0 g of Int. 8 (92%).

The intermediates in the table below were prepared according to an analogous reaction protocol as used for Int. 8:

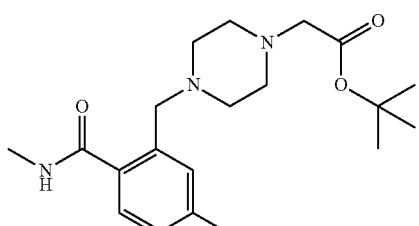

Int. 40

(starting from Int. 39)

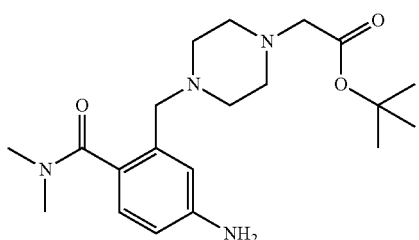

Int. 51

(starting from Int. 50)

e) Preparation of Int. 9

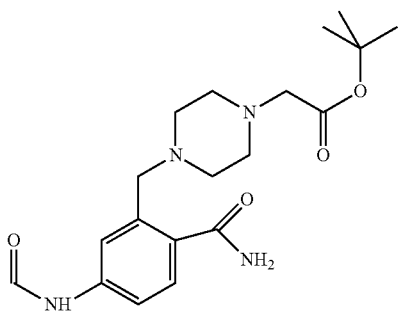 [SMILES: CC(C)(C)OC(=O)CN1CCN(Cc2cc(NC=O)ccc2C(N)=O)CC1]

Phenyl formate (5.748 mL 51.658 mmol) was added to a solution of Int. 8 (4.5 g; 12.915 mmol) in DCM (62 ml) at room temperature. The reaction mixture was stirred at room temperature for 7 days. The precipitate was filtered off and dried. Yield: 3.3 g of Int. 9 (68%).

The Intermediates in the table below were prepared according to an analogous reaction protocol as used for Int. 9:

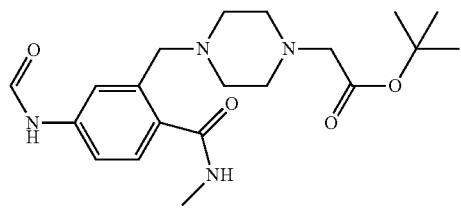

Int. 41

(starting from Int. 40)

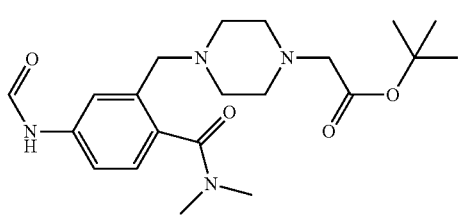

Int. 52

(starting from Int. 51)

f) Preparation of Int. 38

Int. 9 was further reacted according to analogous synthesis protocols as described successively for Int. 4 (A1.d), Int. 10 (A1.e) and Int. 11 (A1.f), to obtain Int. 38, which was used for the synthesis of compound 10:

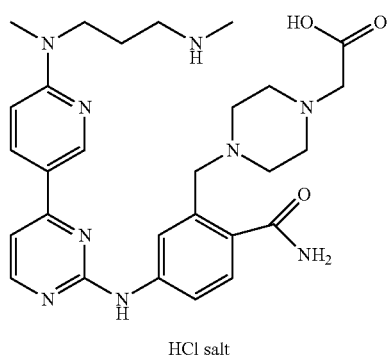 [SMILES: CNCCCN(C)c1ccc(-c2ccnc(Nc3ccc(C(N)=O)c(CN4CCN(CC(=O)O)CC4)c3)n2)cn1]

HCl salt

The intermediates in the table below were prepared according to an analogous reaction protocol as used for Int. 38:

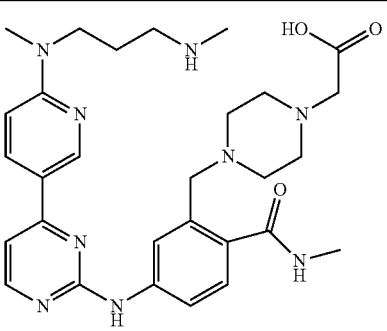

Int. 42

HCl salt
(from Int. 41 and $N^1,N^3$-dimethyl-1,3-propanediamine; used for Co. 12)

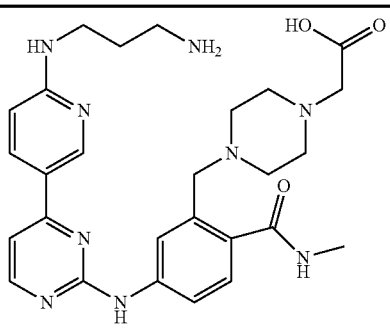

Int. 43

HCl salt
(from Int. 41 and 1,3-
propanediamine; used for Co. 13)

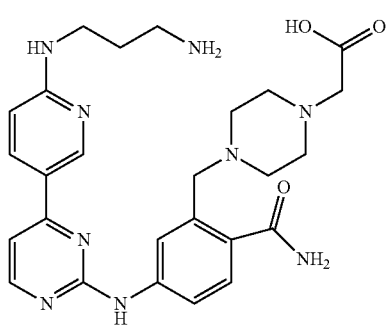

Int. 48

HCl salt
(from Int. 9 and 1,3-
propanediamine; used for Co. 15)

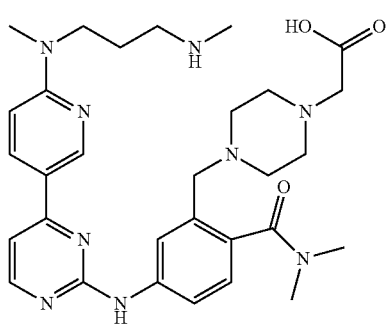

Int. 53

HCl salt
(from Int. 52 and $N^1,N^3$-
dimethyl-1,3-propanediamine; used for
Co. 17)

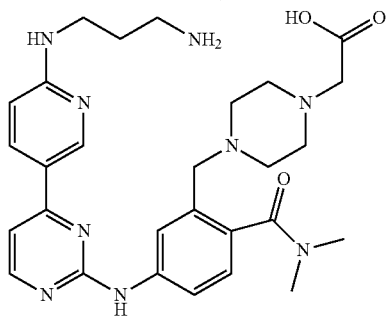

Int. 54

HCl salt
(from Int. 52 and 1,3-
propanediamine; used for Co. 18)

Example A3 a-1) Preparation of Int. 12

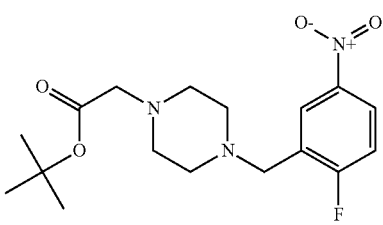 [SMILES: CC(C)(C)OC(=O)CN1CCN(Cc2cc([N+](=O)[O-])ccc2F)CC1]

Piperazine-1-acetic acid tert-butyl ester (25.67 g, 128 mmol) was added to a suspension of 3-bromomethyl-4-fluoronitrobenzene (Journal of Medicinal Chemistry (1994), 37(9), 1362-70) (30 g, 128 mmol) and $K_2CO_3$ (35.3 g, 256 mmol) in $CH_3CN$ (400 ml). The mixture was stirred at room temperature for 2 h and was then filtered.

The organic solvent was evaporated in vacuo. The residue was purified by chromatography on silica gel (PE/EtOAc 8/1 to EtOAc). The desired fractions were collected and the solvent was evaporated. Yield: 28 g of Int. 12 (62% yield).

The intermediates in the table below were prepared according to an analogous reaction protocol as used for Int. 12:

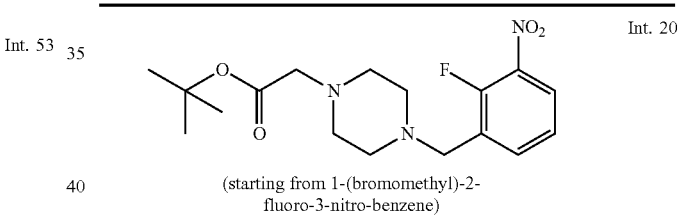

Int. 20

(starting from 1-(bromomethyl)-2-fluoro-3-nitro-benzene)

a-2) Preparation of Int. 16

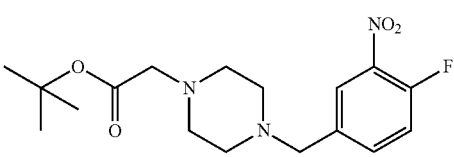 [SMILES: CC(C)(C)OC(=O)CN1CCN(Cc2ccc(F)c([N+](=O)[O-])c2)CC1]

Acetic acid (29.8 g, 400 mmol) was added to a solution of 3-nitro-4-fluorobenzaldehyde (49 g, 290 mmol) and piperazine-1-acetic acid tert-butyl ester (66.3 g, 331 mmol) in DCM (400 ml) and the mixture was stirred for 60 minutes. Then sodium triacetoxyborohydride (77 g, 364 mmol) was added and the reaction mixture was stirred overnight. Water was added to the mixture (200 ml) and the resulting biphasic mixture was extracted twice with DCM (200 ml). The organic layer was washed with saturated NaCl, dried, filtered and the solvent was evaporated. The residue was purified by chromatography on silica gel (PE/EtOAc 40/1 to 10/1). The desired fractions were collected and the solvent was evaporated. Yield: 45 g of Int. 16 (44%).

The intermediates in the table below were prepared according to an analogous reaction protocol as used for Int. 16:

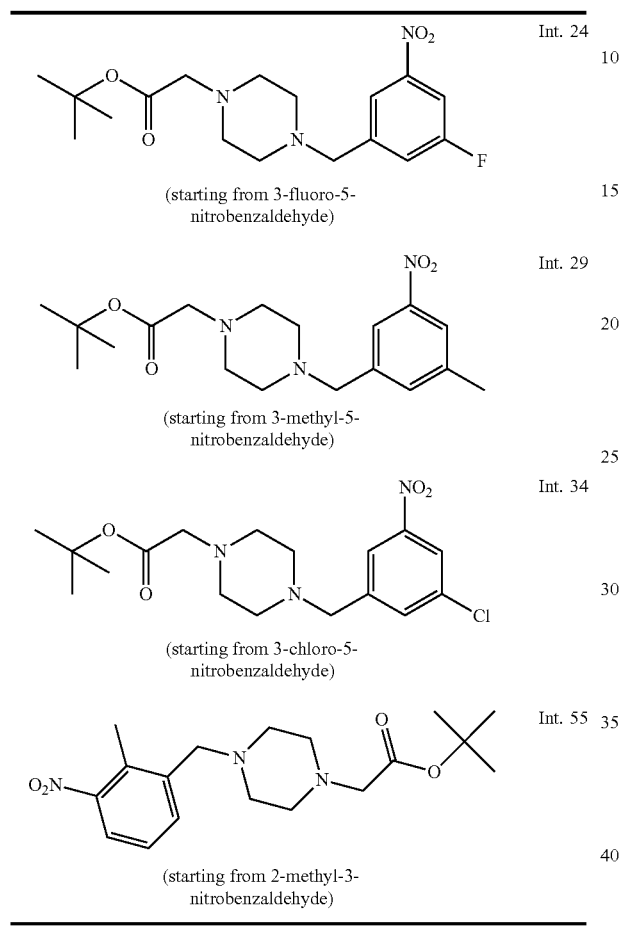

| | |
|---|---|
| (starting from 3-fluoro-5-nitrobenzaldehyde) | Int. 24 |
| (starting from 3-methyl-5-nitrobenzaldehyde) | Int. 29 |
| (starting from 3-chloro-5-nitrobenzaldehyde) | Int. 34 |
| (starting from 2-methyl-3-nitrobenzaldehyde) | Int. 55 | a-3) Preparation of Int. 68

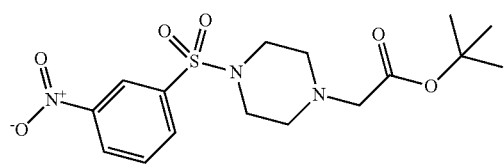

A solution of 3-nitrobenzenesulfonyl chloride (5 g, 22.561 mmol) in DCM (20 ml) was added dropwise to a stirred solution of Et₃N (10.035 mL, 72.195 mmol) and piperazine-1-acetic acid tert-butyl ester (22.561 mmol) in DCM (80 ml) at room temperature. After addition, the reaction mixture was stirred at room temperature for 18 h. The reaction was quenched by the addition of water and the aqueous mixture was extracted twice with DCM. The organic layer was washed with water, dried with MgSO₄, filtered and the filtrate was evaporated. Yield: 10.08 g of Int. 68.

a-4) Preparation of Int. 72

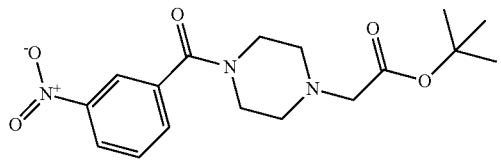

A solution of 3-nitrobenzoyl chloride (11.03 g, 59.44 mmol) in DCM (100 mL) was added dropwise to a stirred solution of piperazine-1-acetic acid tert-butyl ester (12.297 mL, 59.44 mmol) and DIPEA (11.267 mL, 65.384 mmol) in DCM (300 mL) at room temperature. After addition the reaction mixture was stirred at room temperature for 2 h. The reaction was quenched by the addition of water. The mixture was diluted with DCM and then shaken vigorously. The organic layer was separated, washed with water, washed with brine, dried with MgSO₄, filtered and the solvents of the filtrate evaporated. Yield: 21.86 g of Int. 72 (100%).

a-5) Preparation of Int. 76

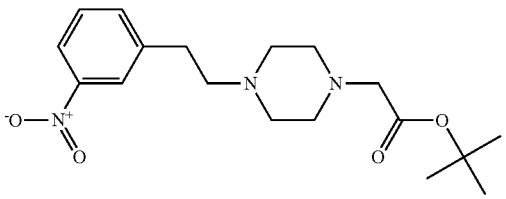

A solution of 1-(2-bromoethyl)-3-nitrobenzene (8.4 g, 36.512 mmol), piperazine-1-acetic acid tert-butyl ester (8043.937 mg, 40.163 mmol) and DIPEA (6.921 mL, 40.163 mmol) in DMA (73 ml) was stirred at 70° C. for 16 h. After cooling, the reaction mixture was poured into water and extracted with EtOAc. The organic layer was separated, dried, filtered and the solvent was evaporated. The residue was purified by flash liquid chromatography on silica gel (eluent DCM/MeOH 98/2). The desired fractions were collected and the solvent was evaporated. Yield: 10.5 g of Int. 76 (82%).

b-1) Preparation of Int. 13

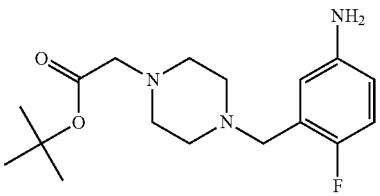 [SMILES: CC(C)(C)OC(=O)CN1CCN(Cc2cc(N)ccc2F)CC1]

Int. 12 (28 g, 79.2 mmol) was dissolved in a mixture of THF (40 ml), H₂O (40 ml) and MeOH (80 ml). Fe (44.2 g, 792 mmol) and NH₄Cl (42.3 g, 792 mmol) were added. The mixture was refluxed for 2 h. After cooling, the mixture was filtered. Brine and DCM were added to the filtrate. The organic layer was separated, dried over Na$_2$SO$_4$ and evaporated to dryness. Yield: 24.3 g of Int. 13 (95%).

The intermediates in the table below were prepared according to an analogous reaction protocol as used for Int. 13:

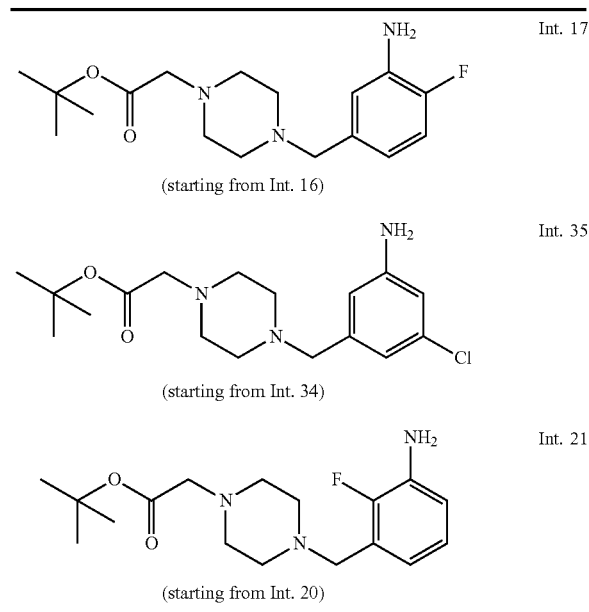

(starting from Int. 16) — Int. 17

(starting from Int. 34) — Int. 35

(starting from Int. 20) — Int. 21 b-2) Preparation of Int. 25

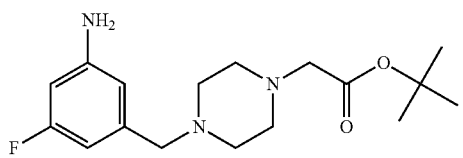 [SMILES: CC(C)(C)OC(=O)CN1CCN(Cc2cc(N)cc(F)c2)CC1]

A suspension of Int. 24 (12 g, 33.95 mmol) and Pt/C 5% (1.5 g) as a catalyst in EtOH (300 ml) was hydrogenated overnight at room temperature under H$_2$-gas atmosphere. The suspension was filtered under reduced pressure. The filtrate was evaporated and the residue was purified by column chromatography over silica gel (gradient eluent: PE/EtOAc from 2/1 to 1/1). The desired fractions were collected and the solvent was evaporated. Yield: 7.2 g of Int. 25 (65.6%).

The intermediates in the table below were prepared according to an analogous reaction protocol as used for Int. 25:

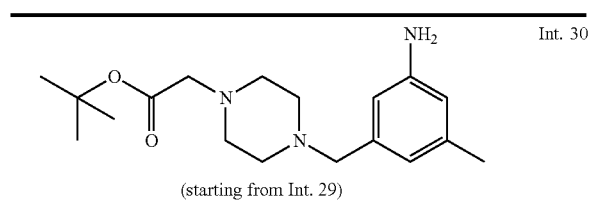

(starting from Int. 29) — Int. 30

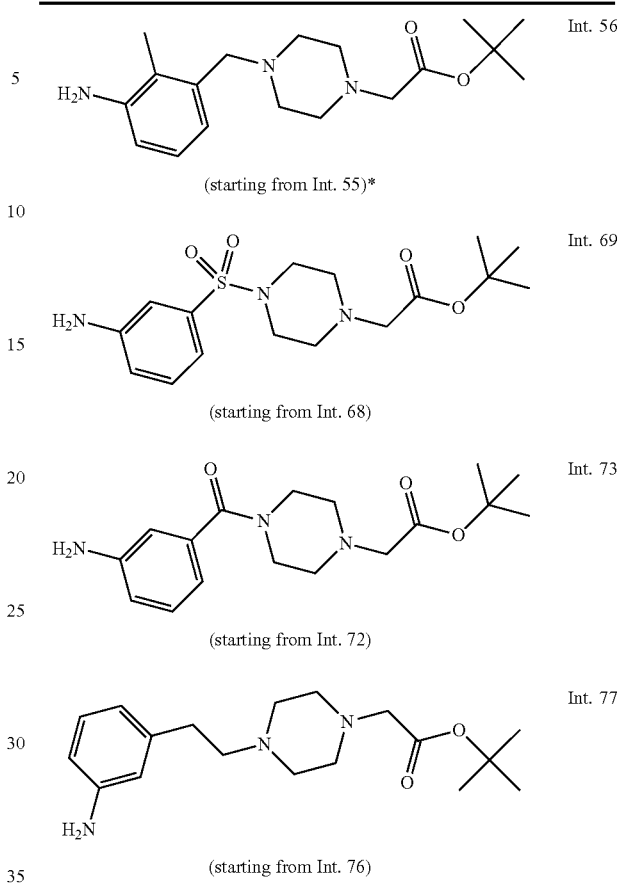

(starting from Int. 55)* — Int. 56

(starting from Int. 68) — Int. 69

(starting from Int. 72) — Int. 73

(starting from Int. 76) — Int. 77

*For the synthesis of Int. 56, 10% Pd/C in MeOH was used under H$_2$ atmosphere at 40 psi pressure for 5 h, after which the mixture was filtered on Celite ®. The crude residue was purified by column chromatography over silica gel (eluent: PE/EtOAc 1/1).

c-1) Preparation of Int. 14

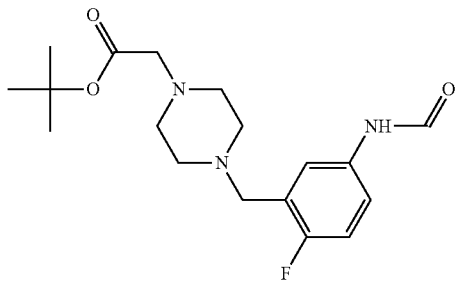 [SMILES: CC(C)(C)OC(=O)CN1CCN(Cc2cc(NC=O)ccc2F)CC1]

Phenyl formate (13.24 g, 108.45 mmol) was added to a solution of Int. 13 (23.4 g, 72.3 mmol) in DCM (200 ml). The mixture was stirred at room temperature for 24 h. The organic solvent was evaporated in vacuo. The residue was purified by chromatography on silica gel (PE/EtOAc 8/1 to EtOAc). The desired fractions were collected and the solvent was evaporated. Yield: 17 g of Int. 14 (67% yield).

The intermediates in the table below were prepared according to an analogous reaction protocol as used for Int. 14:

Int. 18
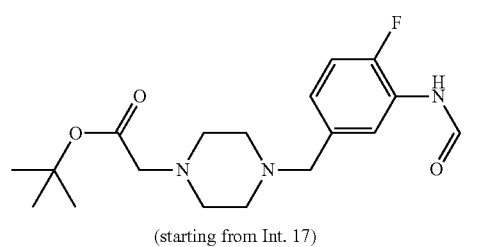 [SMILES: CC(C)(C)OC(=O)CN1CCN(Cc2ccc(F)c(NC=O)c2)CC1]
(starting from Int. 17)

Int. 26
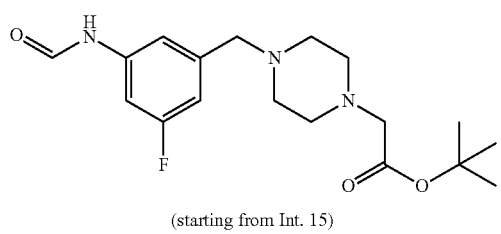 [SMILES: CC(C)(C)OC(=O)CN1CCN(Cc2cc(F)cc(NC=O)c2)CC1]
(starting from Int. 15)

Int. 22
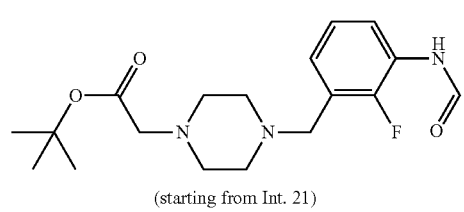 [SMILES: CC(C)(C)OC(=O)CN1CCN(Cc2cccc(NC=O)c2F)CC1]
(starting from Int. 21)

Int. 31
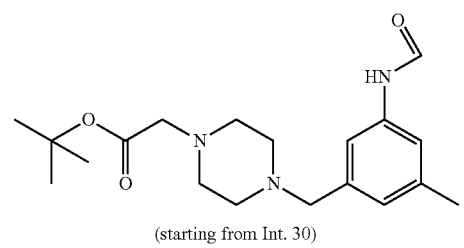 [SMILES: Cc1cc(CN2CCN(CC(=O)OC(C)(C)C)CC2)cc(NC=O)c1]
(starting from Int. 30)

Int. 36
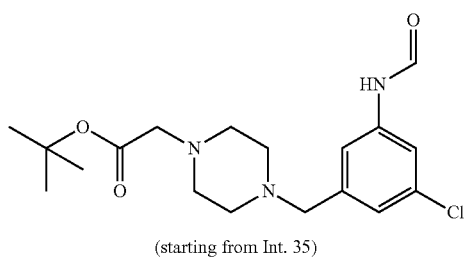 [SMILES: CC(C)(C)OC(=O)CN1CCN(Cc2cc(Cl)cc(NC=O)c2)CC1]
(starting from Int. 35)

Int. 57
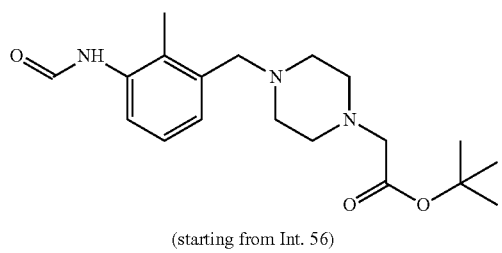 [SMILES: Cc1c(CN2CCN(CC(=O)OC(C)(C)C)CC2)cccc1NC=O]
(starting from Int. 56)

Int. 78
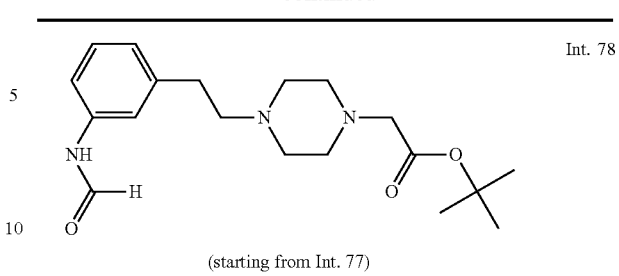
(starting from Int. 77)

c-2) Preparation of Int. 70

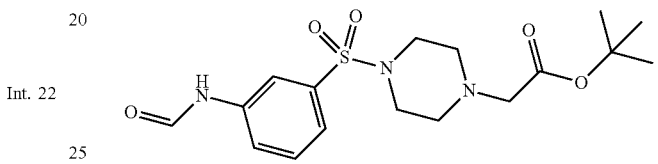

Phenyl formate (2.098 mL, 19.239 mmol) was added dropwise to a stirred mixture of Int. 69 (4.85 g, 12.826 mmol) in DCM (100 ml) at room temperature. After addition the reaction mixture was stirred at room temperature for 2 days. The reaction was quenched by the addition of water. The mixture was diluted with DCM and then shaken vigorously. The organic layer was separated, washed with water, dried with MgSO$_4$, filtered and the filtrate was evaporated. The residue was dissolved in DCM and purified over a SiO$_2$ column, type Grace Reveleris SRC, 80 g, Si 40, on a Armen Spot II Ultimate purification system using DCM and MeOH as eluent in a gradient starting from 100% DCM and ending with 5% MeOH and 95% DCM. The desired fractions were combined and the solvent was evaporated. Yield: 3.78 g of Int. 70 (76%).

The intermediates in the table below were prepared according to an analogous reaction protocol as used for Int. 70:

Int. 74
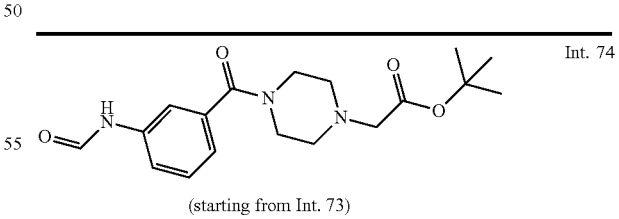
(starting from Int. 73)

d) Preparation of Int. 15

Int. 14 was further reacted according to analogous synthesis protocols as described successively for Int. 4 (A1.d), Int. 10 (A1.e) and Int. 11 (A1.f), to obtain Int. 15, which was used for the synthesis of compound 2:

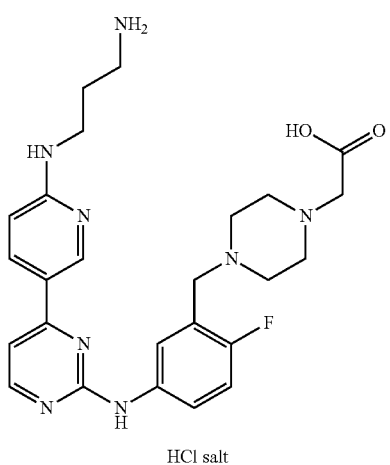 [SMILES: NCCCNc1ccc(-c2ccnc(Nc3ccc(F)c(CN4CCN(CC(=O)O)CC4)c3)n2)cn1]

HCl salt

The intermediates in the table below were prepared according to an analogous reaction protocol as used for Int. 15:

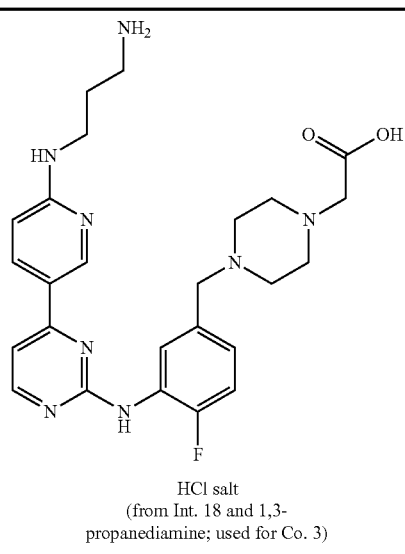

Int. 19

HCl salt
(from Int. 18 and 1,3-
propanediamine; used for Co. 3)

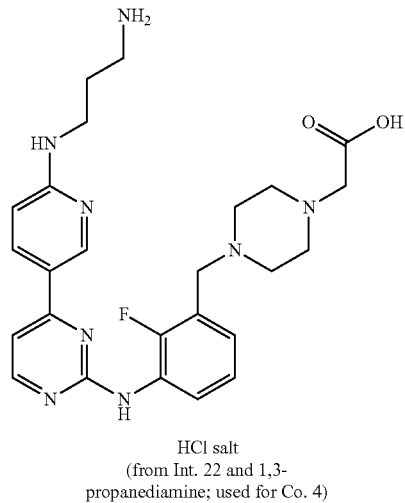 [SMILES: NCCCNc1ccc(-c2ccnc(Nc3cccc(CN4CCN(CC(=O)O)CC4)c3F)n2)cn1]

Int. 23

HCl salt
(from Int. 22 and 1,3-
propanediamine; used for Co. 4)

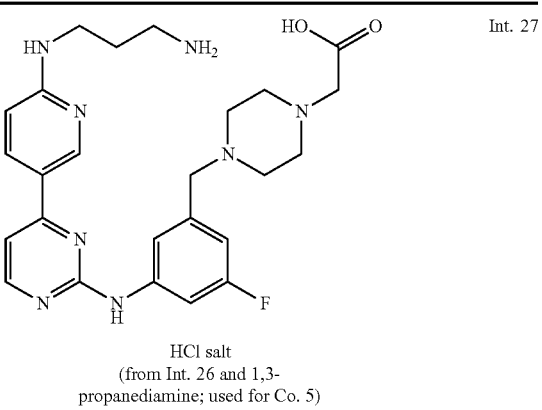

Int. 27

HCl salt
(from Int. 26 and 1,3-
propanediamine; used for Co. 5)

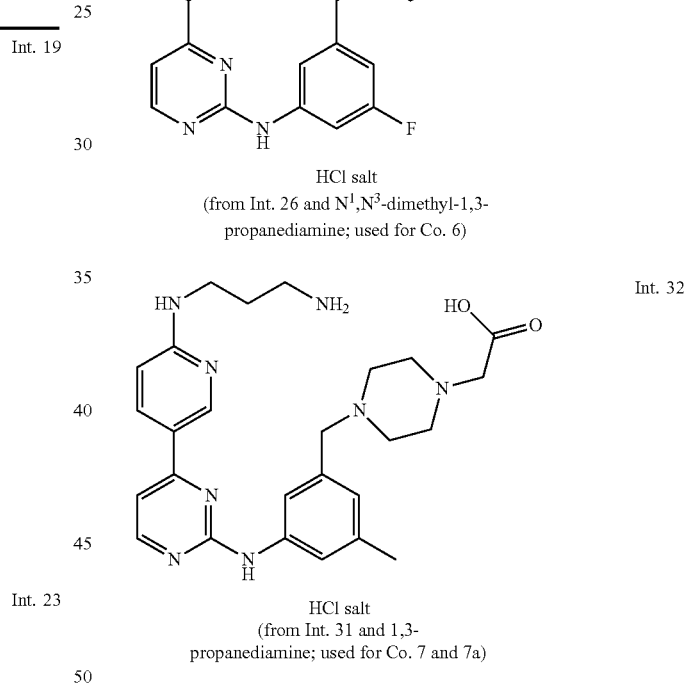

Int. 28

HCl salt
(from Int. 26 and $N^1,N^3$-dimethyl-1,3-
propanediamine; used for Co. 6)

Int. 32

HCl salt
(from Int. 31 and 1,3-
propanediamine; used for Co. 7 and 7a)

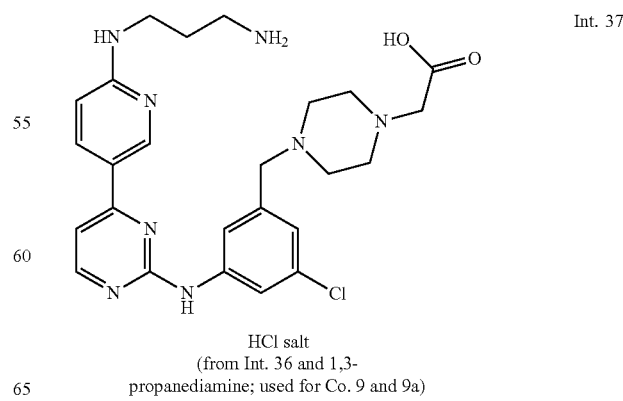

Int. 37

HCl salt
(from Int. 36 and 1,3-
propanediamine; used for Co. 9 and 9a)

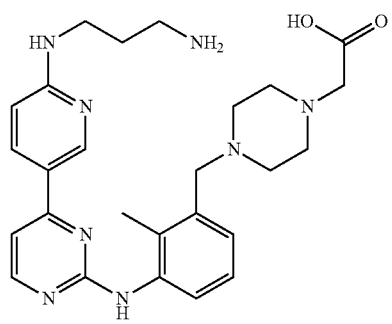

HCl salt
(from Int. 57 and 1,3-propanediamine;
used for Co. 19)

Int. 58

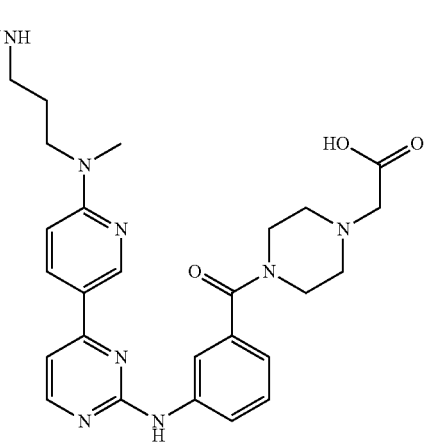

HCl salt
(from Int. 74 and N¹,N³-dimethyl-1,3-
propanediamine; used for Co. 28)

Int. 75

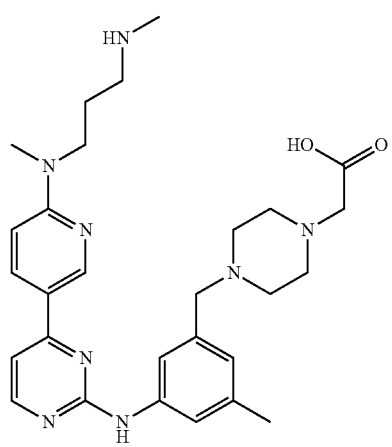

HCl salt
(from Int. 31 and N¹,N³-dimethyl-1,3-
propanediamine; used for Co. 8 and 8a)

Int. 33

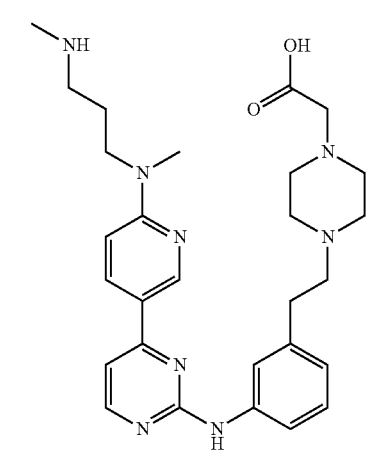

HCl salt
(from Int. 78 and N¹,N³-dimethyl-1,3-
propanediamine; used for Co. 29)

Int. 79

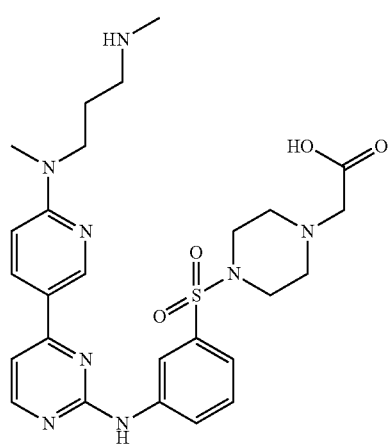

HCl salt
(from Int. 70 and N¹,N³-dimethyl-1,3-
propanediamine; used for Co. 27)

Int. 71

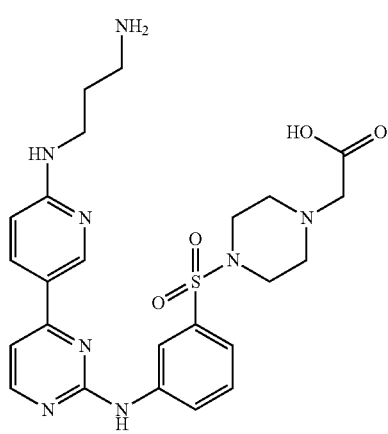

HCl salt
(from Int. 70 and 1,3-propanediamine;
used for Co. 116)

Int. 339

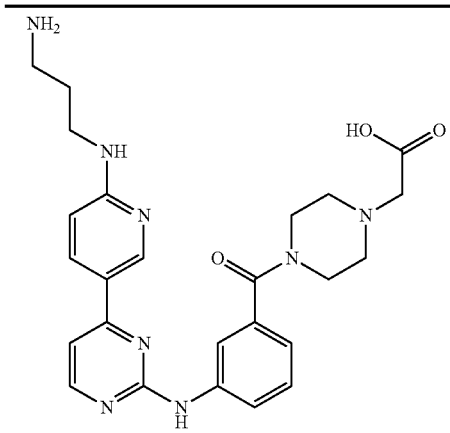

Int. 340

HCl salt
(from Int. 75 and 1,3-propanediamine;
used for Co. 117)

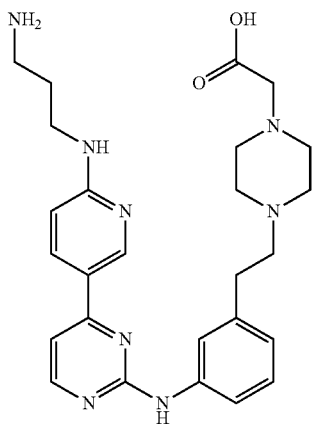

Int. 341

HCl salt
(from Int. 78 and 1,3-propanediamine; used for Co. 118)

Example A4 a) Preparation of Int. 44

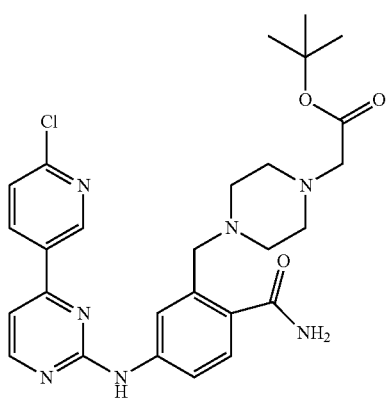 [SMILES: CC(C)(C)OC(=O)CN1CCN(Cc2cc(Nc3nccc(-c4ccc(Cl)nc4)n3)ccc2C(N)=O)CC1]

NaH (60% dispersion in mineral oil) (1.052 g, 26.298 mmol) was added portionwise to a stirred solution of Int. 9 (3.3 g, 8.766 mmol) in DMF (117 ml) under nitrogen atmosphere at room temperature. The reaction mixture was stirred 20 minutes at room temperature under nitrogen atmosphere. 2-chloro-4-(6-chloro-3-pyridinyl)-pyrimidine (1.982 g, 8.766 mmol) was added to the reaction mixture and the resulting solution was stirred at room temperature for 16 h. The reaction mixture was poured out on ice/water. The water layer was stirred for 1 h at room temperature. The precipitate was filtered off and dissolved in EtOAc. The organic layer was dried, filtered and concentrated under reduced pressure. The residue was crystallized from ACN (60 ml). The precipitate was filtered off and dried. Yield: 3.43 g of Int. 44 (72%).

b) Preparation of Int. 45

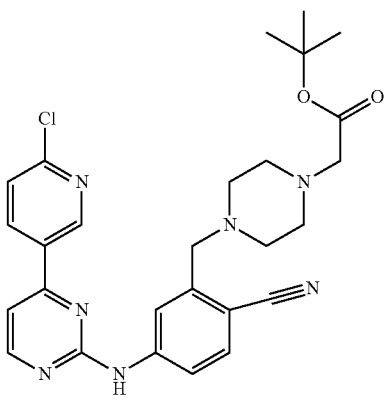

TFA salt

Trifluoroacetic anhydride (1.671 g, 7.955 mmol) was added dropwise to a solution of Int. 44 (2.14 g, 3.977 mmol) and Et$_3$N (1.106 mL, 7.955 mmol) in DCM (24 ml) at room temperature. The solution was stirred for 1 h at room temperature. The solution was concentrated to ¹⁄₁₀ volume. After standing overnight at room temperature, the precipitate was filtered off and dried. Yield: 2.3 g of Int. 45.

c) Preparation of Int. 46

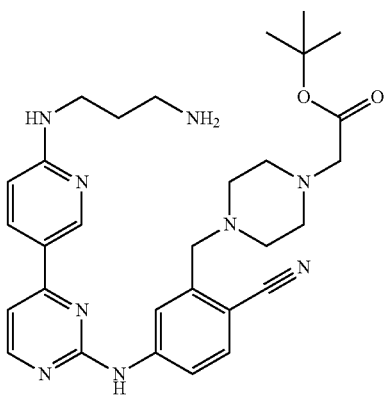 [SMILES: CC(C)(C)OC(=O)CN1CCN(Cc2cc(Nc3nccc(-c4ccc(NCCCN)nc4)n3)ccc2C#N)CC1]

A mixture of Int. 45 (500 mg) and 1,3-diaminopropane (1.126 mL, 13.368 mmol) was stirred at 80° C. for 4 h. Subsequently, water (20 ml) was added to the reaction mixture at room temperature. The reaction mixture was stirred at room temperature for 1 h. The water layer was decanted. The residue was stirred in DIPE at room temperature for 1 h. The DIPE layer was decanted. The residue was dried under vacuum. Yield: 330 mg of Int. 46.

d) Preparation of Int. 47

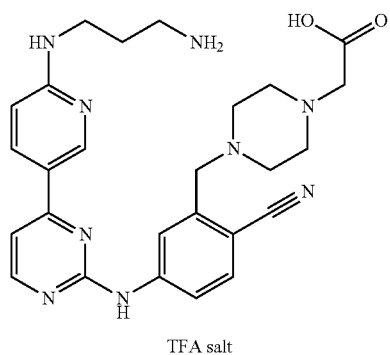 [SMILES: N#Cc1ccc(Nc2nccc(-c3ccc(NCCCN)nc3)n2)cc1CN1CCN(CC(=O)O)CC1]

TFA salt

A solution of Int. 46 (330 mg, 0.592 mmol) in a mixture of trifluoroacetic anhydride (10 ml) and DCM (20 ml) was stirred at room temperature for 48 h. The solution was concentrated under reduced pressure. The residue was co-evaporated with toluene till dryness. Yield: 330 mg of Int. 47 (used for the synthesis of compound 14).

Example A5 a) Preparation of Int. 49

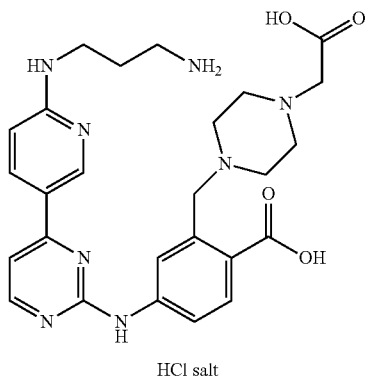 [SMILES: NCCCNc1ccc(-c2ccnc(Nc3ccc(C(=O)O)c(CN4CCN(CC(=O)O)CC4)c3)n2)cn1]

HCl salt

Compound 15 (380 mg, 0.409 mmol) was stirred in HCl (4 M in 1,4-dioxane) (8.929 mL, 35.716 mmol) at 60° C. for 32 h. HCl (4 M in 1,4-dioxane) (4 mL) was added to the solution. The solution was stirred at 60° C. for 16 h. The reaction mixture was concentrated under reduced pressure. The residue was co-evaporated twice with toluene (2×50 ml). The residue (crude Int. 49) was used as such in the next reaction step (the synthesis of compound 16).

Example A6 a) Preparation of Int. 80

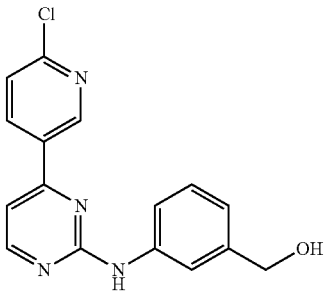 [SMILES: OCc1cccc(Nc2nccc(-c3ccc(Cl)nc3)n2)c1]

A mixture of 2-chloro-4-(6-chloro-3-pyridinyl)-pyrimidine (WO 2009112439) (3 g, 13.271 mmol) and 3-aminobenzyl alcohol (1.63 g, 13.271 mmol) in n-butanol (16.8 mL) was heated in a microwave reactor at 180° C. for 5 minutes. The reaction mixture was taken up into MeOH, diluted with dichloromethane and washed with 10% $K_2CO_3$ aqueous solution. The organic layer was separated, dried over $MgSO_4$, filtered and evaporated, yielding 13.27 g of an orange foam. The reaction was repeated 3 times. The combined residues were purified by preparative LC on irregular SiOH 20-45 μm 1000 g DAVISIL using $NH_4OH$, DCM, MeOH 0.1/97/3 as an eluent. The desired fractions were collected and the solvent was evaporated. Yield: 5.7 g of Int. 80 (45.77%).

The intermediates in the table below were prepared according to an analogous reaction protocol as used for Int. 80:

Int. 342

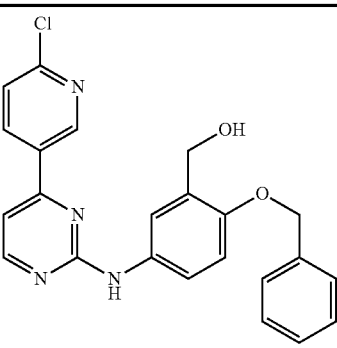

(from 5-amino-2-(phenylmethoxy)-benzenemethanol)

Int. 343

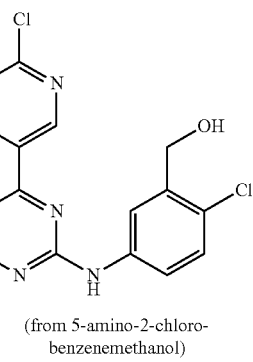

(from 5-amino-2-chloro-benzenemethanol)

b-1) Preparation of Int. 81

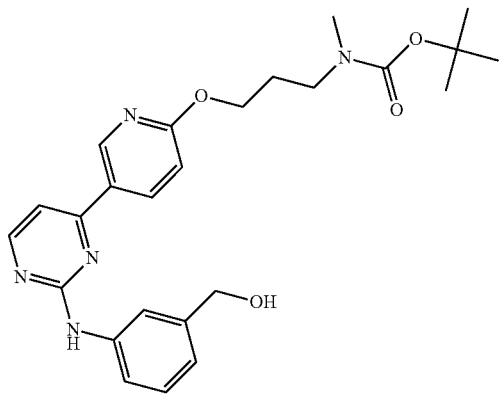 [SMILES: CN(CCCOc1ccc(-c2ccnc(Nc3cccc(CO)c3)n2)cn1)C(=O)OC(C)(C)C]

Reaction was executed twice on the amounts described below.

A suspension of Int. 80 (0.5 g, 1.6 mmol) and 3-(N-tert-butoxycarbonyl-N-methylamino)propanol (1.5 g, 8 mmol) in potassium tert-butoxide 1 M in 2-methyl-2-propanol (14 mL, 14 mmol) was stirred at 110° C. for 5 minutes in a microwave (Biotage) in a sealed tube, monomode, 400 W. The reaction mixture was poured into water. The precipitate was filtered over Celite® and washed with DCM (3×). The combined organic layers were separated, dried over MgSO$_4$, filtered and evaporated. The residue was purified by preparative liquid chromatography on irregular SiOH 15-40 μm 300 g (Merck). Mobile phase NH$_4$OH, DCM, MeOH 0.1/97/3). The desired fractions were collected and the solvent was evaporated. The residue was purified by preparative LC (2-ethylpyridine 6 μm 150×21.2 mm); mobile phase (iPrNH$_2$, CO$_2$, MeOH 0.3/75/25). Yield: 332 mg of Int. 81 (22%).

b-2) Preparation of Int. 85

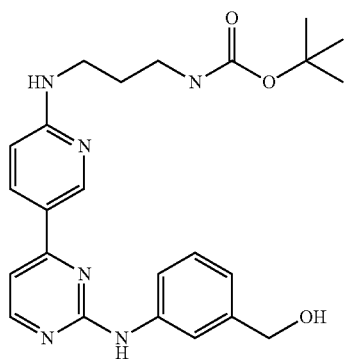 [SMILES: CC(C)(C)OC(=O)NCCCNc1ccc(-c2ccnc(Nc3cccc(CO)c3)n2)cn1]

A mixture of Int. 80 (30 g, 96 mmol), N-(3-aminopropyl)-carbamic acid 1,1-dimethylethyl ester (84 g, 480 mmol) and NMP (120 ml) was stirred for 15 h at 80° C. Subsequently, the solvent was evaporated in vacuo. The residue was purified by column chromatography on silica gel (PE/EtOAc) from 20/1 to 1/2). The desired fractions were collected and the solvent was evaporated. Yield: 17 g of Int. 85 (39%).

b-3) Preparation of Int. 344

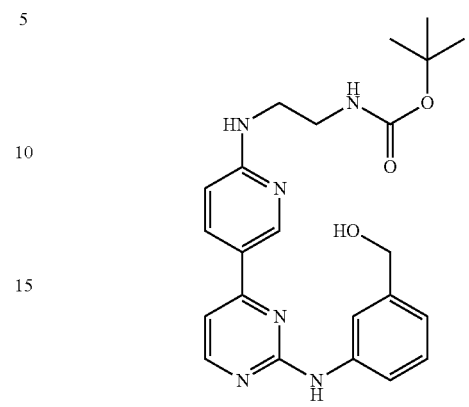

A mixture of int. 80 (1 g; 3.2 mmol) in ethylenediamine (2 ml) was stirred at 150° C. for 3 h. The reaction mixture was poured out onto ice water and the water layer was extracted with a mixture of DCM/MeOH 9/1. The organic layer was dried with MgSO$_4$, filtered and evaporated to dryness. The residue was taken up into DCM (75 ml) and was treated with di-tert-butyl dicarbonate (973 mg; 4.46 mmol) and stirred at room temperature for 16 h. The reaction mixture was washed with a saturated aqueous NaHCO$_3$ solution and water. The organic layer was dried with MgSO$_4$, filtered and evaporated to dryness. The crude residue (containing Int. 344) was used as such in the next reaction step.

The intermediates in the table below were prepared according to an analogous reaction protocol as used for Int. 344:

Int. 345

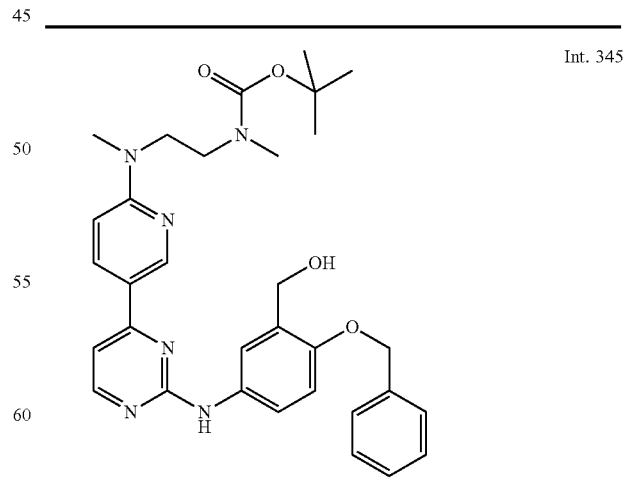

(from Int. 342 and N$^1$,N$^2$-dimethyl-1,2-ethanediamine)

-continued

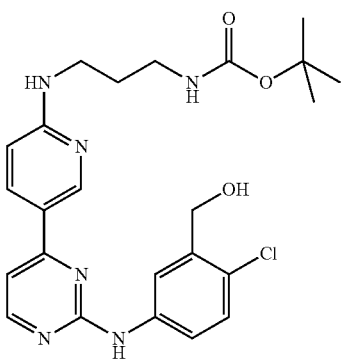

Int. 346

(from Int. 343 and 1,3-propanediamine)

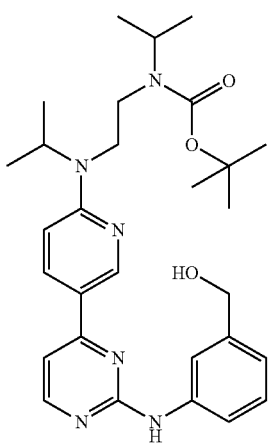

Int. 347

(from Int. 80 and N¹,N²-dimethyl-1,2-ethanediamine)

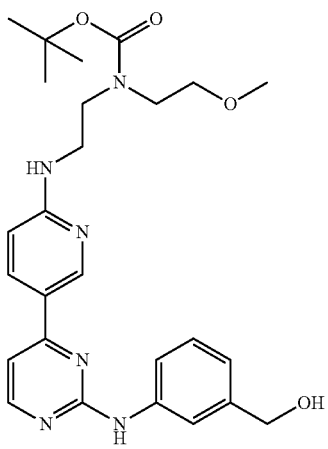

Int. 349

(from Int. 80 and N¹-(2-methoxyethyl)-1,2-ethanediamine)

c) Preparation of Int. 82

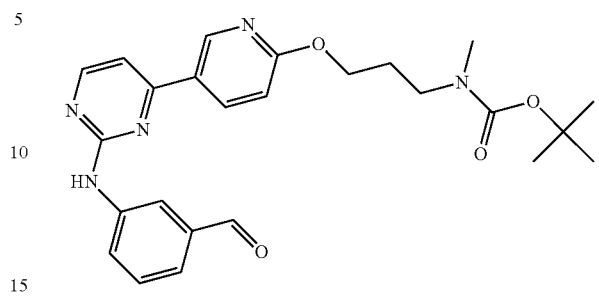

Manganese dioxide (3.4 g, 40.204 mmol) was added to a solution Int. 81 (340 mg, 0.73 mmol) in DCM (5 mL). The reaction mixture was stirred overnight at room temperature. The reaction mixture was filtered through Celite® which was subsequently washed with DCM (3×). The filtrate was evaporated. Yield: 209 mg of Int. 82 (62%).

The Intermediates in the table below were prepared according to an analogous reaction protocol as used for Int. 82:

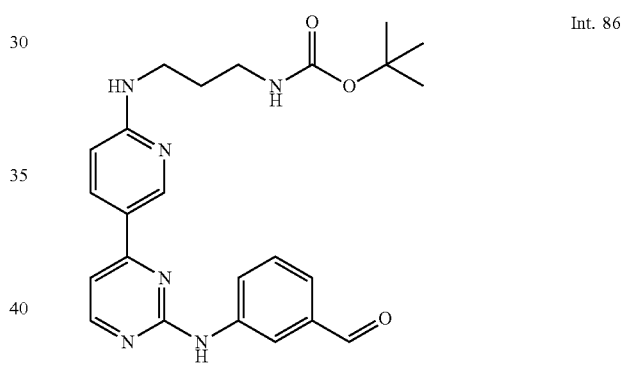

Int. 86

(from Int. 85)

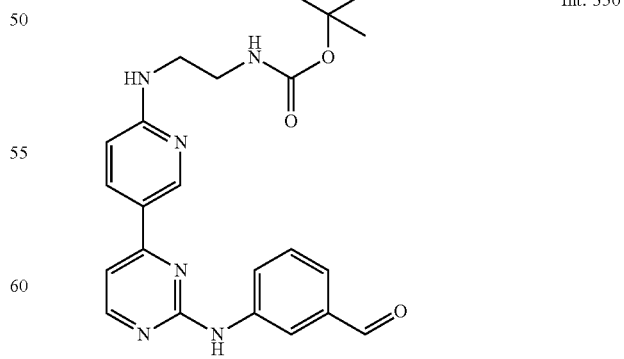

Int. 350

(from Int. 344)

123
-continued

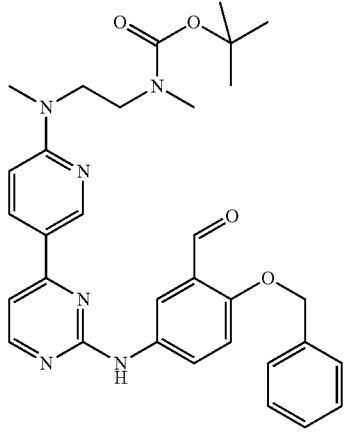

Int. 351

(from Int. 345)

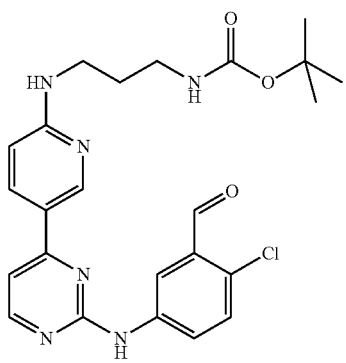

Int. 352

(from Int. 346)

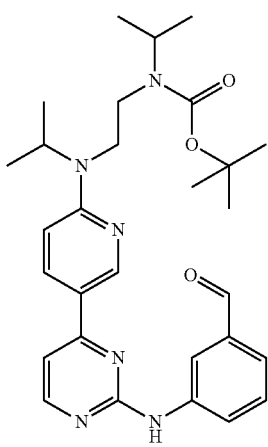

Int. 353

(from Int. 347)

124
-continued

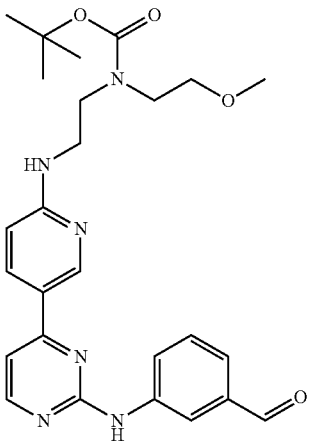

Int. 355

(from Int. 349)

d) Preparation of Int. 83

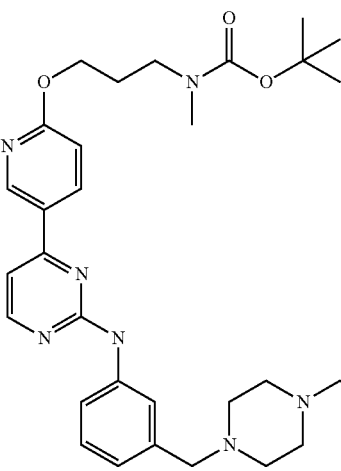

Sodium triacetoxyborohydride (132 mg, 0.621 mmol) was added to a stirred solution of Int. 82 (192 mg, 0.414 mmol), DIPEA (142 µL, 0.828 mmol) and piperazine-1-acetic acid tert-butyl ester (166 mg, 0.828 mmol) in 1,2-dichloroethane (1.9 mL). The mixture was stirred at 120° C. for 20 minutes in a biotage microwave in a sealed tube, monomode, 400 W. Water, potassium carbonate 10% and DCM were added. The reaction mixture was extracted with DCM (3×). The organic layer was separated, dried (MgSO₄), filtered and the solvent was evaporated. The residue was purified by liquid chromatography on silica gel (15-40 µm/30 g; eluent DCM gradient to DCM-MeOH 4%-NH₄OH 0.4%). The solvent was evaporated to give 196 mg of Int. 83 (73%).

The intermediates in the table below were prepared according to an analogous reaction protocol as used for Int. 83:

Int. 87
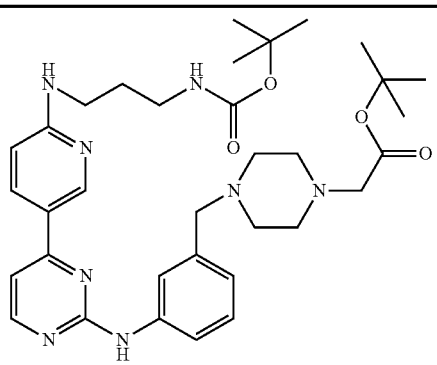
(from Int. 86)
Int. 356
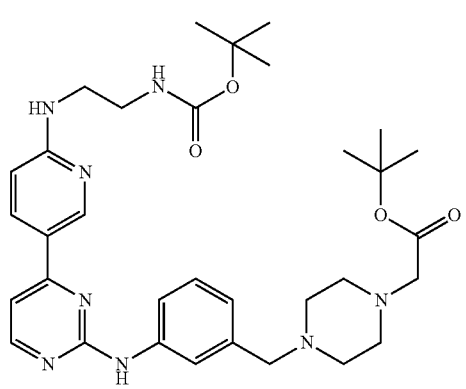
(from Int. 350)
Int. 357
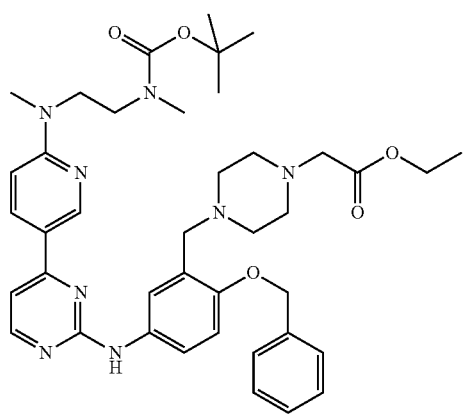
(from Int. 351)
Int. 358
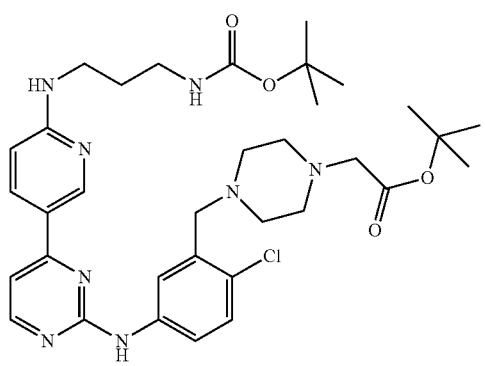
(from Int. 352)
Int. 359
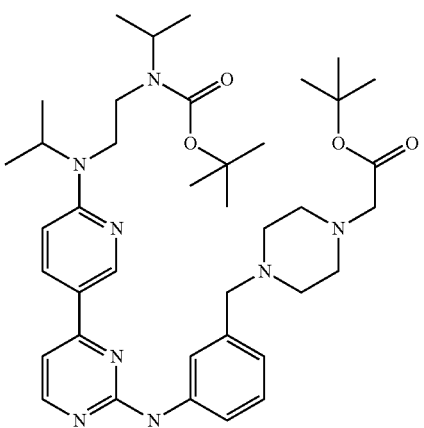
(from Int. 353)
Int. 361
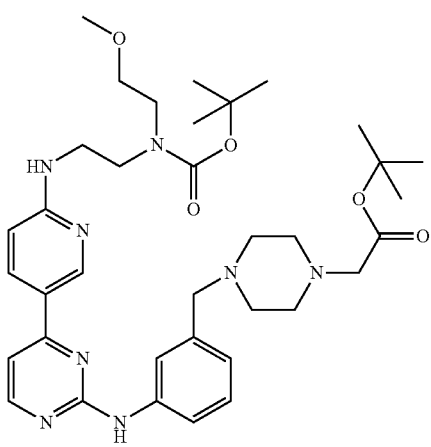
(from Int. 355)
e) Preparation of Int. 84
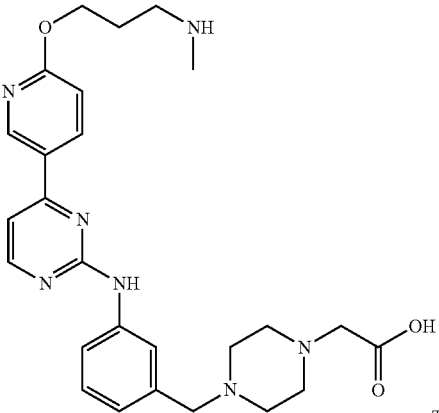
TFA salt
TFA (6.1 mL, 82.552 mmol) was added to a solution of Int. 83 (260 mg, 0.401 mmol) in DCM (6.2 mL) at room temperature. The reaction mixture was stirred at room temperature for 5 h. The solvent was evaporated to give 600 mg of Int. 84 which was used as such without purification for the next reaction step.

The intermediates in the table below were prepared according to an analogous reaction protocol as used for Int. 88:

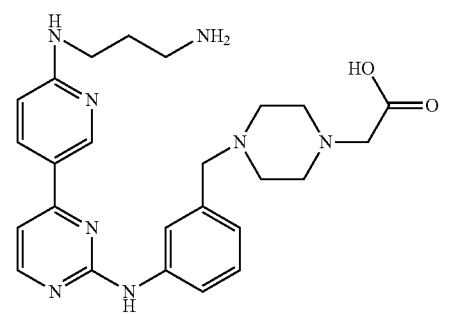

Int. 88

TFA salt
(from Int. 87; used for Co. 31)

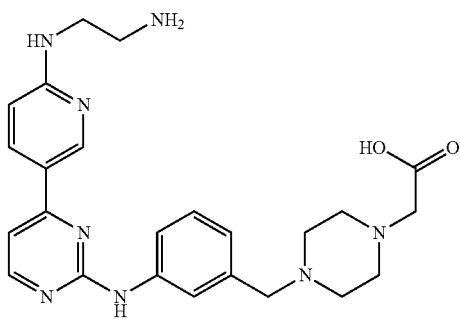

Int. 362

TFA salt
(from Int. 356; used for Co. 119)

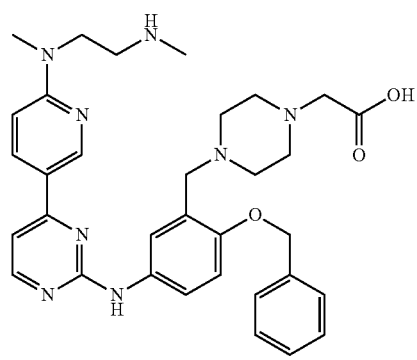

Int. 363

HCl salt
(from Int. 357; used for Int. 379)

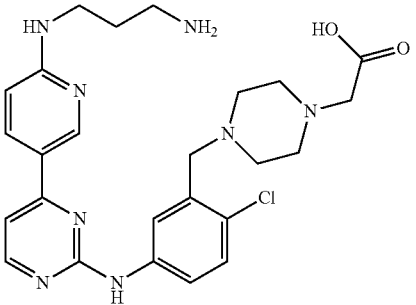

Int. 364

HCl salt
(from Int. 358; used for Co. 120)

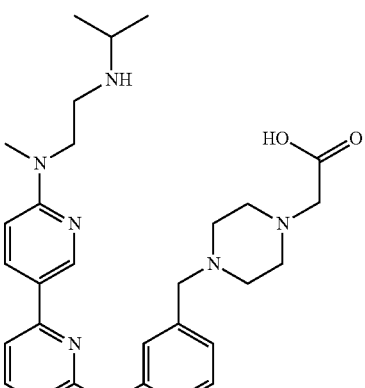

Int. 365

HCl salt
(from Int. 359; used for Co. 121)

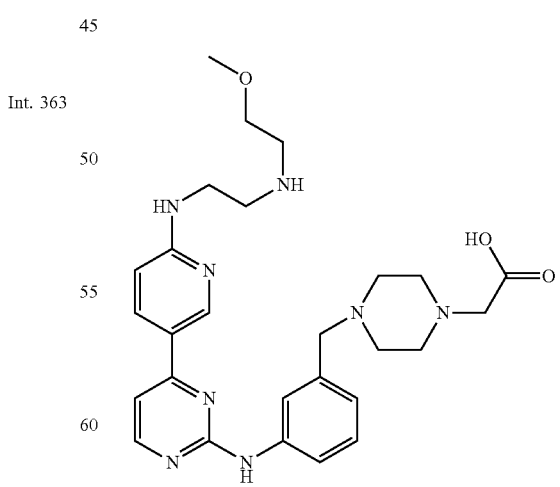

Int. 367

HCl salt
(from Int. 361; used for Co. 123)

Example A7 aa) Preparation of Int. 96

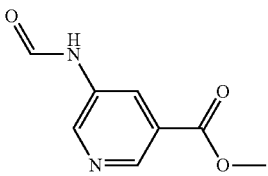

A suspension of 3-amino-5-(methoxycarbonyl)pyridine (3.34 g, 21.95 mmol) and phenyl formate (4.8 mL, 43.90 mmol) in DCM (10 mL) was stirred at room temperature for 72 h. The reaction mixture was diluted with diisopropyl-ether. The precipitate was filtered off and dried. Yield: 4.59 g of Int. 96 as an off-white solid (69%).

a) Preparation of Int. 89

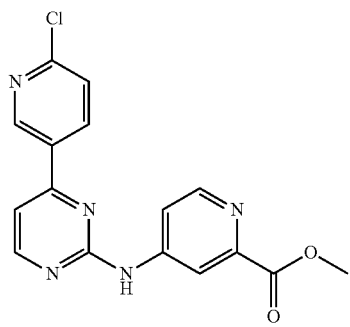 [SMILES: COC(=O)c1cc(Nc2nccc(-c3ccc(Cl)nc3)n2)ccn1]

NaH (60% dispersion in mineral oil) (610 mg; 15.25 mmol) was added portionwise to a solution of 4-(formylamino)-2-pyridinecarboxylic acid, methyl ester (Journal of Antibiotics (1984), 37(5), 532-45) (2.29 g; 12.71 mmol) in DMF (50 mL) at room temperature. The reaction mixture was stirred for 1 h at room temperature and then 2-chloro-4-(6-chloro-3-pyridinyl)-pyrimidine (WO 2009112439) (3.45 g; 15.25 mmol) was added. The reaction mixture was stirred at room temperature overnight. Water was added and the mixture was stirred for 1 h. The mixture was filtered. The precipitate was washed with water (2×), then dried. The residue was combined with the product of the same reaction conducted on 4-(formylamino)-2-pyridinecarboxylic acid, methyl ester (300 mg; 1.67 mmol) and 2-chloro-4-(6-chloro-3-pyridinyl)-pyrimidine (376 mg; 1.67 mmol). The combined residues were purified by preparative liquid chromatography on (Irregular SiOH 20-45 μm, 450 g MATREX). Mobile phase (NH$_4$OH, DCM, MeOH 0.1/96/4). The desired fractions were collected and the solvent was evaporated. Yield: 1.24 g of Int. 89 (yellow solid) (25%).

The intermediates in the table below were prepared according to an analogous reaction protocol as used for Int. 89:

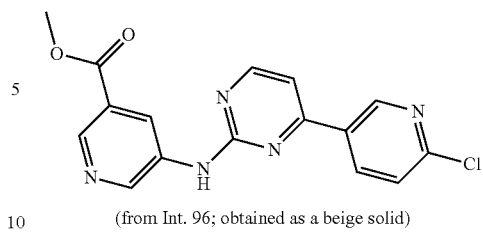

Int. 97

(from Int. 96; obtained as a beige solid)

b) Preparation of Int. 90

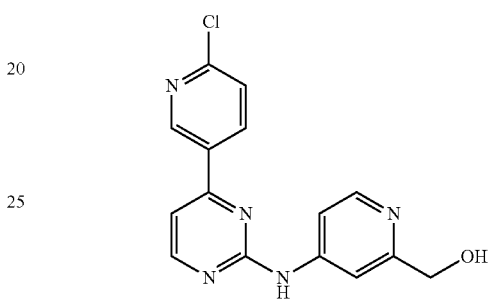

NaBH$_4$ (800 mg, 21 mmol) was added to a suspension of Int. 89 (1.2 g; 3.5 mmol) in MeOH (75 mL) and THF (75 mL). The reaction mixture was stirred for 12 h. Water was added and the organic solvents were evaporated. The precipitate was filtered off, washed with water and dried. The residue was purified by liquid chromatography over silica gel [(Irregular SiOH, 20-45 μm, 40 g). Mobile phase: gradient from DCM, MeOH, NH$_4$OH 97/3/0.1 to DCM, MeOH, NH$_4$OH 90/10/0.1 The pure fractions were collected and the solvent was evaporated. Yield: 460 mg of Int. 90 (41%).

The intermediates in the table below were prepared according to an analogous reaction protocol as used for Int. 90:

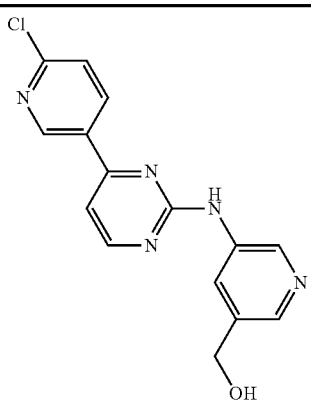

Int. 98

(from Int. 97; LiAlH$_4$ was used as reducing agent (1M in THF); THF was used as solvent)

c) Preparation of Int. 91

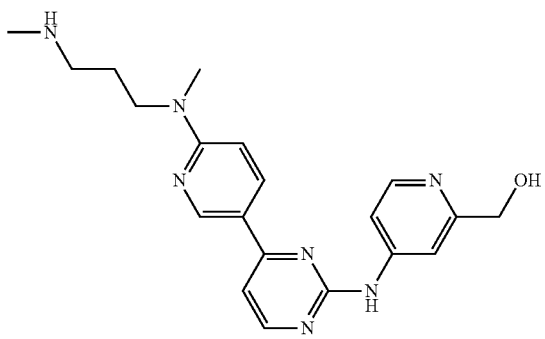 [SMILES: CNCCCN(C)c1ccc(-c2ccnc(Nc3ccnc(CO)c3)n2)cn1]

A mixture of Int. 90 (460 mg; 1.47 mmol) and $N^1,N^3$-dimethyl-1,3-propanediamine (1.2 g; 11.7 mmol) in NMP (3.5 mL) in a sealed tube was heated at 135° C. using one single mode microwave (Biotage Initiator EXP 60) with a power output ranging from 0 to 400 W for 30 min. The solvent was evaporated. The residue was purified by preparative liquid chromatography (Stability Silica 5 μm 150× 30.0 mm). Mobile phase: gradient from NH$_4$OH, DCM, MeOH 0.5/95/5 to NH$_4$OH, DCM, MeOH 0.5/75/25. The desired fractions were collected and the solvent was evaporated. Yield: 540 mg of Int. 91 (97%).

The intermediates in the table below were prepared according to an analogous reaction protocol as used for Int. 91:

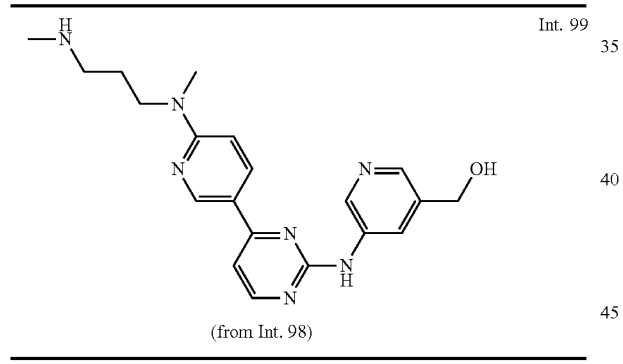

(from Int. 98)

Int. 99 d) Preparation of Int. 92

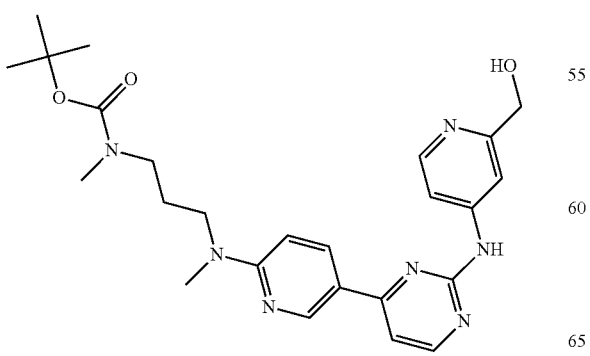

Di-tert-butyl dicarbonate (509 mg; 2.3 mmol) was added to a stirred solution of Int. 91 (0.54 g; 1.2 mmol) in DCM (10 mL) and MeOH (10 mL) at room temperature. The reaction mixture was stirred at room temperature for 2 days. The solvent was evaporated. The residue was purified by preparative LC (Stability Silica 5 μm 150×30.0 mm). Mobile phase: gradient from DCM, MeOH, NH$_4$OH 98/2/0.5 to DCM, MeOH, NH$_4$OH 80/20/0.5. The pure fractions were evaporated and the solvent evaporated until dryness. Yield: 220 mg of Int. 92 (39%).

The intermediates in the table below were prepared according to an analogous reaction protocol as used for Int. 92:

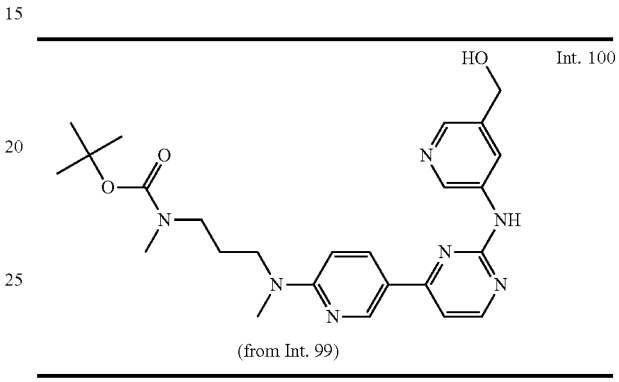

Int. 100

(from Int. 99)

e) Preparation of Int. 93

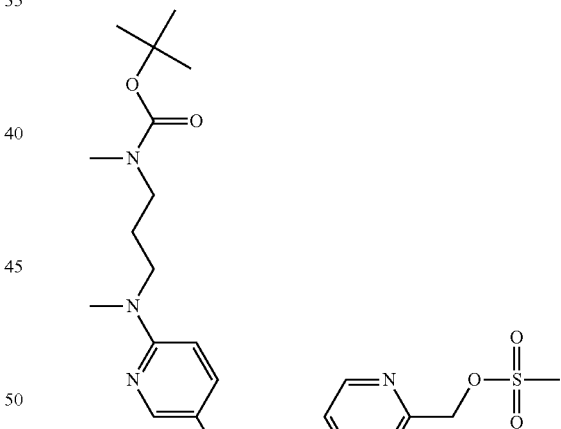

Methanesulfonyl chloride (136 μL; 1.75 mmol) was added dropwise to a solution of Int. 92 (210 mg; 0.44 mmol), DIPEA (383 mg; 2.2 mmol) in DCM (4 mL) at 5° C. under N$_2$ flow. The reaction mixture was stirred at 5° C. for 10 min.

Water and DCM were added. The mixture was extracted with DCM (2×). The organic layer was dried over MgSO$_4$, filtered and the solvent was evaporated. Yield: 280 mg of Int. 93.

The intermediates in the table below were prepared according to an analogous reaction protocol as used for Int. 93:

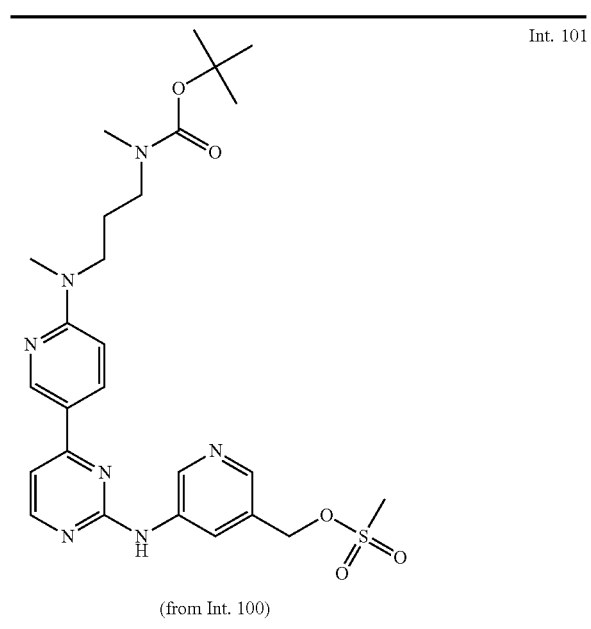

(from Int. 100)

Int. 93 and 101 were typically obtained together with a derivative of these compounds wherein the mesylate moiety is replaced by a chloro moiety. These intermediates were used as mixtures (not quantified) in the next reaction step.

f) Preparation of Int. 94

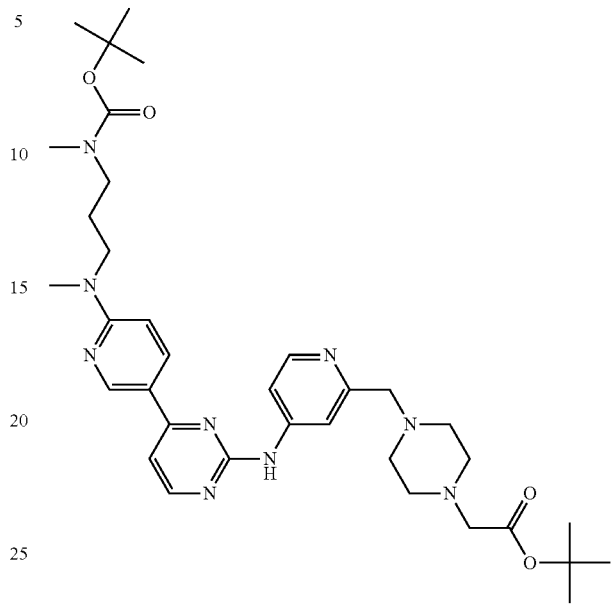

Piperazine-1-acetic acid tert-butyl ester (279 mg; 1.4 mmol) was added to a suspension of Int. 93 (480 mg; 0.47 mmol) and K$_2$CO$_3$ (257 mg; 1.86 mmol) in DMF (2.5 mL). The mixture was stirred at 70° C. for 3 h. Water was added. The mixture was extracted twice with EtOAc. The combined organic layers were washed with water, dried over MgSO$_4$, filtered and evaporated. The residue was purified by preparative liquid chromatography on (Stability Silica 5 μm 150×30.0 mm). Mobile phase: gradient from NH$_4$OH, DCM, MeOH 0.2/98/2 to NH$_4$OH, DCM, MeOH 1.1/89/11). The desired fractions were collected and the solvent was evaporated. Yield: 133 mg of Int. 94 (yellow oil) (43%).

The intermediates in the table below were prepared according to an analogous reaction protocol as used for Int. 94:

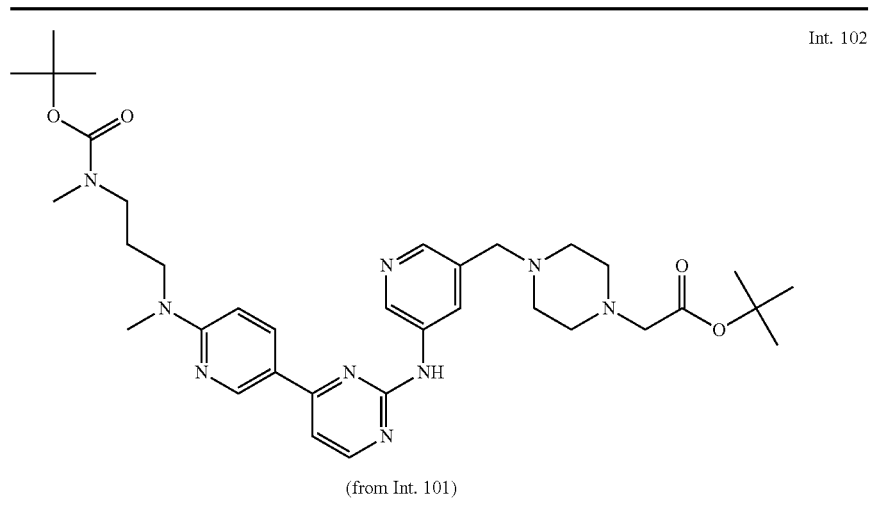

(from Int. 101)

g) Preparation of Int. 95

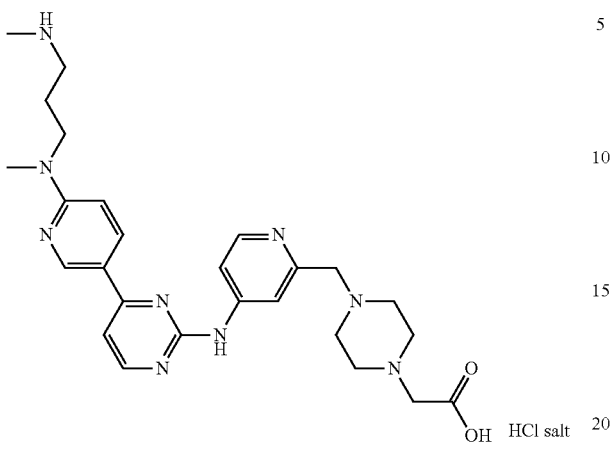

HCl salt

HCl (37% in H₂O) (71 μL; 0.86 mmol) and distilled water (0.5 mL) were added successively to a solution of intermediate 94 (133 mg; 0.17 mmol) in 1,4-dioxane (3 mL). The reaction mixture was stirred at 100° C. for 2 h. The solution was evaporated under reduced pressure and the residue was co-evaporated twice with toluene. Yield: 105 mg of Int. 95.

The intermediates in the table below were prepared according to an analogous reaction protocol as used for Int. 95:

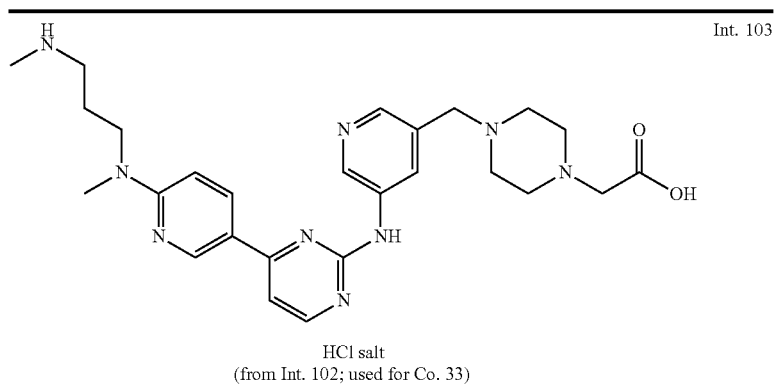

Int. 103

HCl salt
(from Int. 102; used for Co. 33)

Example A8 a) Preparation of Int. 104

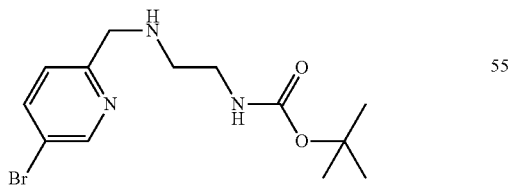

N-(tert-Butoxycarbonyl)-1,2-diaminoethane (8.613 g, 53.761 mmol) and MgSO₄ (9.707 g, 80.642 mmol) were added to a solution of 5-bromo-2-formylpyridine (10 g, 53.761 mmol) in DCM (208 ml). The reaction mixture was stirred 30 min at room temperature under N₂-flow. NaBH (OAc)₃ (10 g, 53.761 mmol) was added portion wise to the reaction mixture at room temperature, and was then stirred at room temperature for 16 h. Subsequently, the reaction mixture was washed twice with an aqueous 2 M NaHCO₃ solution (2×100 ml). The organic layer was separated, dried, filtered and the solvent was evaporated. The residue (21 g) was purified by silicagel filter: eluens DCM/MeOH// from 99.5/0.5 to 96/4. The pure fractions were collected and concentrated under reduced pressure. Yield: 9.2 g of Int. 104 (51.82%).

b) Preparation of Int. 105

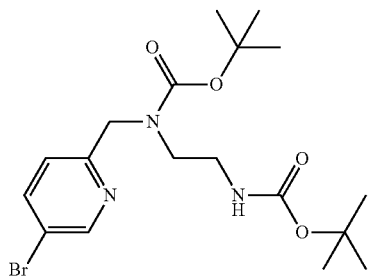 [SMILES: CC(C)(C)OC(=O)NCCN(Cc1ccc(Br)cn1)C(=O)OC(C)(C)C]

Tert-Butyl dicarbonate (14.958 g; 68.535 mmol) was added to a solution of Int. 104 (9.2 g, 27.86 mmol) in DCM at room temperature. The reaction mixture was stirred for 72 h at room temperature, and was subsequently washed with water (2×200 ml). The organic layer was separated, dried, filtered and the solvent was evaporated. The residue (34 g) was stirred in DIPE (25 ml). The precipitate was filtered off and dried under vacuum at 50° C. Yield: 9.6 g of Int. 105 (80.07%).

c) Preparation of Int. 106

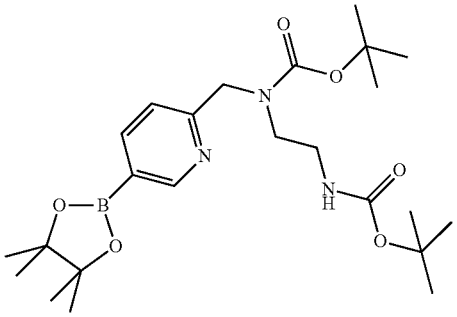 [SMILES: CC(C)(C)OC(=O)NCCN(Cc1ccc(B2OC(C)(C)C(C)(C)O2)cn1)C(=O)OC(C)(C)C]

PdCl$_2$(dppf)-DCM (0.336 g, 0.407 mmol) was added to Int. 105 (5 g, 11.619 mmol), potassium acetate (34.856 mmol) and bis(pinacolate)diboron (3.613 g, 13.942 mmol) in 1,4-dioxane (50 ml) at room temperature. The reaction mixture was stirred at 100° C. for 48 h and was then diluted with 1,4-dioxane (80 ml). The organic layer was filtered through Dicalite®. The filtrate was concentrated under reduced pressure. The residue (Int. 106) was used as such in the next reaction step.

d) Preparation of Int. 107

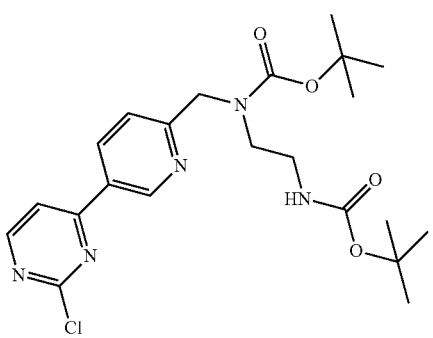 [SMILES: CC(C)(C)OC(=O)NCCN(Cc1ccc(-c2ccnc(Cl)n2)cn1)C(=O)OC(C)(C)C]

PdCl$_2$(dppf)-DCM (0.256 g, 0.349 mmol) was added to a solution of crude Int. 106 (5.547 g) and 2,4-dichloropyrimidine (5.193 g, 34.86 mmol) in 1,4-dioxane (50 ml) at room temperature. 2 M aqueous sodium carbonate (8.715 ml, 17.43 mmol) was added to the reaction mixture at room temperature. The mixture was stirred at 80° C. for 16 h and was then diluted with 1,4-dioxane (160 ml). The organic layer was filtered through Dicalite®. The filtrate was concentrated under reduced pressure. The residue (13.25 g) was purified by flash chromatography on silica gel: eluens DCM/MeOH// from 100/0 to 95/5. The pure fractions were collected and concentrated under reduced pressure. Yield: 5.15 g of Int. 107 (86.93%).

e) Preparation of Int. 108

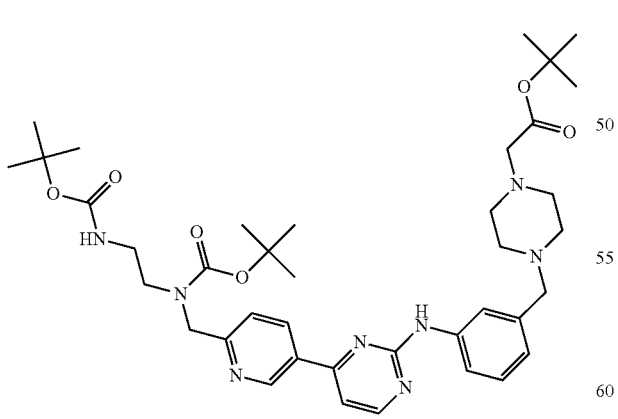

NaH (60% dispersion in mineral oil) (0.577 g, 14.416 mmol) was added portion wise to a stirred solution of intermediate 3 (3.717 g, 11.148 mmol) in DMA (54.26 ml) under N$_2$ atmosphere at room temperature. The reaction mixture was stirred 40 min at room temperature under N$_2$ atmosphere. Int. 107 (2.1 g, 3.44 mmol) was added to the reaction mixture and was then stirred at room temperature for 16 h. Subsequently, the mixture was poured out on ice/water. The water layer was extracted with EtOAc (2×200 ml). The organic layer was separated, dried, filtered and the solvent was evaporated. The residue (14 g) was purified by Prep HPLC (Uptisphere® C18 ODB-10 μm, 200 g, 5 cm). Mobile phase: 0.25% NH$_4$HCO$_3$ solution in water, MeOH. The desired fractions were collected and the solvent was evaporated. Yield: 1.513 g of Int. 108 (60.01%).

f) Preparation of Int. 109

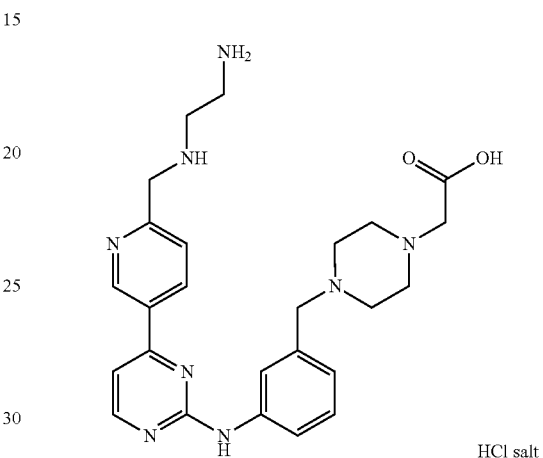

HCl salt

Int. 108 (5 g, 6.822 mmol) was stirred in 4 M HCl in 1,4-dioxane (200 ml) at 60° C. for 16 h. The reaction mixture was concentrated under reduced pressure. The residue was co-evaporated twice with toluene (2×50 ml). The residue (Int. 109) (6.8 g) was used as such in the next reaction step.

Example A9 a-1) Preparation of Int. 110

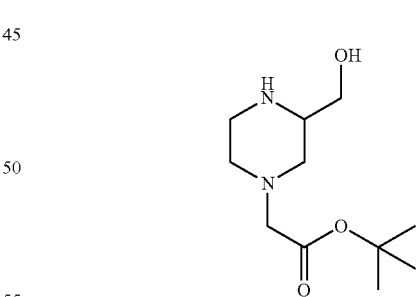

Tert-butyl bromoacetate (3.2 mL; 21.52 mmol) in ACN (20 mL) was added dropwise during 90 min to a solution of 2-piperazinemethanol (5 g; 43.04 mmol) and K$_2$CO$_3$ (4.5 g; 32.28 mmol) in ACN (30 mL) at 0° C. After the addition the reaction mixture was filtered. The precipitate was washed with a mixture of DCM/MeOH (95/5) (3×). The filtrate was evaporated to yield 5.02 g of a yellow oil. The residue was purified by preparative LC (Irregular SiOH 20-45 μm 450 g MATREX). Mobile phase: NH$_4$OH, DCM, MeOH 1/87/12. The desired fractions were collected and the solvent was evaporated. Yield: 1.4 g of a Int. 110 as a yellow oil (28%).

The intermediates in the table below were prepared according to an analogous reaction protocol as used for Int. 110:

| | |
|---|---|
| 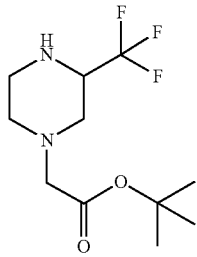<br>(starting from 2-(trifluoromethyl)piperazin) | Int. 119 |
| 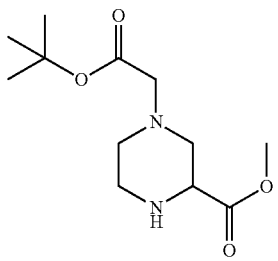<br>(starting from 2-piperazinecarboxylic acid, methyl ester; DMF was used as solvent) | Int. 126 |
| 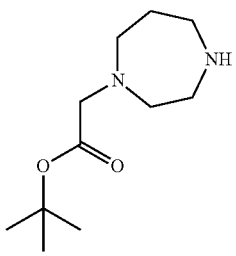<br>(starting from homopiperazine; DCM was used as solvent; no additional base was added) | Int. 129 |
| 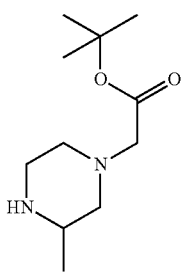<br>(starting from 2-methylpiperazine; DCM was used as solvent; no additional base was added) | Int. 134 | a-2) Preparation of Int. 115

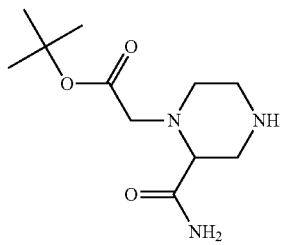

Int. 115

$1^{st}$ Step:

Tert-butyl bromoacetate (2.23 mL) was added dropwise to a suspension of 4-(phenylmethyl)-2-piperazinecarboxamide (4 g; 18.24 mmol) in DCM (63 mL) at room temperature. The reaction mixture was stirred overnight at 50° C. The suspension was filtered off. The precipitate was washed twice with DCM. The filtrate was evaporated to give 4.16 g of a off-white solid. The off-white solid (4.16 g) was purified by preparative LC (Stability Silica 50 μm, 40 g). Mobile phase: DCM, MeOH, NH$_4$OH 97/3/0.1). The pure fractions were collected and the solvent was evaporated until dryness, yielding 2.67 g of a white solid Int. 115a (53%):

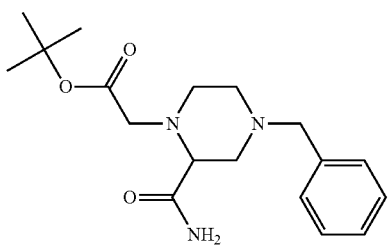

Int. 115a $2^{nd}$ Step

A mixture of Int. 115a (1.47 g; 4.41 mmol) in MeOH (14.7 mL) was hydrogenated at room temperature with Pd/C (150 mg) as a catalyst under a pressure of 3 bar of H$_2$ atmosphere. The reaction mixture was stirred at room temperature overnight. The reaction was performed a $2^{nd}$ time with 1.2 g (3.6 mmol) of Int. 115a, and both reaction mixtures were combined for work-up. The catalyst was filtered off on a pad of Celite® and filtrate was evaporated to give a white sticky solid. The solid was purified by preparative LC (Stability Silica 30-45 μm, 24 g). Mobile phase: Gradient from DCM, MeOH, NH$_4$OH 97/3/0.1 to DCM, MeOH, NH$_4$OH 90/10/0.1). The pure fractions were collected and the solvent was evaporated until dryness to give Int. 115 as a off-white solid (71%).

The intermediates in the table below were prepared according to an analogous reaction protocol as used for Int. 115:

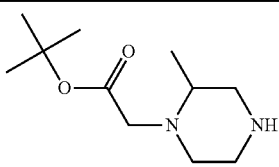

Int. 116

(starting from 3-methyl-1-(phenylmethyl)piperazine); (1st step of the reaction: NaH was added, DMF was used as solvent)

a-3) Preparation of Int. 137

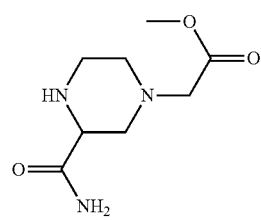

Int. 137

TFA salt

1st Step:

Methyl bromoacetate (1.89 mL; 19.89 mmol) was added drop wise to a solution of 2-(aminocarbonyl)-1-piperazinecarboxylic acid, 1,1-dimethylethyl ester (4.56 g; 19.89 mmol) and $K_2CO_3$ (4.1 g; 29.83 mmol) in DMF (45 mL) at room temperature. The reaction mixture was stirred at room temperature for 90 min. Water and EtOAc were added. The mixture was extracted with EtOAc (3×). The organic layer was washed with brine, dried over $MgSO_4$, filtered and the solvent was evaporated to give 6 g of a yellow oil. The oil was purified by preparative LC (Stability Silica 30-45 μm, 80 g). Mobile phase: Gradient: from pure DCM to DCM, MeOH, $NH_4OH$ 97/3/0.1). The pure fractions were collected and evaporated until dryness to give 5.32 g of a yellow oil Int. 137a (88%):

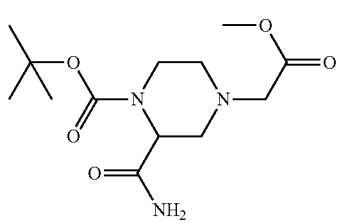

Int. 137a

2nd Step:

TFA (13 mL; 170.24 mmol) was added to a solution of Int. 137a (5.13 g; 17.02 mmol) in DCM (33 mL) at 0° C. The reaction mixture was stirred at room temperature overnight. The solvent was evaporated to yield 10.6 g of an off-white solid as a TFA salt The intermediates in the table below were prepared according to an analogous reaction protocol as used for Int. 137:

Int. 143

TFA salt (starting from methyl 2-bromo-3-hydroxypropionate and 1-piperazinecarboxylic acid, 1,1-dimethylethyl ester, acetate (1:1); DIPEA was used as base in the 1st step)

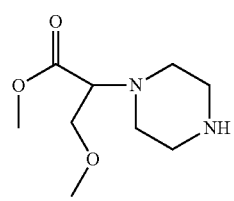

Int. 146

TFA salt (starting from methyl 2-bromo-3-methoxypropionate and 1-piperazinecarboxylic acid, 1,1-dimethylethyl ester, acetate (1:1); $CH_3CN$ was used as solvent in the 1st step)

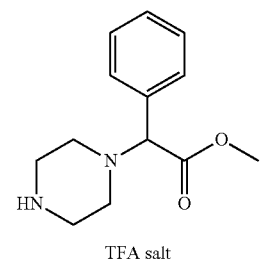

Int. 196

TFA salt (starting from methyl 2-bromophenylacetate and 1-piperazinecarboxylic acid, 1,1-dimethylethyl ester)

a-4) Preparation of Int. 142

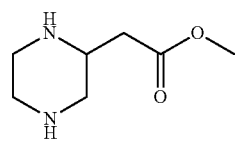

HCl salt

MeOH (250 mL) was added to palladium hydroxide on activated charcoal (4.558 g; 32.454 mmol) under $N_2$-gas atmosphere. Methyl 1,4-dibenzylpiperazine-2-carboxylate (WO2004084898) (21.3 g; 40.907 mmol; 65% purity), HCl (6 M in iPrOH)(15 mL, 90.0 mmol) and $H_2$ gas (1834.4 mL, 81.81 mmol) were added. The reaction mixture was hydrogenated at room temperature under $H_2$-gas until 2 eq. $H_2$ were absorbed. The catalyst was removed by filtration over Dicalite® under $N_2$-gas atmosphere. The filtrate was evaporated. Yield: 13.52 g of Int. 142.

b) Preparation of Int. 85

Alternative for the Procedure in A6.b-2

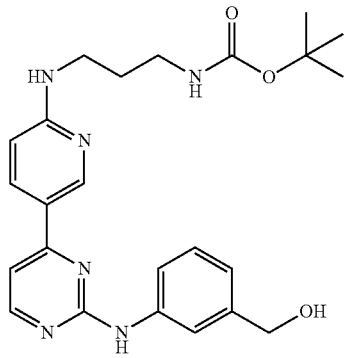 [SMILES: CC(C)(C)OC(=O)NCCCNc1ccc(-c2ccnc(Nc3cccc(CO)c3)n2)cn1]

Int. 80 (1.54 g; 4.92 mmol) and N-(3-aminopropyl)-carbamic acid, 1,1-dimethylethyl ester (4.29 g; 24.62 mmol) in NMP (3.9 mL) were stirred at 140° C. for 6 h. Water and DCM were added. The reaction mixture was extracted with DCM. The organic layer was washed with brine, dried over MgSO$_4$, filtered and the solvent was evaporated. Yield: 4.48 g of a brown oil. The residue was purified by preparative LC (Irregular SiOH 20-45 μm 450 g MATREX). Mobile phase: NH$_4$OH, DCM, MeOH 0.1/93/7). The desired fraction were collected and the solvent was evaporated. Yield: 1.4 g of Int. 85.

The intermediates in the table below were prepared according to an analogous reaction protocol as used in A9.b) for Int. 85:

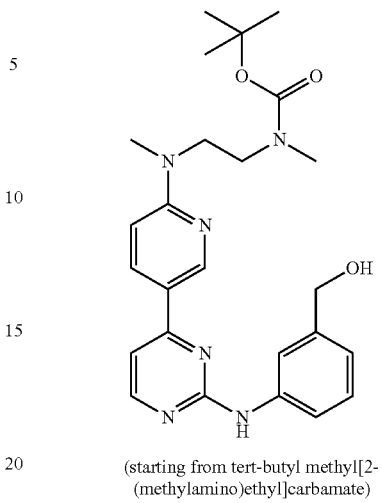

Int. 149

(starting from tert-butyl methyl[2-(methylamino)ethyl]carbamate)

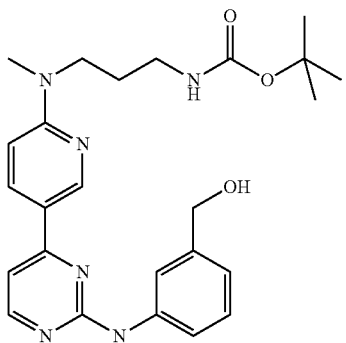

Int. 150

(starting from tert-butyl [3-(methylamino)propyl]carbamate)

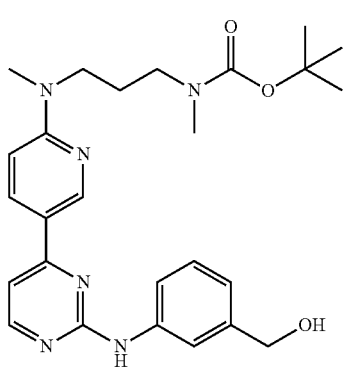

Int. 122

(starting from tert-butyl methyl[3-(methylamino)propyl]carbamate)

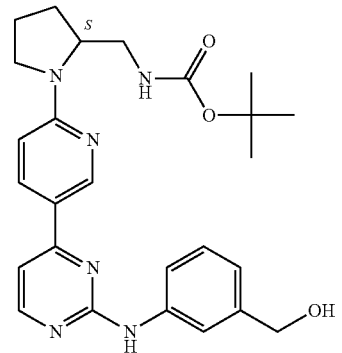

Int. 171

(starting from N-[(2S)-2-pyrrolidinylmethyl]-carbamic acid, 1,1-dimethylethyl ester)

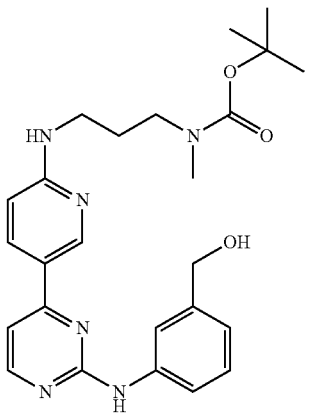

Int. 368

(starting from Int. 80 and N-(3-aminopropyl)-N-methyl-carbamic acid, ,1,1-dimethylethyl ester)

c) Preparation of Int. 112

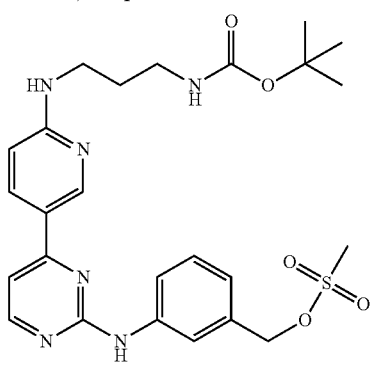

Methanesulfonyl chloride (945 µL; 12.21 mmol) was added dropwise to a solution of Int. 85 (1.1 g; 2.44 mmol), DIPEA (2.13 mL; 12.21 mmol) in DCM (70 mL) at 5° C. under N₂ flow. The reaction mixture was stirred at 5° C. for 15 min. Water and K₂CO₃ were added. The mixture was extracted twice with DCM. The organic layer was dried (MgSO₄), filtered and the solvent was evaporated. Yield: 1.79 g of crude Int. 112 as a yellow solid, used as such in the next reaction step without further purification.

The intermediates in the table below were prepared according to an analogous reaction protocol as used for Int. 112:

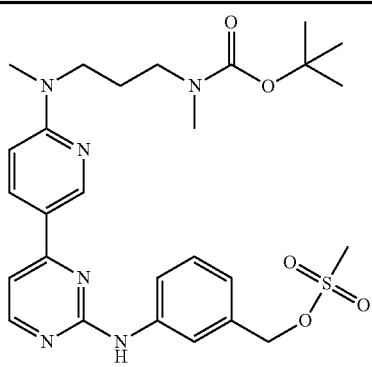

Int. 123

(from Int. 122)

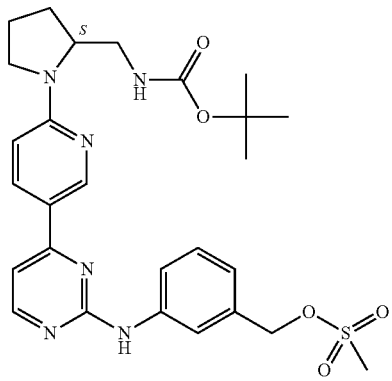

Int. 172

(from Int. 171)

Int. 112, 123 and 172 were typically obtained together with a derivative of these compounds wherein the mesylate moiety is replaced by a chloro moiety. These intermediates were used as mixtures (not quantified) in the next reaction step.

d-1) Preparation of Int. 113

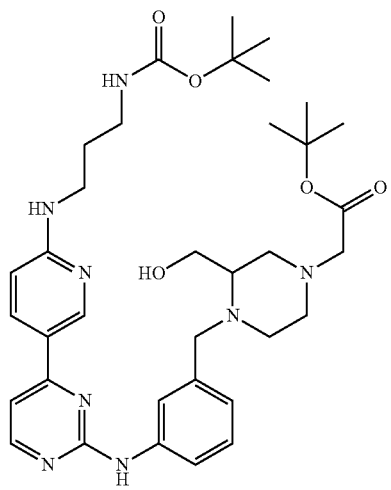 [SMILES: CC(C)(C)OC(=O)CN1CCN(Cc2cccc(Nc3nccc(-c4ccc(NCCCNC(=O)OC(C)(C)C)nc4)n3)c2)C(CO)C1]

Int. 112 (1.87 g; 2.48 mmol) dissolved in DMF (5.4 mL) was added dropwise to a suspension of Int. 110 (1.14 g; 4.95 mmol) and K₂CO₃ (1.37 g; 9.91 mmol) in DMF (1 mL). The mixture was stirred at room temperature for 30 min. Water and EtOAc were added. The mixture was extracted with EtOAc (3×). The organic layer was dried over MgSO₄, filtered and the solvent was evaporated, yielding 2.78 g of a brown oil. The residue was purified by preparative LC (irregular SiOH 15-40 µm 300 g MERCK). Mobile phase: NH₄OH, DCM, MeOH 0.1/94/6. The desired fractions were collected and the solvent was evaporated. Yield: 645 mg of Int. 113 as a yellow foam (39%).

The intermediates in the table below were prepared according to an analogous reaction protocol as used for Int. 113:

Int. 117
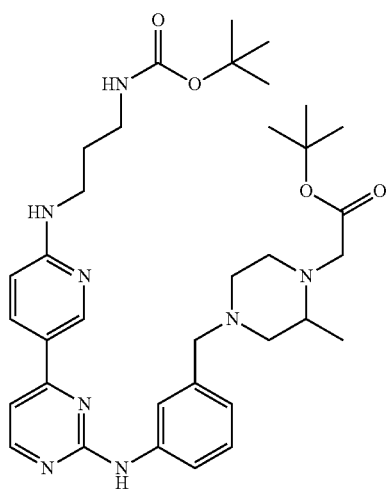
(from Int. 112 and Int. 116)
Int. 120
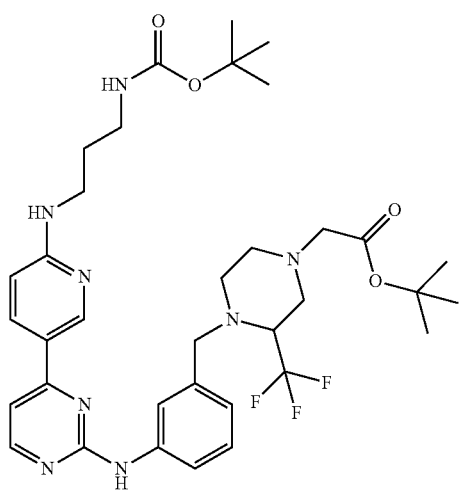
(from Int. 112 and Int. 119)
Int. 124
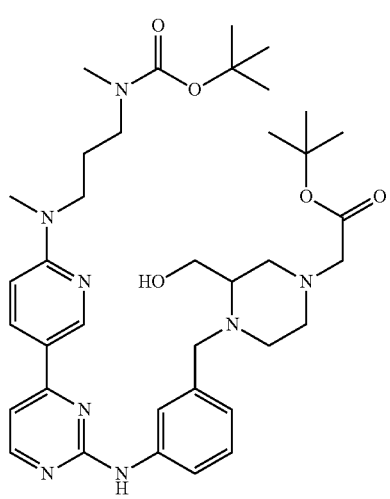
(from Int. 123 and Int. 110)
Int. 127
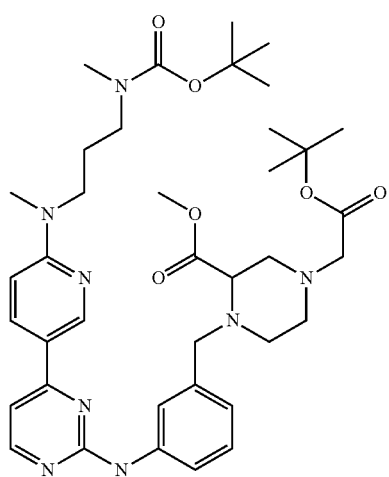
(from Int. 123 and Int. 126)
Int. 130
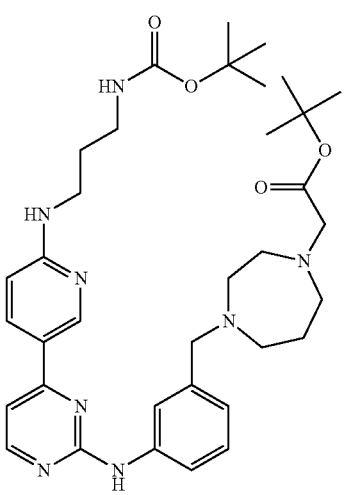
(from Int. 112 and Int. 129)
Int. 132
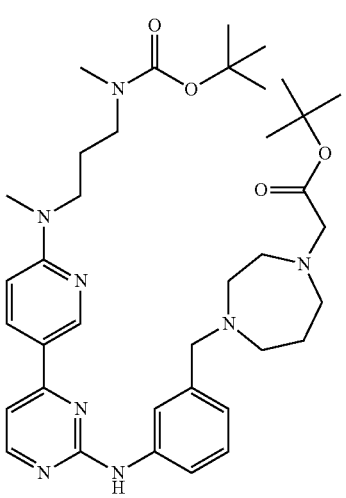
(from Int. 123 and Int. 129)

| | |
|---|---|
| 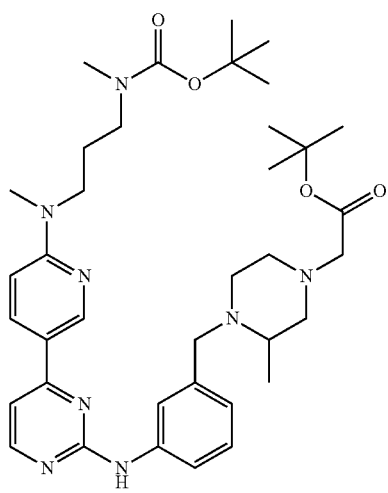<br>(from Int. 123 and Int. 134) Int. 135 | 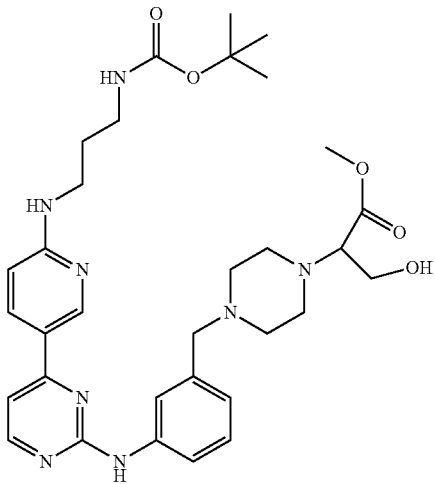<br>(from Int. 112 and Int. 143) Int. 144 |
| 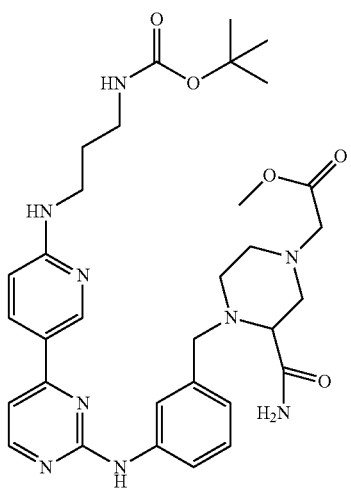<br>(from Int. 112 and Int. 137) Int. 138 | 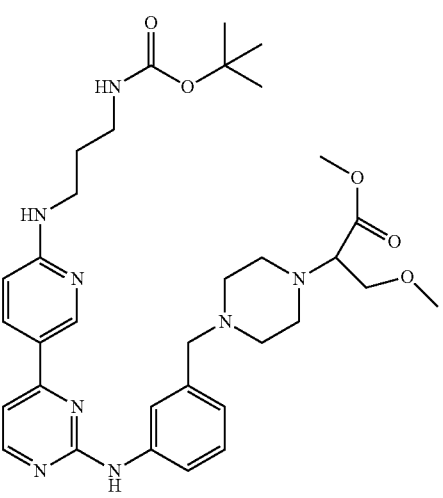<br>(from Int. 112 and Int. 146) Int. 147 |
| 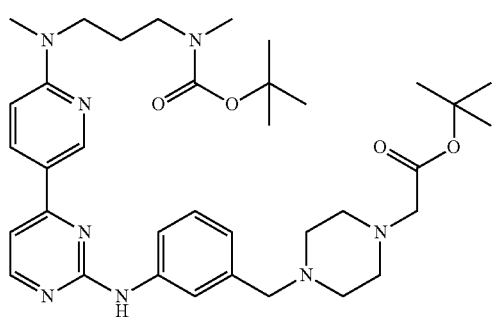<br>(from Int. 123 and (piperazin-1-yl)acetic acid, tert-butyl ester (WO9322303 and commercial)) Int. 140 | 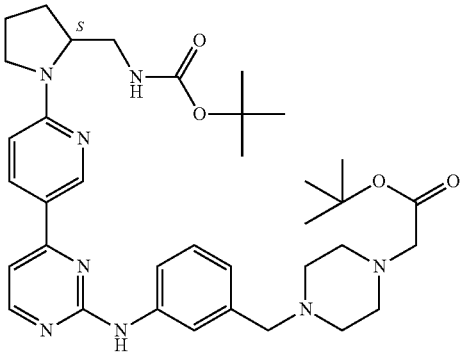<br>(from Int. 172 and 1-piperazineacetic acid, 1,1-dimethyl ethyl ester Int. 173 |

-continued

Int. 197

(from Int. 123 and Int. 196)

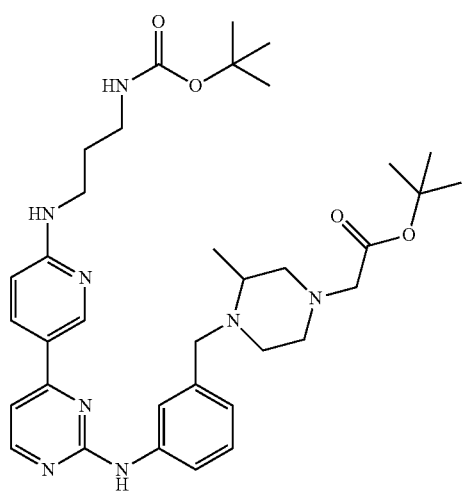

Int. 199

(from Int. 112 and Int. 134)

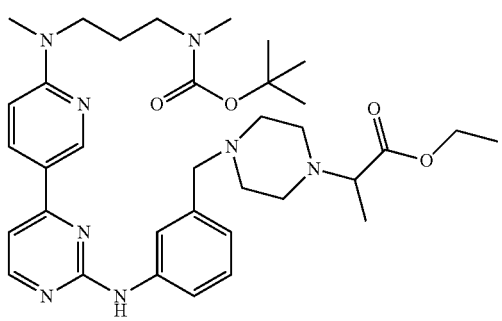

Int. 312

(from Int. 123 and α-methyl-1-piperazineacetic acid, methyl ester)

d-2) Preparation of Int. 151

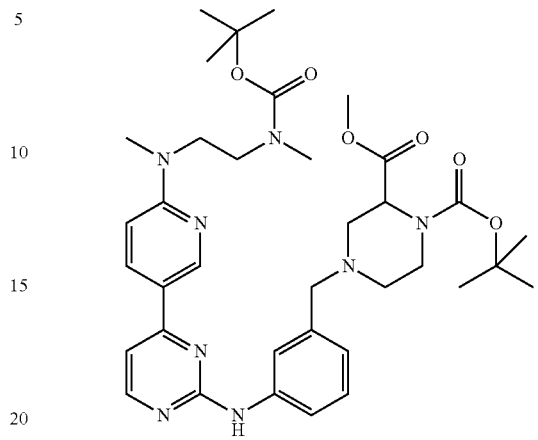

Int. 149 (0.7 g; 1.51 mmol) and DIPEA (0.77 mL; 4.53 mmol) were dissolved in DMF (8 mL) at 0° C. under $N_2$-gas atmosphere. Methanesulfonyl chloride (0.234 mL; 3.02 mmol) was added portionwise (3×0.078 mL) at intervals of 5 min. The reaction mixture was allowed to warm up to room temperature. The mixture was reacted for 1 h, and then 1,2-piperazinedicarboxylic acid, 1-(1,1-dimethylethyl) ester (0.738 g; 3.02 mmol) was added. The reaction mixture was heated at 80° C. overnight. Subsequently, the mixture was concentrated to dryness. The residue was dissolved in DCM/MeOH 10/1 v/v (25 mL) and this solution was washed with 1 M $NaCO_3$ solution in $H_2O$ (15 mL). The organic layers were combined, dried ($MgSO_4$), filtered and concentrated to dryness. The residue was purified by column chromatography over silica gel eluting with a gradient from 100% DCM to 100% DCM/MeOH 9/1 v/v. The desired fractions were collected and the solvent was evaporated. Yield: 0.978 g of Int. 151 (94%).

The intermediates in the table below were prepared according to an analogous reaction protocol as used for Int. 151:

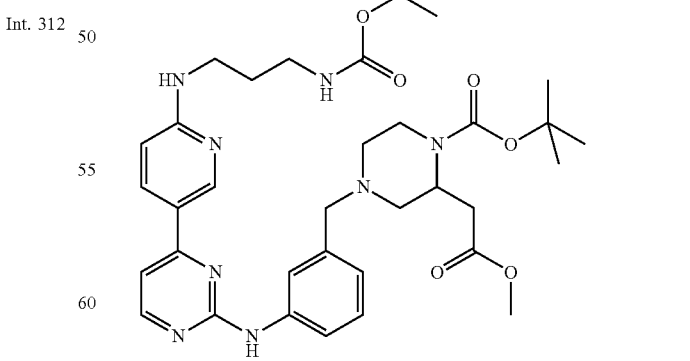

Int. 158

(from Int. 85 and Int. 157);
reaction mixture was not cooled at 0° C.
under $N_2$-gas Int. 160

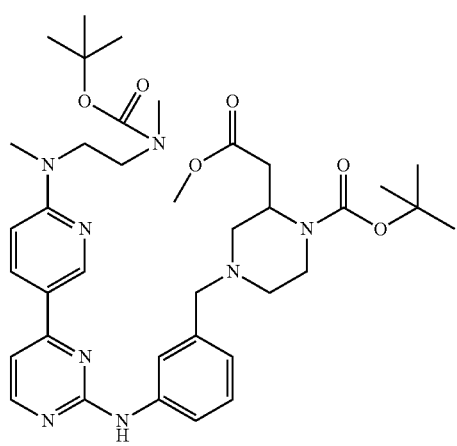

(from Int. 149 and Int. 157)

Int. 162

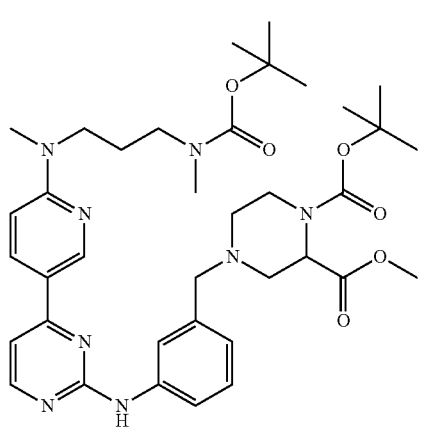

(from Int. 122 and 1,2-piperazinedicarboxylic acid, 1-(1,1-dimethylethyl) 2-methyl ester)

Int. 164

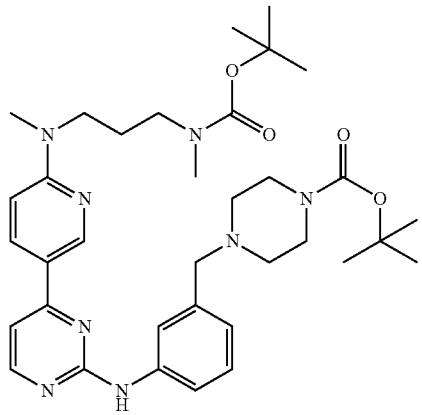

(from Int. 122 and 1-piperazinecarboxylic acid, 1,1-dimethylethyl ester); reaction mixture was not cooled at 0° C. under N$_2$-gas Int. 111

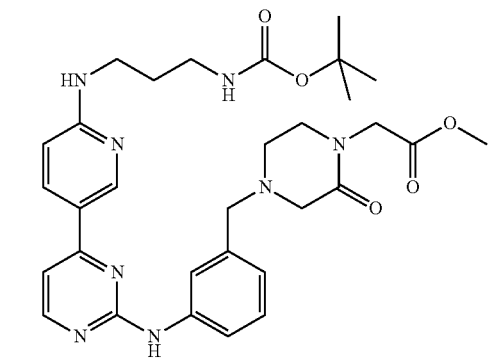

(from Int. 85 and methyl 2-(2-oxopiperazin-1-yl) acetate hydrochloride; reaction mixture was not cooled at 0° C. under N$_2$-gas Int. 167

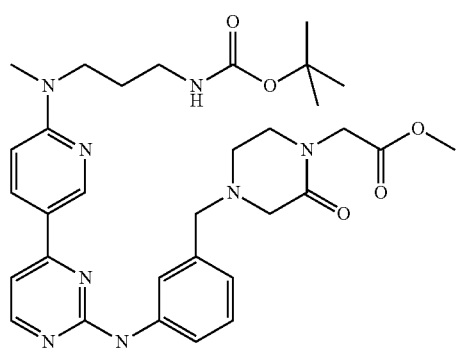

(from Int. 150 and methyl 2-(2-oxopiperazin-1-yl)acetate hydrochloride; reaction mixture was not cooled at 0° C. under N$_2$-gas Int. 169

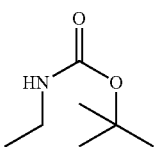
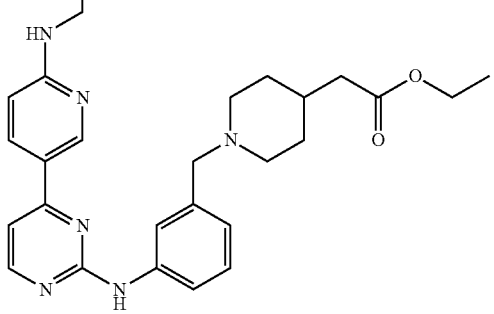

(from Int. 85 and methyl 2-(piperidin-4-yl)acetic acid, ethyl ester); reaction mixture was not cooled at 0° C. under N$_2$-gas -continued
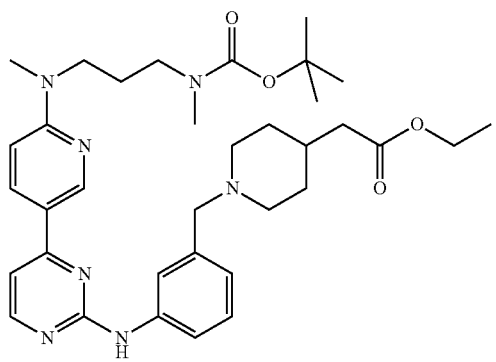
Int. 175
(ethoxycarbonylmethyl)piperidine);
reaction mixture was not cooled at 0° C.
under N₂-gas
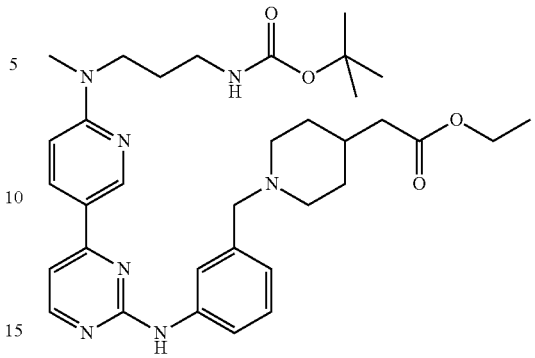
Int. 370
(from Int. 150 and 4-piperidineacetic acid,
ethyl ester)
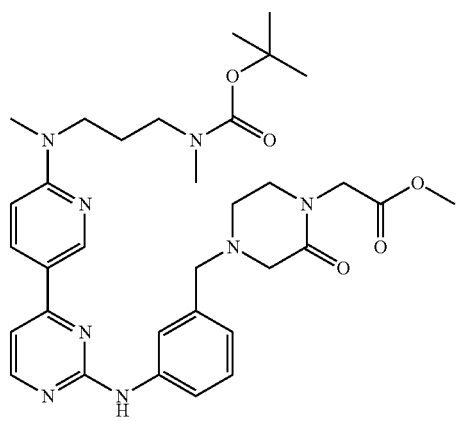
Int. 180
(from Int. 122 and Int. 179)
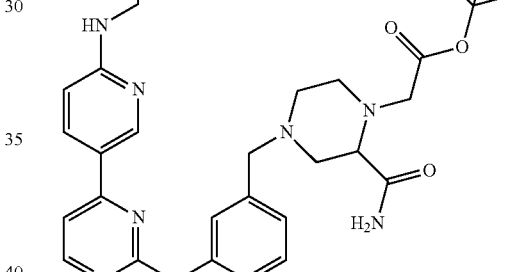
Int. 371
(from Int. 85 and Int. 115)
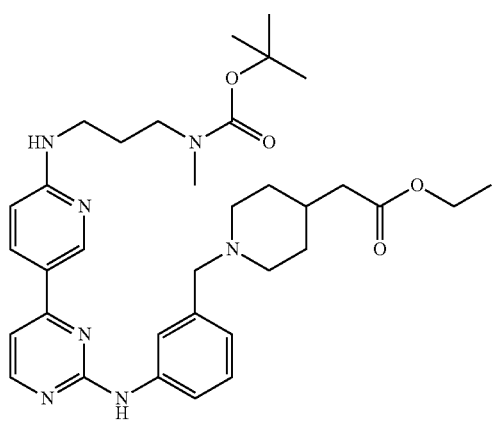
Int. 369
(from Int. 368 and 4-piperidineacetic acid, ethyl ester)
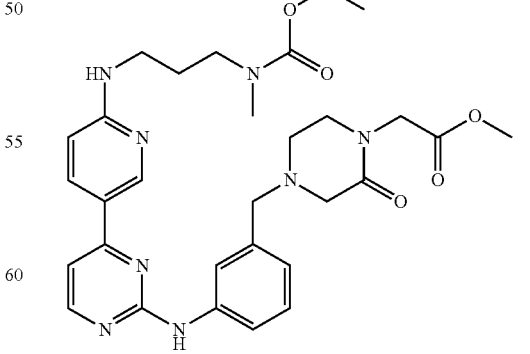
Int. 372
(from Int. 368 and methyl 2-(2-
oxopiperazin-1-yl)acetate hydrodrochloride Int. 373

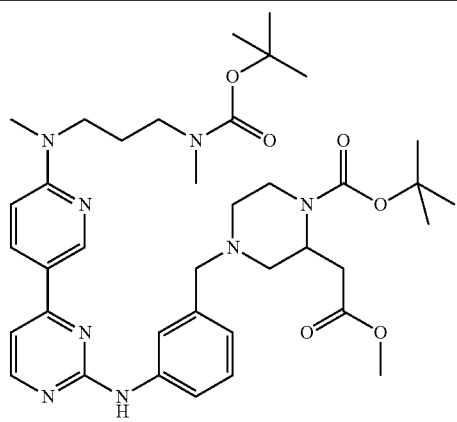

(from Int. 122 and 1-[(1,1-dimethylethoxy)carbonyl]-2-piperazineacetic acid, methyl ester)

Int. 118

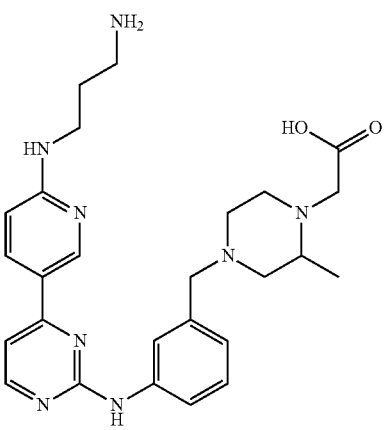

HCl salt
(from Int. 117; used for Co. 49)

e-1) Preparation of Int. 114

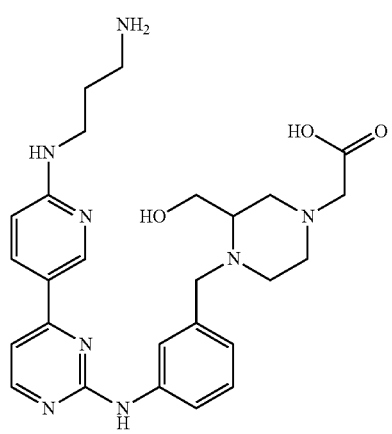

HCl salt

Int. 121

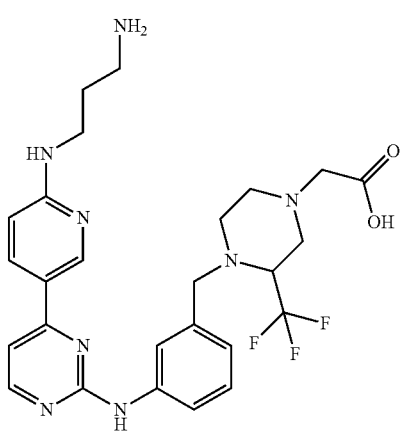

HCl salt
(from Int. 120; used for Co. 50)

Int. 125

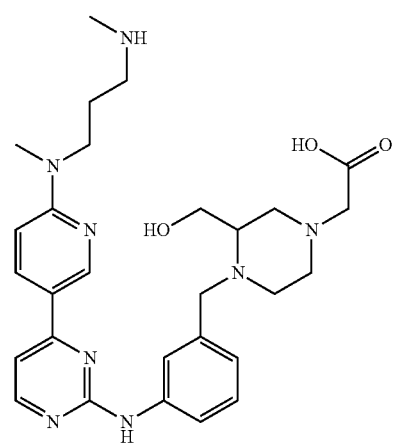

HCl salt
(from Int. 124; used for Co. 51)

HCl (37% in H$_2$O) (334 μL; 4.0 mmol) then distilled water (2.9 mL) were added to a solution of Int. 113 (624 mg; 0.8 mmol) in 1,4-dioxane (22 mL). The reaction mixture was stirred at 100° C. for 2 h. The solution was evaporated under reduced pressure and the residue was co-evaporated twice with toluene. The residue was dried in vacuo at 70° C. Yield: 674 mg of Int. 114 as a brown foam which was used as such without further purification for the next reaction step.

The intermediates in the table below were prepared according to an analogous reaction protocol as used for Int. 114:

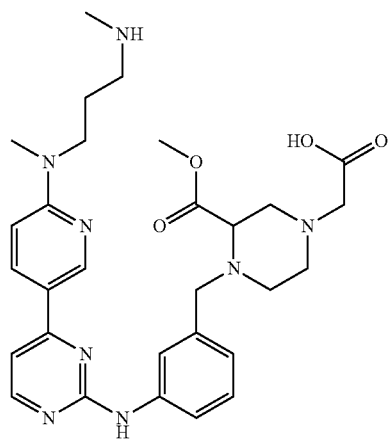
Int. 128
HCl salt
(from Int. 127; used for Co. 55)
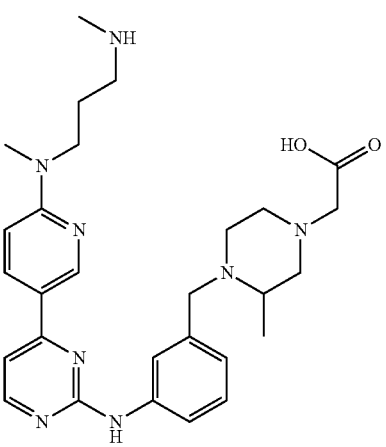
Int. 136
HCl salt
(from Int. 135; used for Co. 58)
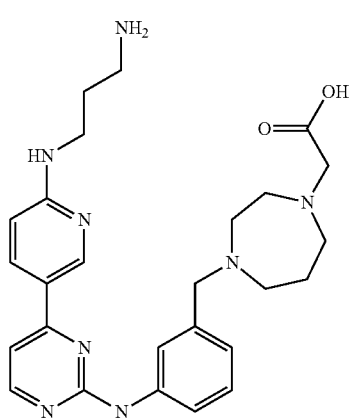
Int. 131
HCl salt
(from Int. 130; used for Co. 56)
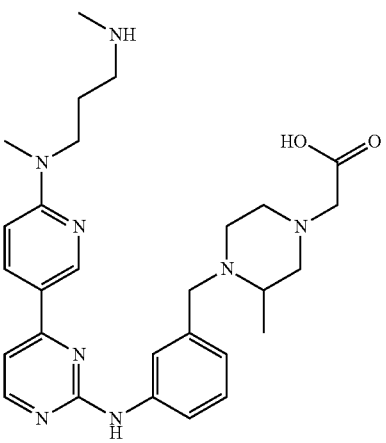
Int. 11
HCl salt
(alternative preparation for A1.f)
(from Int. 140; used for Co. 1)
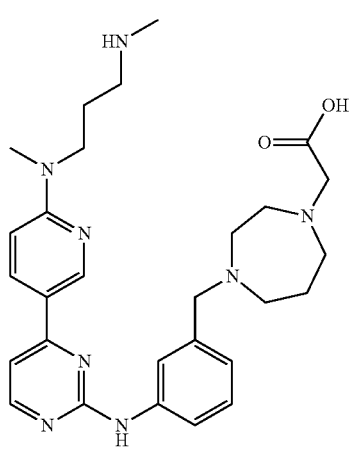
Int. 133
HCl salt
(from Int. 132; used for Co. 57)
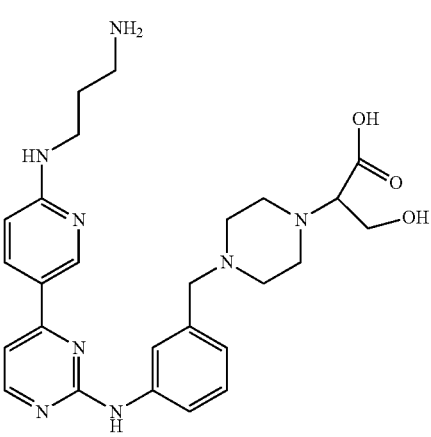
Int. 145
HCl salt
(from Int. 144; used for Co. 65)

-continued
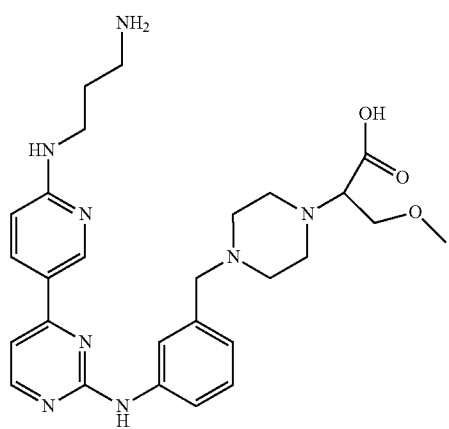
Int. 148
HCl salt
(from Int. 147; used for Co. 66)
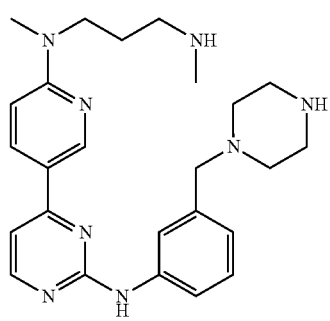
Int. 165
HCl salt
(from Int. 164; used for Co. 76)
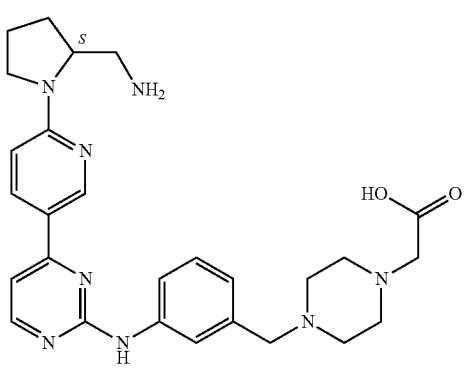
Int. 174
HCl salt
(from Int. 173; used for Co. 80)
-continued
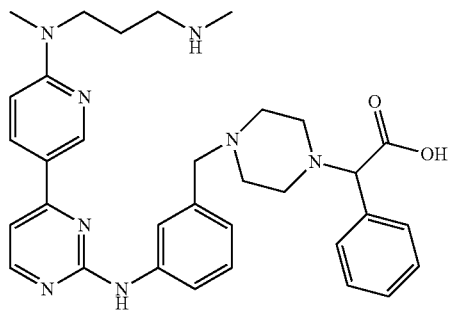
Int. 198
HCl salt
(from Int. 197; used for Co. 64; HCl 4M in 1,4-dioxane was used, no water was added)
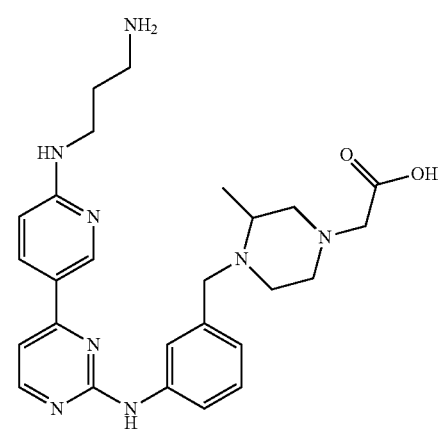
Int. 200
HCl salt
Int. 200 (from Int. 199; used for Co. 60)
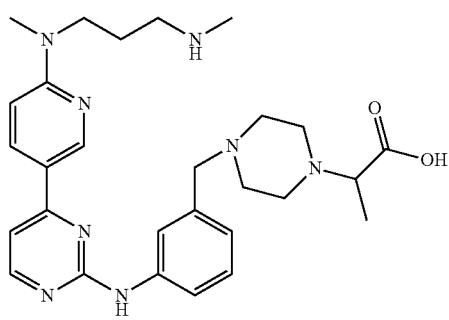
Int. 313
HCl salt
(from Int. 312; used for Co. 67; HCl 4M in 1,4-dioxane was used, no water was added)

-continued

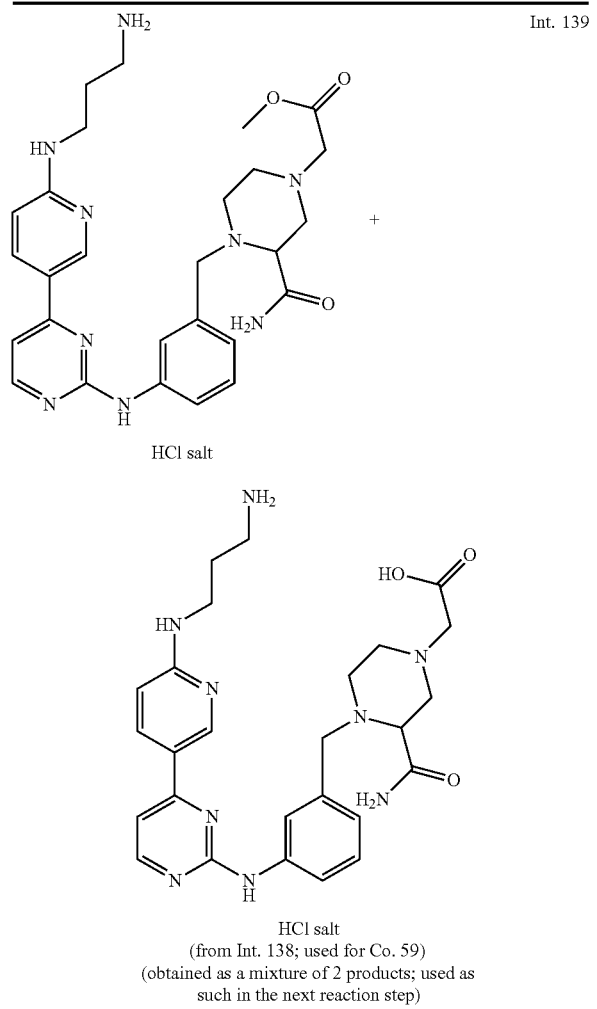

Int. 139

HCl salt

HCl salt
(from Int. 138; used for Co. 59)
(obtained as a mixture of 2 products; used as such in the next reaction step)

e-2) Preparation of Int. 152

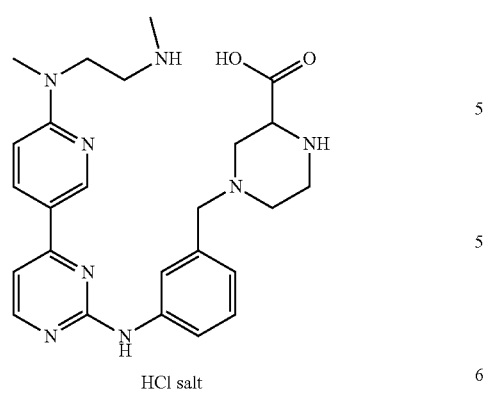

HCl salt

Int. 151 (0.978 g; 1.42 mmol) was dissolved in a mixture of NaOH (1 M; 14.2 mL; 14.2 mmol), THF (7 mL) and MeOH (2 mL). The reaction mixture was heated at 40° C. overnight. Subsequently, HCl (37% in H$_2$O) (3 mL) was added and the reaction mixture was heated at 40° C. for 7 h. The reaction mixture was concentrated to dryness and dried under high vacuum (at room temperature). The residue, containing Int. 152, was used as such in the next reaction step (preparation of Co. 68 and Co. 69).

The intermediates in the table below were prepared according to an analogous reaction protocol as used for Int. 152:

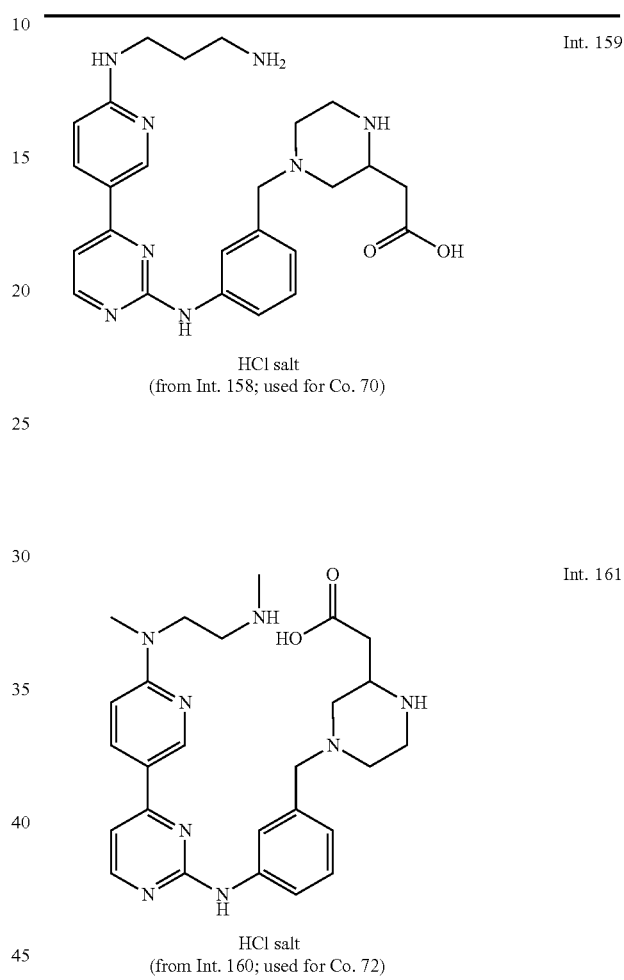

Int. 159

HCl salt
(from Int. 158; used for Co. 70)

Int. 161

HCl salt
(from Int. 160; used for Co. 72)

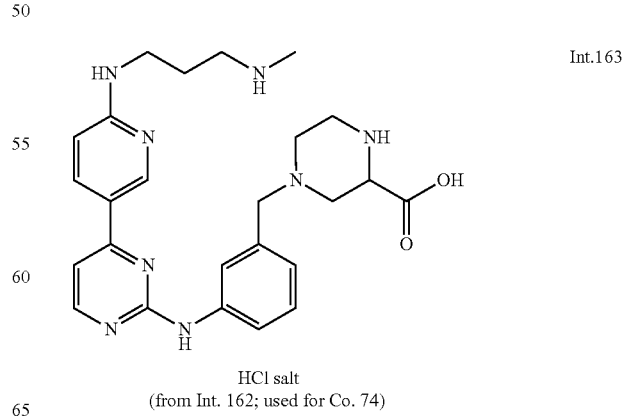

Int.163

HCl salt
(from Int. 162; used for Co. 74)

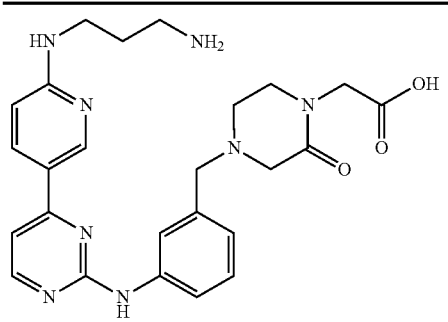
Int. 166
HCl salt
(from Int. 111; used for Co. 77)
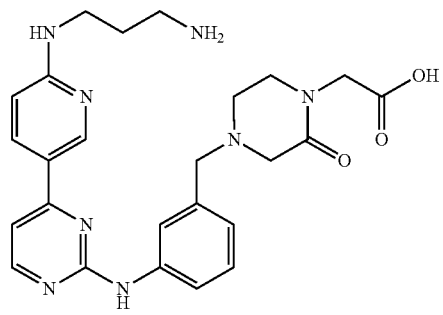
Int. 168
HCl salt
(from Int. 167; used for Co. 78)
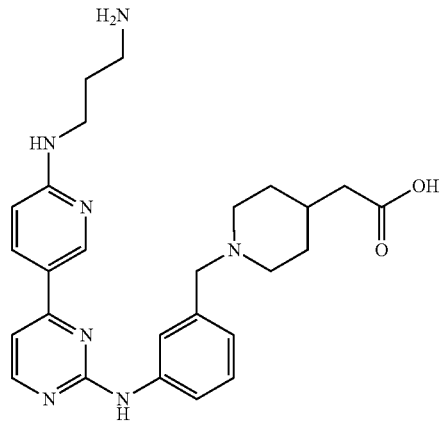
Int. 170
HCl salt
(from Int. 169; used for Co. 79)
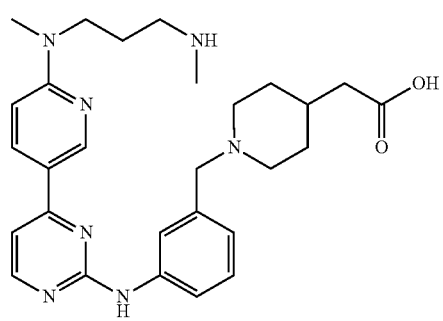
Int. 176
HCl salt
(from Int. 175; used for Co. 81)
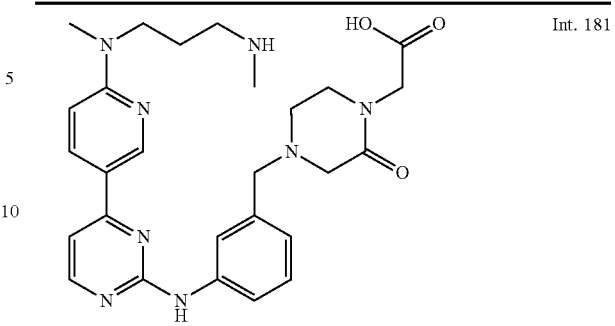
Int. 181
HCl salt
(from Int. 180; used for Co. 82)
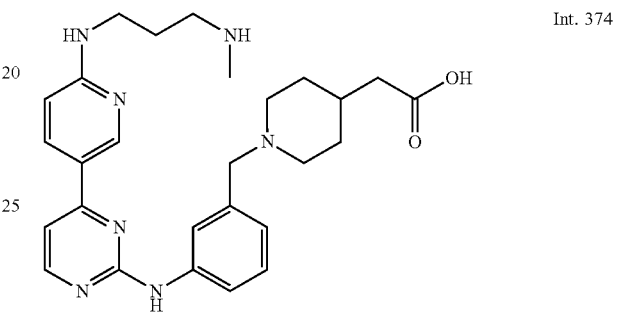
Int. 374
HCl salt
(from Int. 369; used for Co. 124)
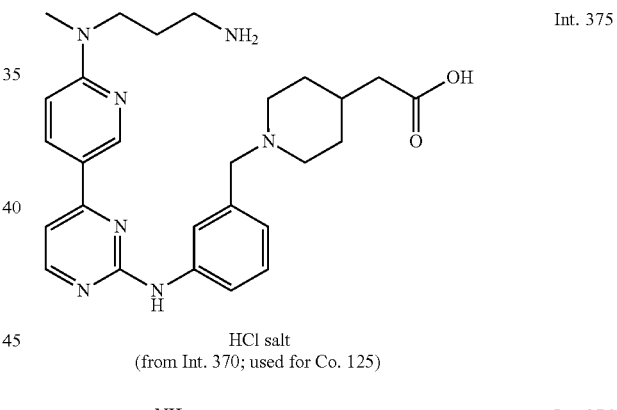
Int. 375
HCl salt
(from Int. 370; used for Co. 125)
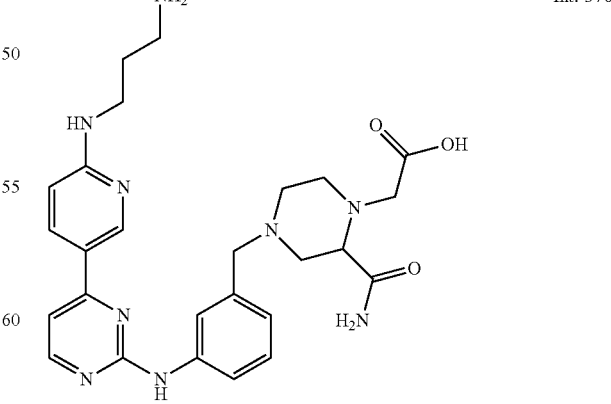
Int. 376
HCl salt
(from Int. 371; used for Co. 126)

-continued

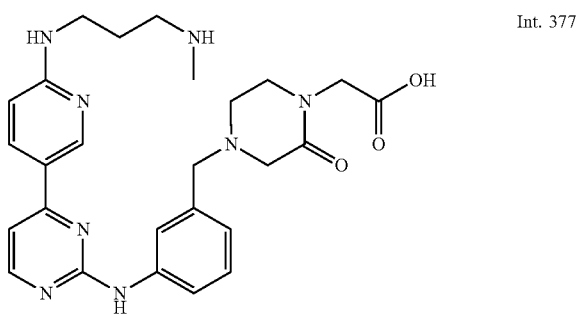

Int. 377

HCl salt
(from Int. 372; used for Co. 127)

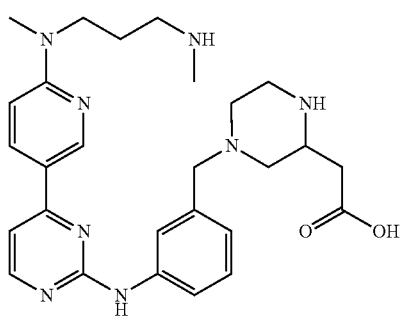

Int. 378

HCl salt
(from Int. 373; used for Co. 128)

Example A10 a) Preparation of Int. 153

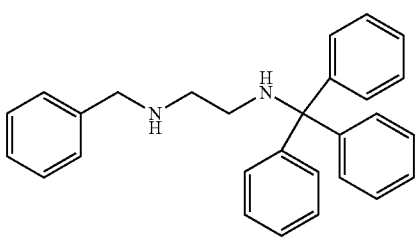 [SMILES: c1ccc(CNCCNC(c2ccccc2)(c2ccccc2)c2ccccc2)cc1]

A solution of triphenylmethyl chloride (27.9 g, 0.1 mmol) in DCM (150 mL) was added dropwise to an ice cold solution of N-benzyl-1,2-ethanediamine (15 g, 0.1 mmol) and Et$_3$N (10.5 mL, 0.075 mmol) in DCM (20 ml) over 3 h. The mixture was then allowed to warm up to room temperature and stirred for an additional hour. The insoluble material was filtered off and the filtrate concentrated. The residue was purified by chromatography over silica gel eluting with a gradient of EtOAc in heptane from 20 to 100%. The desired fractions were collected and the solvent was evaporated. Yield: 11.6 g of Int. 153 (30%).

b) Preparation of Int. 154

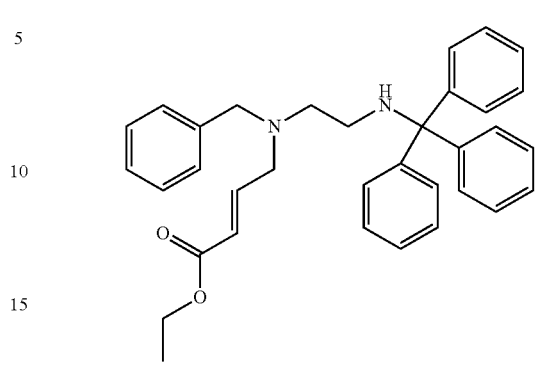

A solution of (E)-4-bromo-2-butenoic acid ethyl ester (7.6 g, 29.5 mmol, 75% purity) in DCM (200 ml) was added dropwise to a solution of Int. 153 (11.6 g, 29.5 mmol) and K$_2$CO$_3$ (8.17 g, 59.1 mmol) in DCM (200 ml) over 3 h. The mixture was then stirred overnight. The reaction mixture was filtered and the filtrate was concentrated. The residue was purified by column chromato-graphy over silica gel eluting with a gradient of EtOAc in heptane from 20 to 100%. The desired fractions were collected and the solvent was evaporated. Yield: 13.6 g of Int. 154.

c) Preparation of Int. 155

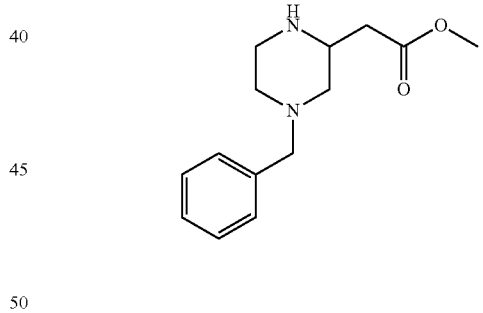

Acetyl chloride (32 mL, 450 mmol) was added to MeOH (225 mL) with ice cooling under N$_2$-gas atmosphere. The mixture was then allowed to warm up to room temperature and stirred for 30 min. The resulting 2 M HCl solution in MeOH was added to Int. 154 (13.6 g, 26.9 mmol) and the mixture refluxed for 10 min. The reaction was allowed to cool to room temperature and concentrated. The residue was partitioned between DCM (150 mL) and 2 M Na$_2$CO$_3$ (250 mL; aqueous solution). The organic layer was separated, dried over MgSO$_4$, filtered and concentrated. The oil was then purified by column chromatography over silica gel eluting first with DCM and then with 10% MeOH in DCM. The desired fractions were collected and the solvent was evaporated. Yield: 5.93 g of Int. 155 (88%).

d) Preparation of Int. 156

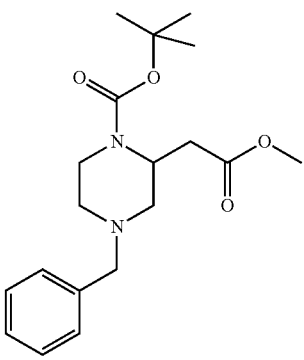 [SMILES: COC(=O)CC1CN(Cc2ccccc2)CCN1C(=O)OC(C)(C)C]

A solution of tert-butoxycarbonyl anhydride (5.2 g, 23.8 mmol) in DCM (50 ml) was added dropwise to Int. 155 (5.93 g, 23.8 mmol) with ice cooling. The mixture was then allowed to warm up to room temperature and stirred for 4 h. The solvent was evaporated under reduced pressure. The crude oil obtained was then purified by column chromatography over silica gel eluting with a mixture 8 to 1 of heptane/EtOAc (v/v). The desired fractions were collected and the solvent was evaporated. Yield: 5.64 g of Int. 156 (68%).

e) Preparation of Int. 157

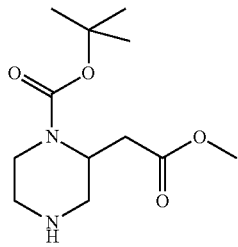 [SMILES: COC(=O)CC1CNCCN1C(=O)OC(C)(C)C]

A solution of Int. 156 (5.64 g, 16.2 mmol) and Pd/C (10%) (0.56 g) as a catalyst in MeOH (100 mL) was hydrogenated under $H_2$ atmosphere overnight at room temperature. The reaction mixture was filtered through a pad of Celite® and the filtrate concentrated. Yield: 4.2 g of Int. 157 as a clear oil (100%).

Example A11 a) Preparation of Int. 63

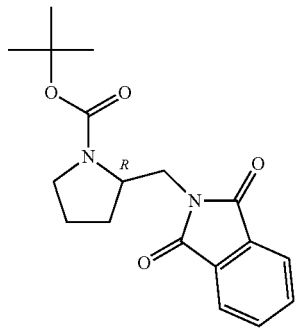

Diisopropylazodicarboxylate (3.5 mL; 18 mmol) was added dropwise to a stirred solution of Boc-D-prolinol (3 g; 15 mmol), phtalimide (2.6 g; 18 mmol) and $PPh_3$ (6 g; 18 mmol) in THF (40 mL) at 0-5° C. The reaction mixture was stirred at room temperature for 12 h. Water was added and this mixture was extracted twice with DCM. The separated organic layer was dried over $MgSO_4$, filtered and evaporated. The residue was crystallised from $Et_2O$. The solid was filtered off and the filtrate was evaporated. The residue was purified by preparative liquid chromatography (Irregular SiOH 20-45 µm 450 g MATREX). Mobile phase (75% heptane, 25% EtOAc). The pure fractions were combined and the solvent was evaporated. Yield: 4.6 g of Int. 63 (93%).

b) Preparation of Int. 64

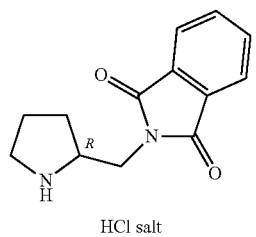

HCl salt

Int. 63 (830 mg; 2.5 mmol) in HCl 5 M (10 mL; aqueous) was stirred at room temperature for 24 h. Subsequently, the reaction mixture was diluted with $Et_2O$. The precipitate was filtered off and dried. Yield: 494 mg of Int. 64.

c) Preparation of Int. 65

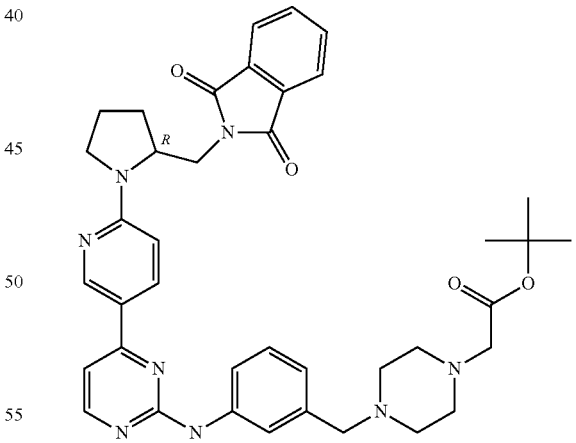

Int. 4 (224 mg, 0.45 mmol), Int. 64 (301 mg) and $Na_2CO_3$ (239 mg; 2.3 mmol) in DMSO (0.8 mL) were stirred at 130° C. for 18 h. Water was added. The solid was filtered off and taken up into DCM. The organic layer was dried with $MgSO_4$, filtered and evaporated. The residue was purified by preparative LC on (Sunfire Silica 5 µm 150×30.0 mm). Mobile phase (Gradient from 71% heptane, 1% MeOH, 28% EtOAc to 0% Heptane, 20% MeOH, 80% EtOAc). The pure fractions were combined and the solvent was evaporated. Yield: 128 mg of Int. 65.

d) Preparation of Int. 66

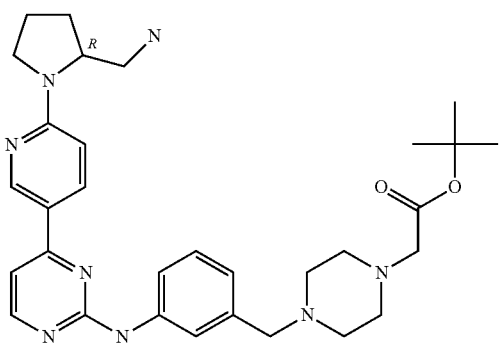

Hydrazine monohydrate (180 µL, 3.7 mmol) was added to a suspension of a mixture of Int. 65 (128 mg, 0.19 mmol) in EtOH (3 ml) and 1,4-dioxane (2 ml). The reaction mixture was heated at reflux for 4 h. Water was added and the organic solvent was evaporated. The aqueous mixture was extracted twice with DCM. The organic layer was dried (MgSO$_4$), filtered and evaporated. Yield: 83 mg of Int. 66 (80%).

e) Preparation of Int. 67

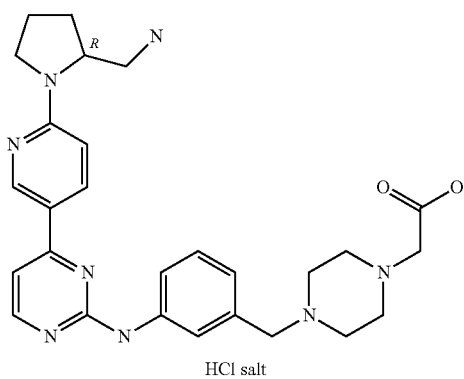

HCl salt

HCl (37% in H$_2$O) (62 µL, 0.74 mmol) and distilled water (0.8 ml) were added to a solution of Int. 66 (83 mg, 0.15 mmol) in 1,4-dioxane (3 ml). The reaction mixture was stirred at 100° C. for 12 h. The solution was evaporated under reduced pressure and the residue was co-evaporated twice with toluene. Yield: 91 mg of Int. 67 as a yellow foam, used as such without further purification in the next reaction step (the synthesis of compound 26).

Example A12 a) Preparation of Int. 177

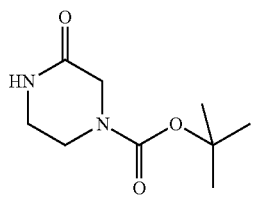

2-Piperazinone (2.5 g; 24.97 mmol) was dissolved in DCM (55 ml). A solution of tert-butyloxycarbonyl anhydride (5.45 g, 24.97 mmol) in DCM (20 ml) was added dropwise. The reaction mixture was stirred at room temperature for 4 h. The reaction mixture was concentrated to dryness and dried under high vacuum, at room temperature. The residue containing Int. 177 (5.1 g) was used as such in the next reaction step.

b) Preparation of Int. 178

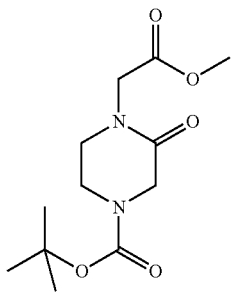 [SMILES: COC(=O)CN1CCN(C(=O)OC(C)(C)C)CC1=O]

NaH (60% in mineral oil) (0.24 g; 5.99 mmol) was added to a solution of Int. 177 (1 g; 4.99 mmol) in DMF (8 ml) and cooled to 0° C. under N$_2$-gas atmosphere. The mixture was stirred at this temperature for 10 min. Methyl bromoacetate (0.522 mL; 5.49 mmol) was added. The cooling bath was removed and the reaction stirred overnight. Subsequently, the reaction was quenched with H$_2$O (2 ml). A saturated NaCl aqueous solution (20 ml) was added and the mixture was extracted with EtOAc (14 ml). The organic layer was dried over MgSO$_4$, filtered and concentrated to dryness. The residue was purified by chromatography over silica gel eluting with a gradient from 100% DCM to 40% DCM and 60% DCM/MeOH 9/1, v/v. The desired fractions were collected and the solvent was evaporated. Yield: 1.14 g of Int. 178 (84%).

c) Preparation of Int. 179

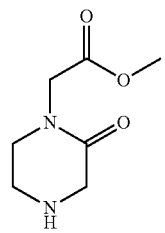

Int. 178 (1.14 g; 4.19 mmol) was dissolved in HCl 4 M in 1,4-dioxane (10.5 mL; 41.9 mmol) and stirred at room temperature overnight. Diethyl ether was added and the mixture was stirred for 30 min. The mixture was filtered. The solid product was dried under high vacuum, at room temperature. The residue was suspended in DCM. Amberlyst A-26 (OH) ion exchange resin (q.s.) was added until basic pH and the mixture was shaken for 20 min. The mixture was filtered and the ion exchange resin washed alternating with DCM (3×5 ml) and MeOH (2×5 ml). The combined solutions were evaporated to give 0.498 g of Int. 179 (69%).

Example A13 a) Preparation of Int. 182

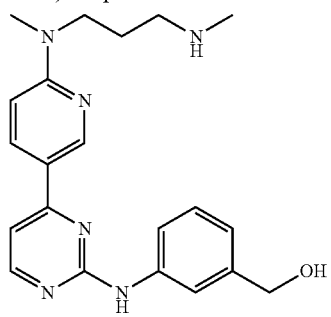

N1,N3-dimethyl-1,3-propanediamine (9.05 g; 88.55 mmol) was added to Int. 80 (5.54 g; 17.71 mmol). The reaction mixture was heated at 110° C. for 5 h. The reaction mixture was concentrated to dryness. The residue was stirred with 1 M NaOH (25 ml) for 1 h. The solid product was filtered off, washed with $H_2O$ (50 ml) and dried under high vacuum, at room temperature to give 5.95 g of Int. 182 (89%).

b) Preparation of Int. 183

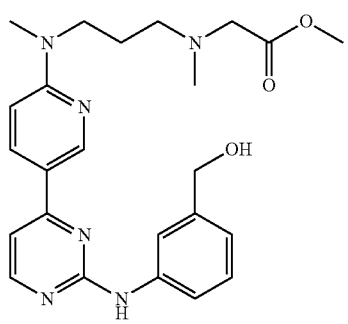 [SMILES: COC(=O)CN(C)CCCN(C)c1ccc(-c2ccnc(Nc3cccc(CO)c3)n2)cn1]

Int. 182 (0.7 g; 1.85 mmol) was suspended in a mixture of $CH_3CN$ (6 mL) and DMF (2 mL). $K_2CO_3$ (0.282 g; 2.04 mmol) and methyl bromoacetate (0.176 mL; 1.85 mmol) were added successively. The reaction mixture was stirred at room temperature overnight. The reaction mixture was diluted with EtOAc (30 mL) and washed with $H_2O$ (15 mL). The aqueous layer was again extracted with EtOAc (30 mL). The combined organic layers were dried over $MgSO_4$, filtered and concentrated to dryness. The residue was purified by column chromatography over silica gel eluting with a gradient of 100% DCM to 30% DCM and 70% DCM/MeOH 9/1, v/v. The desired fractions were collected and the solvent was evaporated. Yield: 0.512 g of Int. 183 (61%).

Example A14 a) Preparation of Int. 186

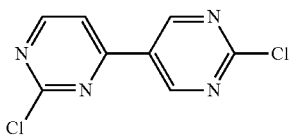

$Pd(OAc)_2$ (3.52 g) and $PPh_3$ (3.93 g) were added to a mixture of (2-chloropyrimidin-5-yl)boronic acid (47.5 g; 300 mmol), 2,4-dichloropyrimidine (49.16 g; 330 mmol), $K_2CO_3$ (124.2 g), THF (720 mL) and $H_2O$ (750 mL) under $N_2$-gas atmosphere. The mixture was heated to reflux for 4 h. The reaction mixture was cooled to 50° C. The organic layer was separated at 50° C. The solvent was evaporated. The residue was purified by column chromatography over silica gel (eluent: DCM). The desired fractions were collected and the solvent was evaporated. Yield: 30 g of Int. 186 (44%).

b) Preparation of Int. 187

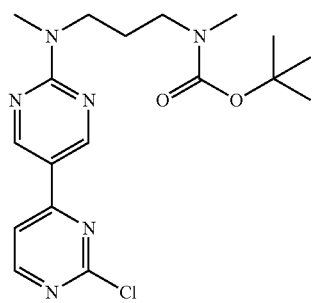 [SMILES: CN(CCCN(C)c1ncc(-c2ccnc(Cl)n2)cn1)C(=O)OC(C)(C)C]

N,N'-dimethyl-1,3-propanediamine (0.512 mL; 4.096 mmol) was added dropwise to Int. 186 (500 mg; 2.202 mmol) in DCM (10 ml) at 0° C. and the reaction was stirred for 1 h. Subsequently, DCM (10 mL) was added to the reaction mixture. Then di-tert-butyl dicarbonate (1.6 g; 7.331 mmol) was added to the reaction mixture at 0° C. and the reaction mixture was stirred for 1 h. The solvent was evaporated under reduced pressure. The residue was triturated with diisopropyl ether and filtered. The filtrate was evaporated under reduced pressure to yield a yellow translucent oil. The crude oil was purified using normal phase flash column chromatography on silica gel SF25-60 g; eluent 2% MeOH in DCM. The desired fractions were collected and the solvent was evaporated under reduced pressure. Yield: 808 mg of Int. 187 as a pale yellow translucent (93%).

c) Preparation of Int. 188

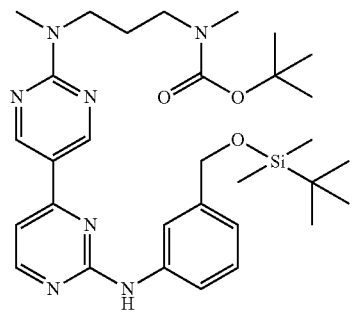 [SMILES: CN(CCCN(C)c1ncc(-c2ccnc(Nc3cccc(CO[Si](C)(C)C(C)(C)C)c3)n2)cn1)C(=O)OC(C)(C)C]

LiHMDS (1 M in THF) (0.2 mL; 0.2 mmol) was added to a solution of tert-butyldimethylsilyl 3-aminobenzyl ether (30 mg; 0.126 mmol) in THF (2.5 mL) at 0° C. and the reaction was stirred for 10 min. Subsequently, Int. 187 (24 mg; 0.0611 mmol) was added and the reaction mixture was stirred for 1 h. The reaction mixture was poured in acidic water and extracted with EtOAc. The organic layers were concentrated under reduced pressure and the residue was co-evaporated twice with toluene. Yield: 50 mg of Int. 188 as dark red oil which used as such in the next reaction step.

d) Preparation of Int. 189

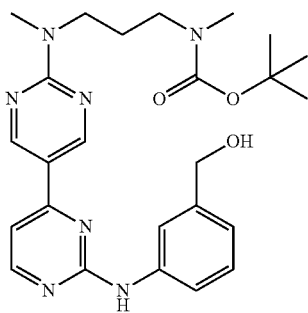 [SMILES: CN(CCCN(C)c1ncc(-c2ccnc(Nc3cccc(CO)c3)n2)cn1)C(=O)OC(C)(C)C]

Acetic acid was added to a solution of Int. 188 (50 mg; 0.053 mmol) in a mixture of water (0.45 mL) and THF (0.45 mL). The resulting mixture was stirred at room temperature overnight. The reaction mixture was neutralized with 1 M NaOH aqueous solution. EtOAc and water were added to the mixture. The layers were separated and the aqueous layer was extracted with EtOAc (3×20 mL). The combined organic layers were dried over $Na_2SO_4$, filtered and the solvent was evaporated under reduced pressure. The residue was purified by reverse phase high performance chromatography on Hyperprep C18 HS BDS, pore size 100 Å, particle size 8 μm (Shandon). Mobile phase: Gradient from 80% ammoniumbicarbonate in $H_2O$ (0.25%) and 20% acetonitrile, to 40% ammoniumbicarbonate in $H_2O$ (0.25%) and 60% acetonitrile in 40 min. The desired fractions were collected and the solvent was evaporated. Yield: 71 mg of Int. 189 as a yellow solid.

e) Preparation of Int. 190

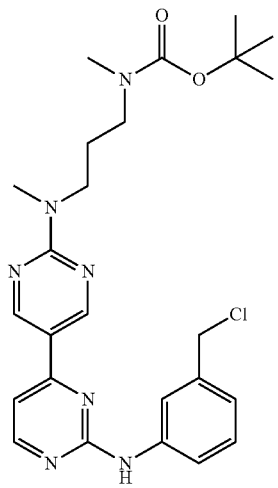 [SMILES: CN(CCCN(C)c1ncc(-c2ccnc(Nc3cccc(CCl)c3)n2)cn1)C(=O)OC(C)(C)C]

Methanesulfonyl chloride (0.0573 mL; 0.74 mmol) was added drop wise to a stirred solution of Int. 189 (71 mg; 0.148 mmol) and $Et_3N$ (0.123 mL; 0.888 mmol) in DCM (5 mL). The reaction mixture was stirred at room temperature for 18 h. Subsequently, the mixture was quenched by the addition of water. The product was extracted twice with DCM. The organic layer was washed with water, dried with $MgSO_4$, filtered and the filtrate was evaporated. Yield: 10 mg of Int. 190 (9%).

Int. 190 was obtained together with a derivative wherein the chloro moiety is replaced by a mesylate moiety. Int. 190 was used as a mixture (not quantified) in the next reaction step.

f) Preparation of Int. 191

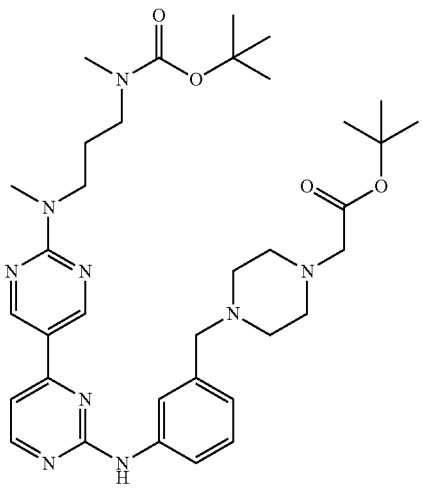 [SMILES: CN(CCCN(C)c1ncc(-c2ccnc(Nc3cccc(CN4CCN(CC(=O)OC(C)(C)C)CC4)c3)n2)cn1)C(=O)OC(C)(C)C]

A solution of piperazine-1-acetic acid tert-butyl ester (10 mg; 0.0137 mmol) and Int. 190 (11.277 mg; 0.0546 mmol) and $Et_3N$ (0.00228 mL; 0.0164 mmol) in DMF (0.13 mL) was stirred at 70° C. for 1 h. The reaction mixture was quenched by the addition of water. The product was extracted twice with DCM. The organic layer was washed with water, dried with $MgSO_4$, filtered and the filtrate was evaporated. Yield: 10 mg of Int. 191.

Example A15 a) Preparation of Int. 192

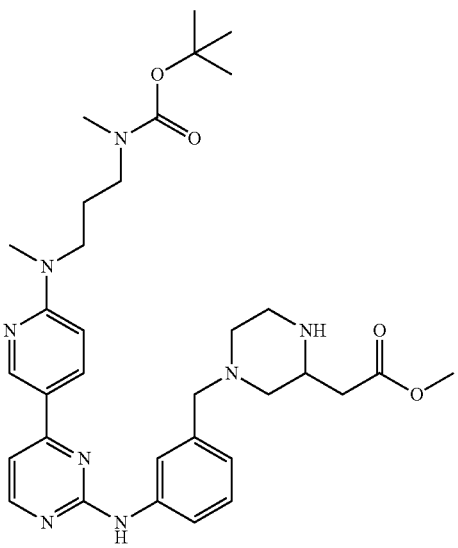 [SMILES: COC(=O)CC1CN(Cc2cccc(Nc3nccc(-c4ccc(N(C)CCCN(C)C(=O)OC(C)(C)C)nc4)n3)c2)CCN1]

Methanesulfonyl chloride (0.575 ml; 7.423 mmol) was added dropwise to a stirred solution of Int. 122 (1.91 g; 3.711 mmol) in DCM (50 mL) and Et$_3$N (5.159 mL; 37.115 mmol). The reaction mixture was stirred at room temperature for 4 h. Subsequently, Int. 142 (2.828 g) was added and the reaction mixture was stirred at room temperature for 18 h. Then water was added, and the product was extracted twice with DCM. The combined organic layers were washed with water, dried (MgSO$_4$), filtered, and the solvent was evaporated. The residue was used in the next reaction step without further purification. Yield: 3.05 g of Int. 192.

b) Preparation of Int. 193

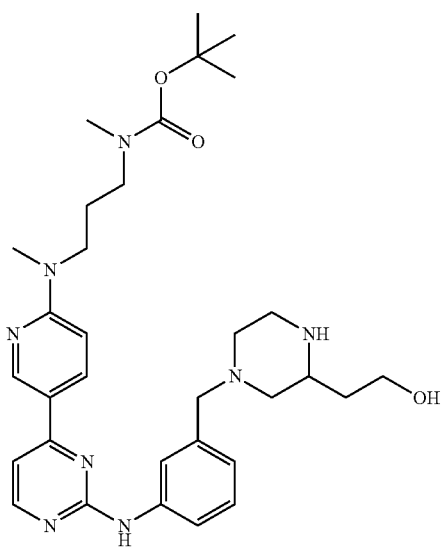 [SMILES: CN(CCCN(C)c1ccc(-c2ccnc(Nc3cccc(CN4CCNC(CCO)C4)c3)n2)cn1)C(=O)OC(C)(C)C]

LiBH$_4$ (1.422 mL; 2.844 mmol) was added to a solution of Int. 192 (2 g; 1.422 mmol) in THF (30 mL) at room temperature. The reaction mixture was stirred at reflux temperature for 18 h, and then cooled to room temperature. Subsequently MeOH (10 mL) and water (10 mL) were added and the product was extracted with DCM. The combined organic layers were washed with water, brine, dried (MgSO$_4$), filtered and the solvent was evaporated. The residue was dissolved in DCM and purified over a SiO$_2$ column (Grace Reveleris SRC, 80 g, Si 40) on an Armen Spot II Ultimate purification system using DCM and MeOH as eluents, gradient: from 100% DCM to 95% DCM/5% MeOH. The desired fractions were collected and the solvent was evaporated. Yield: 316 mg of crude Int. 193 (used as such in the next reaction step without further purification).

c) Preparation of Int. 194

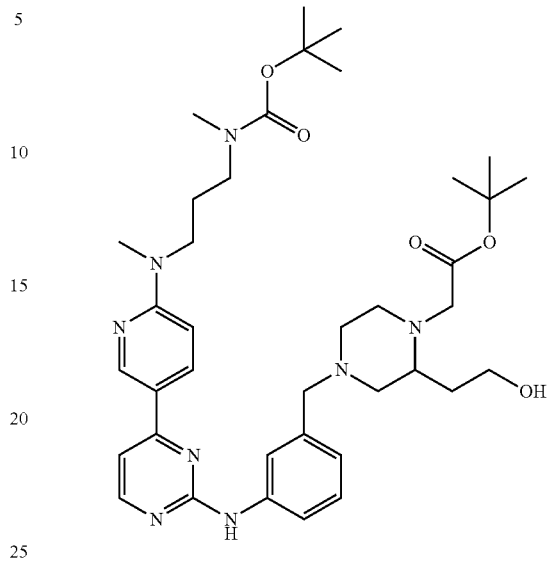

Tert-butyl bromoacetate (0.0474 mL; 0.321 mmol) was added dropwise to a stirred solution of Int. 193 (0.316 g) and Na$_2$CO$_3$ (0.034 g; 0.321 mmol) in DMF (134.933 mL) at room temperature. The reaction mixture was stirred at 80° C. for 18 h. Subsequently, water was added and the product was extracted twice with DCM. The organic layer was washed with water, dried (MgSO$_4$), filtered and the solvent was evaporated. The residue was dissolved in DCM and purified over a SiO$_2$ column (Grace Reveleris SRC, 80 g, Si 40) on an Armen Spot II Ultimate purification system using DCM and MeOH as eluens, gradient: from 100% DCM to 95% DCM/5% MeOH. The desired fractions were collected and the solvent was evaporated. Yield: 46 mg of Int. 194.

d) Preparation of Int. 195

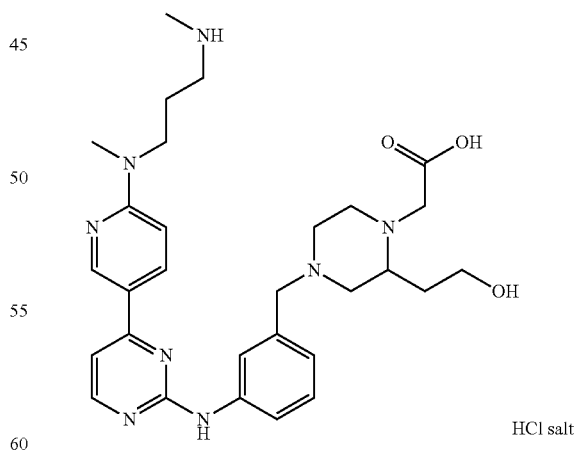

HCl salt

HCl (4 M in 1,4-dioxane; 0.144 mL; 0.574 mmol) was added to a stirred solution of Int. 194 (46 mg; 0.0574 mmol) in 1,4-dioxane (5 mL) at room temperature. The reaction mixture was stirred at 80° C. for 2 h. The solvent was evaporated. Yield: 57 mg of Int. 195 (used without further purification for the preparation of Co. 63).

Example A16 a) Preparation of Int. 201

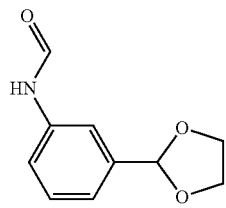 [SMILES: O=CNc1cccc(C2OCCO2)c1]

Phenylformate (10.56 mL; 96.86 mmol) was added to 3-aminobenzaldehyde ethylene acetal (8 g; 48.43 mmol) solution in DCM (5 mL) at room temperature. The reaction mixture was stirred for 40 minutes. The solvent was evaporated and the residue was purified by preparative LC (Irregular SiOH 20-45 μm 400 g MATREX, mobile phase: 90% Heptane, 10% EtOAc). The pure fractions were collected and the solvent was evaporated. Yield: 9.3 g of Int. 201.

b) Preparation of Int. 202

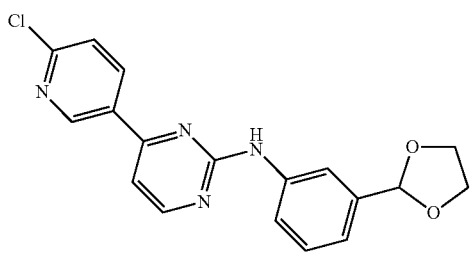 [SMILES: Clc1ccc(-c2ccnc(Nc3cccc(C4OCCO4)c3)n2)cn1]

NaH (60% in oil) (955 mg; 23.887 mmol) was added portionwise to a solution of Int. 201 (3.85 g; 19.906 mmol) in DMF (70 mL) at room temperature. The reaction mixture was stirred for 30 min. Then 2-chloro-4-(6-chloro-3-pyridinyl)-pyrimidine (4.5 g; 19.906 mmol) was added. The reaction mixture was stirred overnight at room temperature. Then 22.2 mL of a 2 N NaOH solution in H₂O and 30 mL of MeOH were added and the reaction mixture was stirred at room temperature for 2 h. The reaction mixture was diluted with water, extracted twice with DCM, dried over MgSO₄, filtered and the solvent was evaporated. The residue was purified by preparative LC on Irregular SiOH 20-45 μm 450 g MATREX: Mobile phase 50% heptane, 50% EtOAc. The pure fractions were collected and the solvent was evaporated. Yield: 4.06 g of Int. 202 (58%).

c) Preparation of Int. 203

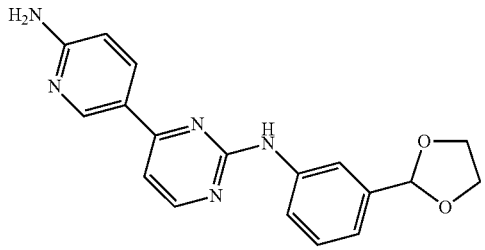 [SMILES: Nc1ccc(-c2ccnc(Nc3cccc(C4OCCO4)c3)n2)cn1]

Ammonia (50 mL; condensed at −78° C.) was added to Int. 202 (4 g; 11.274 mmol) in THF (35 mL) in a sealed vessel. The mixture was stirred at 150° C. for 15 h, under a pressure of 82 bars. A precipitate was filtered off and dried to give 2.4 g of Int. 203 as a brown solid (64%). The filtrate was evaporated and the residue was purified by preparative LC on irregular SiOH 15-40 μm 300 g MERCK. Mobile phase: NH₄OH, DCM, MeOH 0.1/97/3. The desired fractions were collected and the solvent was evaporated. Yield: 1.2 g of Int. 203 (32%).

d) Preparation of Int. 204

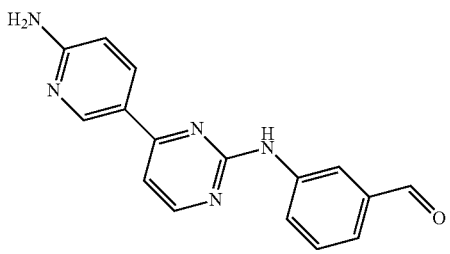 [SMILES: Nc1ccc(-c2ccnc(Nc3cccc(C=O)c3)n2)cn1]

A solution of Int. 203 (3.3 g; 8.561 mmol) and p-toluenesulfonic acid (1.68 g; 8.561 mmol) in acetone (50 mL) and water (10 mL) was stirred at room temperature for 12 h. The mixture was diluted with DCM and K₂CO₃ 10% in H₂O. The organic layer was decanted, dried over MgSO₄, filtered and the solvent was evaporated. Yield: 2.5 g of Int. 204 (100%).

e) Preparation of Int. 205

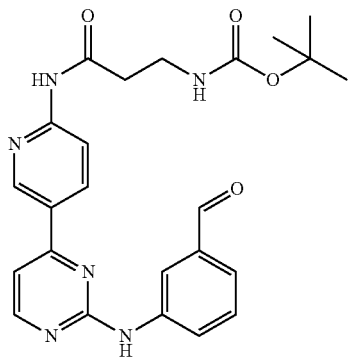 [SMILES: CC(C)(C)OC(=O)NCCC(=O)Nc1ccc(-c2ccnc(Nc3cccc(C=O)c3)n2)cn1]

A solution of Int. 204 (2.5 g; 8.582 mmol), N-[(1,1-dimethylethoxy)carbonyl]-β-alanine, (4.9 g; 25.746 mmol), HATU (9.8 g; 25.746 mmol), and Et₃N (8.4 mL; 60.073 mmol) in THF (100 mL) was stirred at reflux for 14 h. The mixture was diluted with EtOAc and H₂O. The organic layer was decanted, dried over MgSO₄, filtered and the solvent was evaporated. The residue was purified by preparative LC on irregular SiOH 15-40 μm 300 g MERCK. Mobile phase: 98% DCM, 2% MeOH. The desired fractions were collected and the solvent was evaporated to give 6 g of Int. 205 (100%).

f) Preparation of Int. 206

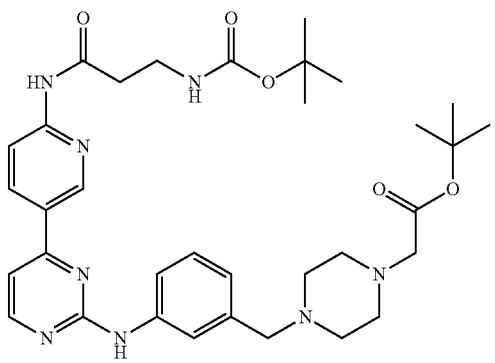 [SMILES: CC(C)(C)OC(=O)CN1CCN(Cc2cccc(Nc3nccc(-c4ccc(NC(=O)CCNC(=O)OC(C)(C)C)nc4)n3)c2)CC1]

The reaction was performed in a microwave-apparatus (Biotage) in a sealed tube, (monomode 400 W).

Sodium triacetoxyborohydride (1.7 g, 7.823 mmol) was added to a stirred solution of Int. 205 (3.6 g, 5.215 mmol) and piperazine-1-acetic acid tert-butyl ester (2.1 g, 10.43 mmol) in DCE (16 mL) and DIPEA (1.8 mL, 10.43 mmol). The mixture was stirred at 120° C. for 20 minutes. Water, $K_2CO_3$ 10% in $H_2O$ and DCM were added. The reaction mixture was extracted with DCM (3×). The organic layer was separated, dried over $MgSO_4$, filtered and the solvent was evaporated. The residue was purified by preparative LC on irregular SiOH 15-40 µm 300 g MERCK. Mobile phase: $NH_4OH$, DCM, MeOH 0.5/96/4. The desired fractions were collected and the solvent was evaporated. Yield: 285 mg of Int. 206.

g) Preparation of Int. 207

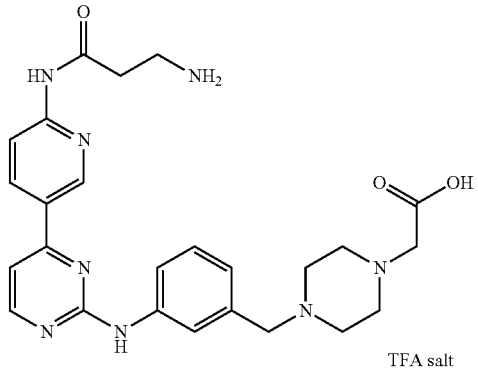 [SMILES: NCCC(=O)Nc1ccc(-c2ccnc(Nc3cccc(CN4CCN(CC(=O)O)CC4)c3)n2)cn1]

TFA salt

TFA (6.6 mL; 85.864 mmol) was added to a solution of Int. 206 (270 mg; 0.417 mmol) in DCM (8 mL) at room temperature. The reaction mixture was stirred for 5 h at room temperature. The solvent was evaporated to give Int. 207 as a brown oil which was used as such in the next reaction step without further purification.

Example A17 a) Preparation of Int. 208

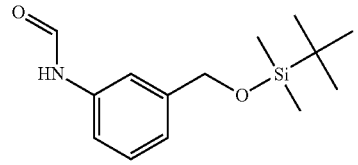 [SMILES: CC(C)(C)[Si](C)(C)OCc1cccc(NC=O)c1]

Phenyl formate (10.6 mL; 96.876 mmol) was added to a solution of 3-[[(ter-butyldimethylsilyl)oxy]methyl]aniline (Journal of Medicinal Chemistry (2009), 52(23), 7503-7511) (11.5 g; 48.438 mmol) in DCM (10 mL) at room temperature. The reaction mixture was stirred for 40 minutes at room temperature. The solvent was evaporated. The residue was purified by preparative liquid chromatography on Irregular SiOH 15-40 µm 330 g. Mobile phase: 80% Heptane, 20% EtOAc. The pure fractions were collected and the solvent removed in vacuo. Yield: 2.7 g (21%) of Int. 208, and 18.7 g of impure material. The impure material was purified by preparative liquid chromatography on Irregular SiOH 20-45 µm 450 g MATREX. Mobile phase: 75% Heptane, 25% EtOAc. The pure fractions were collected and the solvent removed in vacuo. Yield: 9.4 g (73%) of Int. 208.

b) Preparation of Int. 209

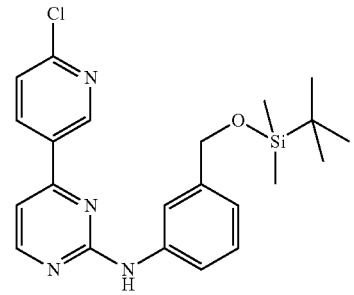 [SMILES: CC(C)(C)[Si](C)(C)OCc1cccc(Nc2nccc(-c3ccc(Cl)nc3)n2)c1]

The reaction was conducted 5 times on similar quantities of Int. 208 (10 g; 37.675 mmol). NaH (60% dispersion in mineral oil) (9 g; 226.05 mmol) was added to a solution of Int. 208 (50 g; 188.375 mmol) in DMF (600 mL) at room temperature. The reaction mixture was stirred for 30 minutes and then 2-chloro-4-(6-Chloropyridin-3-yl)pyrimidine (Journal of Organic Chemistry (2002), 67(21), 7541-7543) (42.6 g; 188.375 mmol) was added. The reaction mixture was stirred at room temperature overnight. NaOH 2 N solution in water (60 ml) and MeOH (80 mL) were added and the reaction mixture was stirred at room temperature for 2 h. The reaction mixture was diluted with water and extracted twice with EtOAc. The organic layer was washed with water, dried over $MgSO_4$, filtered and the solvent was evaporated. The residue was purified by preparative liquid chromatography on Irregular SiOH 20-45 µm 1000 g DAVISIL. Mobile phase: 70% heptane, 30% EtOAc). The solvent was evaporated. Yield: 61.7 g of Int. 209 (77%).

c) Preparation of Int. 311

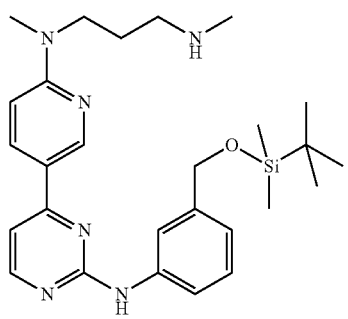 [SMILES: CNCCCN(C)c1ccc(-c2ccnc(Nc3cccc(CO[Si](C)(C)C(C)(C)C)c3)n2)cn1]

A mixture of Int. 209 (10 g; 23.42 mmol) and N,N'-dimethyl-1,3-propane diamine (11.8 mL; 93.67 mmol) was stirred at 135° C. for 1 h. The mixture was evaporated. The residue was purified by preparative liquid chromatography on Irregular SiOH 20-45 µm 450 g MATREX. Mobile phase: NH₄OH, DCM, MeOH 1/90/10. The pure fractions were combined and the solvent evaporated yielding 9.58 g of Int. 311.

Example A18 a) Preparation of Int. 210

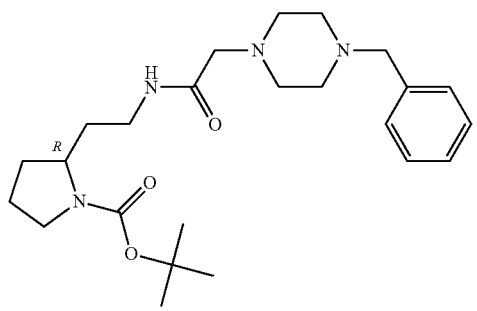

A solution of chloroacetyl chloride (1 mL; 12.74 mmol) in ACN (8 mL) was added dropwise to stirred solution of tert-butyl(2R)-2-(2-aminoethyl)-1-pyrrolidinecarboxylate (2.1 g; 9.80 mmol) and Et₃N (2.7 mL; 19.60 mmol) in ACN (24 mL) at room temperature. The reaction mixture was stirred for 1 h at room temperature. 1-Benzylpiperazine (5.1 mL; 29.40 mmol) was added and the reaction mixture was stirred at 60° C. for 2 h. Water was added and the mixture was extracted with DCM. The organic layer was dried over MgSO₄, filtered and the solvent was evaporated. The residue was purified by preparative liquid chromatography on Irregular SiOH 20-45 µm 450 g MATREX. Mobile phase: NH₄OH, DCM, MeOH 0.5/95/5 The desired fractions were collected and the solvent was evaporated. The oily residue (brown) was purified by preparative liquid chromatography on Irregular SiOH 20-45 µm 450 g MATREX. Mobile phase: NH₄OH, DCM, MeOH 0.5/95/5. The desired fractions were collected and solvent was evaporated. Yield: 3.2 g of Int. 210 (76%).

The intermediates in the table below were prepared according to an analogous reaction protocol as used for Int. 210:

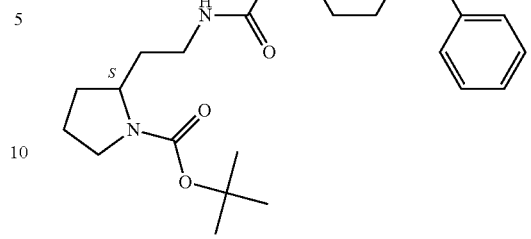

(from S)-2-(aminomethyl)-1-N-boc-pyrrolidine and 1-benzylpiperazine; used for Int. 218)

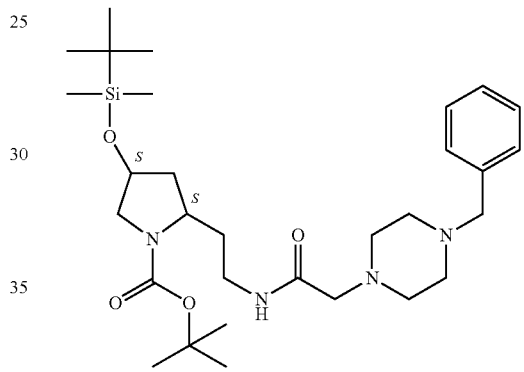

(from Int. 224 and 1-benzylpiperazine; used for Int. 226)

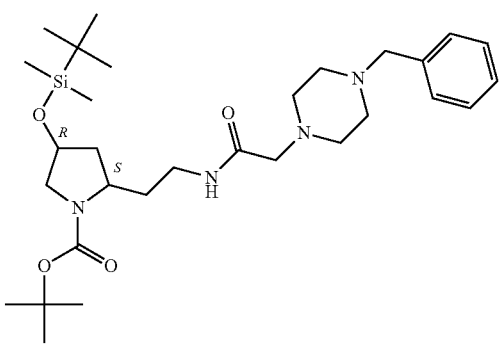

(from Int. 236 and 1-benzylpiperazine; used for Int. 238)

b) Preparation of Int. 211

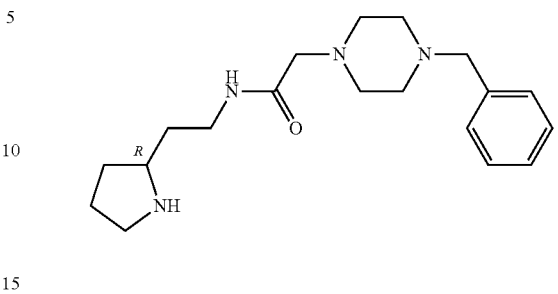

Int. 245

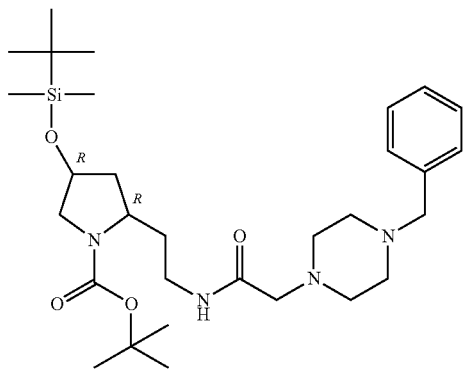

(from tert-butyl (2R,4R)-2-(2-aminoethyl)-
4-[(tert-butyldimethyl-
silyl)oxy]pyrrolidine-1-carboxylate
(WO2010138666) and 1-
benzylpiperazine; used for Int. 246)

TFA (11 mL; 145.85 mmol) was added to a solution of Int. 210 (3.14 g; 7.29 mmol) in DCM (50 mL) at 0-5° C. The reaction mixture was stirred at room temperature for 4 h. Additional TFA (30 eq.; 16.3 mL; 218.77 mmol) was added. The reaction mixture was stirred at room temperature for 2 h. Water and solid $K_2CO_3$ were added. The mixture was extracted with DCM, the organic layer was separated, dried over $MgSO_4$, filtered and the solvent was evaporated. The residue was purified by preparative liquid chromatography on Silica 15-40 μm, 80 g. Mobile phase: Gradient from DCM, MeOH, $NH_4OH$ 95/5/0.1 to DCM, MeOH, $NH_4OH$ 90/10/0.1. The desired fractions were collected and the solvent was evaporated. Yield: 1.9 g of Int. 211 (79%).

The intermediates in the table below were prepared according to an analogous reaction protocol as used for Int. 211:

Int. 258

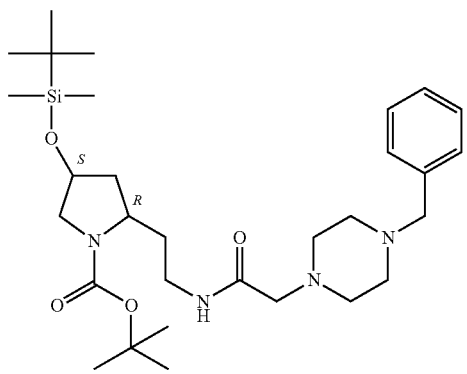

(from Int. 257 and 1-benzylpiperazine; used for Int. 259

Int. 218

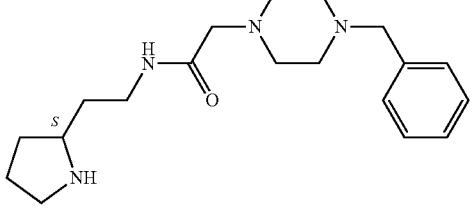

(from Int. 217; used for Int. 219)

Int. 279

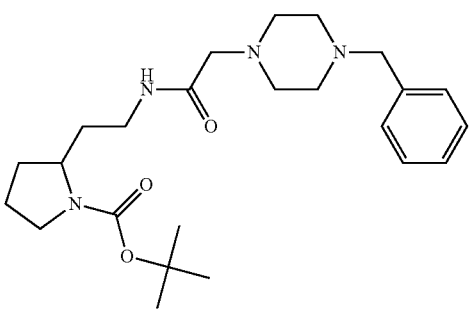

(from tert-butyl 2-(2-aminoethyl)-1-
pyrrolidinecarboxylate and 1-benzylpiperazine;
used for Int. 280)

Int. 280

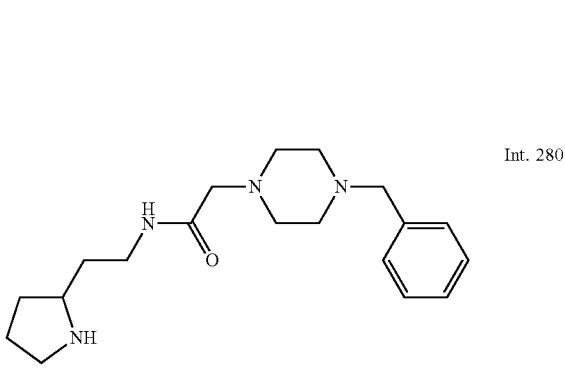

(from Int. 279; used for Int. 281)

c) Preparation of Int. 212

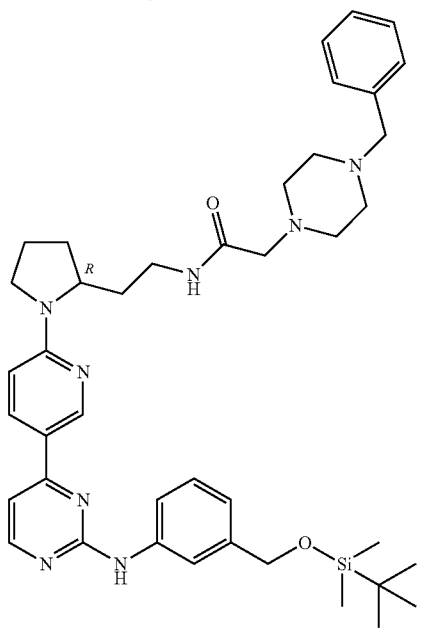

A solution of Int. 209 (500 mg; 1.17 mmol), Int. 211 (697 mg; 2.11 mmol) and K$_2$CO$_3$ (809 mg; 5.86 mmol) in DMF (800 µL) were stirred at 100° C. for 18 h. Water and DCM were added. The organic layer was separated dried over MgSO$_4$, filtered and the solvent was evaporated. The residue was purified by preparative liquid chromatography on irregular SiOH 15-40 µm 300 g MERCK. Mobile phase: 40% heptane, 10% MeOH, 50% EtOAc. The solvent was evaporated and the residue was purified by preparative liquid chromatography on irregular SiOH 15-40 µm 300 g MERCK. Mobile phase: 40% heptane, 10% MeOH, 50% EtOAc. The desired fractions were collected and the solvent was evaporated. Yield: 637 mg of Int. 212 (75%).

The intermediates in the table below were prepared according to an analogous reaction protocol as used for Int. 212:

Int. 219

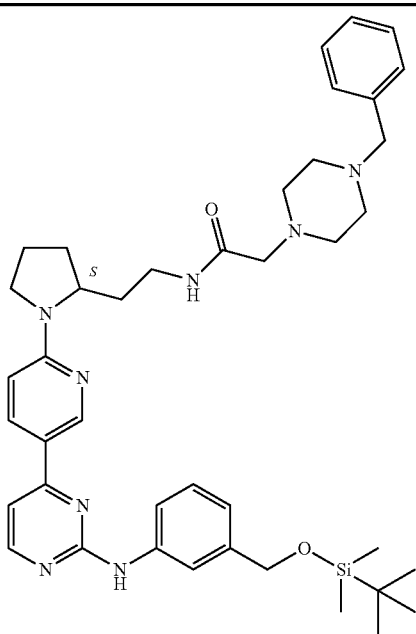

(from Int. 218 and Int. 209; used for Int. 220)

Int. 281

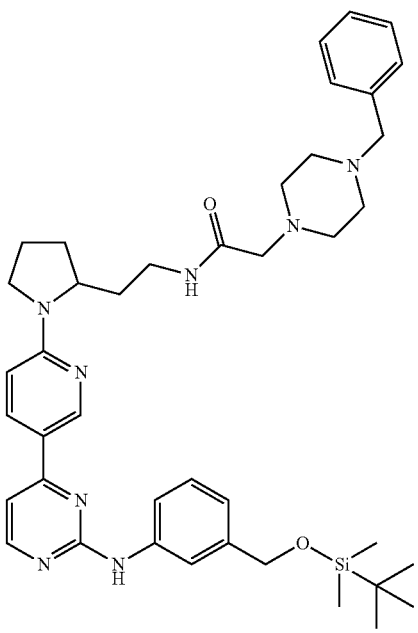

(from Int. 280 and Int. 209; used for Int. 282)

d-1) Preparation of Int. 213

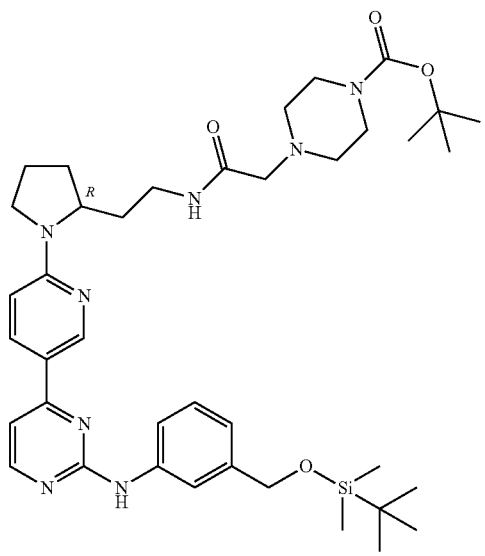

A suspension of Int. 212 (633 mg; 0.88 mmol), tert-butyloxycarbonyl anhydride (230 mg; 1.05 mmol) and Pd/C (10%) as a catalyst (63 mg) in MeOH (6.5 mL) was hydrogenated under H$_2$ atmosphere of 5 bars at 50° C. in a sealed vessel for 12 h. The catalyst was filtered off on a pad of Celite®. The Celite® was washed with a mixture of DCM/MeOH (3×). The filtrate was evaporated. The residue was purified by preparative liquid chromatography on Silica 15-40 µm, 30 g. Mobile phase: Gradient from DCM, MeOH, NH$_4$OH 99/1/0.1 to DCM, MeOH, NH$_4$OH 97/3/0.1. The pure fractions were collected and the solvent was evaporated. Yield: 298 mg of Int. 213 as a yellow oil (46%).

The intermediates in the table below were prepared according to an analogous reaction protocol as used for Int. 213:

Int. 220

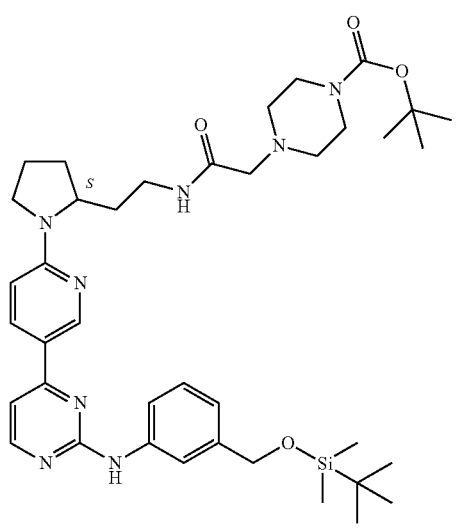

(from Int. 219; used for Int. 221)

Int. 249

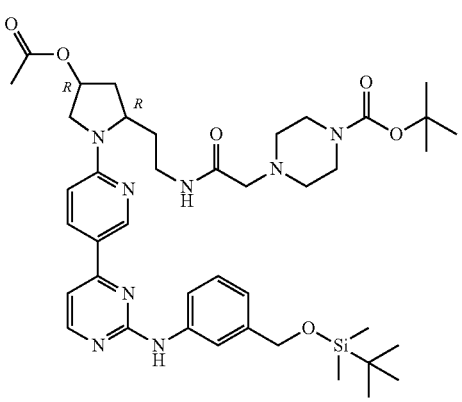

(from Int. 248; used for Int. 250)

Int. 263

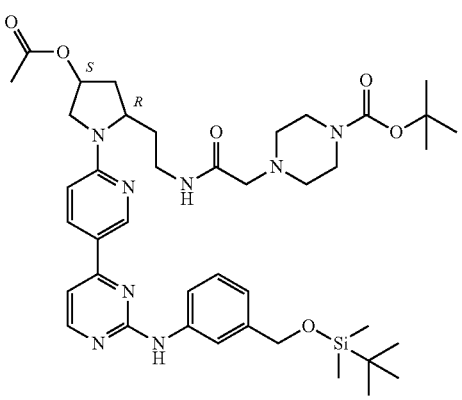

(from Int. 262; used for Int. 264)

d-2) Preparation of Int. 282

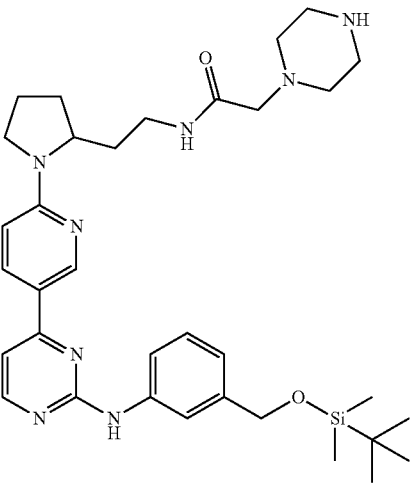 [SMILES: CC(C)(C)[Si](C)(C)OCc1cccc(Nc2nccc(-c3ccc(N4CCCC4CCNC(=O)CN4CCNCC4)nc3)n2)c1]

A suspension of Int. 281 (520 mg; 0.72 mmol) and Pd/C (10%) as a catalyst (50 mg) in MeOH (10 mL) was hydrogenated at 50° C. under 5 bar of $H_2$ atmosphere in a sealed vessel for 12 h. The catalyst was filtered off on a pad of Celite®. Celite@ was washed with a mixture of DCM/MeOH (3×). The filtrate was evaporated to give 472 mg of Int. 282 (oily).

e) Preparation of Int. 214

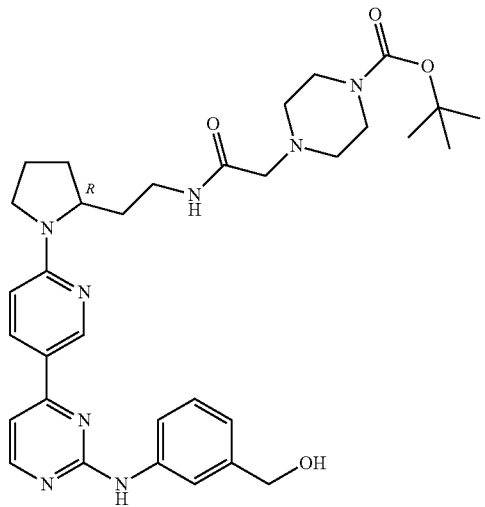

Tetrabutylammonium fluoride 1M (0.80 mL; 0.80 mmol) was added dropwise to a solution of Int. 213 (292 mg; 0.40 mmol) in THF (5.5 mL) at room temperature. The reaction mixture was stirred at room temperature for 12 h. Water was added and the organic solvent was evaporated. The mixture was extracted with DCM. The organic layer was washed with water, dried over $MgSO_4$, filtered and the solvent was evaporated. The residue was purified by preparative liquid chromatography on irregular SiOH 15-40 μm 24 g. Mobile phase: from DCM, MeOH, $NH_4OH$ 98/2/0.1 to DCM, MeOH, NH₄OH 96/4/0.1). The pure fractions were collected and the solvent was evaporated. Yield: 191 mg of Int. 214 as a yellow oil (78%).

The intermediates in the table below were prepared according to an analogous reaction protocol as used for Int. 214:

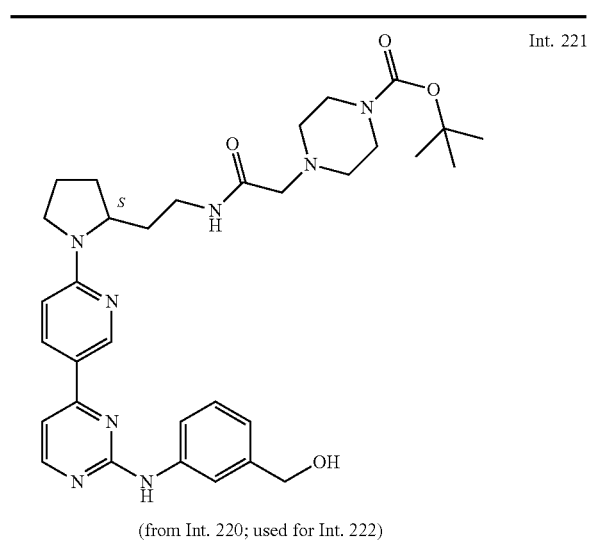
Int. 221
(from Int. 220; used for Int. 222)

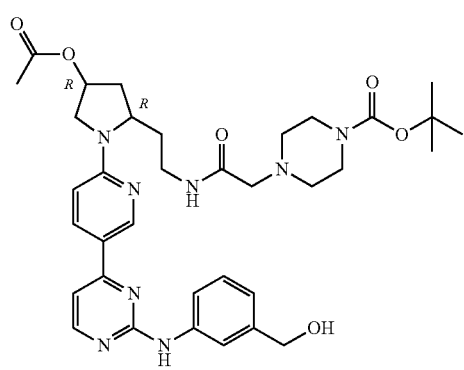
Int. 250
(from Int. 249; used for Int. 251)

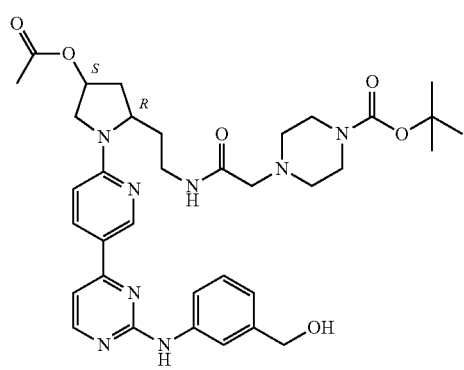
Int. 264
(from Int. 263; used for Int. 265)

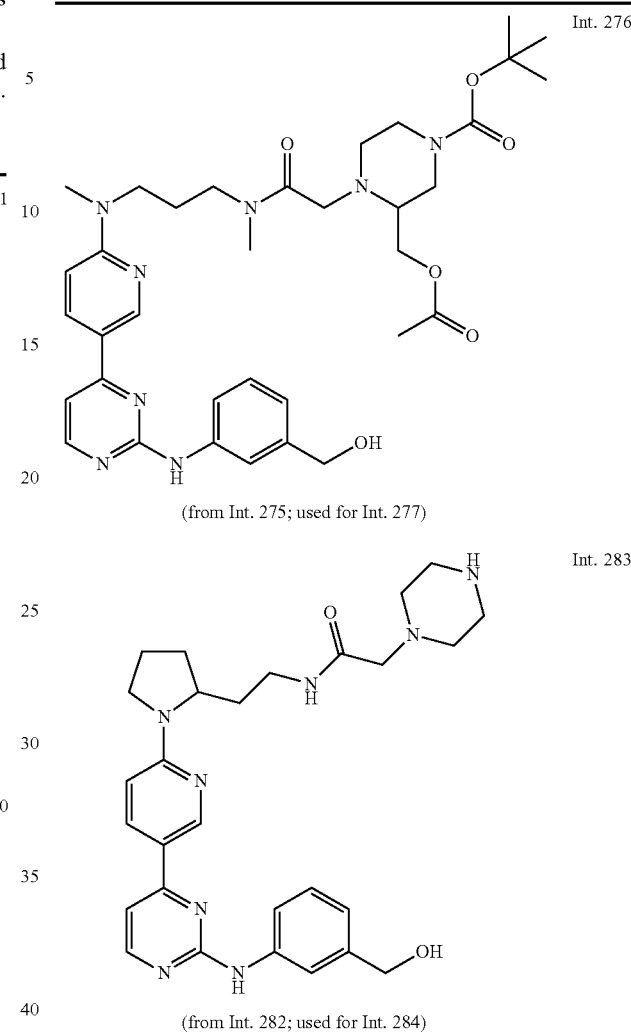
Int. 276
(from Int. 275; used for Int. 277)

Int. 283
(from Int. 282; used for Int. 284)

f) Preparation of nt. 215

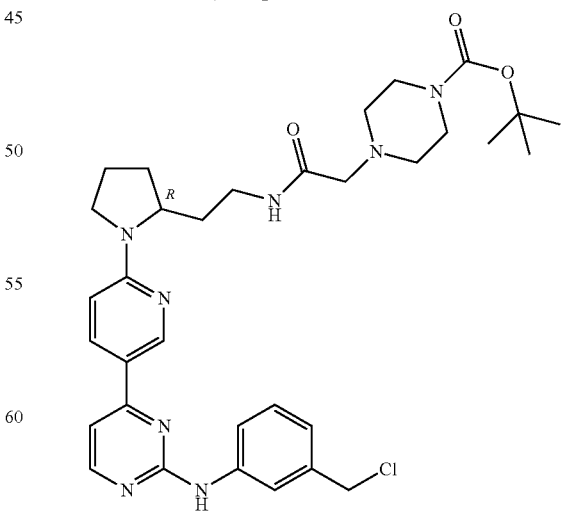

Methanesulfonyl chloride (117 µL; 1.52 mmol) was added dropwise to a solution of Int. 214 (187 mg; 0.30 mmol) and DIPEA (265 µL; 1.52 mmol) in DCM (7.3 mL) at 0° C. The reaction mixture was stirred at room temperature overnight. Water was added. The mixture was extracted with DCM (2×). The organic layer was dried over MgSO₄, filtered and the solvent was evaporated. Yield: 303 mg of Int. 215 as an orange oil which was used as such without any purification in the next reaction step.

The intermediates in the table below were prepared according to an analogous reaction protocol as used for Int. 215:

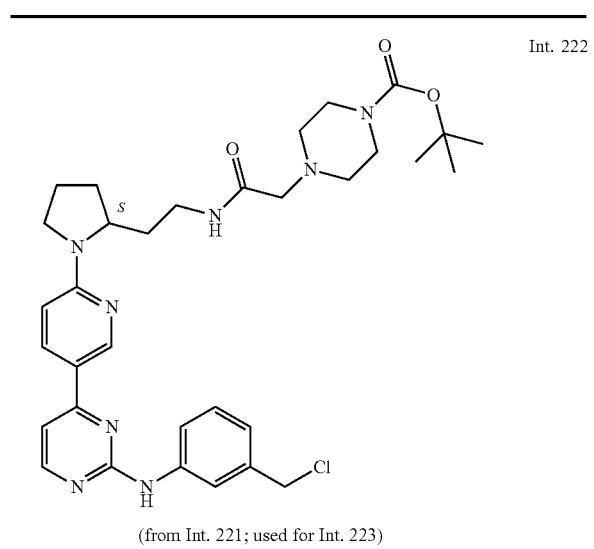

(from Int. 221; used for Int. 223)

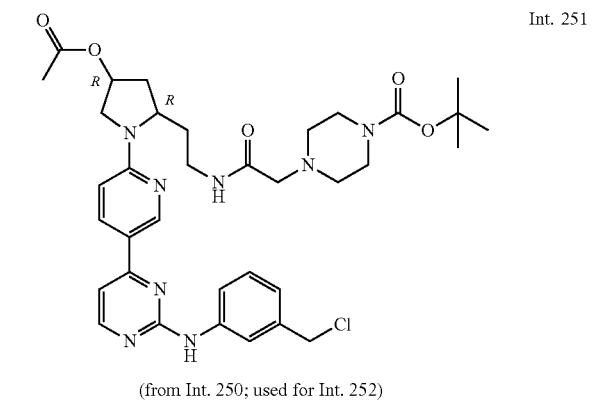

(from Int. 250; used for Int. 252)

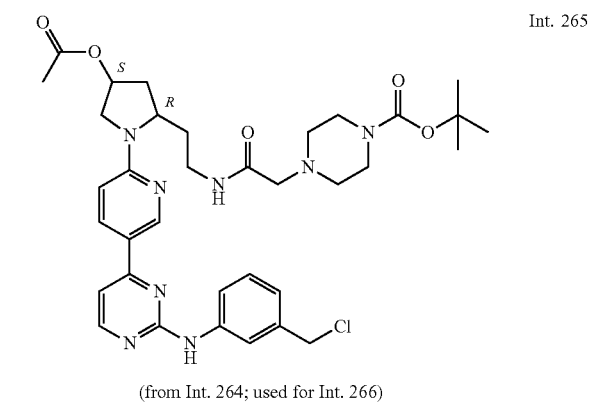

(from Int. 264; used for Int. 266)

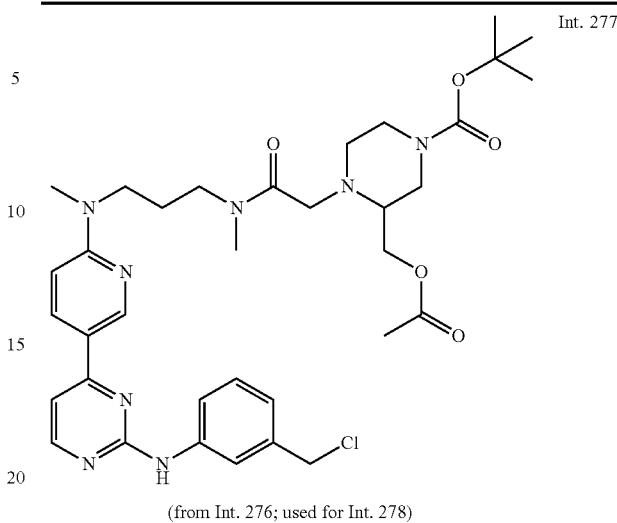

(from Int. 276; used for Int. 278)

Int. 215, 222, 251, 277 and 265 were obtained together with a derivative of these compounds wherein the chloro moiety is replaced by a mesylate moiety. These intermediates were used as mixtures (not quantified) in the next reaction step.

g-1) Preparation of Int. 216

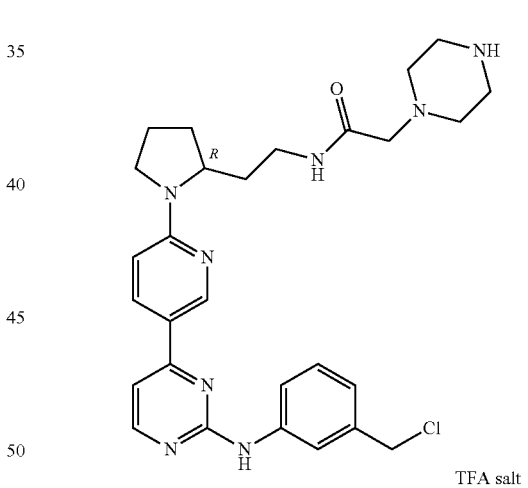

TFA salt

Trifluoroacetic acid (3 mL) was added dropwise to a solution of Int. 215 (303 mg; crude) in DCM (10 mL) at room temperature. The reaction mixture was stirred at room temperature for 3 h. The solvent was evaporated. The residue was taken up into DCM and the solvent was evaporated (repeated 3×). Yield: 600 mg of Int. 216 as a yellow oil which used as such without any purification in the next reaction step (synthesis compound 86).

The intermediates in the table below were prepared according to an analogous reaction protocol as used for Int. 216:

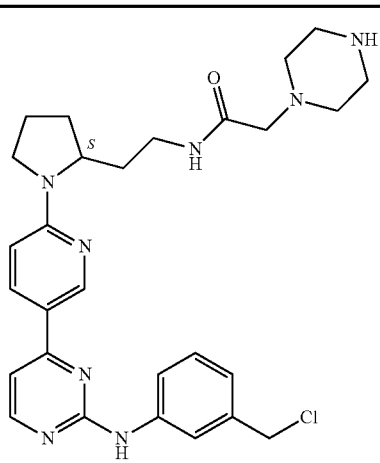

Int. 223

TFA salt
(from Int. 222; used for Co. 88)

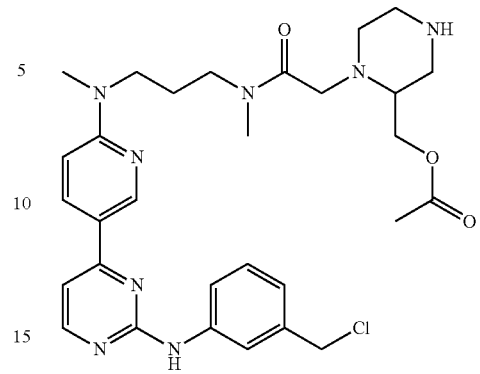

Int. 278

TFA salt
(from Int. 277; used for compound 93)

g-2) Preparation of Int. 284

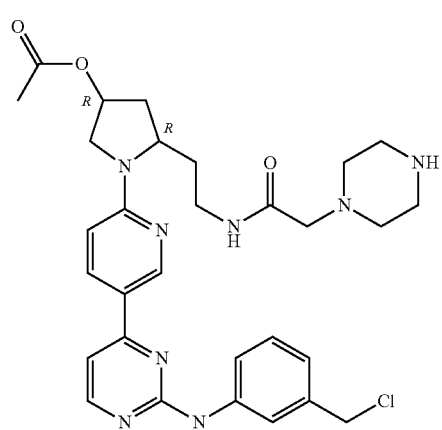

Int. 252

TFA salt
(from Int. 251; used for Co. 253)

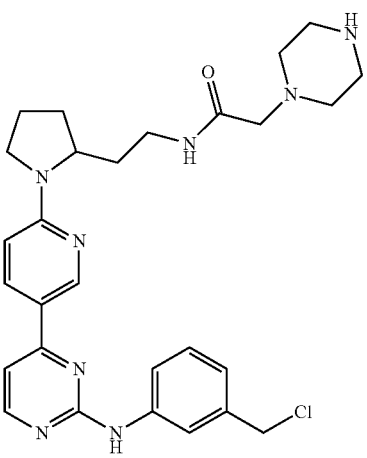

HCl salt

Thionyl chloride (1.65 mL; 22.55 mmol) was added dropwise to a stirred solution of Int. 283 (233 mg; 0.45 mmol) in DCE (54 mL) at room temperature. The reaction mixture was stirred at 60° C. for 18 h. The solvent was evaporated to dryness to give 387 mg of Int. 284 (used for the synthesis of compound 87).

Example A19 a) Preparation of Int. 224

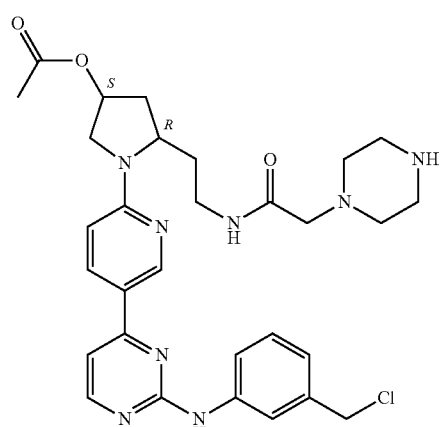

Int. 266

TFA salt
(from Int. 265; used for Co. 267)

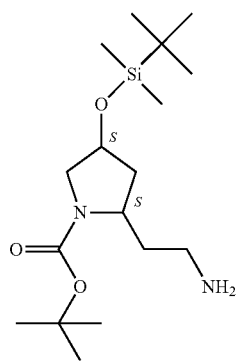

A suspension of 1,1-dimethylethyl(2S,4S)-2-(cyanomethyl)-4-[[(1,1-dimethylethyl)dimethylsilyl]oxy]-1-pyrrolidinecarboxylate (WO/2009026197) (4.59 g; 13.48 mmol), Raney nickel as a catalyst (4.8 g) and Et₃N (3.75 mL; 26.96 mmol) in MeOH (25 mL) was hydrogenated overnight under a H₂ atmosphere of 3.5 bar at room temperature in a sealed vessel The catalyst was filtered off on a pad of Celite@. The Celite@ was washed with DCM and MeOH (3×). The filtrate was evaporated. The residue was purified by preparative liquid chromatography on Irregular SiOH 20-45 µm 450 g MATREX. Mobile phaseNH₄OH, DCM, MeOH 0.6/90/10. The desired fractions were collected and the solvent was evaporated. Yield: 2.65 g of Int. 224 (57%).

b) Preparation of Int. 225

See in the table of Example A18.a c) Preparation of Int. 226

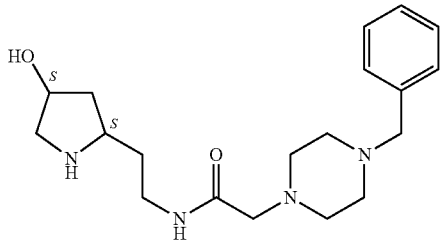

A suspension of Int. 225 (2.47 g; 4.404 mmol) in HCl 5 M (17.6 mL) was stirred at room temperature for 24 h. The reaction mixture was diluted with diisopropylether. The precipitate (brownish) was filtered off and was dissolved in a DCM/MeOH mixture. The solution was evaporated (35° C.) to give 2 g of Int. 226.

The intermediates in the table below were prepared according to an analogous reaction protocol as used for Int. 226:

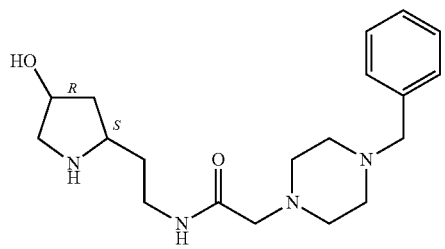

Int. 238

(from Int. 237; used for Int. 238)

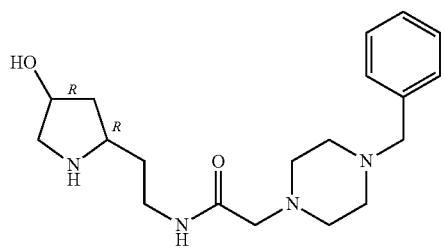

Int. 246

(from Int. 245; used for Int. 247)

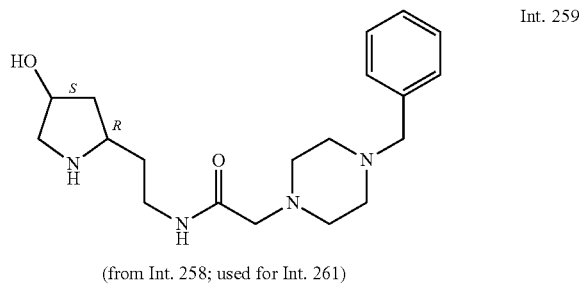

Int. 259

(from Int. 258; used for Int. 261)

d) Preparation of Int. 227

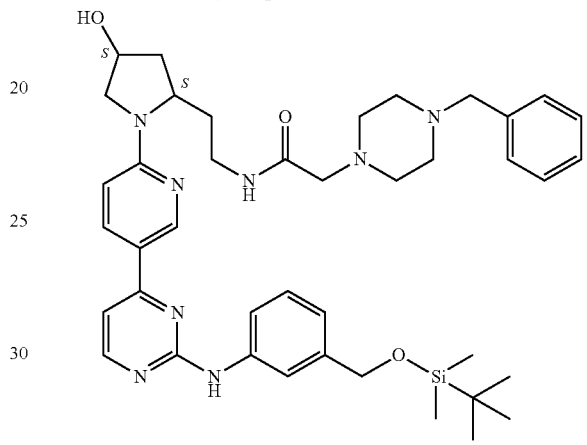

A suspension of Int. 226 (1.9 g; 5.045 mmol), Na₂CO₃ (1.7 g; 16.144 mmol) in DMSO (3.8) was stirred at room temperature for 40 minutes. Then d for Int. 209 (862 mg; 2.018 mmol) was added to the reaction mixture. The solution was stirred at 130° C. for 18 h. Water was added and the mixture was extracted twice with DCM, dried over MgSO₄, filtered and evaporated. The residue was purified by preparative liquid chromatography on irregular SiOH 15-40 µm 300 g MERCK. Mobile phase: NH₄OH, DCM, MeOH 0.5/95/5. The desired fractions were collected and the solvent was evaporated to give 1 g of Int. 227 (67%).

The intermediates in the table below were prepared according to an analogous reaction protocol as used for Int. 227:

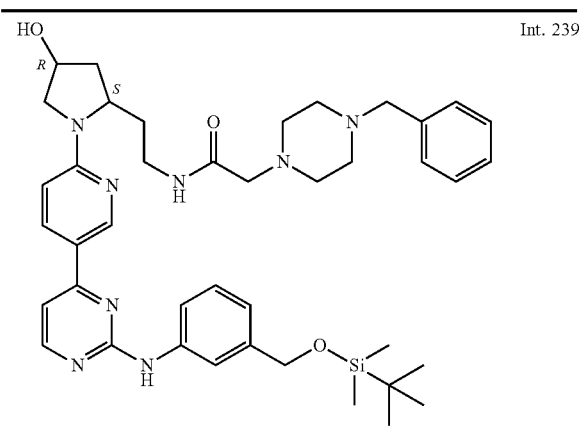

Int. 239

(from Int. 238; used for Int. 240)

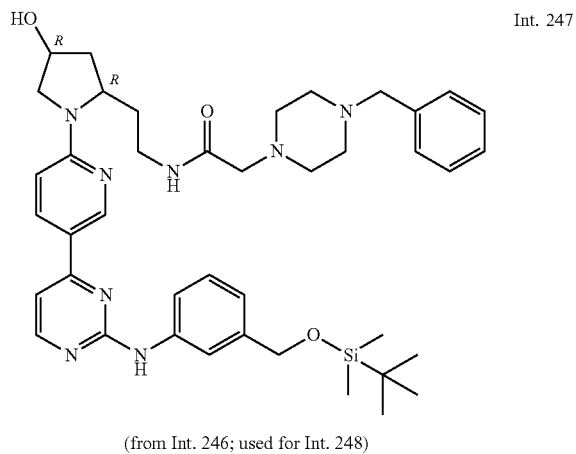

(from Int. 246; used for Int. 248)

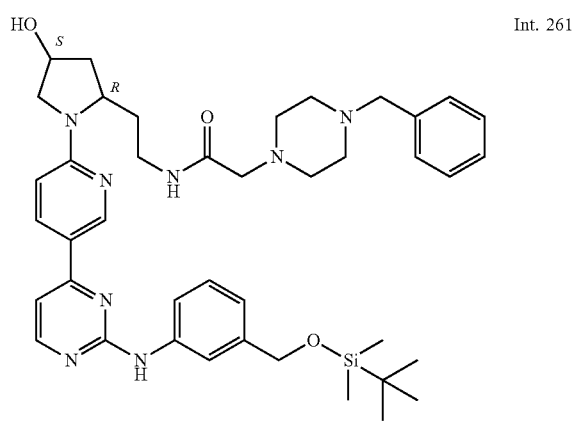

(from Int. 259; used for Int. 262)

e) Preparation of Int. 228

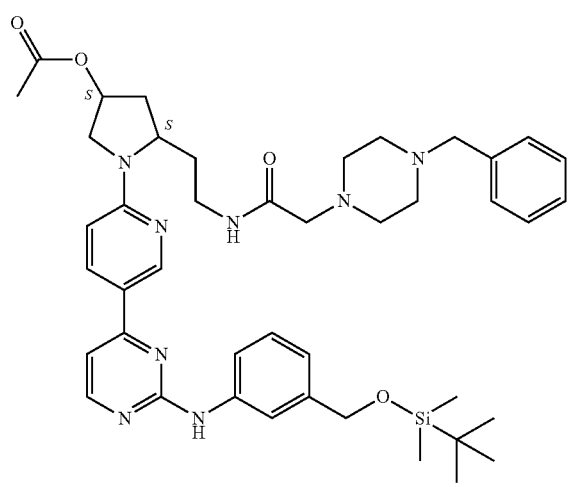

Acetic anhydride (192 μL; 2 mmol) was added to a solution of Int. 227 (1 g; 1.4 mmol), pyridine (164 μL; 2 mmol) and 4-dimethylaminopyridine (17 mg; 0.14 mmol) in DCM (2.6 mL) at room temperature. The reaction mixture was stirred at room temperature for 6 h. Water was added and the mixture was extracted with DCM (2×). The organic layer was dried over $MgSO_4$, filtered and the solvent was evaporated. The residue was purified by preparative liquid chromatography on (Stability Silica 5 μm 150×30.0 mm). Mobile phase: Gradient from $NH_4OH$, DCM, MeOH 0/100/0 to $NH_4OH$, DCM, MeOH 0.5/95/5. The pure fractions were combined and the solvent was evaporated. Yield: 492 mg of Int. 228 (46%).

The intermediates in the table below were prepared according to an analogous reaction protocol as used for Int. 228:

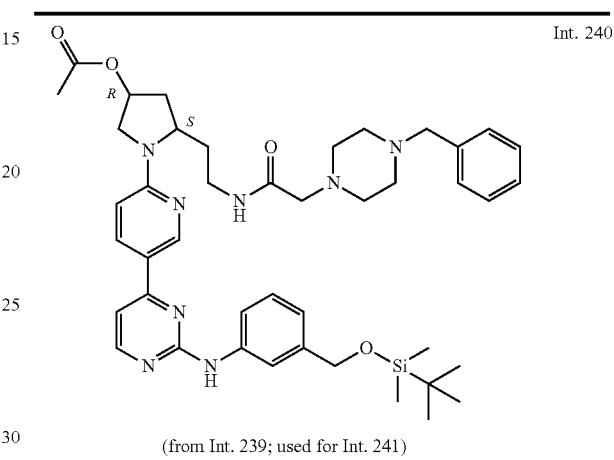

(from Int. 239; used for Int. 241)

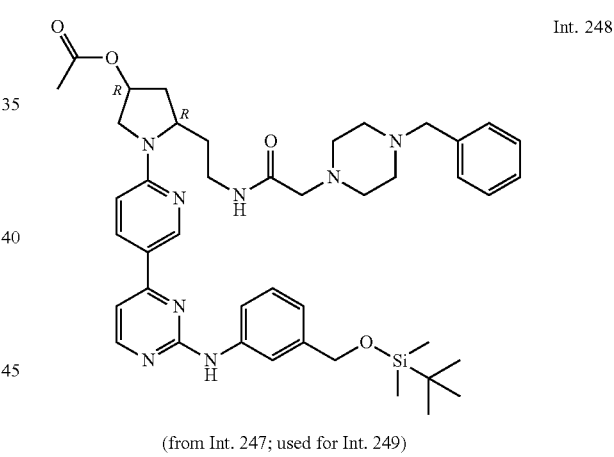

(from Int. 247; used for Int. 249)

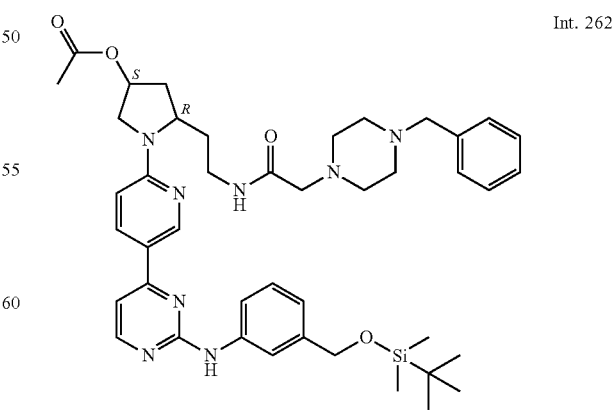

(from Int. 261; used for Int. 263)

f) Preparation of Int. 229

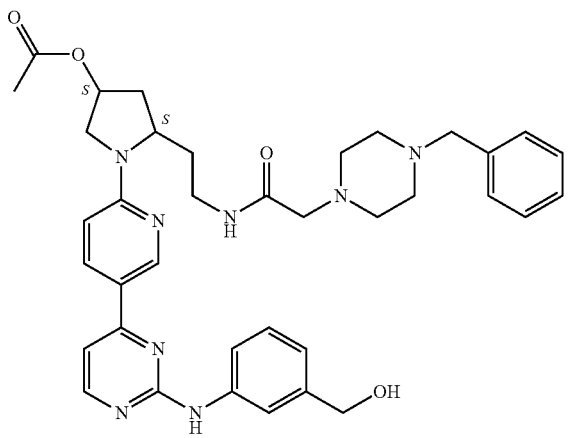

Tetrabutylammonium fluoride 1M (1.3 mL; 1.3 mmol) was added dropwise to a solution of Int 228 (492 mg; 0.63 mmol) in THF (8 mL) at 0° C. The reaction mixture was stirred at 0° C. for 30 minutes and was then stirred at room temperature for 2 h. Water and 10% NH$_4$Cl aqueous solution were added. The mixture was extracted with DCM. The organic layer was washed with water, dried over MgSO$_4$, filtered and the solvent was evaporated. The residue was purified by preparative liquid chromatography on Stability Silica 5 μm 150×30.0 mm. Mobile phase: Gradient from NH$_4$OH, DCM, MeOH 0/100/0 to % NH$_4$OH, DCM, MeOH 0.7/90/10. The desired fractions were collected and the solvent was evaporated. Yield: 476 mg of Int. 229.

The intermediates in the table below were prepared according to an analogous reaction protocol as used for Int. 229:

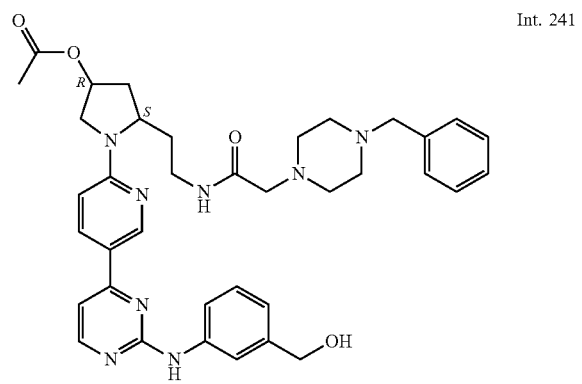

Int. 241

(from Int. 240; used for Int. 242)

g) Preparation of Int. 230

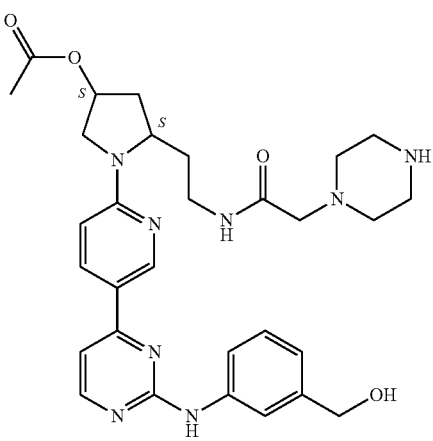

A suspension of Int. 229 (476 mg; 0.72 mmol) and Pd/C (10%) as a catalyst (50 mg) in MeOH (15 mL) was hydrogenated under H$_2$ atmosphere of 4 bars at 30° C. in a sealed vessel for 12 h. The catalyst was filtered off on a pad of Celite@. The Celite@ was washed with a mixture of DCM/MeOH (3×). The filtrate was evaporated. Yield: 398 mg of Int. 230.

The intermediates in the table below were prepared according to an analogous reaction protocol as used for Int. 230:

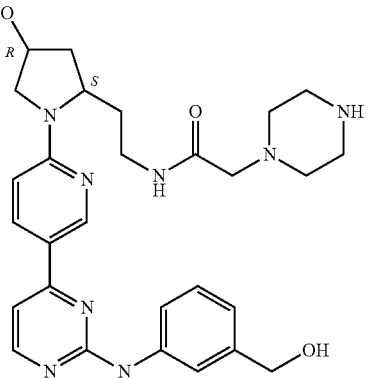

Int. 242

(from Int. 241; used for Int. 243)

h) Preparation of Int. 231

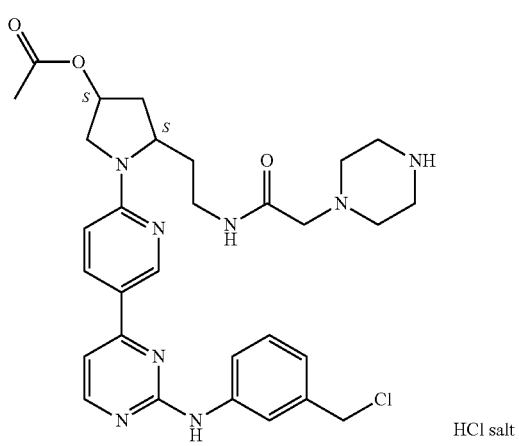

HCl salt i) Preparation of Int. 232

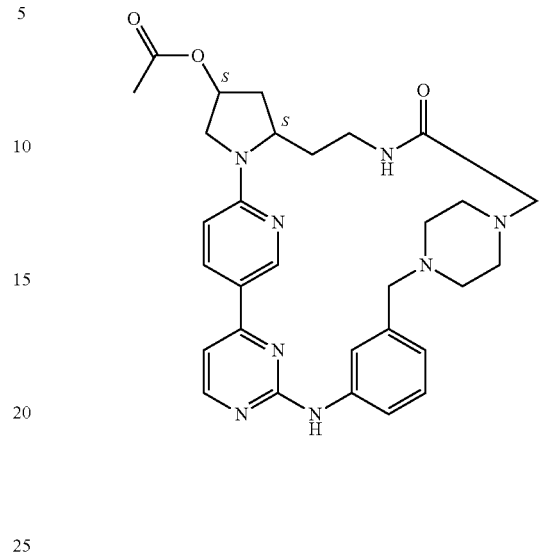

Thionyl chloride (2 mL; 28 mmol) was added dropwise to a stirred solution of Int. 230 (350 mg; 0.56 mmol) in DCE (80 mL) at room temperature. The reaction mixture was stirred at 65° C. for 2 h. The solvent was evaporated to dryness. Yield: 393 mg of Int. 231 which was used as such without any purification for the next reaction step.

The intermediates in the table below were prepared according to an analogous reaction protocol as used for Int. 231:

$K_2CO_3$ (1.7 g; 12 mmol) was added to a solution of Int. 231 (393 mg) in DMF (130 mL) at room temperature. The reaction mixture was stirred at 50° C. for 18 h. The solvent was evaporated. The residue was taken up into water, extracted twice with DCM, dried over $MgSO_4$, filtered and evaporated. The residue was purified by preparative liquid chromatography on irregular 15-40 μm 30 g Merck. Mobile phase: $NH_4OH$/DCM/MeOH 0.3/97/3. The pure fractions were combined and the solvent was evaporated. Yield: 110 mg of Int. 232.

The intermediates in the table below were prepared according to an analogous reaction protocol as used for Int. 232:

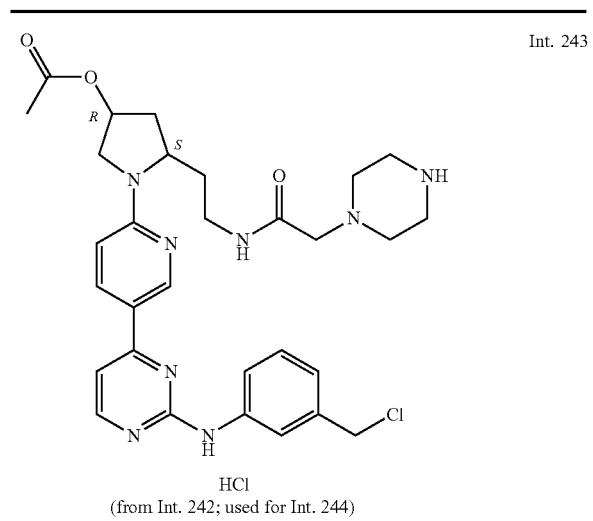

Int. 243

HCl
(from Int. 242; used for Int. 244)

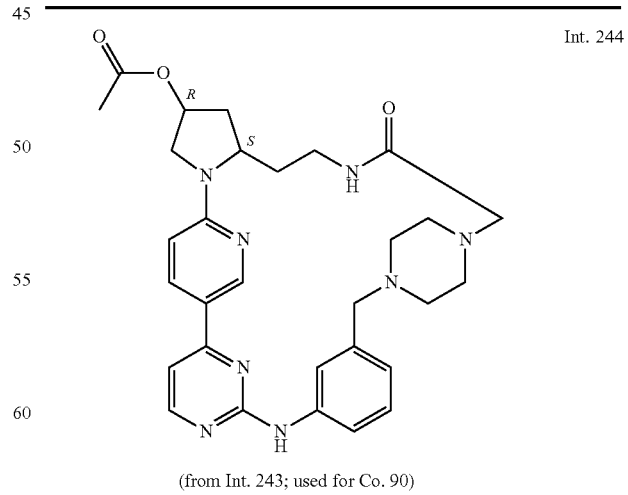

Int. 244

(from Int. 243; used for Co. 90)

Int. 253

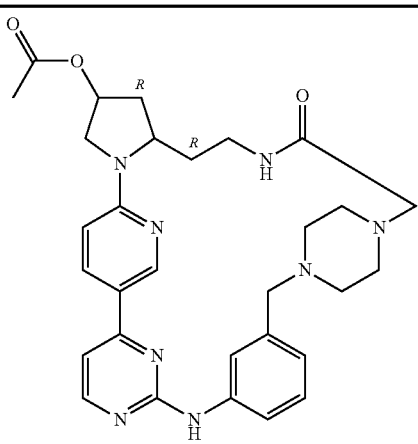

(from Int. 252; used for Co. 91)

Int. 267

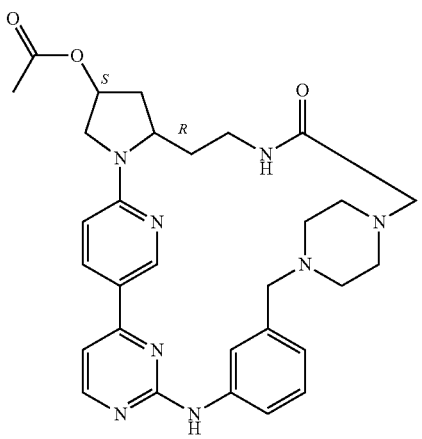

(from Int. 266; used for Co. 96)

Example A20 a-1) Preparation of Int. 260

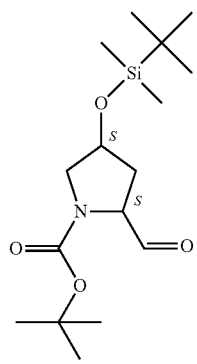

Lithium borohydride (69 mL; 138 mmol; 2 M in THF) was added to a stirred solution of (2S,4S)-4-[[(1,1-dimethylethyl)dimethylsilyl]oxy]-1,2-pyrrolidinedicarboxylic acid, 1-(1,1-dimethylethyl) 2-methyl ester (32 g, 89 mmol) in THF (58 mL) at 0-5° C. under N₂ atmosphere. The reaction mixture was stirred for 12 hours. Ice was added and the mixture was extracted with EtOAc (2×). The combined organic layers were washed with a 10% NH₄Cl aqueous solution, dried (MgSO₄), filtered, and the solvent was evaporated. The residue (29.8 g) was dissolved in DMSO (27 mL) and DCM (123 mL) at 0° C. under N₂ atmosphere. Et₃N (21.5 mL; 154.59 mmol) and then pyridine sulphur trioxide (48-50%) (19.7 g; 123.67 mmol) were added to the stirred solution under N₂ atmosphere. The reaction mixture was stirred at 0° C. for 2 h. EtOAc was added. The mixture was first washed with HCl 0.5 N and then with brine. Subsequently, the mixture was evaporated. The residue was taken up in Et₂O/heptane 70/30, washed successively with HCl 1 M and brine, dried (MgSO₄), filtered and the solvent was evaporated. Yield: 9.76 g of Int. 260 as a colourless oil which was used as such in the next reaction step (preparation of Int. 254).

a-2) Preparation of Int. 233

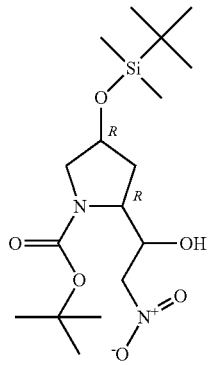

Et₃N (1.9 mL; 13.4 mmol) was added dropwise to a stirred solution of (2R,4R)-4-[[(1,1-dimethylethyl)dimethylsilyl]oxy]-2-formyl-1-pyrrolidinecarboxylic acid, 1,1-dimethylethyl ester (4.4 g; 13.4 mmol) (Bioorganic & Medicinal Chemistry 10 (2002) 1595-1610) in nitromethane (22 mL) at 0° C. under N₂ atmosphere. The reaction mixture was stirred at room temperature for 14 h. The mixture was concentrated and the residue was dissolved in toluene and evaporated three times to give 5.2 g of int. 233 which was used as such without any purification for the next reaction step.

The intermediates in the table below were prepared according to an analogous reaction protocol as used for Int. 233:

Int. 254

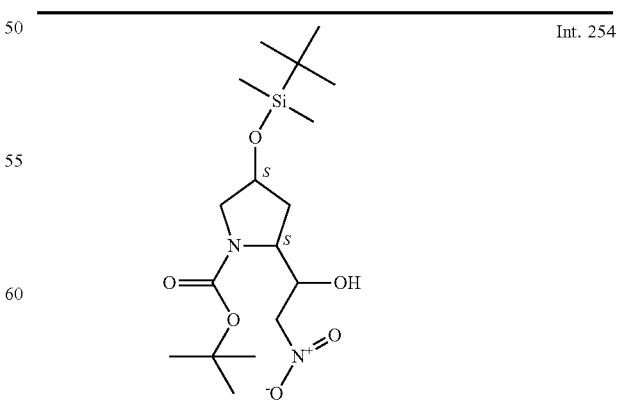

(from Int. 260; used for Int. 255)

b) Preparation of Int. 234

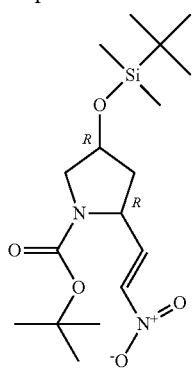

A solution of SOCl$_2$ (1.3 mL; 17 mmol) in DCM (20 mL) was added dropwise to a stirred solution of Int. 233 (5.2 g) and Et$_3$N (7.4 mL; 53 mmol) in DCM (65 mL) at −78° C. over a period of 10 minutes. The reaction mixture was then stirred for an additional 15 minutes. The solvent was evaporated. The residue was taken up into Heptane/EtOAc (70/30). The precipitate was filtered off and the filtrate was evaporated. The residue was purified by preparative liquid chromatography on Irregular SiOH 20-45 μm 450 g MATREX). Mobile phase: 70% Heptane, 30% EtOAc. The pure fractions were combined and the solvent was evaporated to give 3.1 g of Int. 234.

The intermediates in the table below were prepared according to an analogous reaction protocol as used for Int. 234:

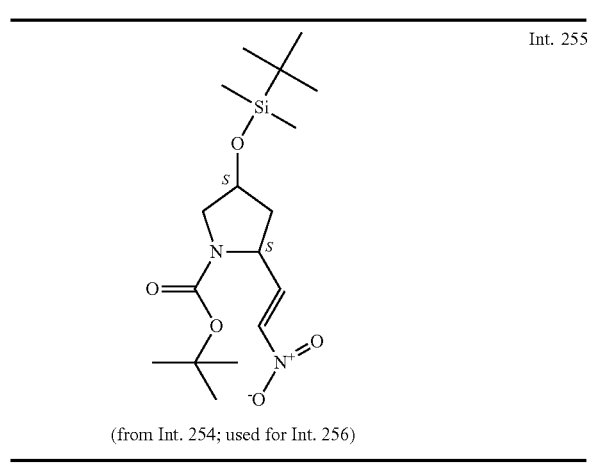

Int. 255

(from Int. 254; used for Int. 256)

c) Preparation of Int. 235

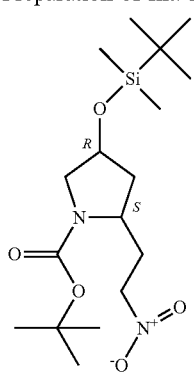

Distilled water (25 mL) was added to a suspension of NaBH$_4$ (1.6 g; 41.6 mmol) in THF (150 mL) at −20° C. under N$_2$ atmosphere. A solution of Int. 234 (3.1 g; 8.3 mmol) in THF (26 mL) was added dropwise at −20° C. over 30 minutes. After an additional 30 minutes, the cold reaction was carefully quenched with HCl 1 N in H$_2$O (30 mL). The reaction mixture was then diluted with EtOAc. The solution was purified by preparative liquid chromatography on irregular SiOH 15-40 μm 300 g MERCK. Mobile phase: 85% heptane, 15% EtOAc). The pure fractions were combined and the solvent was evaporated to give 2.4 g of Int. 235 (77%).

The intermediates in the table below were prepared according to an analogous reaction protocol as used for Int. 235:

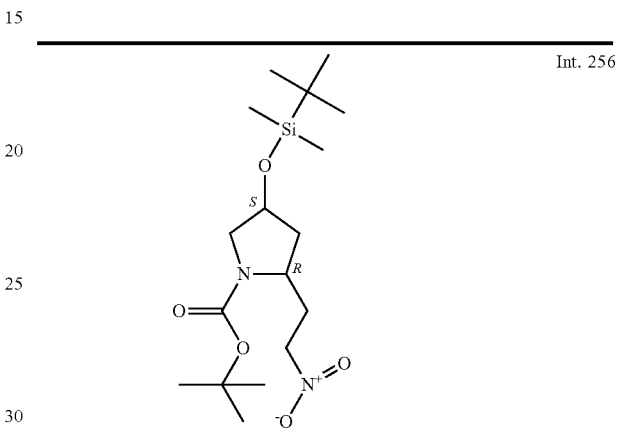

Int. 256

(from Int. 255; used for Int. 257)

d) Preparation of Int. 236

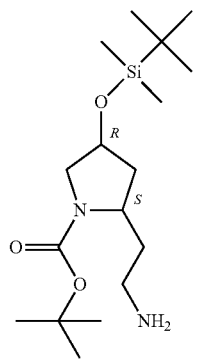

A suspension of Int. 235 (2.4 g; 6.4 mmol) and Raney nickel as a catalyst (2.2 g) in EtOH (22 ml) was hydrogenated under H$_2$ atmosphere of 3.5 bars at room temperature in a sealed vessel The reaction mixture was stirred for 3 h. The catalyst was filtered off on a pad of Celite®. Celite® was washed with DCM and MeOH. The filtrate was evaporated to give 2.28 g of Int. 236.

The intermediates in the table below were prepared according to an analogous reaction protocol as used for Int. 236:

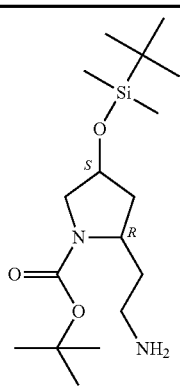

Int. 257

(from Int. 256; used for Int. 258)

Example A21 a) Preparation of Int. 268

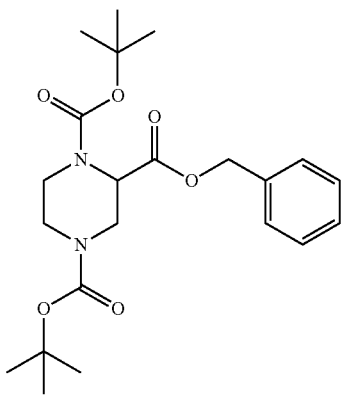 [SMILES: CC(C)(C)OC(=O)N1CCN(C(=O)OC(C)(C)C)C(C(=O)OCc2ccccc2)C1]

Benzyl bromide (2.8 mL; 23.61 mmol) was added dropwise to a suspension of 1,4-bis(tert-butoxycarbonyl)piperazine-2-carboxylic acid (3 g; 9.08 mmol) and $K_2CO_3$ (1.63 g; 11.81 mmol) in DMF (30 mL) at 0° C. under $N_2$ atmosphere. The reaction mixture was stirred at room temperature for 18 h. A portion of the reaction was quenched with water and EtOAc was added. The organic layer was washed with brine, dried over $MgSO_4$, filtered and the solvent was evaporated. The residue was purified by preparative LC (Stability Silica 30-45 µm, 10 g). Mobile phase: Gradient from 90% heptane, 10% EtOAc to 80% heptane, 20% EtOAc. The pure fractions were collected and the solvent was evaporated until dryness to give 112 mg of Int. 268 (3%). Water and EtOAc were added to the remaining reaction mixture. The mixture was extracted with EtOAc (3×). The organic layer was washed with brine, dried over $MgSO_4$, filtered and the solvent was evaporated. The residue was taken up in ACN. The precipitate was filtered, washed with ACN and dried to give 2.05 g of Int. 268 (54%). The filtrate was evaporated and the residue was purified by preparative LC (Stability Silica 30-45 µm, 10 g. Mobile phase: Gradient from 90% heptane, 10% EtOAc to 80% EtOAc. The pure fractions were collected and the solvent was evaporated until dryness to give 1.34 g of a Int. 268 (35%).

b) Preparation of Int. 269

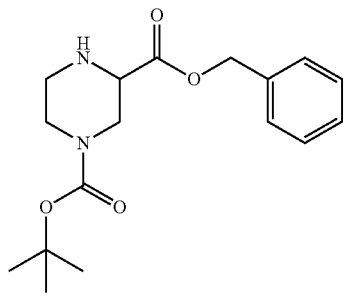 [SMILES: CC(C)(C)OC(=O)N1CCNC(C(=O)OCc2ccccc2)C1]

TFA (6.15 mL; 80.38 mmol) was added to a solution of Int. 268 (3.38 g; 8.04 mmol) in DCM (16 mL) at 0° C. The reaction mixture was stirred at room temperature for 1 h. A solution of $K_2CO_3$ 10% in $H_2O$ and DCM were added. The mixture was extracted with DCM (3×). The organic layer was dried over $MgSO_4$, filtered and the solvent was evaporated. The residue was purified by preparative LC on irregular SiOH 15-40 µm 300 g (MERCK). Mobile phase: Gradient from heptane, MeOH, EtOAc 40/10/50 to $NH_4OH$, DCM, MeOH 0.5/95/5. The desired fractions were collected and the solvent was evaporated. Yield: 315 mg of Int. 269 (12%).

c) Preparation of Int. 270

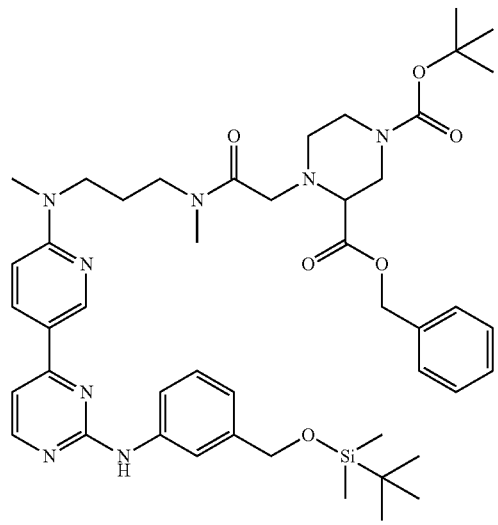 [SMILES: CN(CCCN(C)c1ccc(-c2ccnc(Nc3cccc(CO[Si](C)(C)C(C)(C)C)c3)n2)cn1)C(=O)CN1CCN(C(=O)OC(C)(C)C)CC1C(=O)OCc1ccccc1]

A solution of chloroacetyl chloride (85 µL; 1.07 mmol) in ACN (0.8 mL) was added dropwise to a solution of Int. 311 (404 mg; 0.82 mmol) and $Et_3N$ (228 µL; 1.64 mmol) in ACN (2 mL) at room temperature. The reaction mixture was stirred at room temperature for 11 h. Int. 269 (315 mg; 0.98 mmol) was added and the reaction mixture was stirred at 60° C. for 13 h. Water was added and the mixture was extracted with DCM. The organic layer was separated, dried over $MgSO_4$, filtered and the solvent was evaporated. The residue was purified by preparative liquid chromatography on Stability Silica 5 µm 150×30.0 mm. Mobile phase: Gradient from $NH_4OH$, DCM, MeOH 0.2/98/2 to $NH_4OH$, DCM, MeOH 1/90/10. The desired fractions were collected and the solvent was evaporated. Yield: 242 mg of Int. 270 (35%).

d) Preparation of Int. 271

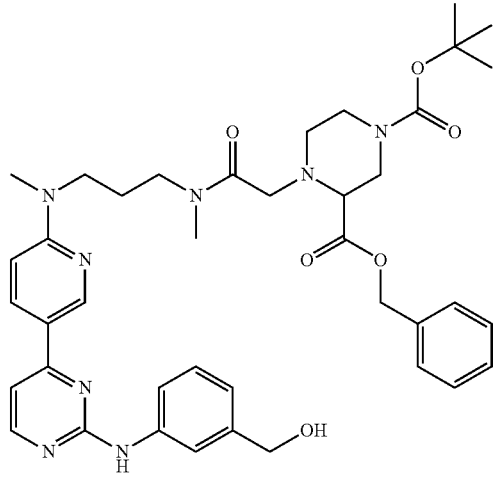 [SMILES: CN(CCCN(C)c1ccc(-c2ccnc(Nc3cccc(CO)c3)n2)cn1)C(=O)CN1CCN(C(=O)OC(C)(C)C)CC1C(=O)OCc1ccccc1]

Tetrabutylammonium fluoride 1M (302 μL; 0.30 mmol) was added dropwise to a solution of Int. 270 (234 mg; 0.27 mmol) in THF (2.9 mL) at room temperature. The reaction mixture stirred at room temperature for 3 h. Water was added. THF was evaporated. The mixture was extracted with DCM. The organic layer was washed with water, dried over MgSO$_4$, filtered and the solvent was evaporated. The residue was purified by preparative liquid chromatography on Stability Silica 5 μm 150×30.0 mm. Mobile phase: Gradient from NH$_4$OH, DCM, MeOH 0.2/98/2 to NH$_4$OH, DCM, MeOH 1/90/10. The desired fractions were collected and the solvent was evaporated. Yield: 138 mg of Int. 271 (68%).

e) Preparation of Int. 272

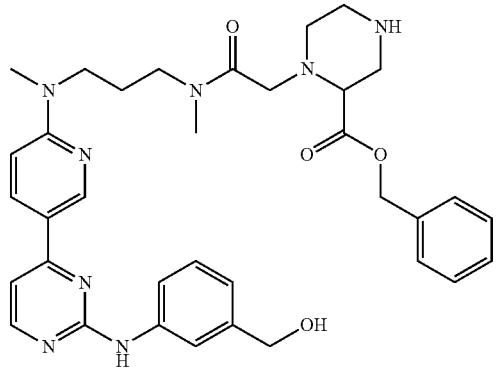 [SMILES: CN(CCCN(C)c1ccc(-c2ccnc(Nc3cccc(CO)c3)n2)cn1)C(=O)CN1CCNCC1C(=O)OCc1ccccc1]

HCl (4 M in dioxane) (149 μL; 0.60 mmol) was added to a solution of Int. 271 (110 mg; 0.15 mmol) in dioxane (330 μL). The reaction mixture was stirred at 80° C. for 4 h. Water and a solution of K$_2$CO$_3$ 10% in H$_2$O were added. The mixture was extracted with EtOAc. The organic layer was washed with brine, dried over MgSO$_4$, filtered and the solvent was evaporated. Yield: 86 mg of Int. 272 which was used as such without purification for the next reaction step.

f) Preparation of Int. 273

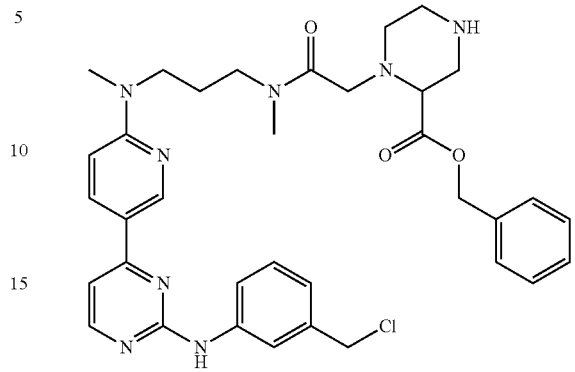

Thionyl Chloride (491 μL; 6.73 mmol) was added dropwise to a stirred solution of Int. 272 (86 mg) in DCE (16 mL) at room temperature. The reaction mixture was stirred at 60° C. for 4 h. The solvent was evaporated to dryness to give 113 mg of Int. 273 which was used as such without purification for the next reaction step (synthesis of compound 92).

Example A22 a) Preparation of Int. 274

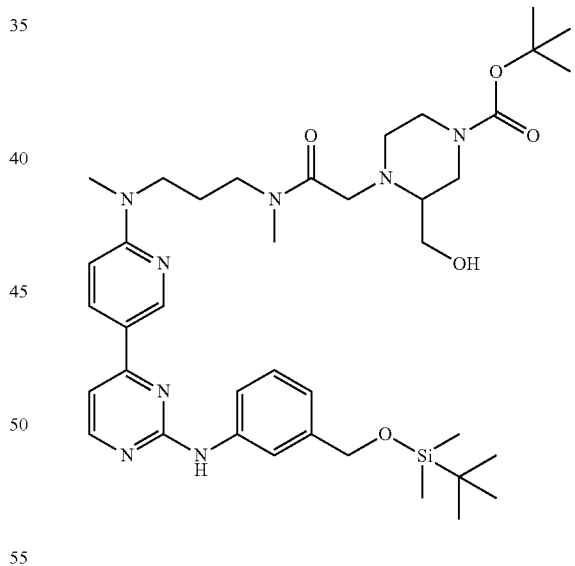

A solution of chloroacetyl chloride (199 μL; 2.50 mmol) in ACN (1.75 mL) was added dropwise to a solution of Int. 311 (949 mg; 1.93 mmol) and Et$_3$N (536 μL; 3.85 mmol) in THF (4.75 mL) at room temperature. The reaction mixture was stirred at room temperature for 1 h. 4-N-Boc-2-hydroxymethylpiperazine (500 mg; 3.85 mmol) was added and the reaction mixture was stirred at 60° C. for 6 h. Water and a solution of K$_2$CO$_3$ 10% in H$_2$O were added and the mixture was extracted with DCM. The organic layer was dried over MgSO$_4$, filtered and the solvent was evaporated. The residue was purified by preparative liquid chromatography on irregular SiOH 15-40 μm 300 g MERCK. Mobile phase: NH₄OH, DCM, MeOH 0.5/95/5. The desired fractions were collected and the solvent was evaporated, yielding Int. 274 in a 68% yield.

b) Preparation of Int. 275

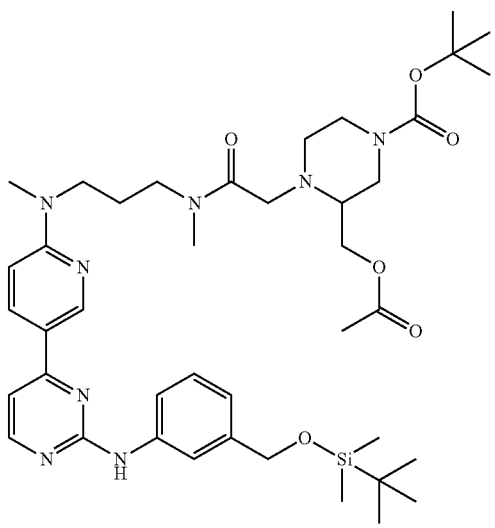 [SMILES: CC(=O)OCC1CN(C(=O)OC(C)(C)C)CCN1CC(=O)N(C)CCCN(C)c1ccc(-c2ccnc(Nc3cccc(CO[Si](C)(C)C(C)(C)C)c3)n2)cn1]

Acetic anhydride (189 µL; 2 mmol) was added to a solution of Int. 274 (1 g; 1.34 mmol), pyridine (161 µL; 2 mmol) and 4-dimethylaminopyridine (16.3 mg; 0.13 mmol) in DCM (2.6 mL) at room temperature. The reaction mixture was stirred at room temperature for 6 h. Water was added and the mixture was extracted with DCM (2×). The organic layer was dried over MgSO₄, filtered and the solvent was evaporated. The residue was purified by preparative liquid chromatography on Irregular SiOH 20-45 µm 450 g MATREX. Mobile phase: NH₄OH, DCM, MeOH 0.1/97/3. The desired fractions were collected and the solvent was evaporated. Yield: 780 mg Int. 275 as a brown foam (74%).

Example A23 a) Preparation of Int. 285

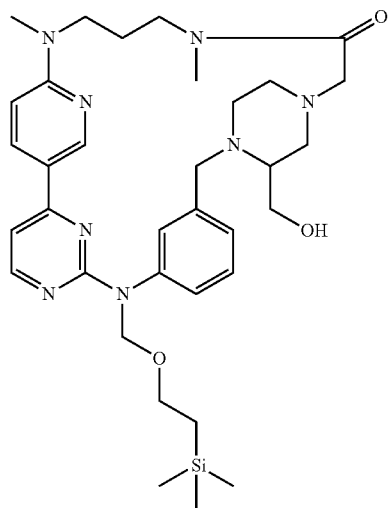 [SMILES: CN1CCCN(C)c2ccc(cn2)-c2ccnc(n2)N(COCC[Si](C)(C)C)c2cccc(c2)CN2CCN(CC1=O)CC2CO]

138 mg (3.46 mmol) of a 60% NaH dispersion in mineral oil was added to a solution of 1.7 g of compound 51 (3.29 mmol) in DMF (25.5 mL) at room temperature under flow of N₂-gas. The reaction mixture was stirred for 1 h at room temperature. 2-(Trimethylsylil)ethoxymethyl chloride (611 µL; 3.46 mmol) was added. The reaction mixture was stirred for 1 h at room temperature. Water was added. The precipitate was filtered off, washed with water and dried to give 1.55 g of Int. 285 as an orange solid which was used as such without further purification for the next reaction step.

b) Preparation of Int. 286

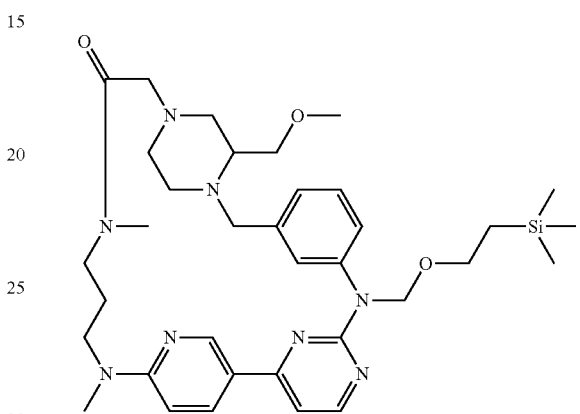

A 60% NaH dispersion in mineral oil (65 mg; 1.62 mmol) was added to a solution of Int. 285 (300 mg; 0.46 mmol) in DMF (4.5 mL) at room temperature under N₂ gas flow. The reaction mixture was stirred at room temperature for 1 h. Iodomethane (92 µL; 1.48 mmol) was added. The reaction mixture was stirred at room temperature for 3 h. The reaction mixture was poured into water. The precipitate was filtered off, taken up into DCM, dried over MgSO₄, filtered and the solvent was evaporated to yield 335 mg of Int. 286.

The intermediates in the table below were prepared according to an analogous reaction protocol as used for Int. 286:

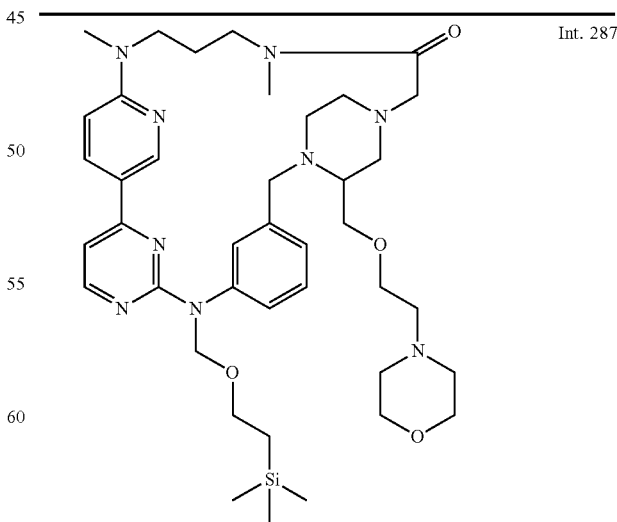

Int. 287

(from Int. 285 and 4-(2-iodoethyl)morpholine; used for Co. 98)

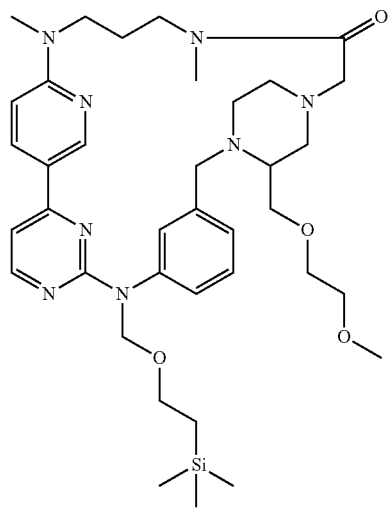

Int. 288

(from Int. 285 and 2-bromoethyl methyl ether; used for Co. 101)

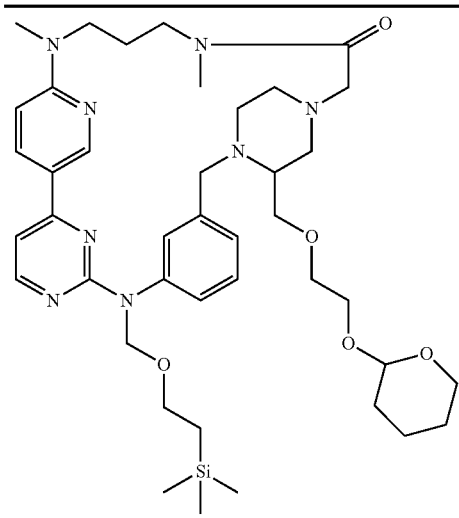

Int. 290

(from Int. 285 and 2-(2-iodoethoxy)tetrahydro-2H-pyran; used for Co. 103)

Example A24 a) Preparation of Int. 291

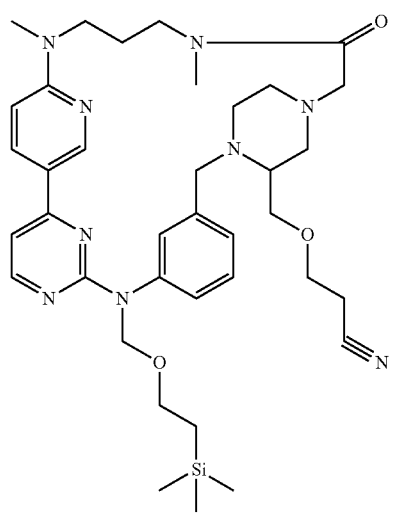

Int. 289

(from Int. 285 and 3-bromopropionitrile; used for Co. 102)

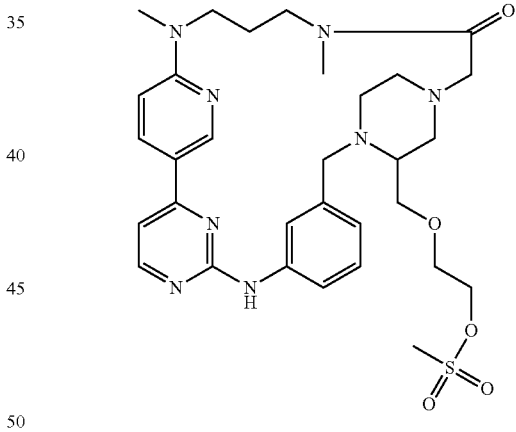

Methane sulfonyl chloride (121 μL; 1.6 mmol) was added dropwise to a solution of compound 103 (175 mg; 0.3 mmol) and DIPEA (273 μL; 1.6 mmol) in DCM (7.6 mL) at room temperature. The reaction mixture was stirred at room temperature for 2 h. Water was added. The mixture was extracted twice with DCM. The organic layer was dried over MgSO$_4$, filtered and the solvent was evaporated. Yield: 200 mg of Int. 291 which was used as such without any purification in the preparation of compound 106 (Int. 291 was obtained together with a derivative of the compound wherein the mesylate moiety is replaced by a chloro moiety. Int. 291 was used as a mixture (not quantified) in the next reaction step.)

Example A25 a-1) Preparation of Int. 292

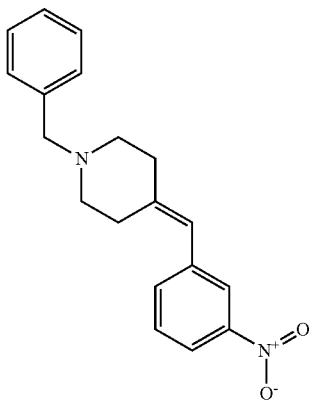 [SMILES: O=[N+]([O-])c1cccc(C=C2CCN(Cc3ccccc3)CC2)c1]

A solution of lithium diisopropylamide was freshly prepared via dropwise addition of n-butyllithium (1.6 M solution in hexanes; 22.7 mL; 36.3 mmol) to a cold solution of diisopropylamine (5.1 mL; 36.3 mmol) in THF (37 mL) under $N_2$ atmosphere. This solution was added dropwise to a cold suspension of [(3-nitrophenyl)methyl]triphenyl-phosphonium chloride (10.5 g; 24.2 mmol) in THF (extra dry; 60 mL) under $N_2$ atmosphere. The reaction mixture was stirred at room temperature for 45 minutes and then at 50° C. for 30 minutes. The reaction mixture was cooled to 0° C. A solution of N-benzyl-4-piperidone (4.5 mL; 24.2 mmol) in THF (extra dry; 23 mL) was added dropwise to this mixture. The reaction mixture was refluxed for 5 h and was then concentrated to dryness. The residue was purified by chromatography over silica gel eluting with a gradient of EtOAc in heptane from 0 to 60%. The desired fractions were collected and the solvent was evaporated. Yield: 1.95 g of Int. 292 (26%).

a-2) Preparation of Int. 298

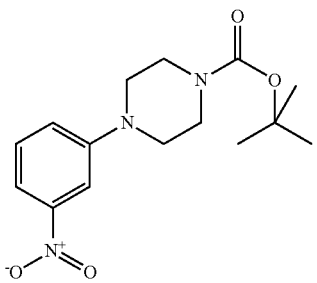

Tert-butyl dicarbonate (2.24 g; 10.26 mmol) and 4-(N,N-dimethylamino)pyridine (0.125 g; 1.03 mmol) were added to a mixture of 1-(3-nitrophenyl)-piperazine monohydrochloride (2.5 g; 10.26 mmol) solution in DCM (40 mL) and sodium carbonate 1 M solution in water (20 mL). The mixture was stirred at room temperature. The organic layer was separated and concentrated and the residue purified by column chromatography eluting with a gradient from 100% DCM to 100% DCM/MeOH 9/1. The desired fractions were collected and the solvent was evaporated. Yield: 2.644 g of Int. 298 (84%).

b) Preparation of Int. 293

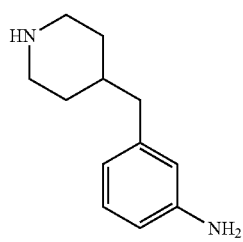 [SMILES: Nc1cccc(CC2CCNCC2)c1]

Int. 292 (1 g; 3.24 mmol) was dissolved in MeOH (3 mL) and cooled to 0° C. (ice-bath) under $N_2$ atmosphere. Palladium on activated carbon 10 wt. % as a catalyst (0.2 g) was added. The reaction mixture was hydrogenated at room temperature under $H_2$ atmosphere overnight. The suspension was filtered through a pad of Celite® and washed with MeOH. The solvent was evaporated under reduced pressure. The residue was used as such in the next reaction step. Yield: 0.604 g of Int. 293 (98%).

The intermediates in the table below were prepared according to an analogous reaction protocol as used for Int. 293:

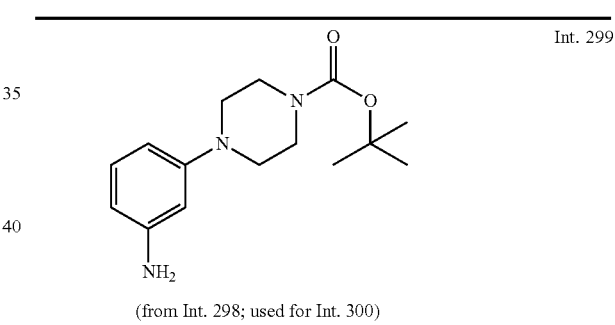

Int. 299

(from Int. 298; used for Int. 300)

c) Preparation of Int. 294

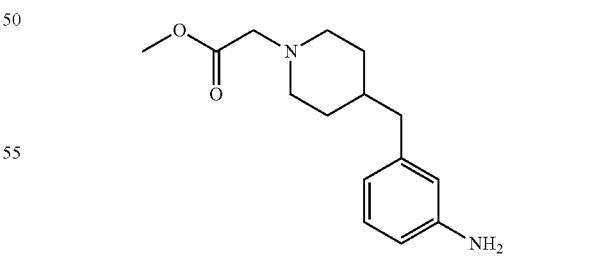

Int. 293 (0.74 g; 3.9 mmol) was dissolved in ACN (10 mL). $K_2CO_3$ (1.08 g; 7.8 mmol) was added followed by methyl bromoacetate (0.37 mL; 3.9 mmol). The reaction mixture was stirred at room temperature overnight. The mixture was filtered. The filtrate was concentrated to dryness. The residue was purified by chromatography over silica gel eluting with a gradient from 100% DCM to 40%

DCM and 60% (DCM/MeOH 9/1 v/v). The desired fractions were collected and the solvent was evaporated. Yield: 0.449 g of int 294 (44%).

d) Preparation of Int. 295

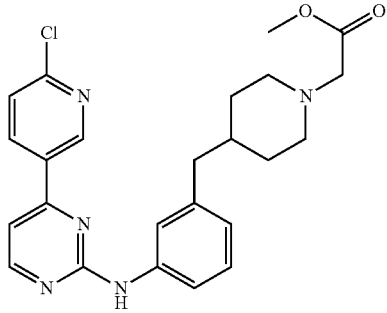 [SMILES: COC(=O)CN1CCC(Cc2cccc(Nc3nccc(-c4ccc(Cl)nc4)n3)c2)CC1]

2-Chloro-4-(6-chloro-3-pyridinyl)-pyrimidine (WO 2009112439) (0.773 g; 3.42 mmol), Int. 294 (0.449 g; 1.71 mmol) and p-toluenesulfonic acid monohydrate (0.325 g; 1.71 mmol) were dissolved in a mixture of 1,4-dioxane (20 mL) and 2-propanol (5 mL). The reaction mixture was heated at 100° C. overnight. The reaction mixture was concentrated to dryness. The residue was dissolved in DCM/MeOH 10/1 v/v (20 ml) and washed with 1 M NaOH aqueous solution (10 ml). The aqueous phase was extracted again with DCM/MeOH 10/1 v/v (20 ml). The combined organic solutions were dried over MgSO$_4$, filtered and concentrated to dryness.

The residue was purified by column chromatography over silica gel eluting with a gradient from 100% DCM to 100% DCM/MeOH 9/1 v/v. The desired fractions were collected and the solvent was evaporated. Yield: 0.232 g of Int. 295 (15%).

The intermediates in the table below were prepared according to an analogous reaction protocol as used for Int. 295:

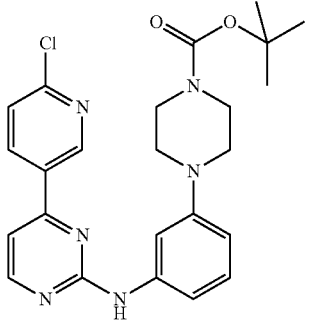

Int. 300

(from Int. 299; used for Int. 301)

e) Preparation of Int. 296

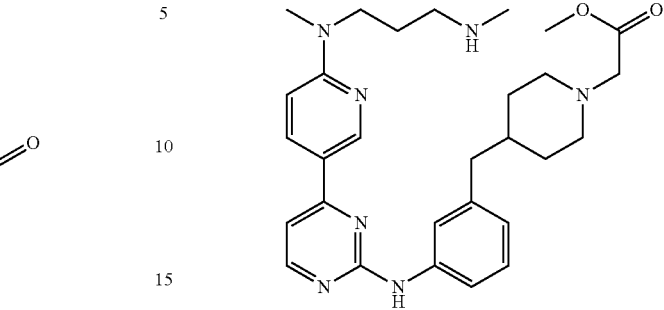

N,N-dimethyl-1,3-propanediamine (0.5 mL) was added to Int. 295 (0.232 g; 0.51 mmol). The reaction mixture was heated at 110° C. for 4 h and was then concentrated to dryness. The residue was purified by chromatography over silica gel eluting with DCM/MeOH 5/1, v/v in DCM from 0 to 100%. Yield: 0.162 g Int. 296 (61%).

The intermediates in the table below were prepared according to an analogous reaction protocol as used for Int. 296:

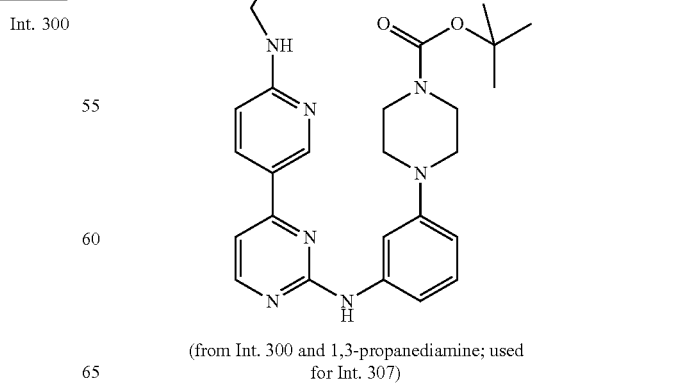

Int. 301

(from Int. 300 and N,N-dimethyl-1,3-propanediamine; used for Int. 302)

Int. 306

(from Int. 300 and 1,3-propanediamine; used for Int. 307)

f) Preparation of Int. 302

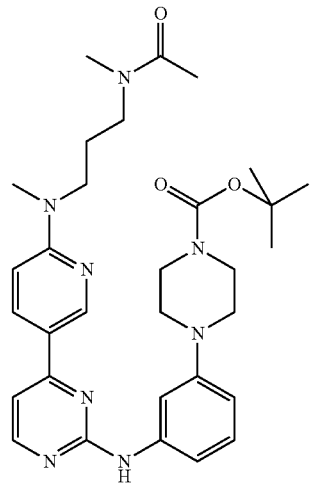 [SMILES: CC(=O)N(C)CCCN(C)c1ccc(-c2ccnc(Nc3cccc(N4CCN(C(=O)OC(C)(C)C)CC4)c3)n2)cn1]

Sodium bicarbonate saturated solution in water (4 mL) was added to a suspension of Int. 301 (0.31 g; 0.58 mmol) in DCM (12 ml) and the mixture was cooled to 0-5° C. in an ice/water bath. A solution of acetyl chloride (0.684 mL; 9.4 mmol) in DCM (5 ml) was added dropwise over 10 minutes. The mixture was allowed to warm up to room temperature and stirred for 1 h. Water was added and the product was extracted with DCM. The organic layer was separated, dried over MgSO$_4$, filtered and concentrated to dryness. Yield: 0.317 g of Int. 302 (60%).

The intermediates in the table below were prepared according to an analogous reaction protocol as used for Int. 302:

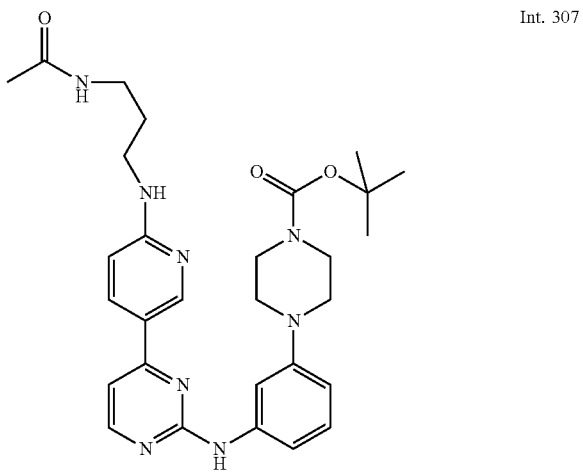

Int. 307

(from Int. 306; used for Int. 308)

g) Preparation of Int. 303

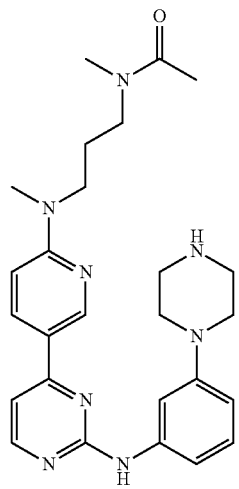 [SMILES: CC(=O)N(C)CCCN(C)c1ccc(-c2ccnc(Nc3cccc(N4CCNCC4)c3)n2)cn1]

A mixture of Int. 302 (0.317 g; 0.55 mmol) in HCl 4 N solution in 1,4-dioxane (5 mL) was stirred at room temperature for 1 h. The crude was concentrated and then dried under high vacuum. NaOH 1 N solution in water was added and the product was extracted with DCM. The organic layer was separated, dried over MgSO$_4$, filtered and concentrated to dryness. Yield: 0.262 g of Int. 303 (100%).

The intermediates in the table below were prepared according to an analogous reaction protocol as used for Int. 303:

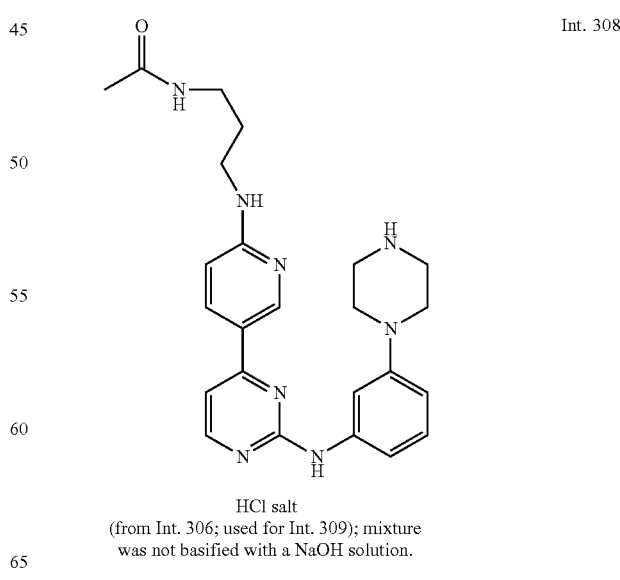

Int. 308

HCl salt
(from Int. 306; used for Int. 309); mixture
was not basified with a NaOH solution.

h) Preparation of Int. 304

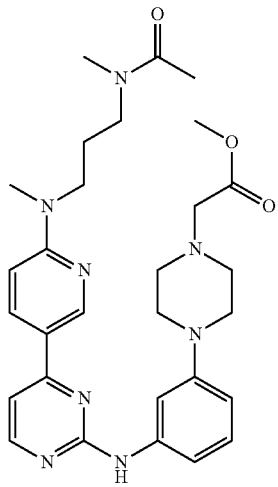 [SMILES: COC(=O)CN1CCN(c2cccc(Nc3nccc(-c4ccc(N(C)CCCN(C)C(C)=O)nc4)n3)c2)CC1]

Methyl bromoacetate (0.063 mL; 0.66 mmol) and $K_2CO_3$ (0.084 g; 0.61 mmol) were added to a solution of Int. 303 (0.262 g, 0.55 mmol) in ACN (12 mL) and DMF (2 mL). The reaction mixture was stirred at room temperature. Water was added. The product was extracted with EtOAc. The organic layer was separated, dried over $MgSO_4$, filtered, concentrated and purified by column chromatography eluting with a gradient from 100% DCM to 100% DCM/MeOH 9/1. The desired fractions were collected and the solvent was evaporated. Yield: 0.298 g of Int. 304 (99%).

The intermediates in the table below were prepared according to an analogous reaction protocol as used for Int. 304:

Int. 309

(from Int. 308; used for Int. 310)

i) Preparation of Int. 297

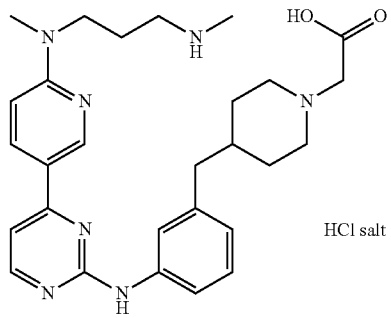 [SMILES: CNCCCN(C)c1ccc(-c2ccnc(Nc3cccc(CC4CCN(CC(=O)O)CC4)c3)n2)cn1]

HCl salt

Int. 296 (0.162 g) was dissolved in a mixture of NaOH 1 M solution in water (3 mL), MeOH (0.5 mL) and THF (0.5 mL). The reaction mixture was stirred at room temperature overnight and was then acidified to pH 6.0 by the addition of HCl 1 M solution in water. The reaction mixture was concentrated to dryness. The residue was dried under high vacuum, at room temperature to give 0.312 g of Int. 297 which was used as such in the next reaction step.

The intermediates in the table below were prepared according to an analogous reaction protocol as used for Int. 297:

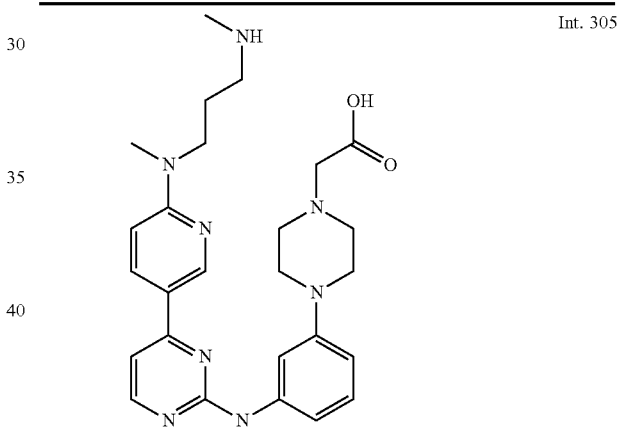

Int. 305

HCl salt
(from Int. 304; used for Co. 110)

Int. 310

HCl salt
(from Int. 309; used for Co. 111)

Example A26 a) Preparation of Int. 314

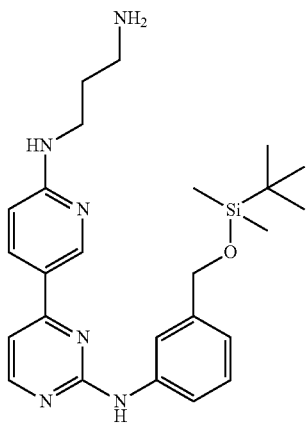 [SMILES: CC(C)(C)[Si](C)(C)OCc1cccc(Nc2nccc(-c3ccc(NCCCN)nc3)n2)c1]

Int. 209 (4.3 g; 10.1 mmol) and 1,3 diaminopropane (7.5 g; 101 mmol) were stirred at 110° C. until complete conversion. NaOH 1 M and H$_2$O were added. The product was filtered and dried to give 3.182 g of Int. 314 (68%).

The intermediates in the table below were prepared according to an analogous reaction protocol as used for Int. 314:

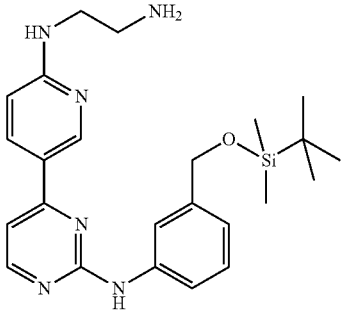

Int. 321

(from 1,2-ethanediamine; used for Int. 322)

b) Preparation of Int. 315

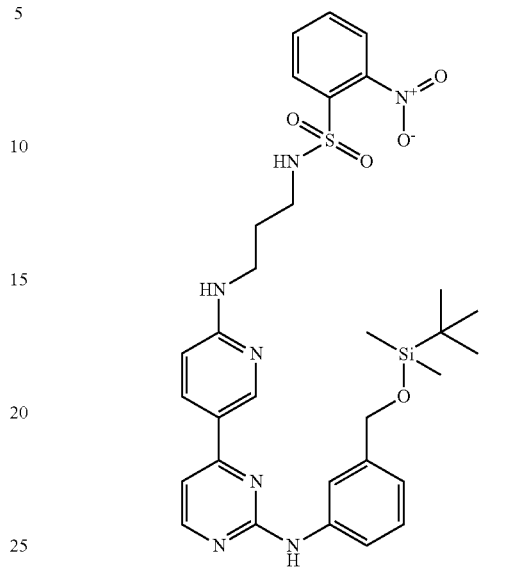

Int. 314 (3.18 g; 6.85 mmol) and DIPEA (2.5 mL; 13.7 mmol) were added to DCM (40 mL). The mixture was stirred at 0° C. under N$_2$ atmosphere. Then 2-nitrobenzene sulfonyl chloride (1.88 g; 8.22 mmol) was added dropwise and the mixture was allowed to reach room temperature. The reaction mixture was washed with Na$_2$CO$_3$ 1 M and the water layer was extracted with DCM. The combined organic layers were dried over MgSO$_4$, filtered, concentrated and purified by column chromatography over silica gel eluting with a gradient from 100% DCM to 30% DCM and 70% DCM/MeOH (9/1). The pure fractions were combined and solvent evaporated to yield 2.516 g of Int. 315 (57%).

The intermediates in the table below were prepared according to an analogous reaction protocol as used for Int. 315:

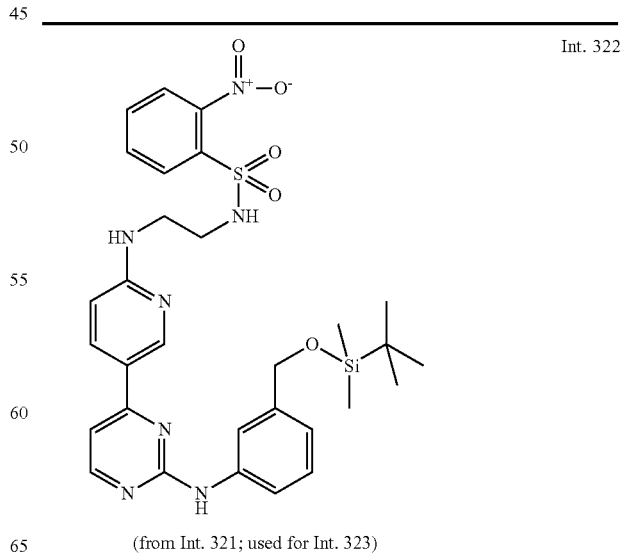

Int. 322

(from Int. 321; used for Int. 323)

c) Preparation of Int. 316

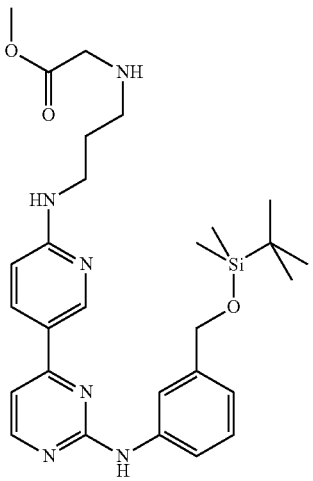 [SMILES: COC(=O)CNCCCNc1ccc(-c2ccnc(Nc3cccc(CO[Si](C)(C)C(C)(C)C)c3)n2)cn1]

Methyl bromoacetate (0.483 ml; 5 mmol) was added to a mixture of Int. 315 (2.516 g; 3.87 mmol) and cesium carbonate (2.52 g; 7.74 mmol) in DMF (40 mL). The mixture was stirred at room temperature for 2 h. Then thiophenol (0.593 ml; 5.81 mmol) was added and the reaction mixture was stirred for an additional 30 min. The reaction mixture was poured into water and extracted with EtOAc. The organic layer was washed with brine and concentrated to dryness. The residue was purified by column chromatography over silica gel eluting with a gradient of MeOH in DCM from 0 to 10%. The pure fractions were combined and solvent evaporated to yield 1.412 g of Int. 316 (68%).

The intermediates in the table below were prepared according to an analogous reaction protocol as used for Int. 316:

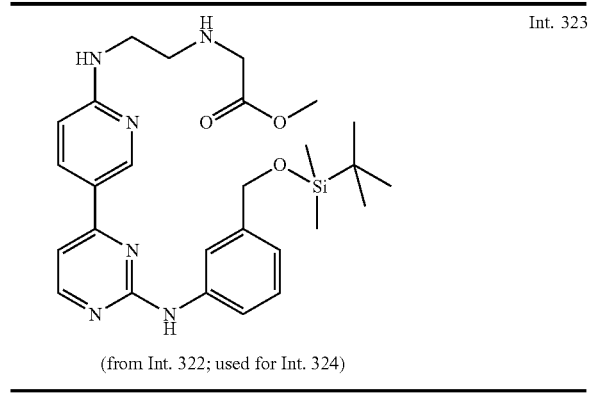

Int. 323

(from Int. 322; used for Int. 324)

d) Preparation of Int. 317

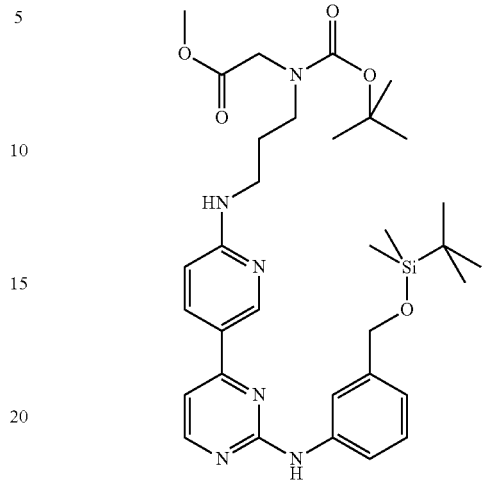

Tert-butyloxycarbonyl anhydride (0.574 g; 2.63 mmol) and DMAP (0.032 g; 0.26 mmol) were added to mixture of Int. 316 (1.412 g; 2.63 mmol) in DCM (25 mL). The mixture was stirred at room temperature until complete conversion. The reaction mixture was concentrated and purified by column chromatography over silica gel eluting with a gradient of 100% DCM to DCM/MeOH 9/1. The pure fractions were combined and solvent evaporated to yield 1.552 g of Int. 317 (93%).

The intermediates in the table below were prepared according to an analogous reaction protocol as used for Int. 317:

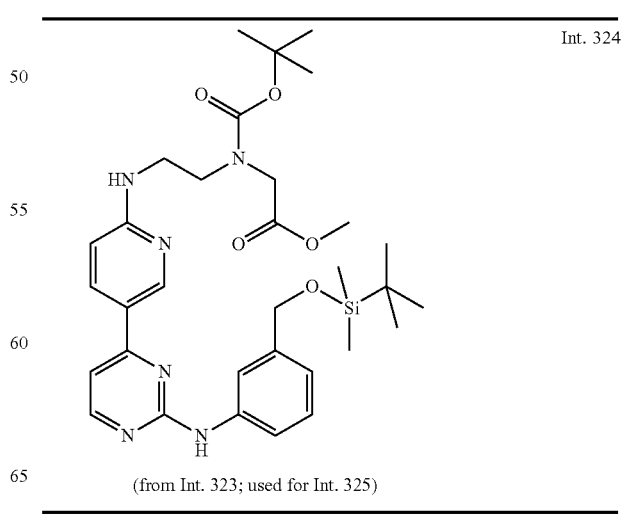

Int. 324

(from Int. 323; used for Int. 325)

e) Preparation of Int. 318

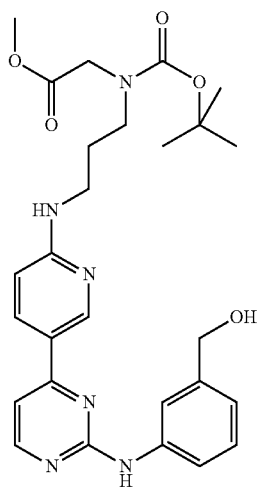 [SMILES: COC(=O)CN(CCCNc1ccc(-c2ccnc(Nc3cccc(CO)c3)n2)cn1)C(=O)OC(C)(C)C]

Int. 317 (1.552 g; 2.44 mmol) was dissolved in THF (25 mL).

Tetrabutylammoniumfluoride trihydrate (1.54 g; 4.88 mmol) was added. The reaction mixture was stirred at room temperature for 5 h and was concentrated to dryness. The residue was taken up into water and was extracted with EtOAc. The organic layer was washed with H₂O and then with saturated NaCl. The organic layer was dried over MgSO₄, filtered and concentrated to dryness. The residue was purified by chromatography over silica gel eluting with a gradient from 100% DCM to 30% DCM and 70% DCM/MeOH 9/1, v/v. The pure fractions were combined and solvent evaporated to yield 0.941 g of Int. 318 (74%).

The intermediates in the table below were prepared according to an analogous reaction protocol as used for Int. 318:

f) Preparation of Int. 319

Methane sulfonyl chloride (0.3 ml; 3.5 mmol) was added in two portions to a solution Int. 318 (0.941 g; 1.8 mmol) and DIPEA (1.6 ml; 9 mmol) in DMF (15 ml). The reaction mixture was stirred for 30 min. 1-Piperazinecarboxylic acid, 1,1-dimethylethyl ester (0.7 g; 3.6 mmol) was added and the reaction mixture was stirred for 1 h at room temperature and then heated at 80° C. for 1 h. The reaction mixture was concentrated. The reaction mixture was taken up into EtOAc and the organic solution was washed with 1 M Na₂CO₃, brine, dried over MgSO₄, filtered and concentrated. The residue was purified by column chromatography eluting with a gradient from 100% DCM to 30% DCM and 70% DCM/MeOH (9/1). The pure fractions were combined and solvent evaporated to yield 1.14 g of Int. 319 (92%).

The intermediates in the table below were prepared according to an analogous reaction protocol as used for Int. 319:

| Int. 325 | Int. 326 |
|---|---|
| 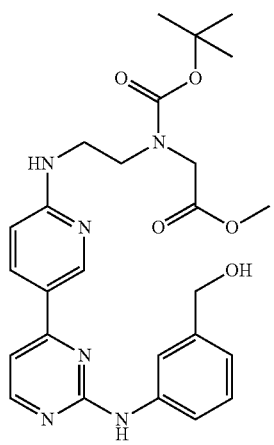 | 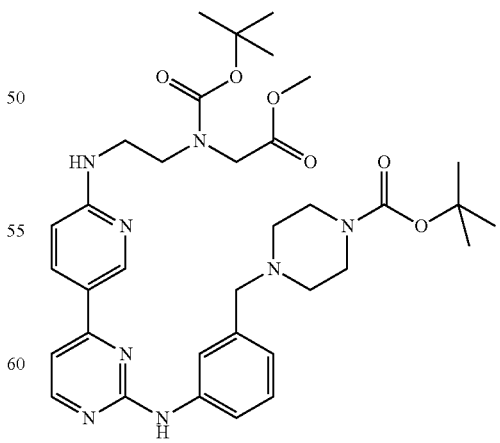 |
| (from Int. 324; used for Int. 326) | (from Int. 325; used for Int. 327) |

Int. 184

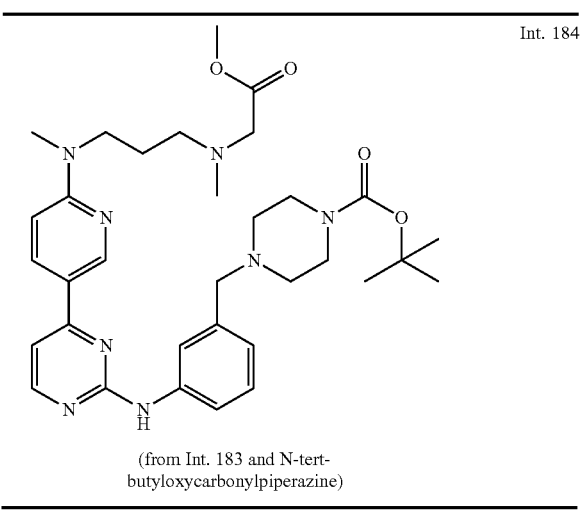

(from Int. 183 and N-tert-butyloxycarbonylpiperazine)

g) Preparation of Int. 320

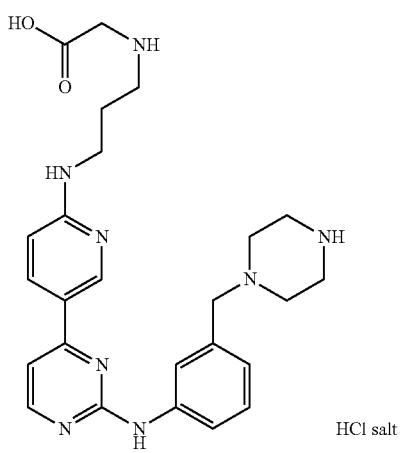 [SMILES: O=C(O)CNCCCNc1ccc(-c2ccnc(Nc3cccc(CN4CCNCC4)c3)n2)cn1]

HCl salt

Int. 319 (1.14 g; 1.65 mmol) was dissolved in a mixture of NaOH 1 N (17 ml; 16.5 mmol) and THF (4 mL). The reaction mixture was stirred overnight at room temperature. HCl (10 mL; 37%) was added. The reaction mixture was heated at 40° C. overnight. The reaction mixture was concentrated to dryness and dried under high vacuum, at room temperature. The residue was used as such in the next reaction step. Yield: 0.786 g of Int. 320.

The intermediates in the table below were prepared according to an analogous reaction protocol as used for Int. 320:

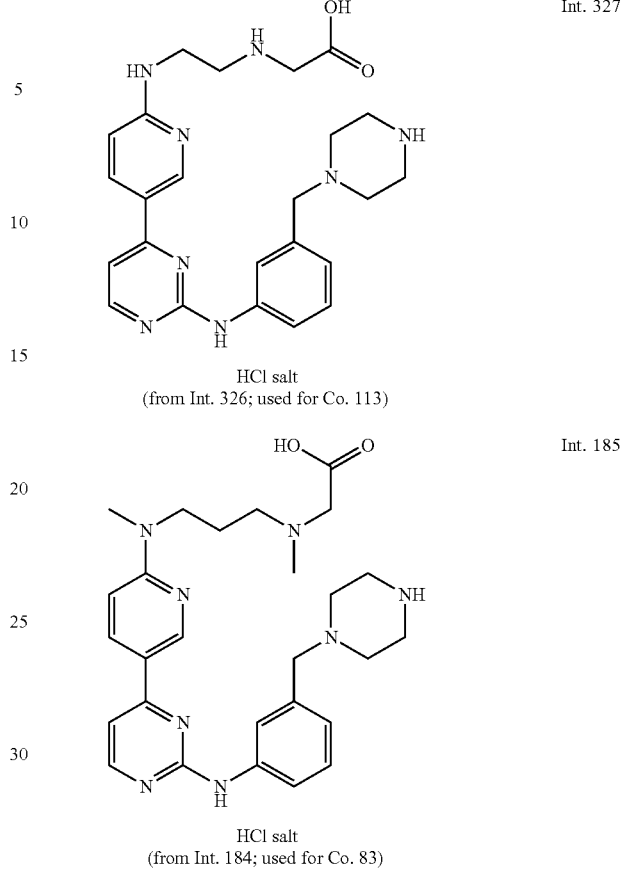

Int. 327

HCl salt
(from Int. 326; used for Co. 113)

Int. 185

HCl salt
(from Int. 184; used for Co. 83)

Example A27 a) Preparation of Int. 328

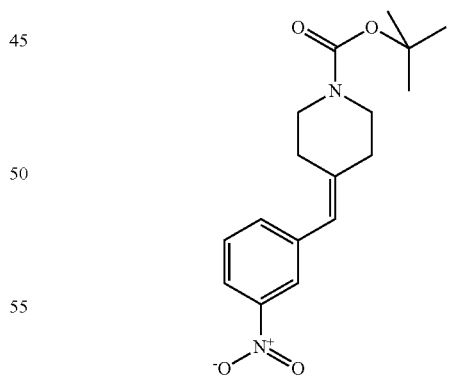

A saturated sodium hydrogenocarbonate solution in water (30 mL) and tert-butoxycarbonyl anhydride (1.28 g; 5.85 mmol) were added successively to a solution of 4-(4-nitrobenzylidene)piperidine (WO 2011051282) (1.35 g; 5.32 mmol) in DCM. The mixture was stirred for 1 h and then the phases were separated. The organic layer was dried over MgSO$_4$, filtered and concentrated. The residue was purified by chromatography over silica gel eluting with a gradient of EtOAc in heptane from 0% to 25%). The solvent was evaporated to yield 1.358 g of Int. 328 (80%).

b) Preparation of Int. 329

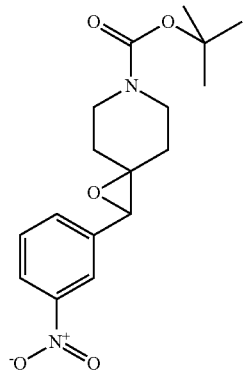

m-Chloroperoxybenzoic acid (0.81 g; 4.69 mmol) was added to an ice cooled solution of Int. 328 (1.358 g; 4.26 mmol) in chloroform (40 mL). The mixture was stirred overnight at room temperature. DCM was added and the solution was washed with 1 M Na₂CO₃. The organic layer was dried over MgSO₄, filtered and concentrated. The residue was purified by chromatography over silica gel eluting with a gradient of EtOAc in heptane from 0% to 35%. The solvent was evaporated to give 0.72 g of Int. 329 (53%).

c) Preparation of Int. 330

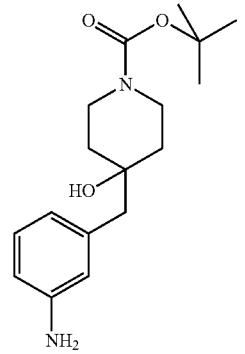 [SMILES: CC(C)(C)OC(=O)N1CCC(O)(Cc2cccc(N)c2)CC1]

Palladium (0.25 g) as a catalyst was added to a solution of Int. 329 (0.5 g; 1.49 mmol) was dissolved in MeOH at 0° C. The reaction mixture was hydrogenated at room temperature under H₂ gas atmosphere for 6 h. The catalyst was filtered off through a pad of Celite®. The filtrate was concentrated to an oil and dried under vacuum to yield 0.315 g of Int. 330 (69%).

d) Preparation of Int. 331

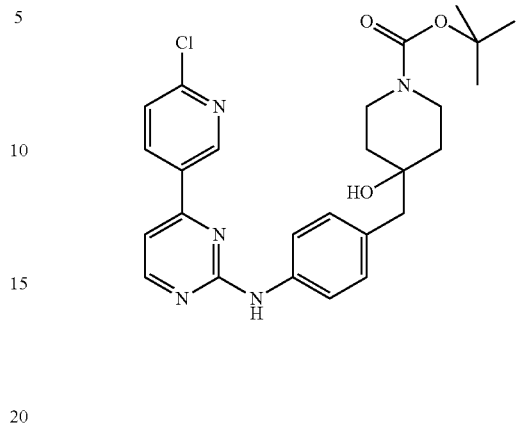

A solution of 2-chloro-4-(6-chloro-3-pyridinyl)-pyrimidine (WO 2009112439) (0.233 g; 1.03 mmol), Int. 330 (0.315 g; 1.03 mmol) and 4-toluenesulfonic acid (0.04 g; 0.206 mmol) were refluxed (110° C.) in 1,4-dioxane (10 mL) for 16 h. The reaction mixture was concentrated, the residue was dissolved in EtOAc and washed with 1 M Na₂CO₃. The organic layer was dried over MgSO₄, filtered and concentrated. The crude was purified by column chromatography eluting with a gradient of EtOAc in Heptane from 0% to 50%. The desired fractions were collected and the solvent was evaporated to give 0.21 g of Int. 331 (41%).

e) Preparation of Int. 332

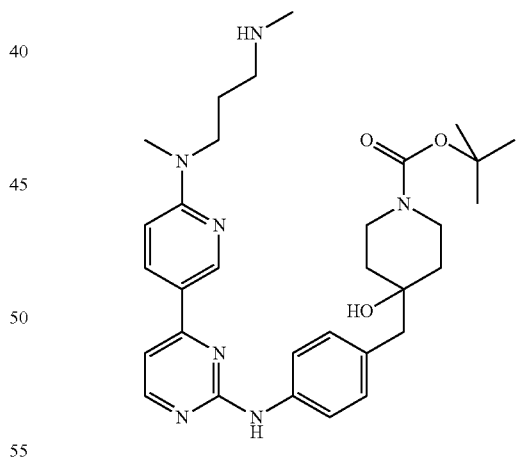

A solution of Int. 331 (0.21 g 0.42 mmol) in N,N'-dimethylpropanediamine (0.25 g; 2.12 mmol) was heated at 100° C. for 3 h. The solvent was evaporated and the residue was purified by column chromatography eluting with a gradient from 100% DCM to 100% DCM/MeOH (5/1). The desired fractions were collected and the solvent was evaporated to give 0.237 g of Int. 332 (100%).

f) Preparation of Int. 333

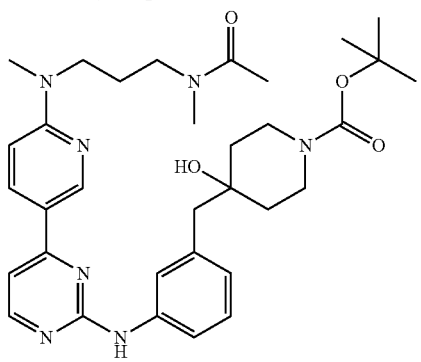 [SMILES: CC(=O)N(C)CCCN(C)c1ccc(-c2ccnc(Nc3cccc(CC4(O)CCN(C(=O)OC(C)(C)C)CC4)c3)n2)cn1]

Acetyl chloride (0.035 mL; 0.5 mmol) was added to a solution of Int. 332 (0.23 g; 0.41 mmol) and Et₃N (0.14 mL; 1 mmol) in DCM (15 mL). After 2 h the reaction was quenched by addition of 1 M Na₂CO₃ (10 mL). The reaction mixture was extracted with DCM (2×20 mL). The organic phase was dried over MgSO₄, filtered and concentrated to dryness. The residue was purified by column chromatography over silica gel eluting with a gradient of MeOH in DCM from 0 to 5%. The desired fractions were collected and the solvent was evaporated to give 0.179 g of Int. 333 (72%).

g) Preparation of Int. 334

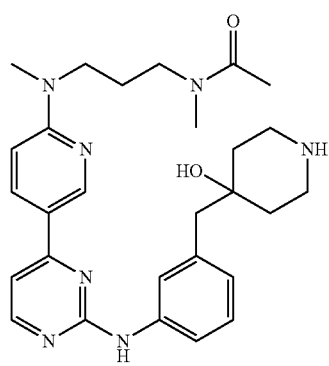 [SMILES: CC(=O)N(C)CCCN(C)c1ccc(-c2ccnc(Nc3cccc(CC4(O)CCNCC4)c3)n2)cn1]

A suspension of Int. 333 (0.179 g; 0.296 mmol) was taken in 4 N HCl in dioxane (4 mL) and stirred overnight. The mixture was concentrated and the crude Int. 334 was used as such in the next step.

h) Preparation of Int. 335

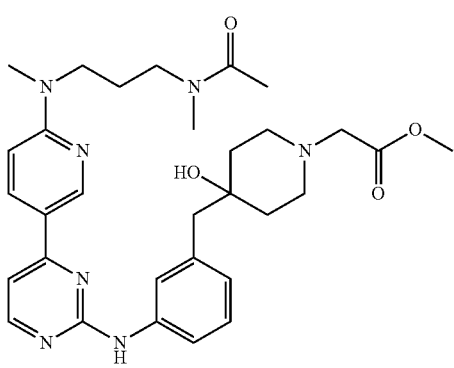 [SMILES: COC(=O)CN1CCC(O)(Cc2cccc(Nc3nccc(-c4ccc(N(C)CCCN(C)C(C)=O)nc4)n3)c2)CC1]

Int. 334 (crude) was suspended in 4 N HCl in dioxane (4 mL). Potassium carbonate (0.082 g; 0.5992 mmol) and methyl bromoacetate (0.029 mL; 0.296 mmol) were added and the suspension was stirred overnight. The reaction mixture was concentrated to dryness and the residue was purified by flash column chromatography over silica gel eluting with a gradient of MeOH in DCM from 0 to 10%. The desired fractions were collected and the solvent was evaporated to yield 0.165 g of Int. 335.

i) Preparation of Int. 336

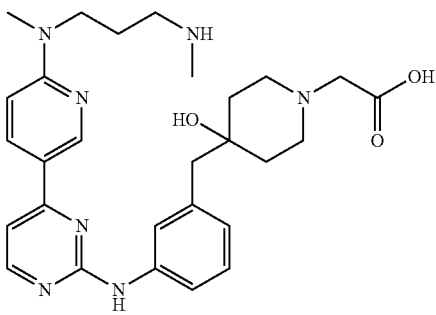 [SMILES: CNCCCN(C)c1ccc(-c2ccnc(Nc3cccc(CC4(O)CCN(CC(=O)O)CC4)c3)n2)cn1]

1 M NaOH (5 mL; 5 mmol) was added to a solution of Int. 335 (0.163 g; 0.283 mmol) in MeOH (1 mL) and THF (1 mL). The mixture stirred for 2 h at room temperature. HCl (37%) (1 mL) was added and the mixture was heated at 100° C. for 36 h. The mixture was concentrated to dryness and the crude Int. 336 was used as such in next reaction step.

Example A28 a) Preparation of Int. 337

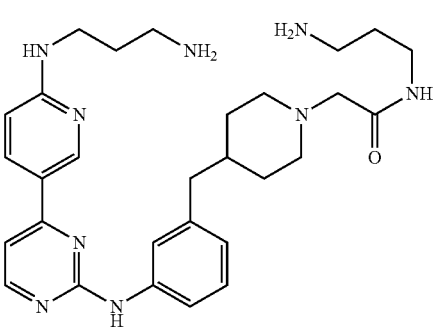 [SMILES: NCCCNC(=O)CN1CCC(Cc2cccc(Nc3nccc(-c4ccc(NCCCN)nc4)n3)c2)CC1]

A mixture of Int. 295 (1.76 g; 3.89 mmol) and 1,3-propanediamine (3.27 mL; 38.9 mmol) was heated at 100° C. overnight. The reaction mixture was concentrated to dryness. The residue was dried under high vacuum to give 4.34 g of Int. 337 which was used as such in the next reaction step.

b) Preparation of Int. 338

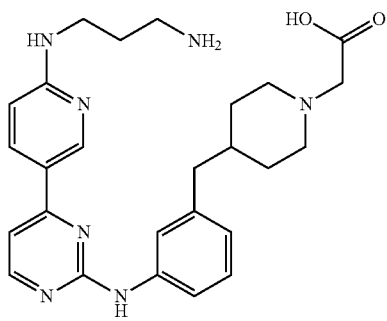 [SMILES: NCCCNc1ccc(-c2ccnc(Nc3cccc(CC4CCN(CC(=O)O)CC4)c3)n2)cn1]

A solution of Int. 337 (4.34 g) in HCl (37%) (20 mL) was refluxed for 5 days. The reaction mixture was concentrated to dryness. The residue was purified by reverse phase chromatography [start (90% H$_2$O—10% CH$_3$CN—CH$_3$OH)-end (54% H$_2$O—46% CH$_3$CN—CH$_3$OH)]—[H$_2$O: 25 mM NH$_4$HCO$_3$]. The desired fractions were collected and the solvent was evaporated to give 0.458 g Int. 338 (used in the preparation of compound 115).

Example A29 a) Preparation of Int. 380

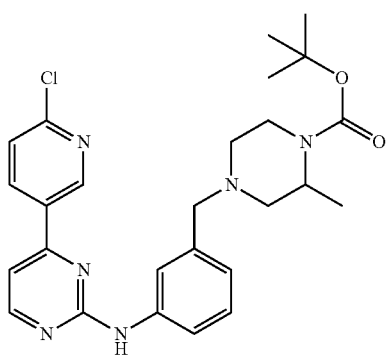 [SMILES: CC1CN(Cc2cccc(Nc3nccc(-c4ccc(Cl)nc4)n3)c2)CCN1C(=O)OC(C)(C)C]

Methanesulfonyl chloride (1.9 mL; 23.98 mmol) was added dropwise to a solution of Int. 80 (1.5 g; 4.80 mmol), DIPEA (4.2 mL; 23.98 mmol) in DCM (118 mL) at 5° C. under N$_2$ flow. The reaction mixture was stirred at 5° C. for 15 min. Water and K$_2$CO$_3$ were added. The mixture was extracted with DCM (2×). The organic layer was dried over MgSO$_4$, filtered and the solvent was evaporated. The residue was dissolved in DMF (7.6 mL) and was added dropwise to a suspension of 2-methyl-1-piperazinecarboxylic acid, 1,1-dimethylethyl ester (1.22 g; 6.08 mmol) and K$_2$CO$_3$ (2.8 g; 20.26 mmol) in DMF (5.5 mL). The mixture was stirred at r.t. for 30 min. Water and EtOAc were added. The mixture was extracted with EtOAc (3×). The organic layer was dried over MgSO$_4$, filtered and the solvent was evaporated. The residue was purified by preparative LC on (irregular SiOH 15-40 μm 300 g Merck). Mobile phase (60% Heptane, 3% MeOH, 37% EtOAc). The desired fractions were collected and the solvent was evaporated, yielding 1.9 g of Int. 380 as a yellow foam (61%).

b) Preparation of Int. 381

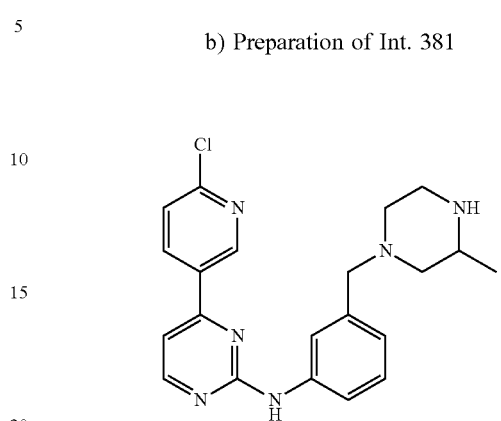

TFA (4.6 mL; 61.41 mmol) was added to a solution of Int. 380 (1.9 g; 3.07 mmol) in DCM (21 mL) at 0-5° C. The reaction mixture was stirred at r.t. for 4 h. More TFA (6.9 mL; 92.12 mmol) was added. The reaction mixture was stirred at r.t. for 2 h The solvent was evaporated. The residue was purified by preparative LC on (Irregular SiOH 20-45 μm 450 g MATREX). Mobile phase NH$_4$OH, DCM, MeOH 0.5/93/7. The desired fractions were collected and the solvent was evaporated, yielding 1.22 g of Int. 381 (78%).

c) Preparation of Int. 382

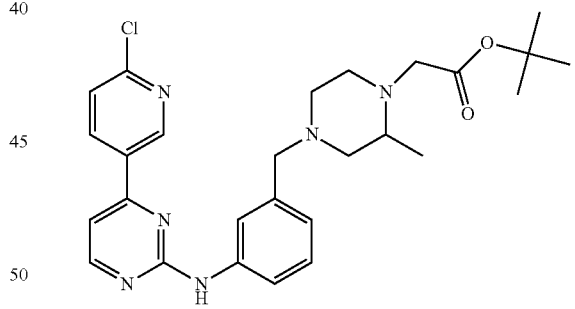

Et$_3$N (327 μL; 2.355 mmol) was added portionwise to a stirred solution of Int. 381 (620 mg; 1.57 mmol) in DCM (4.3 mL; 67.51 mmol) at r.t. The r.m. was stirred for 45 min and was then cooled down to 0-5° C. Tert-butyl bromoacetate (299 μL; 2.041 mmol) was added and the reaction mixture was stirred at r.t. for 5 h and was then poured into water and extracted with DCM. The organic layer was dried, filtered and evaporated. The residue was purified by preparative LC on (irregular SiOH 15-40 μm 30 g MERCK). Mobile phase: pure DCM to DCM, MeOH, NH$_4$OH 97/3/0.3). The desired fractions were collected and the solvent was evaporated to give 650 mg of Int. 382.

d) Preparation of Int. 383

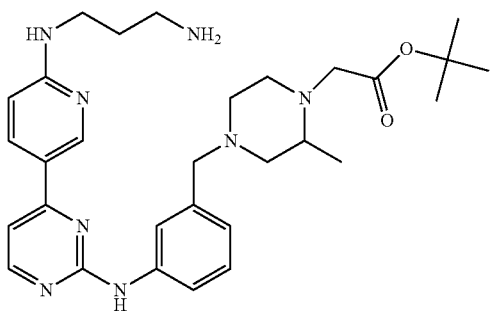 [SMILES: CC1CN(Cc2cccc(Nc3nccc(-c4ccc(NCCCN)nc4)n3)c2)CCN1CC(=O)OC(C)(C)C]

A mixture of Int. 382 (0.63 g; 1.238 mmol) and 1,3-diaminopropane (0.42 mL; 4.95 mmol) in NMP (1.3 mL) in a sealed tube was heated at 110° C. using one single mode microwave (Biotage Initiator EXP 60) with a power output ranging from 0 to 400 W for 90 min [fixed hold time]. The mixture was evaporated to dryness. The residue was purified by preparative LC on (irregular SiOH 15-40 µm 300 g MERCK). Mobile phase NH$_4$OH, DCM, MeOH 1/83/17. The desired fractions were collected and the solvent was evaporated to give 270 mg of Int. 383 (40%).

e) Preparation of Int. 384

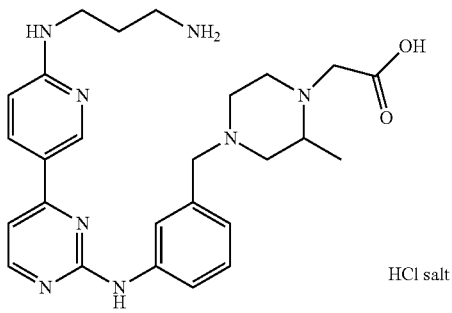 [SMILES: CC1CN(Cc2cccc(Nc3nccc(-c4ccc(NCCCN)nc4)n3)c2)CCN1CC(=O)O]

HCl salt

HCl (37% in H$_2$O) (206 µL; 2.469 mmol) and water (0.72 mL) were added to a solution of Int. 383 (270 mg; 0.494 mmol) in 1,4-dioxane (7.2 mL). The reaction mixture was stirred at 100° C. for 3 h. The solution was evaporated under reduced pressure and the residue was used without any further purification for the next reaction step.

B. Preparation of the Final Compounds

Example B1 a) Preparation of Compound 1

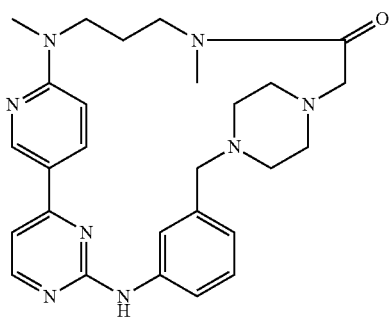 [SMILES: CN1CCCN(C)c2ccc(cn2)-c2ccnc(n2)Nc2cccc(c2)CN2CCN(CC2)CC1=O]

Diethyl cyanophosphonate (0.751 mL, 4.519 mmol) was added to a stirred solution of Int. 11 (1.6 g) and Et$_3$N (6.281 mL, 45.186 mmol) in DMF (100 ml) at room temperature. The reaction mixture was stirred at room temperature for 2 h. The reaction mixture was flushed with N$_2$-gas for 15 minutes and then a saturated aqueous NaHCO$_3$ solution (q.s.) was added. This mixture was stirred for 10 minutes and then diluted with water and a mixture of 10% MeOH and 90% DCM. The organic layer was separated. The water layer was extracted twice with a mixture of 10% MeOH and 90% DCM. The combined organic layers were washed with water, dried with MgSO$_4$, filtered and the filtrate was evaporated. Yield: 0.92 g of compound 1.

b) Preparation of Compound 14

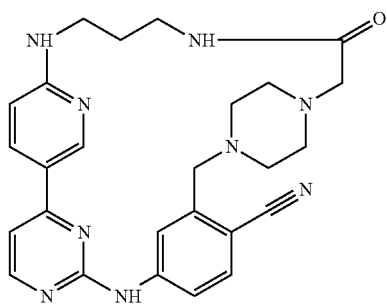 [SMILES: N#Cc1ccc2cc1CN1CCN(CC1)CC(=O)NCCCNc1ccc(cn1)-c1ccnc(n1)N2]

Diethyl cyanophosphonate (0.185 mL, 1.237 mmol) was added to a solution of Int. 47 (330 mg) and Et$_3$N (0.172 mL, 1.237 mmol) in DMF (45 ml) at room temperature. The reaction mixture was stirred at room temperature for 16 h. The solution was concentrated under reduced pressure. The residue was stirred in 0.1 M aqueous NaHCO$_3$ (50 ml) at room temperature for 2 h. The aqueous layer was decanted. The residue was crystallized from MeOH. The precipitate was filtered off and dried. Yield: 182 mg of compound 14.

c) Preparation of Compound 16

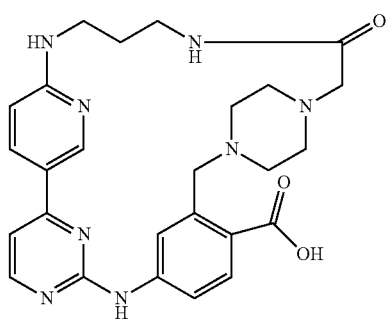 [SMILES: O=C1CN2CCN(CC2)Cc2cc(ccc2C(=O)O)Nc2nccc(n2)-c2ccc(nc2)NCCCN1]

Diethyl cyanophosphonate (0.208 mL, 1.392 mmol) was added to a solution of Int. 49 (251.99 mg) and Et$_3$N (0.194 mL, 1.392 mmol) in DMF (71 ml) at room temperature. The solution was stirred at room temperature for 1 hour. The solution was concentrated under reduced pressure. The residue was stirred in 0.1 M aqueous NaHCO$_3$ (50 ml) at room temperature for 2 h. The aqueous layer was concentrated to a volume of approximately 10 mL. The solution was purified by Preparative HPLC (Uptisphere C18 ODB—

10 μm, 200 g, 5 cm). Mobile phase (0.25% NH₄HCO₃ solution in water, MeOH). The desired fractions were collected and the solvent was evaporated. Subsequently, the residue was dissolved in DCM/MeOH and the solvent was evaporated. The residue was dried under vacuum. Yield: 36 mg of compound 16.

Example B2 a) Preparation of Compound 30

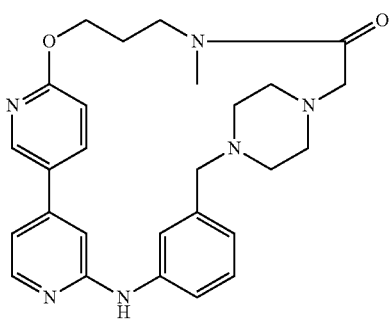

Diethylcyanophosphonate (215 μl, 1.439 mmol) was added to a solution of Int. 84 (600 mg) and DIPEA (1240 μl, 7.197 mmol) in DMF. After addition, the reaction mixture was stirred at 60° C. for 2 h. The solvent was removed under reduced pressure. The residue was dissolved in a mixture of DCM/MeOH 95/5 and washed with a saturated bicarbonate solution and water. The organic layer was dried with MgSO₄, filtered and evaporated to dryness. The residue was purified by preparative liquid chromatography on (Stability Silica 5 μm 150×30.0 mm). Mobile phase (Gradient from NH₄OH, DCM, MeOH 0.2/98/2 to NH₄OH, DCM, MeOH 0.8/92/8). The desired fractions were collected and the solvent was evaporated. Yield: 24 mg of compound 30.

Intermediate 379 was prepared according to an analogous protocol as compound 30, starting from Int. 363:

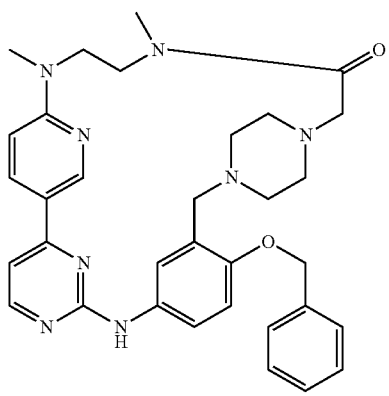 [SMILES: CN1CCN(C)c2ccc(cn2)-c2ccnc(n2)Nc2ccc(OCc3ccccc3)c(c2)CN2CCN(CC2)CC1=O]

Example B3 a) Preparation of Compound 32

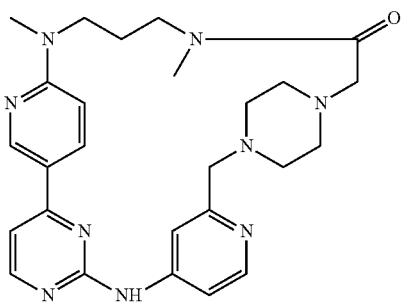 [SMILES: CN1CCCN(C)c2ccc(cn2)-c2ccnc(n2)Nc2ccnc(c2)CN2CCN(CC2)CC1=O]

Diethylcyanophosphonate (0.064 mL; 0.43 mmol) in DMF (10 mL) was added dropwise to a solution of Int. 95 (105 mg) and DIPEA (0.25 mL; 1.4 mmol in DMF (110 mL). After addition, the reaction mixture was heated at 100° C. for 4 h. The solvent was evaporated. The residue was purified by chromatography over silica gel [(Irregular SiOH, 20-45 μm, 40 g). Mobile phase: gradient from DCM, MeOH, NH₄OH 100/0/0 to DCM, MeOH, NH₄OH 80/20/0.1. The desired fractions were collected and the solvent as evaporated until dryness to give 90 mg of compound 32.

Example B4 a) Preparation of Compound 34

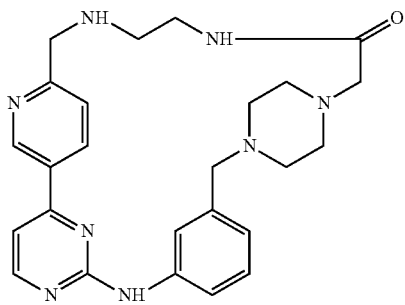 [SMILES: O=C1CN2CCN(CC2)Cc2cccc(c2)Nc2nccc(n2)-c2ccc(nc2)CNCCN1]

Diethyl cyanophosphonate (4.377 ml, 29.279 mmol) was added to a solution of Int. 109 (4.495 g) and Et₃N (4.075 ml, 29.279 mmol) in DMF (434.8 ml) at room temperature. The reaction mixture was stirred at room temperature for 16 h and was then concentrated under reduced pressure. The residue was dissolved in water (500 ml). The water layer was basified with a saturated NaHCO₃ solution (100 ml). The water layer was stirred 1 h at room temperature and was then concentrated under reduced pressure.

The residue was co-evaporated with MeOH (2×150 ml). The residue was purified by flash chromatography on silica gel: eluens DCM/MeOH(NH₃)// from 100/0 to 95/5. The pure fractions were collected and concentrated under reduced pressure. The residue was dried under vacuum at 50° C. for 16 h. Yield: 3.128 g of compound 34.

Example B5 a) Preparation of Compound 46

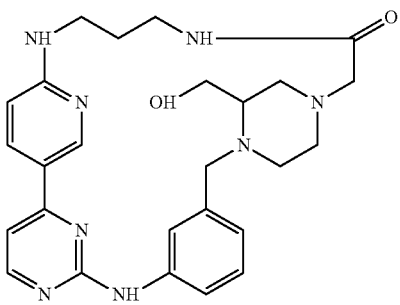 [SMILES: O=C1CN2CCN(Cc3cccc(c3)Nc3nccc(n3)-c3ccc(nc3)NCCCN1)C(CO)C2]

Diethyl cyanophosphonate (382 μL; 2.55 mmol) was added drop wise to a solution of Int. 114 (624 mg) and DIPEA (1.47 mL; 8.51 mmol) in DMF (384 mL). After addition, the reaction mixture was heated at 100° C. for 4 h. DMF was evaporated to give 1.34 g of a brown oil. The residue was purified by preparative LC (Irregular SiOH 20-45 μm 450 g MATREX). Mobile phase: NH$_4$OH, DCM, MeOH 1/93/7. The desired fractions were collected and the solvent was evaporated. Yield: 285 mg of compound 46 as a yellow oil.

Example B6 a) Preparation of Compound 85

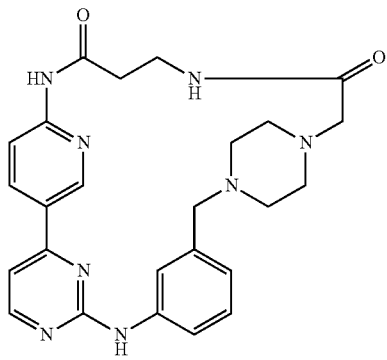 [SMILES: O=C1CN2CCN(CC2)Cc2cccc(c2)Nc2nccc(n2)-c2ccc(nc2)NC(=O)CCN1]

Diethyl cyanophosphonate (321 μL; 2.147 mmol) was added slowly to a solution of Int. 207 (450 mg; 0.716 mmol) and DIPEA (1.2 mL; 7.155 mmol) in DMF (80 mL). The reaction mixture was stirred at 100° C. for 4 h. The solvent was evaporated. The residue was purified by preparative LC on irregular SiOH 15-40 μm 300 g MERCK). Mobile phase: NH$_4$OH, DCM, MeOH 0.5/93/7. The desired fractions were collected and the product was further purified by preparative LC on irregular 15-40 μm 50 g Merck. Mobile phase: NH$_4$OH, DCM, MeOH 0.5/95/5. The desired fractions were collected and the solvent was evaporated. Yield: 21 mg of compound 85 (6%).

Example B7 a) Preparation of Compound 86

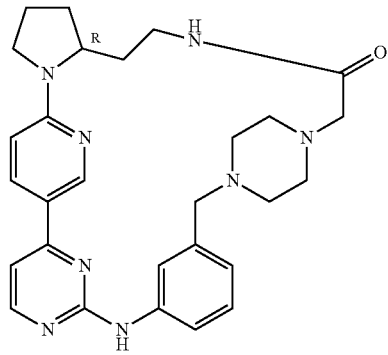

K$_2$CO$_3$ (1.41 g; 10.17 mmol) was added to a solution of Int. 216 (600 mg) in DMF (55 mL) at room temperature. The reaction mixture was stirred at 50° C. for 3 h. Water and DCM were added. The water layer was separated and extracted with DCM (3×). The combined organic solutions were dried over MgSO$_4$, filtered and the solvent was evaporated. The residue was purified by preparative liquid chromatography on irregular 15-40 μm 30 g Merck. Mobile phase: NH$_4$OH, DCM, MeOH 0.5/93/7. The desired fractions were collected and the solvent was evaporated. Yield: 70 mg of a colorless oil. The oil was freeze-dried with water-ACN to give 56 mg of compound 86.

Example B8 a) Preparation of Compound 97

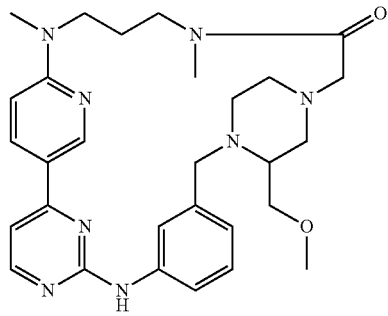 [SMILES: COCC1CN2CCN1Cc1cccc(c1)Nc1nccc(n1)-c1ccc(nc1)N(C)CCCN(C)C(=O)C2]

HCl (2 N; 4.9 mL, 9.7 mmol) was added to a solution of Int. 286 (335 mg; 0.51 mmol) in EtOH (4.9 mL). The reaction mixture was stirred at 50° C. for 5 h. A solution of aqueous K$_2$CO$_3$ 10% and DCM were added. The mixture was extracted twice with DCM. The organic layer was dried with MgSO$_4$, filtered and the solvent was evaporated. The residue was purified by preparative LC on silica gel (irregular 15-40 μm 30 g Merck). Mobile phase: NH$_4$OH, DCM, MeOH 0.1/97/3. The pure fractions were combined and the solvent was evaporated. The residue was crystallised from ACN. The precipitate was filtered off, washed with Et$_2$O and air dried to give 80 mg of compound 97.

Example B9 a) Preparation of Compound 109

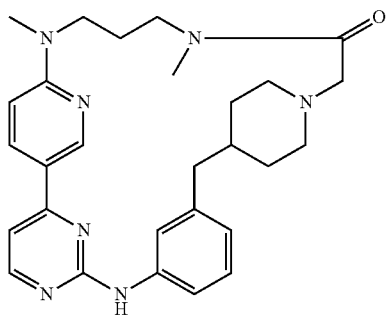 [SMILES: CN1CCCN(C)c2ccc(cn2)-c2ccnc(n2)Nc2cccc(c2)CC2CCN(CC2)CC1=O]

A mixture of Int. 297 (0.312 g; 0.313 mmol) and DIPEA (0.16 mL; 0.94 mmol) dissolved in N,N-dimethylformamide (10 mL) was added dropwise to a solution of 1-[bis(dimethylamino)methylene]-1H-Benzotriazolium-3-oxide (0.356 g; 0.939 mmol) and DIPEA (0.16 mL; 0.94 mmol) in DMF (20 mL). The reaction mixture was stirred for 1 h. The reaction mixture was concentrated to dryness. The residue was dissolved in EtOAc (20 mL) and washed with a $Na_2CO_3$ 1 M solution in water (2×10 ml). The organic layer was separated and washed once more with a saturated NaCl solution in water (10 mL). The organic layer was dried over $MgSO_4$, filtered and concentrated to dryness. The residue was purified by chromatography over silica gel eluting with a gradient from 100% DCM to 100% (DCM/MeOH 9/1, v/v). The desired fractions were collected and the solvent was evaporated. The residue was crystallized from ACN to give 0.054 g of compound 109 (36%) as a white solid.

Co. 111 was prepared according to an analogous reaction protocol as B9, but Amberlyst A-26 (OH) ion exchange resin was used in the work-up procedure.

Example B10 a) Preparation of Compound 112

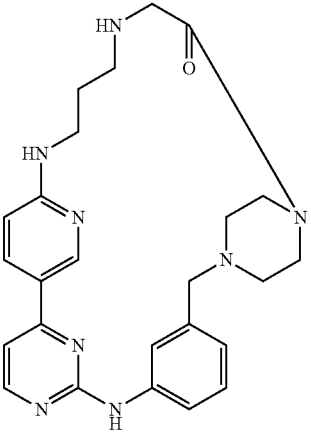 [SMILES: O=C1CNCCCNc2ccc(cn2)-c2ccnc(n2)Nc2cccc(c2)CN2CCN1CC2]

A solution of DIPEA (0.88 ml; 4.95 mmol) and Int. 320 (0; 786 g) in DMF (30 mL) was added dropwise to a solution of HBTU (1.91 g; 4.95 mmol) and DIPEA (0.59 ml; 3.3 mmol) in DMF (30 mL). The mixture was stirred at room temperature for 30 min. The reaction mixture was concentrated and taken up into EtOAc and the organic layer was washed with 1 M $Na_2CO_3$. The organic layer was dried over $MgSO_4$, concentrated and purified by column chromatography eluting over silica gel with a gradient from 100% DCM to 100% of DCM/MeOH (9/1). The pure fractions were combined and the solvent was evaporated. The product was crystallized from $CH_3CN$ to give 0.023 g of compound 112 as a brown solid.

Example B11 a) Preparation of Compound 114

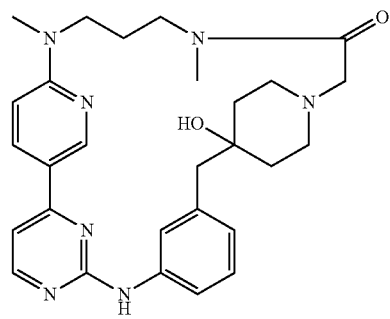 [SMILES: CN1CCCN(C)c2ccc(cn2)-c2ccnc(n2)Nc2cccc(c2)CC2(O)CCN(CC2)CC1=O]

1-[Bis(dimethylamino)methylene]-1H-benzotriazolium hexafluorophosphate(1-)3-oxide (0.3 mL) was added to a solution of Int. 336 (0.283 mmol) in DMF (10 mL) and stirred for 15 min at room temperature. The mixture was filtered and the filtrate was added dropwise over 15 min to a solution of of 1-[bis(dimethylamino)methylene]-1H-benzotriazolium hexafluorophosphate(1-)3-oxide and N-ethyldiisopropylamine (0.2 mL) in DMF (10 mL). The mixture was stirred for 1 h and concentrated to dryness. The residue was partitioned between EtOAc (20 mL) and 1 M $Na_2CO_3$ (20 mL). The aqueous phase was extracted once more with EtOAc (20 mL). The combined organic layers were dried over $MgSO_4$, filtered and concentrated. The residue was purified by chromatography over silica gel eluting with a gradient of MeOH in DCM from 0 to 20%. The product was recrystallized from hot ACN (4 mL) to give 0.035 g of compound 114.

Co. 115 was prepared according to an analogous reaction protocol as B11, but Amberlyst A-26 (OH) ion exchange resin was used in the work-up procedure.

Example B12 a) Preparation of Compound 131

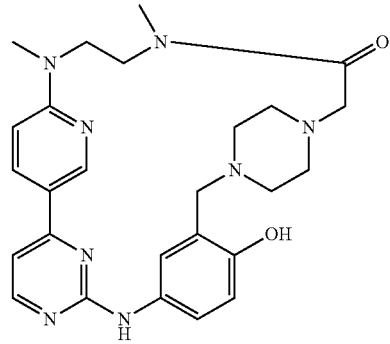 [SMILES: CN1CCN(C)c2ccc(cn2)-c2ccnc(n2)Nc2ccc(O)c(c2)CN2CCN(CC2)CC1=O]

Int. 379 (0.13 g; 0.224 mmol) was taken up in TFA (2.5 ml) and stirred at 100° C. for 4 h. The reaction mixture was concentrated to dryness. The residue was taken up in toluene (30 ml) and concentrated again. The residue was partitioned between DCM (20 ml) and saturated NaHCO₃ (20 ml). The aqueous phase was extracted once more with DCM (20 ml). The combine organic layers were dried over MgSO₄, filtered and concentrated. The residue was purified by column chromatography over silica gel eluting with a gradient of MeOH in DCM from 0 to 10%. The desired fractions were collected and evaporated.

Yield: 0.077 g of Compound 131 (70%).

Example B13 a) Preparation of Compounds 68 and 69

Compound 68

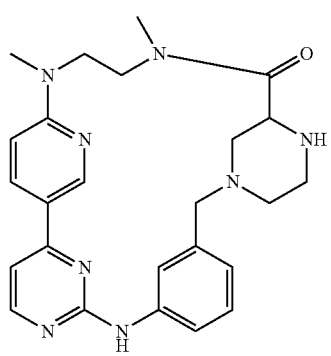

Compound 69

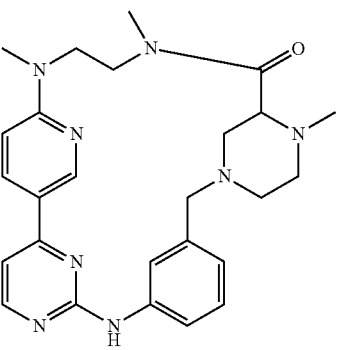

A solution of Int. 152 (1.76 g) and DIPEA (8.52 mmol, 1.45 ml) dissolved in DMF (40 mL) was added dropwise to a solution of HBTU (1.62 g 4.26 mmol) and DIPEA (4.26 mmol, 0.72 ml) dissolved in DMF (90 ml). The reaction mixture was stirred for 1 h. The reaction mixture was concentrated to dryness. The residue was dissolved in DCM/MeOH, 7/1, v/v, (2×50 ml) and washed with 1 M Na₂CO₃ (30 ml). The organic layer was separated, dried over MgSO₄, filtered and concentrated to dryness. The residue was purified over silica gel eluting with a gradient of from 100% DCM to 40% DCM and 60% DCM/NH₃ 3.5 N in MeOH, 9/1, v/v. The desired fractions were collected and the solvent was evaporated. The residue was crystallized from MeOH to give a white solid. The residue was purified by reverse phase chromatography [start (72% H₂O—28% CH₃CN-MeOH)-end (36% H₂O—64%)]-[H₂O: 65 mM NH₄OAc+CH₃CN (90:10)]. Two different product fractions were obtained. The solvent of each fraction was evaporated. Both residues were crystallized from CH₃CN. Yield: 0.065 g of Co. 68; and 0.058 g of Co. 69.

Co. 72 was prepared according to an analogous reaction protocol as B13, but Amberlyst A-26 (OH) ion exchange resin was used in the work-up procedure.

Example B14 a) Preparation of Compound 76

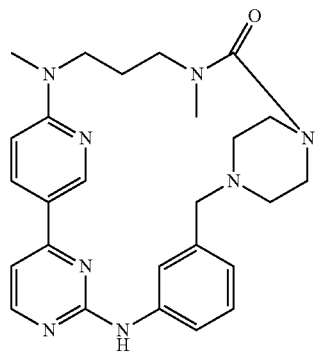 [SMILES: CN1CCCN(C)c2ccc(cn2)-c2ccnc(n2)Nc2cccc(c2)CN2CCN(CC2)C1=O]

A solution of carbonochloridic acid, 4-nitrophenyl ester (0.068 g, 0.326 mmol) in 1,4 dioxane (25 ml) was added to a solution of Int. 165 (0.485 g; 1.086 mmol) and DIPEA (0.58 mL, 3.26 mmol) in 1,4 dioxane (25 ml) at 80° C. The reaction mixture was heated to reflux (110° C.). 1 M NaOH in H₂O (15 ml) was added. The aqueous mixture was extracted with EtOAc (50 ml), dried over MgSO₄, filtered, and the solvent was evaporated. The residue was purified by column chromatography over silica gel eluting with a gradient from DCM 100% to 50% DCM and 50% (MeOH/DCM 9/1). The desired fraction were collected and the solvent was evaporated. Yield: 0.09 g of compound 76 (2%).

Compound 130 was prepared by using successively analogous reaction protocols as used for Int. 164, Int. 165 and compound 76, starting from Int. 85 instead of Int. 122 (which was used for the synthesis of Int. 164).

Example B15 a) Preparation of Compound 84

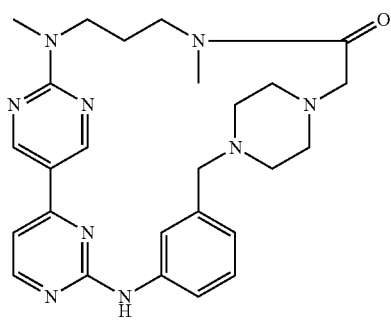

HCl (4 M in dioxane) (0.0212 mL; 0.0846 mmol) was added to a stirred solution of Int. 191 (10 mg; 0.00846 mmol) in 1,4-dioxane (0.31 mL) at room temperature. The reaction mixture was stirred at 60° C. for 2 h. The solvent was evaporated. DMF (1 mL), Et₃N (23.522 µL; 0.169 mmol) and diethylcyanophosphonate (2.811 µL; 0.0169 mmol) were added and the reaction mixture was stirred at room temperature for 2 h. The reaction was quenched by the addition of water. The product was extracted twice with DCM. The organic layer was washed with water, dried with MgSO₄, filtered and the filtrate was evaporated. Yield: 29 mg of compound 84.

Example B16 a) Preparation of Compound 89

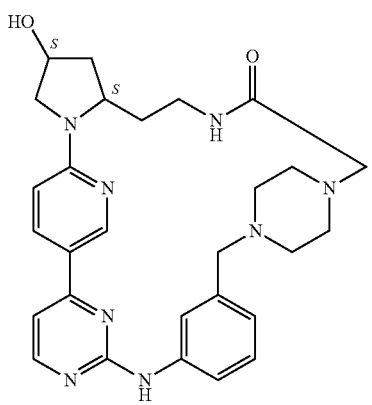

K₂CO₃ (82 mg; 0.59 mmol) was added to a suspension of Int. 232 (110 mg; 0.2 mmol) in MeOH (2 mL) at room temperature. The reaction mixture was stirred at room temperature for 24 h. Water and DCM were added. The mixture was extracted with DCM/MeOH (95/5) (3×). The organic layer was dried over MgSO₄, filtered and the solvent was evaporated. The residue was purified by preparative liquid chromatography on Stability Silica 5 µm 150×30.0 mm). Mobile phase: Gradient from NH₄OH, DCM, MeOH 0.2/98/2 to NH₄OH, DCM, MeOH 1.3/87/13. The pure fractions were combined and the solvent was evaporated. The residue was freeze-dried with water/ACN. Yield: 56 mg of compound 89 (55%).

Example B17 a) Preparation of Compounds 93a and 93

Compound 93a

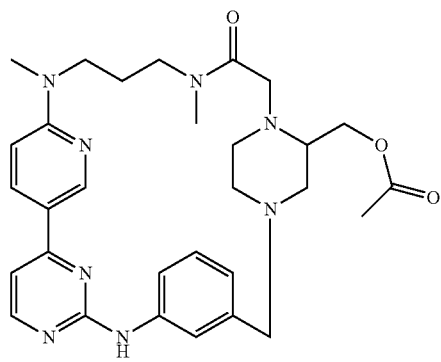

Compound 93

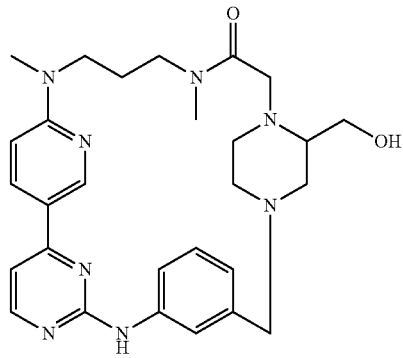

K₂CO₃ (2 g; 14.79 mmol) was added to a solution of int. 278 (1.26 g) in DMF (156 mL) at room temperature. The reaction mixture was stirred at 50° C. for 12 h. Water and DCM were added. The organic layer was separated and washed with water, dried over MgSO₄, filtered and the solvent was evaporated. The residue was purified by preparative liquid chromatography on irregular 15-40 µm 90 g Merck. Mobile phase: NH₄OH, DCM, MeOH 0.1/96/4. The desired fractions were collected and the solvent was evaporated. Yield: 275 mg of compound 93a and 40 mg of compound 93.

Example B18 a) Preparation of Compound 106

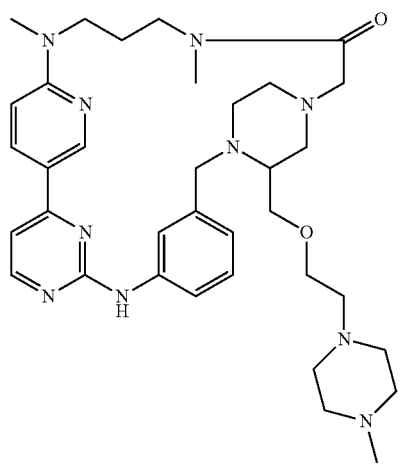 [SMILES: CN1CCN(CCOCC2CN3CCN2Cc2cccc(c2)Nc2nccc(n2)-c2ccc(nc2)N(C)CCCN(C)C(=O)C3)CC1]

A mixture of Int. 291 (182 mg; 0.29 mmol) and 1-methylpiperazine (0.43 g; 4.3 mmol) in THF (2.4 mL) in a sealed tube was heated at 90° C. using one single mode microwave (Biotage Initiator EXP 60) with a power output ranging from 0 to 400 W for 60 min. Subsequently, the solvent was evaporated. The residue was purified by preparative LC on Stability Silica 5 µm 150×30.0 mm. Mobile phase: Gradient from NH₄OH, DCM, MeOH 0.2/98/2 to NH₄OH, DCM, MeOH 1.3/87/13. The pure fractions were combined and the solvent was evaporated. The residue was purified by achiral SFC on 2-ethylpyridine 6 µm 150×21.2 mm. Mobile phase: isopropylamine, CO₂, MeOH. 0.3/85/15. The pure fractions were combined, the solvent was evaporated and the residue was freeze-dried with ACN/water 20/80 to give 52 mg of compound 106.

Co. 107 was prepared according to an analogous reaction protocol as B18, starting from Int. 291 and anhydrous piperazine.

Co. 108 was prepared according to an analogous reaction protocol as B18, starting from Int. 291 and dimethylamine.

Example B19 a) Preparation of Compound 135

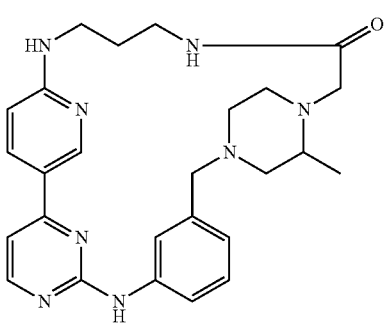 [SMILES: CC1CN2CCN1CC(=O)NCCCNc1ccc(cn1)-c1ccnc(n1)Nc1cccc(c1)C2]

Diethyl cyanophosphonate (222 µL; 1.485 mmol) was added slowly to a solution of Int. 384 (300 mg) and DIPEA (853 µL; 4.951 mmol) in DMF (60 mL). After the addition, the reaction mixture was heated at 100° C. for 4 h. The r.m. was evaporated and the residue was purified by preparative LC on (Stability Silica 5 µm 150×30.0 mm). Mobile phase (Gradient from $NH_4OH$, DCM, MeOH 0.2/98/2 to $NH_4OH$, DCM, MeOH 1.3/87/13). The desired fractions were collected and the solvent was evaporated, yielding 72 mg of compound 135.

C. Conversion Reactions

Example C1 a) Preparation of Compound 11

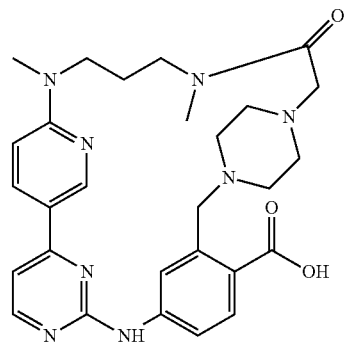 [SMILES: CN1CCCN(C)c2ccc(cn2)-c2ccnc(n2)Nc2ccc(C(=O)O)c(c2)CN2CCN(CC2)CC1=O]

Compound 10 (150 mg, 0.164 mmol) was stirred in HCl (4 M in dioxane) (10.606 mL, 42.422 mmol) at 60° C. for 16 h. The reaction mixture was concentrated under reduced pressure. The residue was co-evaporated twice with 1,4-dioxane (2×50 ml). The residue was stirred in 0.1 M aqueous $NaHCO_3$ (50 ml) at room temperature for 2 h. The solution was concentrated to +10 ml volume. The concentrate was purified by Prep HPLC on (RP Vydac Denali C18-10 µm, 200 g, 5 cm). Mobile phase (0.25% $NH_4HCO_3$ solution in water, $CH_3CN$). The desired fractions were collected, evaporated, dissolved in MeOH and evaporated again. Yield: 62 mg of compound 11 (71%).

Example C2 a) Preparation of Compound 35

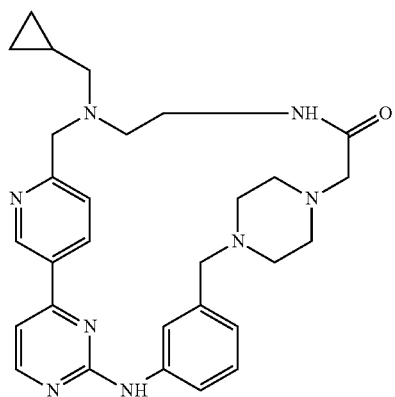 [SMILES: O=C1CN2CCN(CC2)Cc2cccc(c2)Nc2nccc(n2)-c2ccc(nc2)CN(CC2CC2)CCN1]

Cyclopropylmethyl bromide (0.0318 g, 0.236 mmol) dissolved in 3 ml DMF was added dropwise to compound 34 (0.108 g, 0.236 mmol) and $Et_3N$ (0.162 ml, 0.942 mmol) in DMF (15 ml) at 50° C. over 30 min. The reaction mixture was stirred at 70° C. for 16 h and was then concentrated. The residue was purified by Prep HPLC (RP SunFire Prep C18 OBD-10 µm, 30×50 mm). Mobile phase (0.25% $NH_4HCO_3$ solution in water, $CH_3CN$). The desired fractions were collected, evaporated, dissolved in MeOH and evaporated again. Yield: 50 mg of compound 35 (41.4%).

The compounds in the table below were prepared according to an analogous reaction protocol as used for compound 35, but wherein cyclopropylmethyl bromide is replaced by another starting material (as indicated):

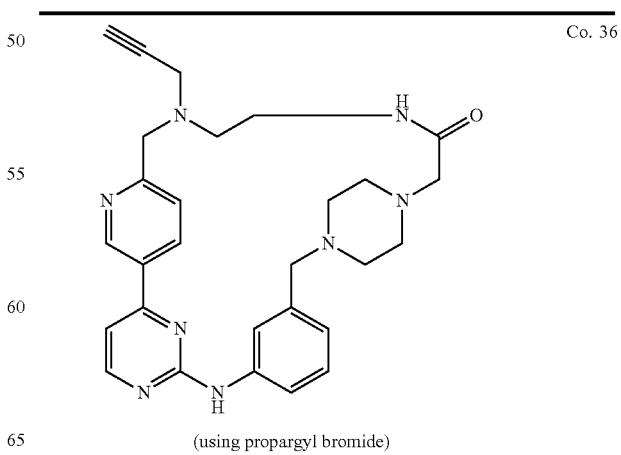

Co. 36

(using propargyl bromide)

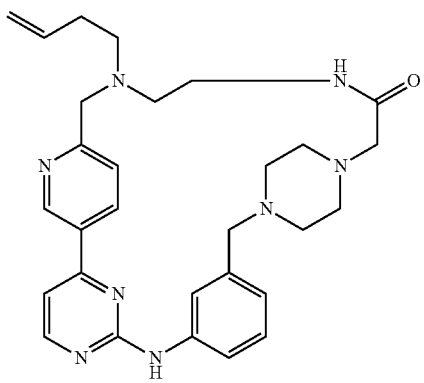
Co. 37
(using homoallyl bromide)
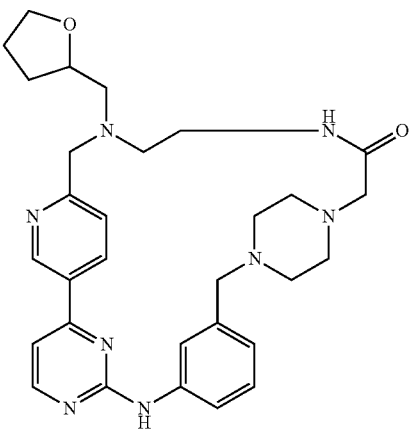
Co. 40
(using (RS)-tetrahydrofurfuryl bromide)
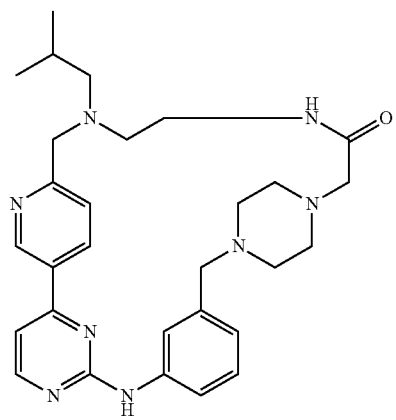
Co. 38
(using 2-methylpropyl bromide)
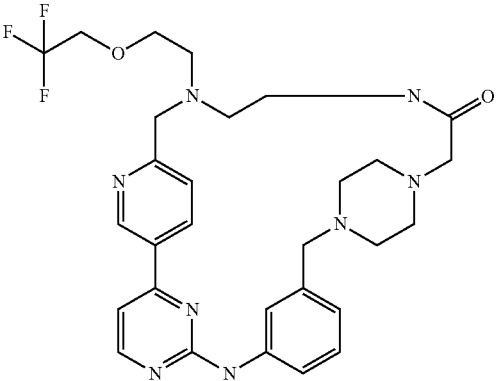
Co. 41
(using 5-chloro-1,1,1-trifluoro-3-oxapentane)
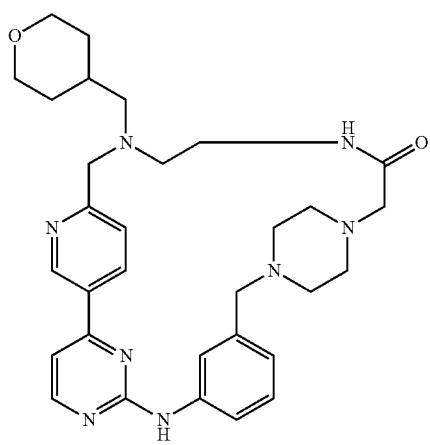
Co. 39
(using (tetrahydropyran-4-yl)methyl bromide)
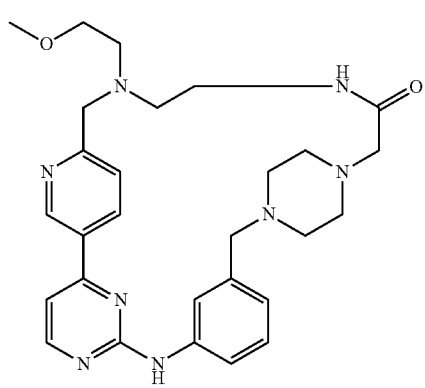
Co. 42
(using methoxyethyl chloride)

-continued

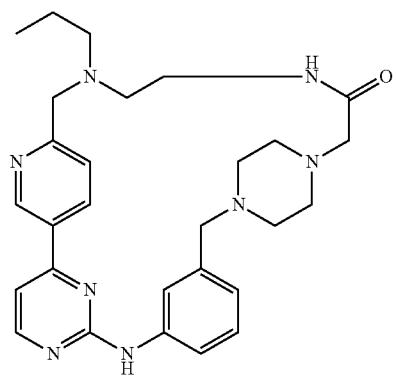

Co. 43

(using 1-propyl bromide)

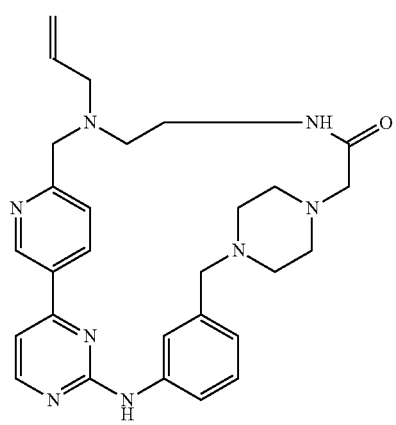

Co. 45

(using allyl bromide)

b) Preparation of Compound 44

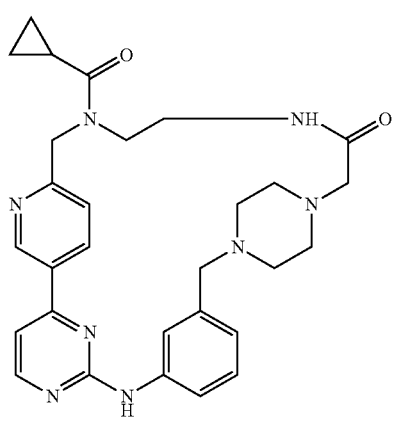 [SMILES: O=C1CN2CCN(CC2)Cc2cccc(c2)Nc2nccc(n2)-c2ccc(nc2)CN(C(=O)C2CC2)CCN1]

Cyclopropanecarbonyl chloride (13.678 mg; 0.131 mmol) was added to compound 34 (50 mg; 0.109 mmol) and DIPEA (0.0752 ml; 0.436 mmol) in DMF (3.5 ml) at room temperature. The reaction mixture was stirred at 70° C. for 16 h. The reaction mixture was concentrated. The residue was purified by Prep HPLC on (RP SunFire Prep C18 OBD-10 μm, 30×150 mm). Mobile phase (0.25% NH$_4$HCO$_3$ solution in water, CH$_3$CN). The desired fractions were collected and the solvent was evaporated, yielding Compound 44 (42 mg; 73.14%).

The compounds in the table below were prepared according to an analogous reaction protocol as used for compound 44, but wherein cyclopropanecarbonyl chloride is replaced by another starting material (as indicated):

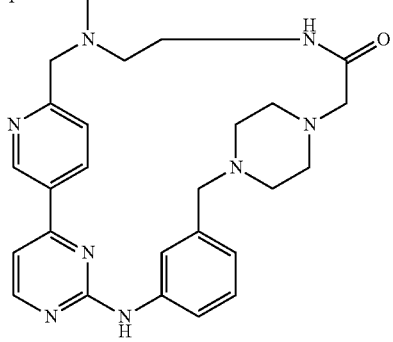

Co. 132

(using TFA anhydride)

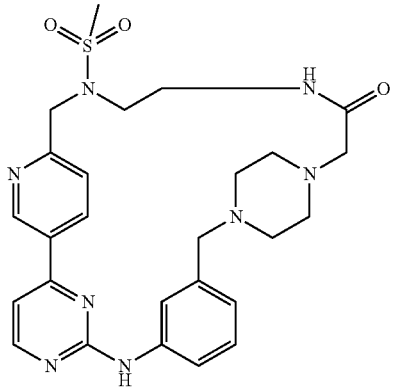

Co. 133

(using mesyl chloride)

c) Preparation of Compound 134

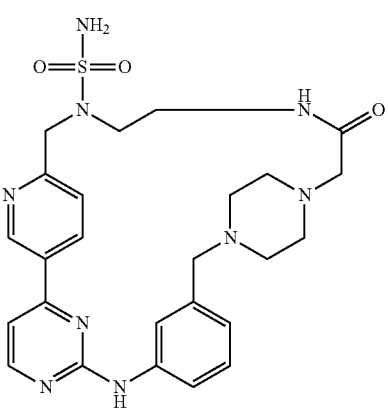 [SMILES: NS(=O)(=O)N1CCNC(=O)CN2CCN(CC2)Cc2cccc(c2)Nc2nccc(n2)-c2ccc(nc2)C1]

Sulfamide (157 mg; 163.4 mmol) was added to Compound 34 (50 mg; 0.11 mmol) in dioxane (3 ml) at room temperature. The reaction mixture was stirred at 80° C. for 4 days. The reaction mixture was concentrated and the residue was purified by Prep HPLC on (RP Vydac Denali C18-10 &m, 200 g, 5 cm). Mobile phase (0.25% NH$_4$HCO$_3$ solution in water, CH$_3$CN), yielding Compound 134 (41 mg; 70%).

Example C3 a) Preparation of Compound 71

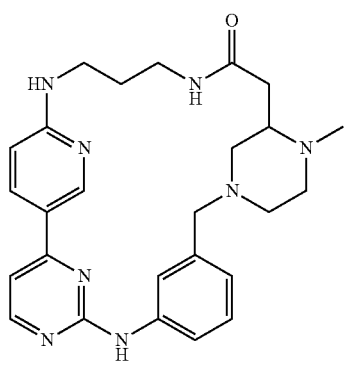 [SMILES: CN1CCN2Cc3cccc(c3)Nc3nccc(n3)-c3ccc(nc3)NCCCNC(=O)CC1C2]

Sodium cyanoborohydride (0.087 g, 1.32 mmol) was added to a solution of compound 70 (0.401 g; 0.875 mmol) and formol (0.04 g; 1.32 mmol) in MeOH (15 mL). The mixture was stirred at room temperature until complete conversion. Subsequently, NaOH 1 M in H$_2$O and DCM were added. The organic layer was separated, dried over MgSO$_4$, concentrated and purified by column chromatography over silica gel eluting with a gradient of DCM/MeOH (5/1, v/v)/DCM from 0% to 100%. The desired fraction were collected and the solvent was evaporated. The residue was crystallized from CH$_3$CN. Yield: 0.120 g of Compound 71 (29%).

Compound 129 was prepared according to an analogous reaction protocol as used for Compound 71, starting from compound 128.

Example C4 a) Preparation of Compounds 93, 94 and 95

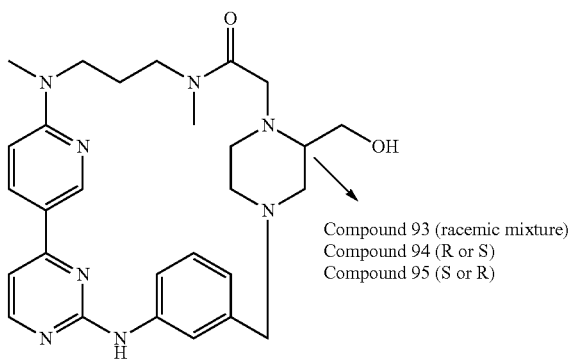 [SMILES: CN1CCCN(C)c2ccc(cn2)-c2ccnc(n2)Nc2cccc(c2)CN2CCN(CC1=O)C(CO)C2]

Compound 93 (racemic mixture)
Compound 94 (R or S)
Compound 95 (S or R)

K$_2$CO$_3$ (191 mg; 1.38 mmol) was added to a suspension of compound 93a (257 mg; 0.46 mmol) in MeOH (3.6 mL) at room temperature. The reaction mixture was stirred at room temperature overnight. Water and DCM were added. The mixture was extracted with DCM/MeOH (95/5) (3×). The organic layer was dried over MgSO$_4$, filtered and the solvent was evaporated. The residue was purified by preparative liquid chromatography on Stability Silica 5 μm 150×30.0 mm. Mobile phase: Gradient from NH$_4$OH, DCM, MeOH 0.3/97/3 to NH$_4$OH, DCM, MeOH 1.3/87/13. The desired fractions were collected and the solvent was evaporated. The residue was purified by chiral SFC on CHIRAL-PAK AD-H 5 μm 250×20 mm. Mobile phase: isopropylamine, CO$_2$, MeOH 0.3/45/55. The desired fractions were collected and the solvent was evaporated, yielding 38 mg of crude compound 94 and 37 mg of crude compound 95. Crude compound 94 was freeze-dried with water/ACN to give 34 mg of compound 94 (14%). Crude compound 95 was freeze-dried with water/ACN to give 20 mg of compound 95 (8%).

Example C5 a) Preparation of Compounds 24 and 25

Compound 24

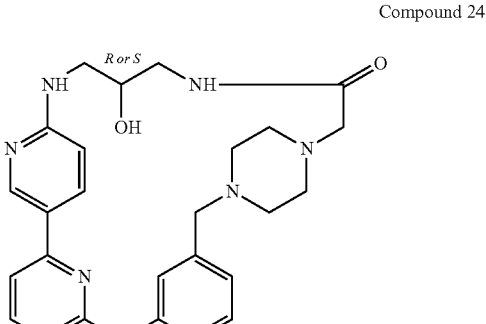

Compound 25

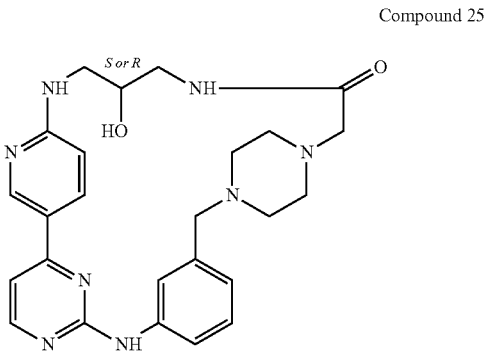

Compound 23 (0.3 g; 0.63 mmol) was purified by chiral SFC (CHIRALPAK AD-H 5 μm 250×20 mm). Mobile phase: iPrNH$_2$, CO$_2$, iPrOH 0.3/55/45. The desired fractions were combined and evaporated until dryness to give 120 mg of compound 25 (40%; R or S) and 160 mg of a second residue which was taken up into DCM (20 mL) and MeOH (7 mL). Tris-(2-aminoethyl)amine resin was added to the second residue and the mixture was stirred for 12 h. The resin was filtered off. The filtrate was evaporated until dryness to give 139 mg of residue which was purified by preparative LC (Stability Silica 5 μm 150×30.0 mm, mobile phase gradient from 95% DCM, 5% MeOH to 90% DCM, 10% MeOH). The desired fractions were collected and the solvent was evaporated. Yield: 77 mg of compound 24 (25%).

b) Preparation of Compounds 47 and 48

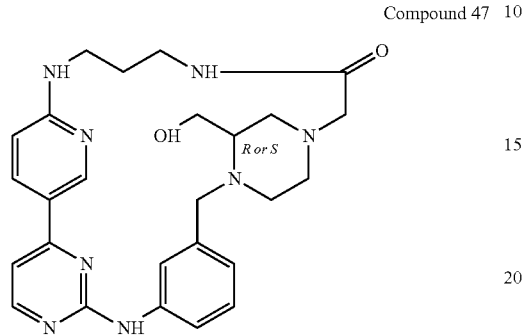
Compound 47

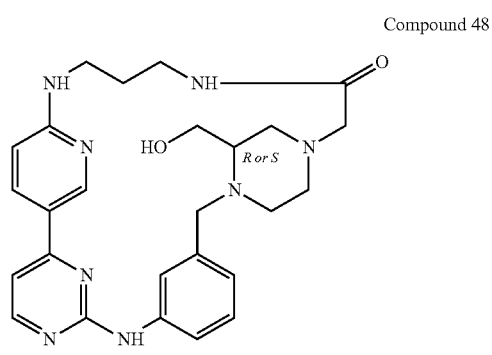
Compound 48

Compound 46 was purified by chiral SFC (CHIRALPAK AD-H 5 μm 250×20 mm). Mobile phase: iPrNH$_2$, CO$_2$, iPrOH 0.3/55/45. The pure fractions were collected and the solvent was evaporated. Yield: 41 mg of compound 47 (43%) and 41 mg of compound 48 (43%).

c) Preparation of Compounds 61 and 62

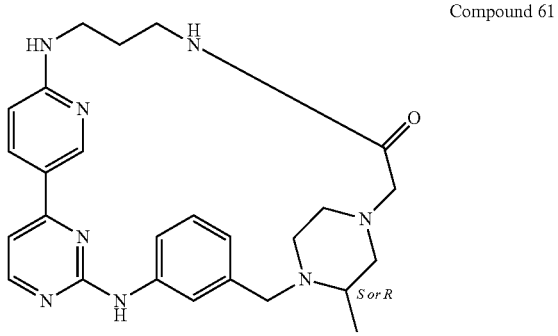
Compound 61

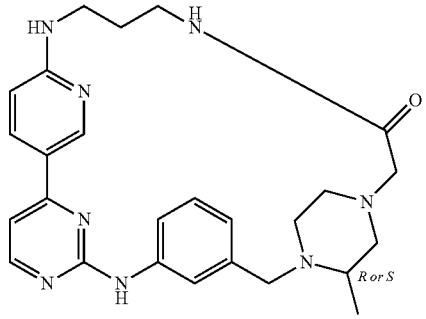
Compound 62

Compound 60 (229 mg; 0.49 mmol) was purified by chiral SFC (CHIRALPAK AD-H 5 μm 250×20 mm). Mobile phase: iPrNH$_2$, CO$_2$, iPrOH 0.3/53/47). The pure fractions were collected and the solvent was evaporated. Yield: 88 mg of an orange oil which was freeze-dried with water/ACN to give 85 mg of compound 62 as a white powder (37%); and 102 mg of an orange oil which was freeze-dried with water/ACN to give 93 mg of a white powder which was taken up in an aqueous K$_2$CO$_3$ solution (10%) and EtOAc mixture. This mixture was extracted with EtOAc (3×) and the solvent was evaporated. The residue was freeze-dried with water/ACN to give 86 mg of compound 61 (37%).

d) Preparation of Compounds 99 and 100

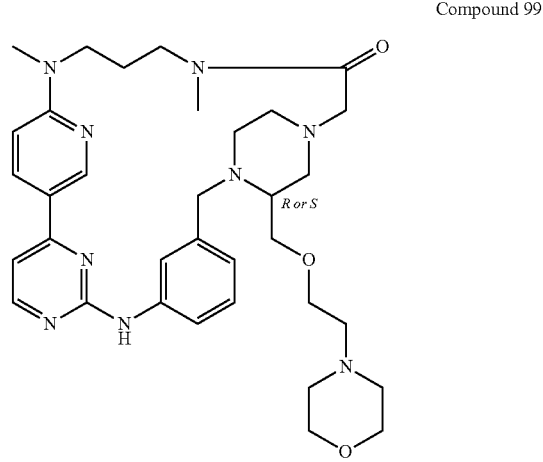
Compound 99

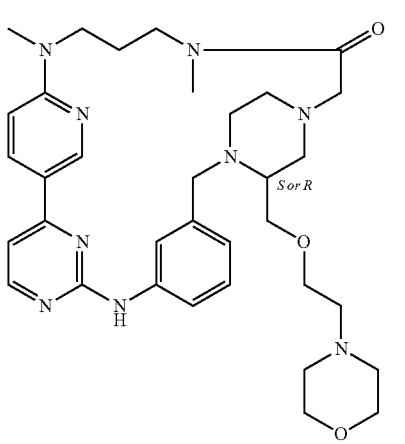
Compound 100

Compound 98 (70 mg, 0.111 mol) was purified by preparative SFC on Chiralcel Diacel OD 20×250 mm. Mobile phase: CO$_2$, MeOH with 0.2% iPrNH$_2$. The desired fractions were collected and the solvent was evaporated. Yield: 32 mg of compound 99 and 32 mg of compound 100.

e) Preparation of Compounds 104 and 105

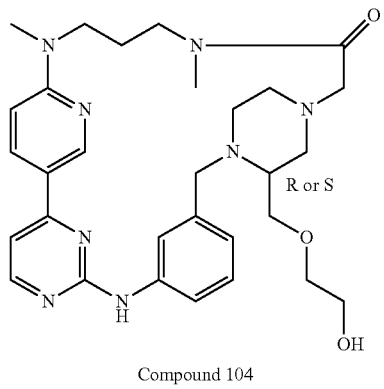

Compound 104

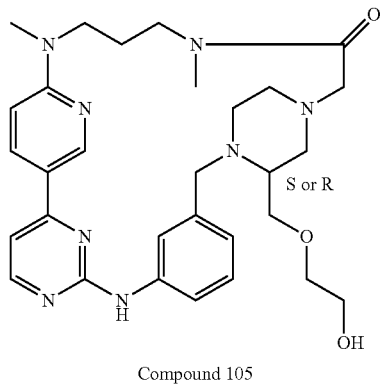

Compound 105

Compound 103 (170 mg) was purified by preparative SFC on Chiralcel Diacel OD 20×250 mm. Mobile phase: CO$_2$, MeOH with 0.2% iPrNH$_2$. The desired fractions were collected and the solvent was evaporated. Yield: 34 mg of compound 104 and 35 mg of compound 105.

f) Preparation of Compounds 136 and 137

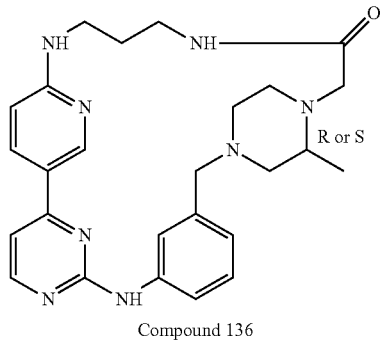

Compound 136

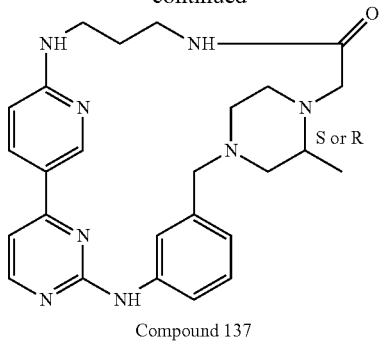

Compound 137

Compound 135 (72 mg) was purified by chiral SFC on Chiralpak AD-H 5 μm 250×20 mm. Mobile phase iPrNH$_2$, CO$_2$, EtOH 0.3/50/50. The desired fractions were collected and the solvent was evaporated. The two enantiomers were freeze-dried with water-ACN yielding 18 mg of Compound 136 and 24 mg of Compound 137.

Example C6 a) Preparation of Compound 54

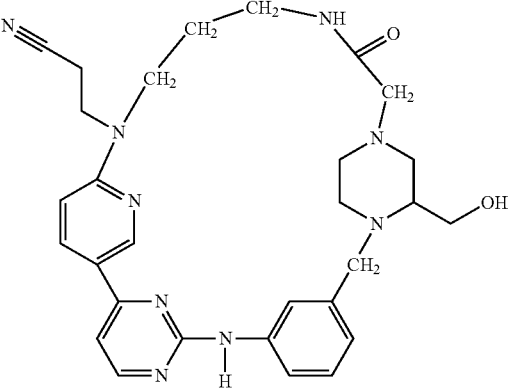 [SMILES: N#CCCN1CCCNC(=O)CN2CCN(Cc3cccc(c3)Nc3nccc(n3)-c3ccc1nc3)C(CO)C2]

NaH (60% dispersion in mineral oil) (4.912 mg; 0.123 mmol) was added to a solution of Co. 46 (20 mg; 0.0409 mmol) in DMF (1 mL) at room temperature under N$_2$-gas atmosphere. The mixture was stirred for 30 min at room temperature. Then 3-bromopropionitrile (4.088 μL; 0.0491 mmol) was added dropwise. After addition the reaction mixture was stirred for 1 h.

The reaction was quenched by the addition of water. The product was extracted twice with DCM. The organic layer was washed with water, dried with MgSO$_4$, filtered and the solvents were evaporated The residue was purified by Prep HPLC on (RP SunFire Prep C18 OBD-10 μm, 30×150 mm). Mobile phase (0.25% NH$_4$HCO$_3$ solution in water, ACN). The pure fractions were combined and the solvent was evaporated yielding 7 mg of compound 54.

Analytical Part and Compound Tables

LCMS General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times (Re) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "ELSD" Evaporative Light Scanning Detector.

By using analogous reaction protocols as described in the foregoing examples, the compounds listed in the Tables below have been prepared.

'Co. No.' means compound number.

'Method' refers to the Example number in analogy to which protocol the compound was synthesized.

In case no specific stereochemistry is indicated for a stereocenter of a compound, this means that the compound was obtained as a mixture of the R and the S enantiomers.

The values of salt stoichiometry or acid content in the compounds as provided herein, are those obtained experimentally and may vary dependent on the analytical method used (for the compounds in Table 2, $^1$H NMR and/or elemental analysis was used).

In case no salt form is indicated, the compound was obtained as a free base.

TABLE 1

LCMS Method codes (Flow expressed in mL/min; column temperature (T) in ° C.; Run time in minutes).

| Method code | Instrument | Column | Mobile phase | Gradient | Flow Col T | Run time |
|---|---|---|---|---|---|---|
| 1 | Waters: Acquity ® UPLC ® - DAD and SQD | Waters: BEH C18 (1.7 μm, 2.1*50 mm) | A: 10 mM $CH_3COONH_4$ in 95% $H_2O$ + 5% $CH_3CN$ B: $CH_3CN$ | From 95% A to 5% A in 1.3 min, held for 0.7 min. | 0.8 55 | 2 |
| 2 | Agilent 1100 - DAD- MSD G1956A | YMC-pack ODS-AQ C18 (50 × 4.6 mm, 3 μm) | A: 0.1% HCOOH in $H_2O$ B: $CH_3CN$ | From 95% A to 5% A in 4.8 min, held for 1.0 min, to 95% A in 0.2 min. | 2.6 35 | 6.0 |
| 3 | Waters: Acquity UPLC ® - DAD and Quattro Micro ™ | Waters: BEH C18 (1.7 μm, 2.1 × 100 mm) | A: 95% $CH_3COONH_4$ 7 mM/ 5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343- 40 | 6.2 |
| 4 | Waters: Alliance ®- DAD - ZQ and ELSD 2000 Alltech | Waters: Xterra MS C18 (3.5 μm, 4.6*100 mm) | A: 25 mM $CH_3COONH_4$ in 95% $H_2O$ + 5% $CH_3CN$ B: $CH_3CN$ C: $CH_3OH$ D: (40% $CH_3CN$ and 40% $CH_3OH$ and 20% $H_2O$ with 0.25% $CH_3COOH$ | From 100% A to 1% A, 49% B and 50% C in 6.5 min, to 1% A and 99% B in 0.5 min, to 100% D in 1 min held for 1.0 min to 100% A in 0.5 min and held for 1.5 min. | 1.6 40 | 11 |
| 5 | Waters: Acquity ® UPLC ® - DAD and SQD | Waters: BEH C18 (1.7 μm, 2.1*50 mm) | A: 0.1% HCOOH + 5% $CH_3OH$ in $H_2O$ B: $CH_3OH$ | From 95% A to 5% A in 1.3 min, held for 0.7 min. | 0.8 55 | 2 |
| 6 | Waters: Acquity ® UPLC ® - DAD and SQD | BEH C18 column (1.7 μm, 2.1 × 50 mm; Waters Acquity) | A: 25 mM ammonium acetate in $H_2O/CH_3CN$ 95/5; B: $CH_3CN$ | 95% A and 5% B to 5% A and 95% B in 1.3 minutes and hold for 0.3 minutes | 0.8 55 | 2 |
| 7 | Waters: Acquity ® UPLC ® - DAD and SQD | Waters: BEH C18 (1.7 μm, 2.1*50 mm) | A: 0.1% HCOOH + 5% $CH_3OH$ in $H_2O$ B: $CH_3OH$ | From 90% A to 20% A in 0.7 min, to 5% A in 0.8 min held for 0.5 min. | 0.8 55 | 2 |

TABLE 2 compounds and physico-chemical data (Co. No. means compound number)

| Co. No. | Compound Structure | Method | HPLC Rt (min) | MS M+ (H+) | LC/GC/MS Method |
|---|---|---|---|---|---|
| 1 | 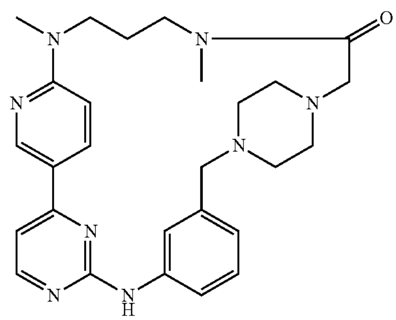 | B1 or B5 | 0.90 | 487 | 1 |
| 131 | 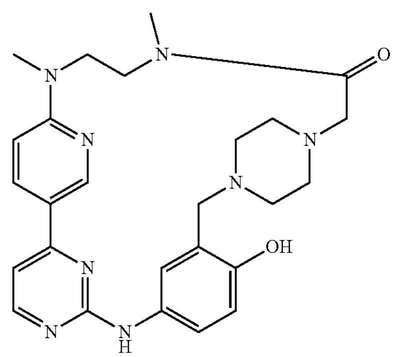 [SMILES: CN1CCN(C)c2ccc(cn2)-c2ccnc(n2)Nc2ccc(O)c(c2)CN2CCN(CC2)CC1=O] | B12 | 1.47 | 489 | 2 |
| 81 | 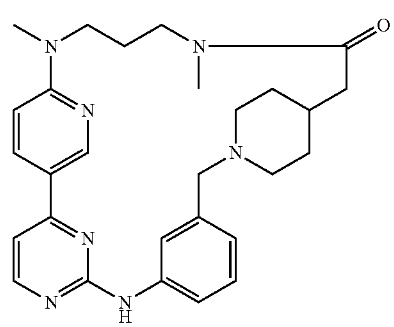 [SMILES: CN1CCCN(C)c2ccc(cn2)-c2ccnc(n2)Nc2cccc(c2)CN2CCC(CC2)CC1=O] | B13 | 1.61 | 486 | 2 |
| 109 | 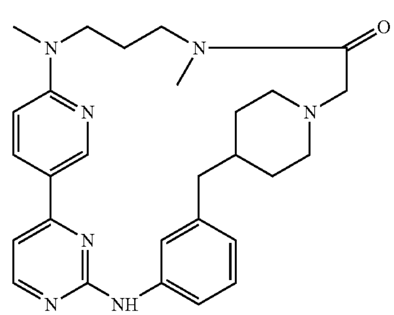 [SMILES: CN1CCCN(C)c2ccc(cn2)-c2ccnc(n2)Nc2cccc(c2)CC2CCN(CC2)CC1=O] | B9 | 1.92 | 486 | 2 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 74 | 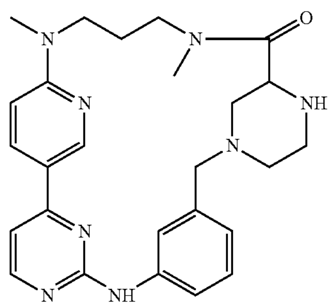 [SMILES: CN1CCCN(C)c2ccc(cn2)-c2ccnc(n2)Nc2cccc(c2)CN2CCNC(C2)C1=O] | B13 | 1.90 | 473 | 2 |
| 31 | 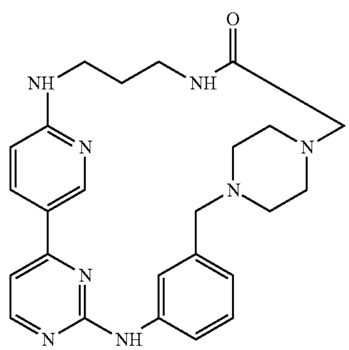 [SMILES: O=C1CN2CCN(CC2)Cc2cccc(c2)Nc2nccc(n2)-c2ccc(nc2)NCCCN1] | B2 | 0.75 | 459 | 6 |
| 75 | 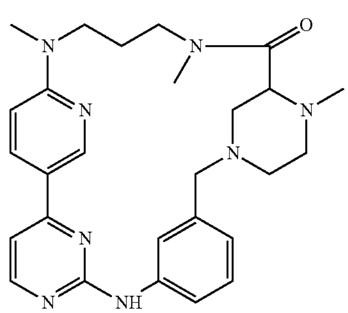 [SMILES: CN1CCCN(C)c2ccc(cn2)-c2ccnc(n2)Nc2cccc(c2)CN2CCN(C)C(C2)C1=O] | C3 | 1.94 | 487 | 2 |
| 82 | 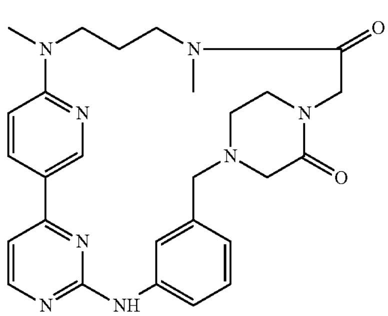 [SMILES: CN1CCCN(C)c2ccc(cn2)-c2ccnc(n2)Nc2cccc(c2)CN2CCN(CC1=O)C(=O)C2] | B13 | 1.39 | 501 | 2 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 114 | 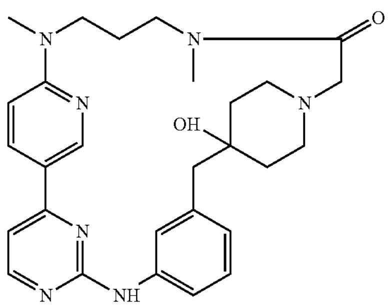 [SMILES: CN1CCCN(C)c2ccc(cn2)-c2ccnc(n2)Nc2cccc(c2)CC2(O)CCN(CC2)CC1=O] | B11 | 1.47 | 502 | 2 |
| 83 | 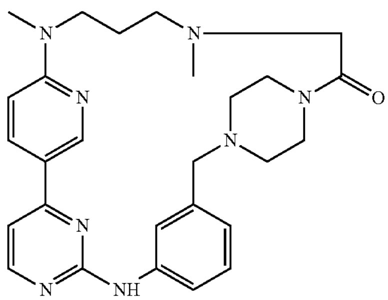 [SMILES: CN1CCCN(C)c2ccc(cn2)-c2ccnc(n2)Nc2cccc(c2)CN2CCN(CC2)C(=O)C1] | B13 | 1.26 | 487 | 2 |
| 68 | 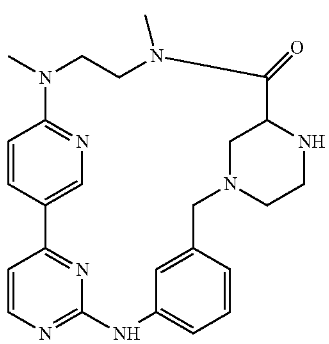 [SMILES: CN1CCN(C)c2ccc(cn2)-c2ccnc(n2)Nc2cccc(c2)CN2CCNC(C2)C1=O] | B13 | 2.06 | 459 | 2 |
| 119 | 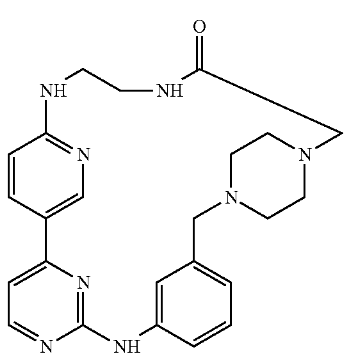 [SMILES: O=C1CN2CCN(CC2)Cc2cccc(c2)Nc2nccc(n2)-c2ccc(nc2)NCCN1] | B2 | 0.67 | 445 | 6 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 21 | 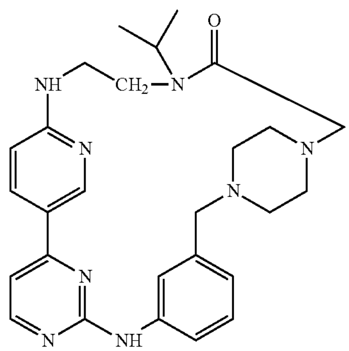 [SMILES: CC(C)N1CCNc2ccc(cn2)-c2ccnc(n2)Nc2cccc(c2)CN2CCN(CC2)CC1=O] | B1 | 2.36 | 487 | 3 |
| 69 | 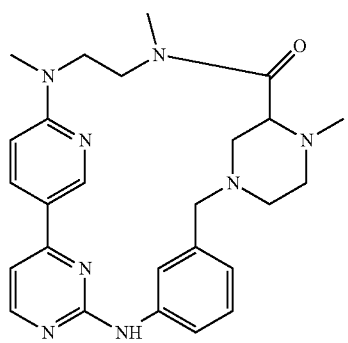 [SMILES: CN1CCN(C)c2ccc(cn2)-c2ccnc(n2)Nc2cccc(c2)CN2CCN(C)C(C2)C1=O] | B13 | 2.06 | 473 | 2 |
| 30 | 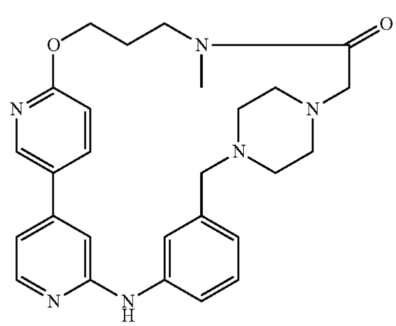 | B2 | 2.48 | 474 | 3 |
| 121 | 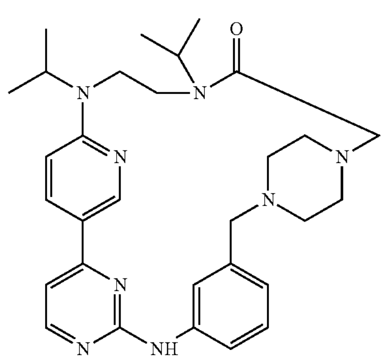 [SMILES: CC(C)N1CCN(C(C)C)c2ccc(cn2)-c2ccnc(n2)Nc2cccc(c2)CN2CCN(CC2)CC1=O] | B2 | 3.04 | 529 | 3 |

TABLE 2-continued
compounds and physico-chemical data (Co. No. means compound number)
| Co. No. | Compound Structure | Method | HPLC Rt (min) | MS M+ (H+) | LC/GC/MS Method |
|---|---|---|---|---|---|
| 79 | 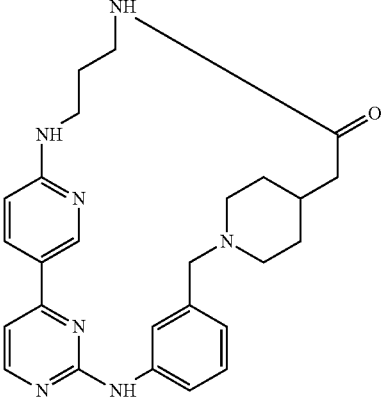 [SMILES: O=C1CC2CCN(CC2)Cc2cccc(c2)Nc2nccc(n2)-c2ccc(nc2)NCCCN1] | B13 | 1.01 | 458 | 2 |
| 22 | 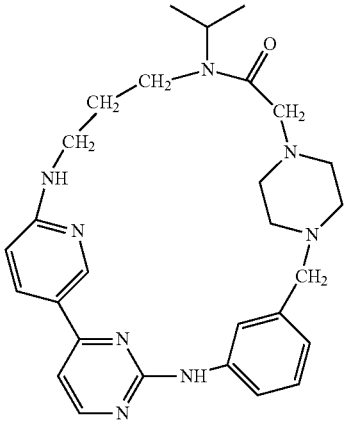 [SMILES: CC(C)N1CCCNc2ccc(cn2)-c2ccnc(n2)Nc2cccc(c2)CN2CCN(CC2)CC1=O] | B1 | 2.52 | 501 | 3 |
| 128 | 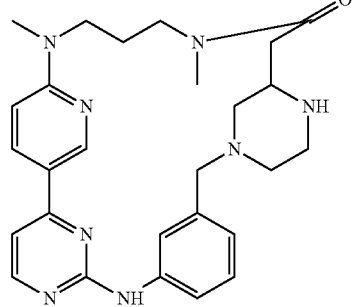 | B5 | 1.54 | 487 | 2 |

TABLE 2-continued compounds and physico-chemical data (Co. No. means compound number)

| Co. No. | Compound Structure | Method | HPLC Rt (min) | MS M+ (H+) | LC/GC/ MS Method |
|---|---|---|---|---|---|
| 110 | 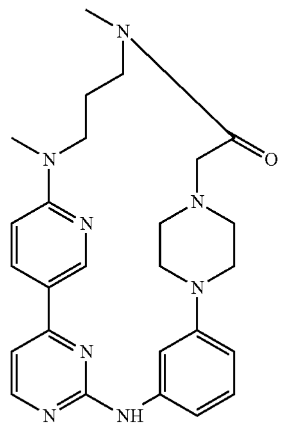 [SMILES: CN1CCCN(C)c2ccc(cn2)-c2ccnc(n2)Nc2cccc(c2)N2CCN(CC2)CC1=O] | B9 | 1.67 | 473 | 2 |
| 77 | 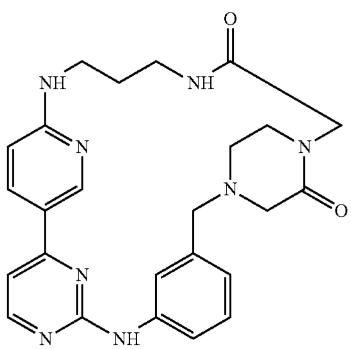 [SMILES: O=C1CN2CCN(CC2=O)Cc2cccc(c2)Nc2nccc(n2)-c2ccc(nc2)NCCCN1] | B13 | 1.20 | 473 | 2 |
| 78 | 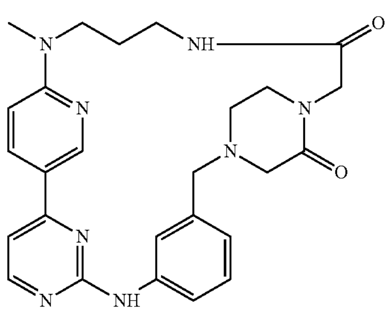 [SMILES: CN1CCCNC(=O)CN2CCN(CC2=O)Cc2cccc(c2)Nc2nccc(n2)-c2ccc1nc2] | B13 | 1.30 | 487 | 2 |
| 125 | 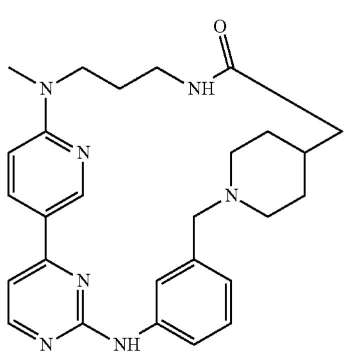 [SMILES: CN1CCCNC(=O)CC2CCN(CC2)Cc2cccc(c2)Nc2nccc(n2)-c2ccc1nc2] | B5 | 1.20 | 472 | 2 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 113 | 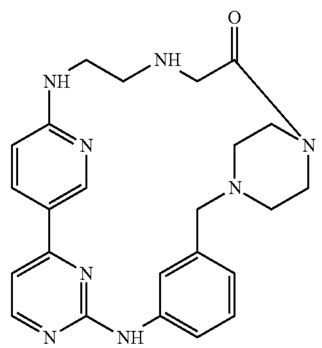 [SMILES: O=C1CNCCNc2ccc(cn2)-c2ccnc(n2)Nc2cccc(c2)CN2CCN1CC2] | B10 | 1.00 | 445 | 2 |
| 129 | 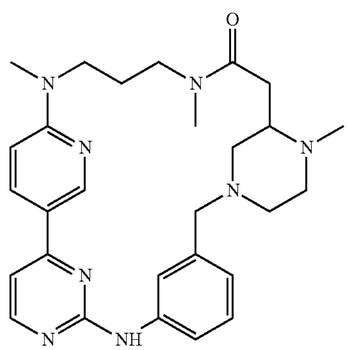 [SMILES: CN1CCCN(C)c2ccc(cn2)-c2ccnc(n2)Nc2cccc(c2)CN2CCN(C)C(CC1=O)C2] | C3 | 1.50 | 501 | 2 |
| 127 | 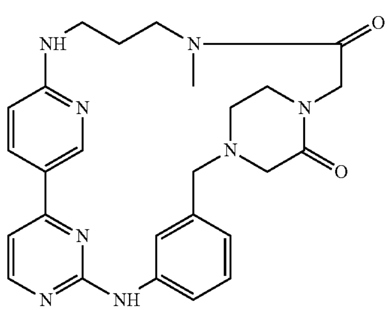 [SMILES: CN1CCCNc2ccc(cn2)-c2ccnc(n2)Nc2cccc(c2)CN2CCN(CC1=O)C(=O)C2] | B5 | 1.20 | 487 | 2 |
| 111 | 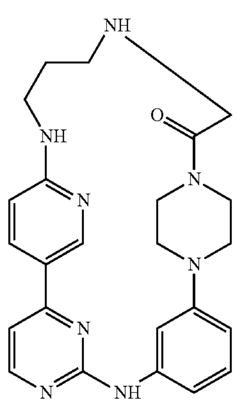 [SMILES: O=C1CNCCCNc2ccc(cn2)-c2ccnc(n2)Nc2cccc(c2)N2CCN1CC2] | B9 | 1.40 | 445 | 2 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 70 | 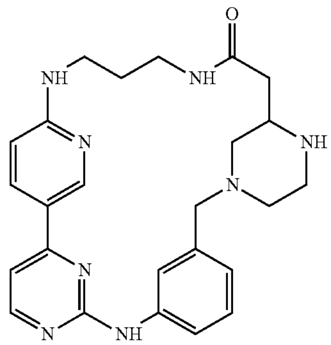 [SMILES: O=C1CC2CN(CCN2)Cc2cccc(c2)Nc2nccc(n2)-c2ccc(nc2)NCCCN1] | B13 | 1.10 | 459 | 2 |
| 112 | 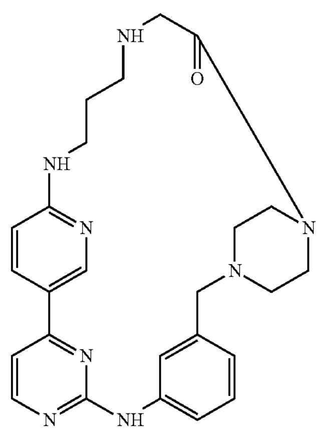 [SMILES: O=C1CNCCCNc2ccc(cn2)-c2ccnc(n2)Nc2cccc(c2)CN2CCN1CC2] | B10 | 1.07 | 459 | 2 |
| 71 | 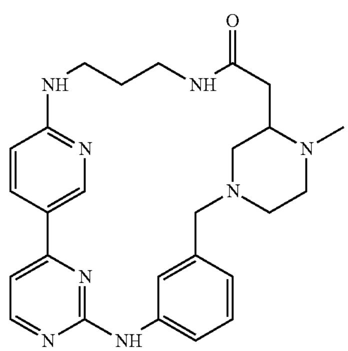 [SMILES: CN1CCN2Cc3cccc(c3)Nc3nccc(n3)-c3ccc(nc3)NCCCNC(=O)CC1C2] | C3 | 1.26 | 473 | 2 |
| 73 | 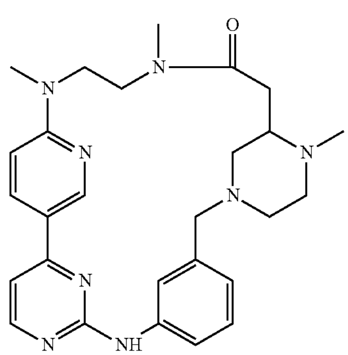 [SMILES: CN1CCN(C)c2ccc(cn2)-c2ccnc(n2)Nc2cccc(c2)CN2CCN(C)C(CC1=O)C2] | C3 | 1.62 | 487 | 2 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 72 | 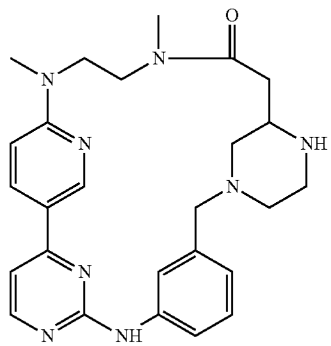 [SMILES: CN1CCN(C)c2ccc(cn2)-c2ccnc(n2)Nc2cccc(c2)CN2CCNC(CC1=O)C2] | B5 | 1.55 | 473 | 2 |
| 124 | 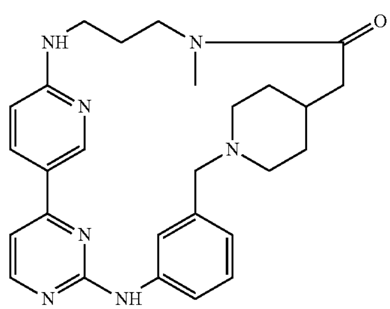 [SMILES: CN1CCCNc2ccc(cn2)-c2ccnc(n2)Nc2cccc(c2)CN2CCC(CC2)CC1=O] | B5 | 1.15 | 472 | 2 |
| 115 | 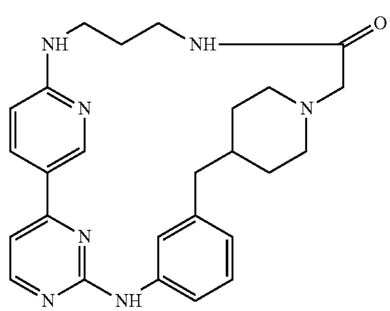 [SMILES: O=C1CN2CCC(CC2)Cc2cccc(c2)Nc2nccc(n2)-c2ccc(nc2)NCCCN1] | B11 | 1.25 | 458 | 2 |
| 76 | 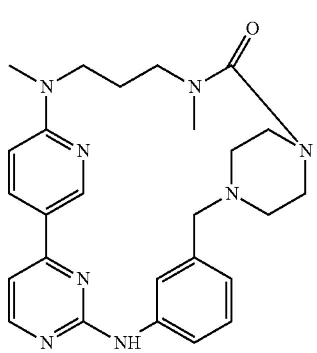 [SMILES: CN1CCCN(C)c2ccc(cn2)-c2ccnc(n2)Nc2cccc(c2)CN2CCN(CC2)C1=O] | B14 | 1.63 | 473 | 2 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 130 | 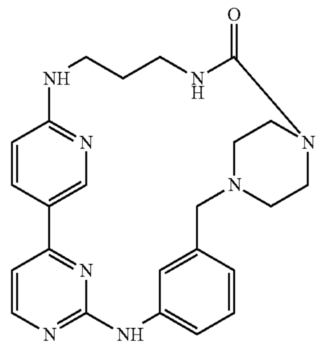 [SMILES: O=C1NCCCNc2ccc(cn2)-c2ccnc(n2)Nc2cccc(c2)CN2CCN1CC2] | B14 | 1.48 | 445 | 2 |
| 123 | 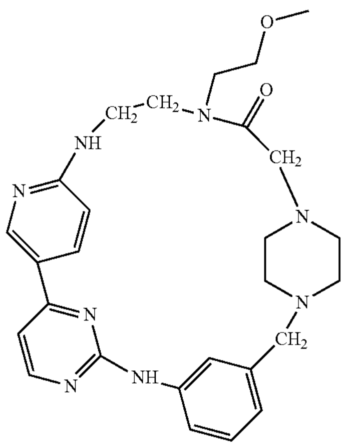 [SMILES: COCCN1CCNc2ccc(cn2)-c2ccnc(n2)Nc2cccc(c2)CN2CCN(CC2)CC1=O] | B2 | 0.76 | 503 | 7 |
| 23 | 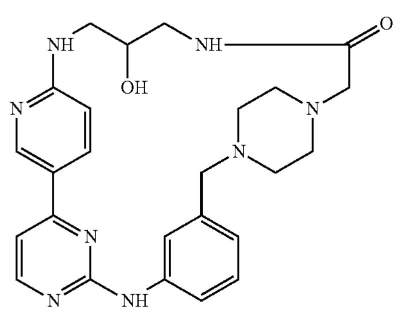 [SMILES: O=C1CN2CCN(CC2)Cc2cccc(c2)Nc2nccc(n2)-c2ccc(nc2)NCC(O)CN1] | B1 | 1.98 | 475 | 3 |
| 120 | 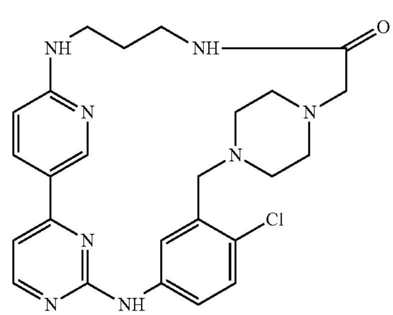 [SMILES: O=C1CN2CCN(CC2)Cc2cc(ccc2Cl)Nc2nccc(n2)-c2ccc(nc2)NCCCN1] | B2 | 5.81 | 493 | 4 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 29 | 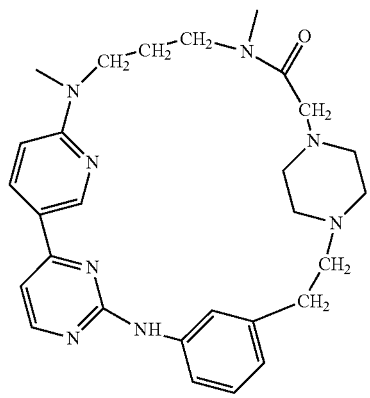 [SMILES: CN1CCCN(C)c2ccc(cn2)-c2ccnc(n2)Nc2cccc(c2)CCN2CCN(CC2)CC1=O] | B1 | 0.92 | 501 | 7 |
| 118 | 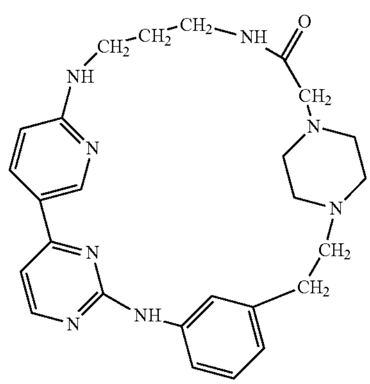 [SMILES: O=C1CN2CCN(CCc3cccc(c3)Nc3nccc(n3)-c3ccc(nc3)NCCCN1)CC2] | B1 | 0.76 | 473 | 7 |
| 28 | 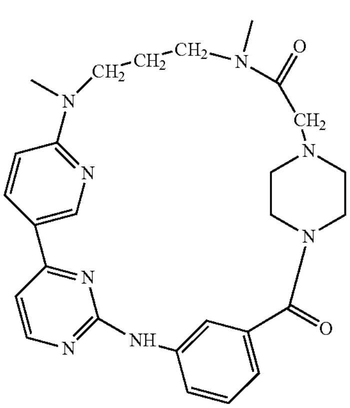 [SMILES: CN1CCCN(C)c2ccc(cn2)-c2ccnc(n2)Nc2cccc(c2)C(=O)N2CCN(CC2)CC1=O] | B1 | 0.77 | 501 | 5 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 117 | 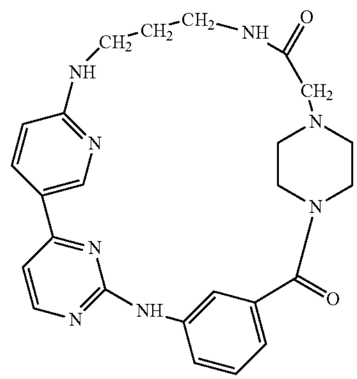 [SMILES: O=C1CN2CCN(CC2)C(=O)c2cccc(c2)Nc2nccc(n2)-c2ccc(nc2)NCCCN1] | B1 | 0.55 | 473 | 5 |
| 67 | 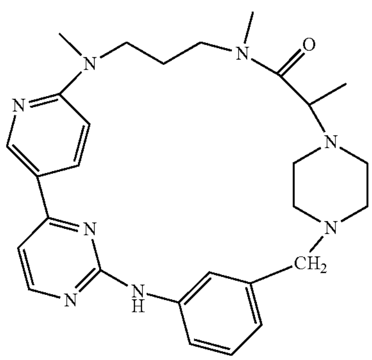 [SMILES: CC1C(=O)N(C)CCCN(C)c2ccc(cn2)-c2ccnc(n2)Nc2cccc(c2)CN2CCN1CC2] | B5 (Et₃N was used instead of DIPEA) | 0.93 | 501 | 6 |
| 64 | 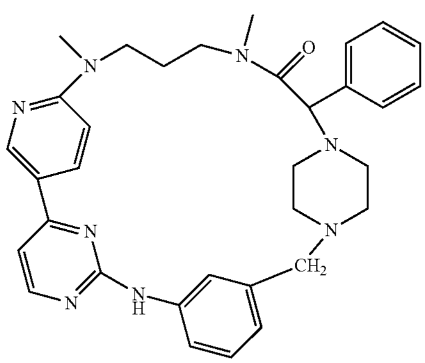 [SMILES: CN1CCCN(C)c2ccc(cn2)-c2ccnc(n2)Nc2cccc(c2)CN2CCN(CC2)C(c2ccccc2)C1=O] | B5 (Et₃N was used instead of DIPEA) | 1.07 | 563 | 6 |
| 80 | 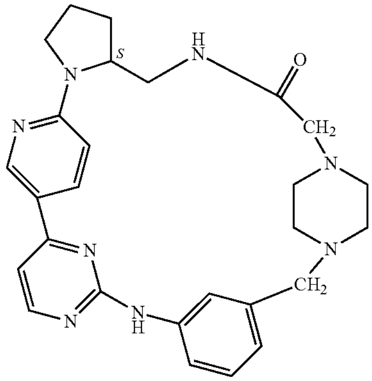 | B5 | 0.87 | 485 | 7 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 20 | (structure) TFA salt (·CF$_3$COOH) | B1 | 0.93 | 501 | 1 |
| 60 | (structure) | B5 | 2.34 | 473 | 3 |
| 33 | (structure) | B3 | 2.27 | 488 | 3 |
| 32 | (structure) | B3 | 2.24 | 488 | 3 |

TABLE 2-continued compounds and physico-chemical data (Co. No. means compound number)

| Co. No. | Compound Structure | Method | HPLC Rt (min) | MS M+ (H$^+$) | LC/GC/MS Method |
|---|---|---|---|---|---|
| 34 | 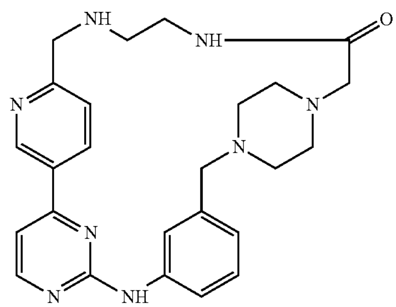 [SMILES: O=C1CN2CCN(CC2)Cc2cccc(c2)Nc2nccc(n2)-c2ccc(nc2)CNCCN1] | B4 | 1.9 | 459 | 3 |
| 126 | 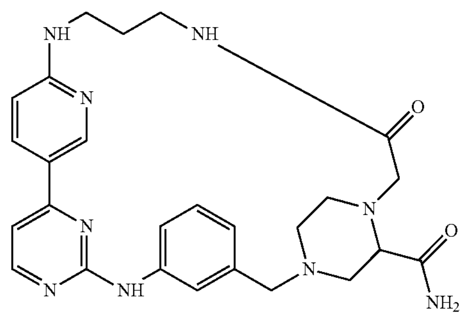 [SMILES: NC(=O)C1CN2CCN1CC(=O)NCCCNc1ccc(cn1)-c1ccnc(n1)Nc1cccc(c1)C2] | B5 | 1.96 | 502 | 3 |
| 46 | 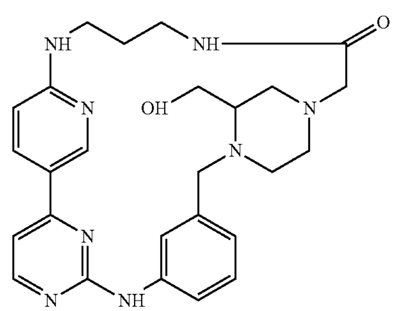 [SMILES: O=C1CN2CCN(Cc3cccc(c3)Nc3nccc(n3)-c3ccc(nc3)NCCCN1)C(CO)C2] | B5 | 1.98 | 489 | 3 |
| 27 | 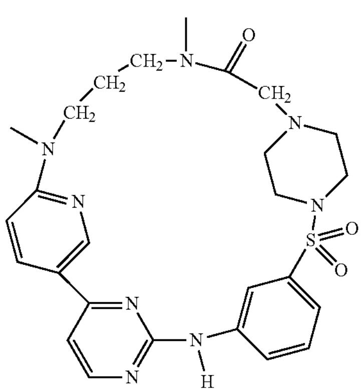 [SMILES: CN1CCCN(C)c2ccc(cn2)-c2ccnc(n2)Nc2cccc(c2)S(=O)(=O)N2CCN(CC2)CC1=O] | B1 | 0.91 | 537 | 1 |

TABLE 2-continued compounds and physico-chemical data (Co. No. means compound number)

| Co. No. | Compound Structure | Method | HPLC Rt (min) | MS M+ (H⁺) | LC/GC/MS Method |
|---|---|---|---|---|---|
| 116 | 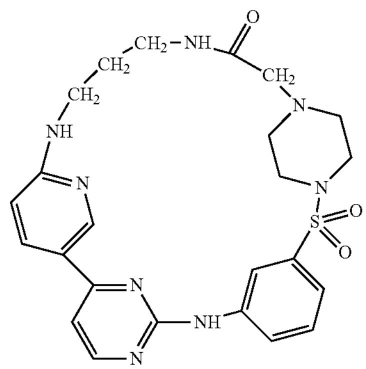 [SMILES: O=C1CN2CCN(CC2)S(=O)(=O)c2cccc(c2)Nc2nccc(n2)-c2ccc(nc2)NCCCN1] | B1 | 0.75 | 509 | 1 |
| 85 | 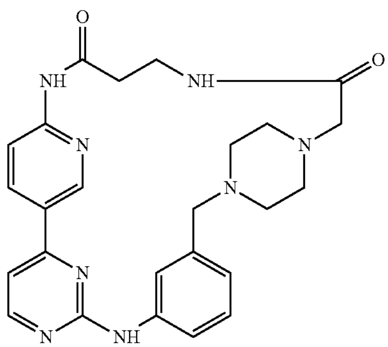 [SMILES: O=C1CN2CCN(CC2)Cc2cccc(c2)Nc2nccc(n2)-c2ccc(nc2)NC(=O)CCN1] | B6 | 1.89 | 473 | 3 |
| 56 | 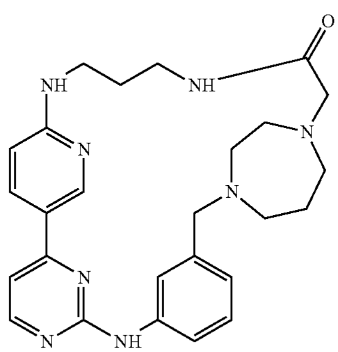 [SMILES: O=C1CN2CCCN(CC2)Cc2cccc(c2)Nc2nccc(n2)-c2ccc(nc2)NCCCN1] | B5 | 2.15 | 473 | 3 |
| 7 | 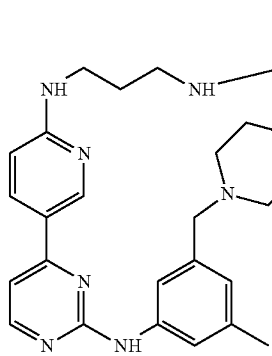 | B1 | 0.89 | 473 | 1 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 7a | (structure) ·4HCl·4H₂O | B1 | 0.81 | 473 | 1 |
| 9 | (structure) | B1 | 0.86 | 493 | 1 |
| 9a | (structure) ·2.6HCl·3H₂O | B1 | 0.89 | 493 | 1 |
| 8 | (structure) | B1 | 0.93 | 501 | 1 |

TABLE 2-continued
compounds and physico-chemical data (Co. No. means compound number)
| Co. No. | Compound Structure | Method | HPLC Rt (min) | MS M+ (H+) | LC/GC/MS Method |
|---|---|---|---|---|---|
| 8a | 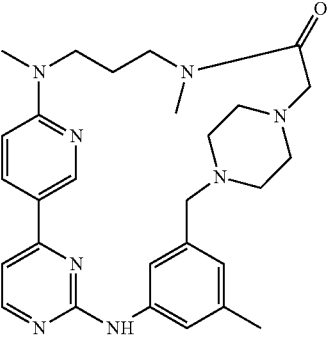 ·3HCl ·5 H$_2$O | B1 | 0.96 | 501 | 1 |
| 5 | 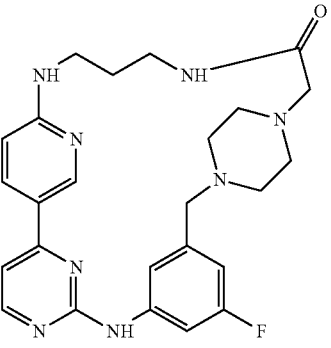 [SMILES: O=C1CN2CCN(CC2)Cc2cc(Cl)cc(c2)Nc2nccc(n2)-c2ccc(nc2)NCCCN1] | B1 | 0.78 | 477 | 1 |
| 6 | 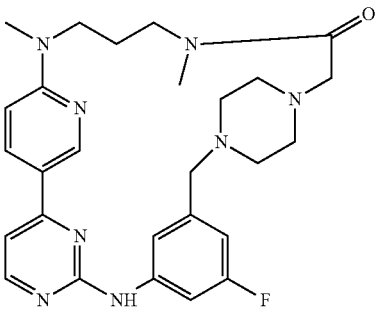 [SMILES: CN1CCCN(C)c2ccc(cn2)-c2ccnc(n2)Nc2cc(F)cc(c2)CN2CCN(CC2)CC1=O] | B1 | 0.93 | 505 | 1 |
| 49 | 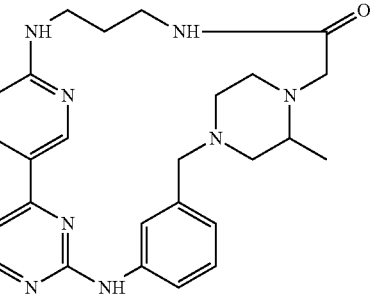 | B5 | 2.32 | 473 | 3 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 59 | 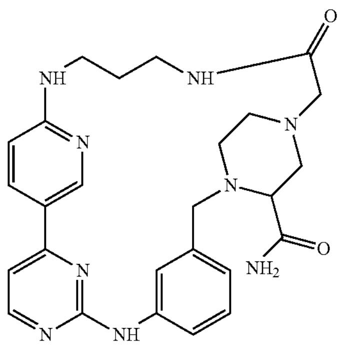 [SMILES: NC(=O)C1CN2CCN1Cc1cccc(c1)Nc1nccc(n1)-c1ccc(nc1)NCCCNC(=O)C2] | B5 | 1.96 | 502 | 3 |
| 25 | 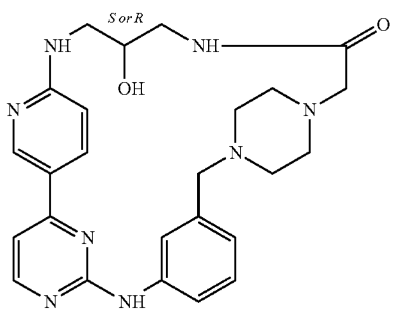 [SMILES: O=C1CN2CCN(CC2)Cc2cccc(c2)Nc2nccc(n2)-c2ccc(nc2)NCC(O)CN1] | C5.a | 1.99 | 475 | 3 |
| 24 | 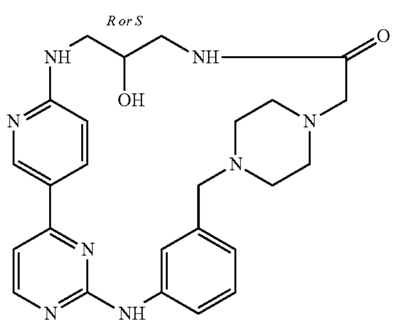 [SMILES: O=C1CN2CCN(CC2)Cc2cccc(c2)Nc2nccc(n2)-c2ccc(nc2)NCC(O)CN1] | C5.a | 2.00 | 475 | 3 |
| 57 | 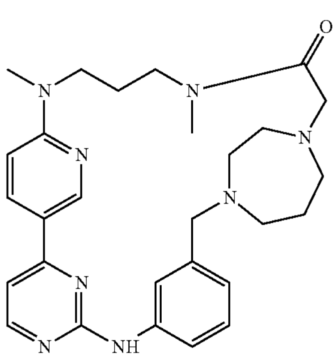 [SMILES: CN1CCCN(C)c2ccc(cn2)-c2ccnc(n2)Nc2cccc(c2)CN2CCCN(CC2)CC1=O] | B5 | 2.43 | 501 | 3 |

TABLE 2-continued compounds and physico-chemical data (Co. No. means compound number)

| Co. No. | Compound Structure | Method | HPLC Rt (min) | MS M+ (H$^+$) | LC/GC/ MS Method |
|---|---|---|---|---|---|
| 58 | 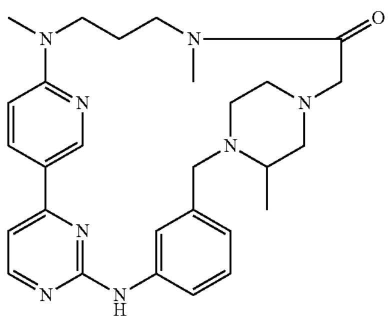 [SMILES: CC1CN2CCN1Cc1cccc(c1)Nc1nccc(n1)-c1ccc(nc1)N(C)CCCN(C)C(=O)C2] | B5 | 2.72 | 501 | 3 |
| 51 | 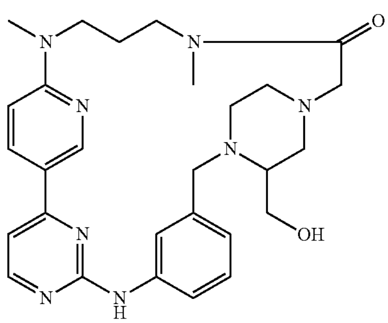 [SMILES: CN1CCCN(C)c2ccc(cn2)-c2ccnc(n2)Nc2cccc(c2)CN2CCN(CC1=O)CC2CO] | B5 | 2.28 | 517 | 3 |
| 84 | 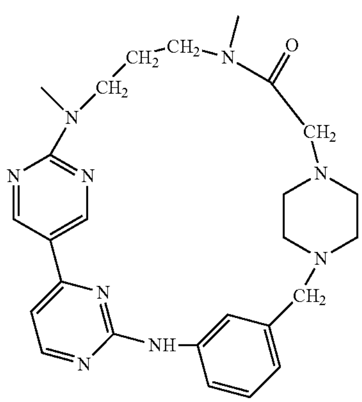 [SMILES: CN1CCCN(C)c2ncc(cn2)-c2ccnc(n2)Nc2cccc(c2)CN2CCN(CC2)CC1=O] | B15 | 0.90 | 488 | 1 |
| 54 | 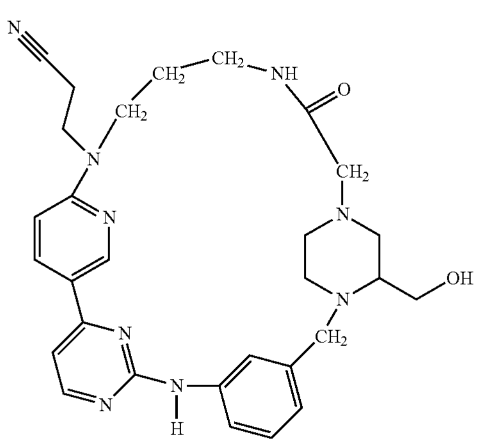 [SMILES: N#CCCN1CCCNC(=O)CN2CCN(Cc3cccc(c3)Nc3nccc(n3)-c3ccc1nc3)C(CO)C2] | C6 | 0.75 | 542 | 1 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 50 | 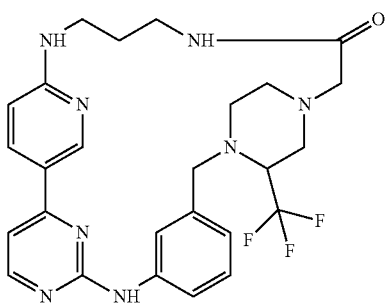 [SMILES: O=C1CN2CCN(Cc3cccc(c3)Nc3nccc(n3)-c3ccc(nc3)NCCCN1)C(C(F)(F)F)C2] | B5 | 2.82 | 527 | 3 |
| 87 | 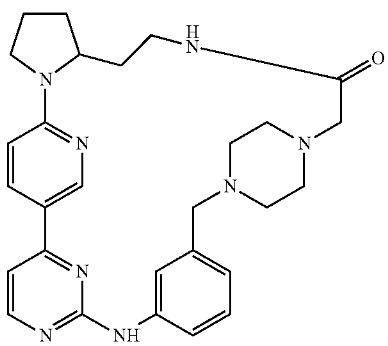 [SMILES: O=C1CN2CCN(CC2)Cc2cccc(c2)Nc2nccc(n2)-c2ccc(nc2)N2CCCC2CCN1] | B7 | 2.56 | 499 | 3 |
| 10 | 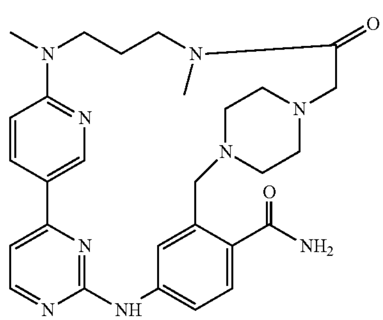 [SMILES: CN1CCCN(C)c2ccc(cn2)-c2ccnc(n2)Nc2ccc(C(N)=O)c(c2)CN2CCN(CC2)CC1=O] | B1 | 5.18 | 530 | 4 |
| 15 | 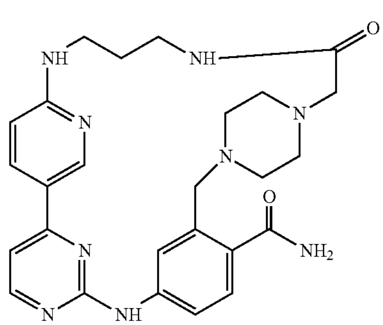 [SMILES: NC(=O)c1ccc2cc1CN1CCN(CC1)CC(=O)NCCCNc1ccc(cn1)-c1ccnc(n1)N2] | B1 | 4.24 | 502 | 4 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 13 | 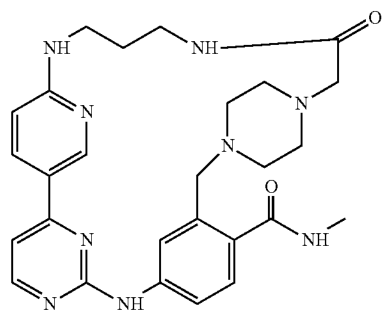 [SMILES: CNC(=O)c1ccc2cc1CN1CCN(CC1)CC(=O)NCCCNc1ccc(cn1)-c1ccnc(n1)N2] | B1 | 0.68 | 516 | 1 |
| 18 | 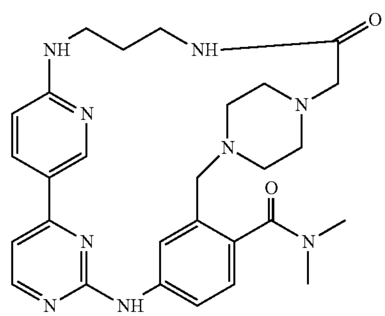 [SMILES: CN(C)C(=O)c1ccc2cc1CN1CCN(CC1)CC(=O)NCCCNc1ccc(cn1)-c1ccnc(n1)N2] | B1 | 0.68 | 530 | 1 |
| 17 | 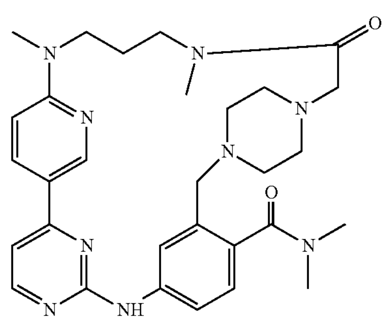 [SMILES: CN(C)C(=O)c1ccc2cc1CN1CCN(CC1)CC(=O)N(C)CCCN(C)c1ccc(cn1)-c1ccnc(n1)N2] | B1 | 0.81 | 558 | 1 |
| 12 | 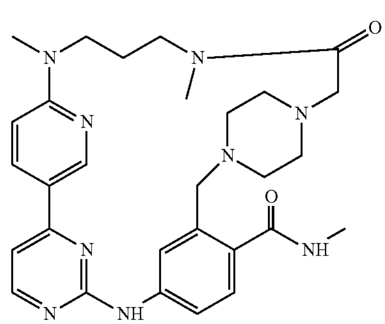 [SMILES: CNC(=O)c1ccc2cc1CN1CCN(CC1)CC(=O)N(C)CCCN(C)c1ccc(cn1)-c1ccnc(n1)N2] | B1 | 0.83 | 544 | 1 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 66 | 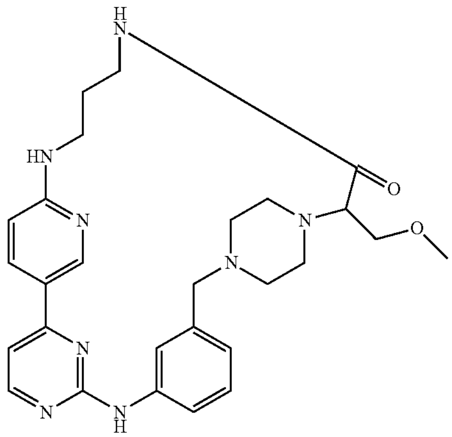 [SMILES: COCC1C(=O)NCCCNc2ccc(cn2)-c2ccnc(n2)Nc2cccc(c2)CN2CCN1CC2] | B5 | 0.77 | 503 | 1 |
| 65 | 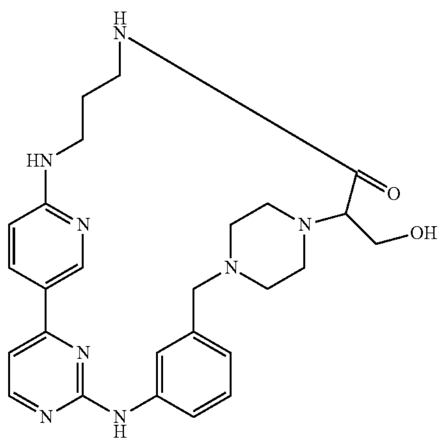 [SMILES: O=C1NCCCNc2ccc(cn2)-c2ccnc(n2)Nc2cccc(c2)CN2CCN(CC2)C1CO] | B5 | 0.67 | 489 | 1 |
| 62 | 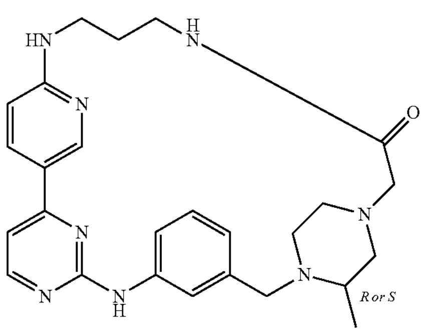 [SMILES: CC1CN2CCN1Cc1cccc(c1)Nc1nccc(n1)-c1ccc(nc1)NCCCNC(=O)C2] | C5.c | 2.33 | 473 | 3 |
| 61 | 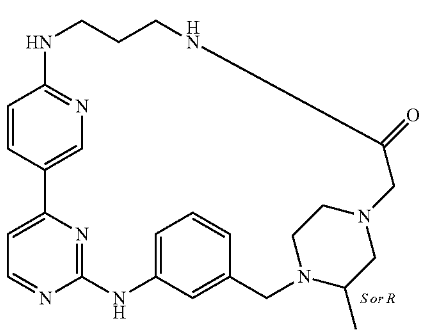 [SMILES: CC1CN2CCN1Cc1cccc(c1)Nc1nccc(n1)-c1ccc(nc1)NCCCNC(=O)C2] | C5.c | 2.33 | 473 | 3 |

TABLE 2-continued
compounds and physico-chemical data (Co. No. means compound number)
| Co. No. | Compound Structure | Method | HPLC Rt (min) | MS M+ (H+) | LC/GC/ MS Method |
|---|---|---|---|---|---|
| 52 | 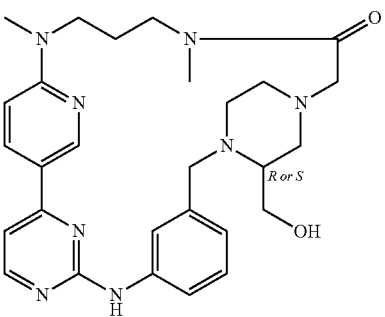 [SMILES: CN1CCCN(C)c2ccc(cn2)-c2ccnc(n2)Nc2cccc(c2)CN2CCN(CC1=O)CC2CO] | C5.b | 2.28 | 517 | 3 |
| 53 | 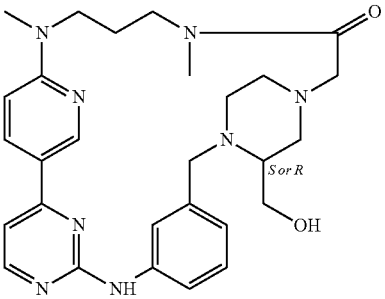 [SMILES: CN1CCCN(C)c2ccc(cn2)-c2ccnc(n2)Nc2cccc(c2)CN2CCN(CC1=O)CC2CO] | C5.b | 2.29 | 517 | 3 |
| 63 | 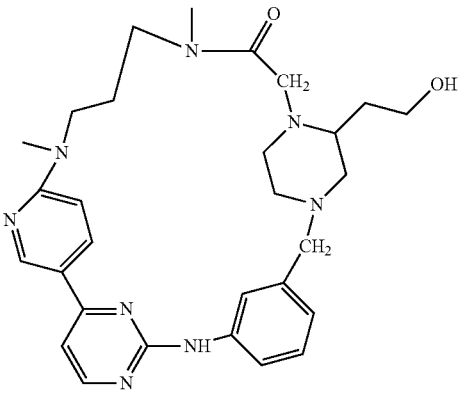 [SMILES: CN1CCCN(C)c2ccc(cn2)-c2ccnc(n2)Nc2cccc(c2)CN2CCN(CC1=O)C(CCO)C2] | B5 (Et$_3$N was used instead of DIPEA) | 0.82 | 531 | 1 |
| 16 | 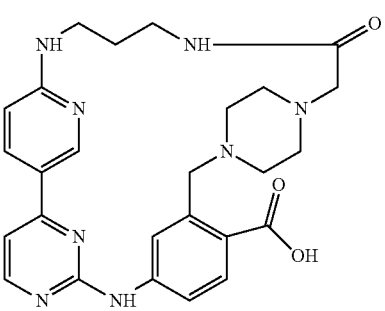 [SMILES: O=C1CN2CCN(CC2)Cc2cc(ccc2C(=O)O)Nc2nccc(n2)-c2ccc(nc2)NCCCN1] | B1.c | 0.50 | 503 | 1 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 19 | 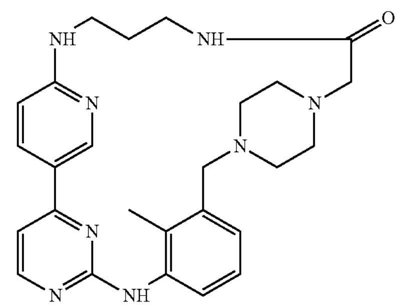 [SMILES: Cc1c2cccc1Nc1nccc(n1)-c1ccc(nc1)NCCCNC(=O)CN1CCN(CC1)C2] | B1 | 0.75 | 473 | 1 |
| 11 | 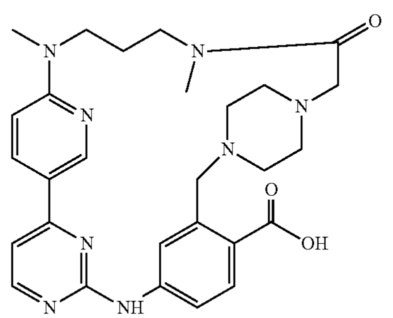 [SMILES: CN1CCCN(C)c2ccc(cn2)-c2ccnc(n2)Nc2ccc(C(=O)O)c(c2)CN2CCN(CC2)CC1=O] | C1 | 0.64 | 531 | 1 |
| 26 | 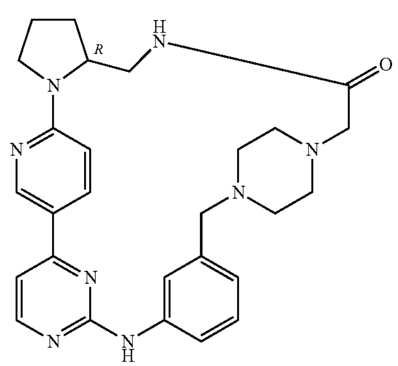 | B1 | 2.43 | 485 | 3 |
| 92 | 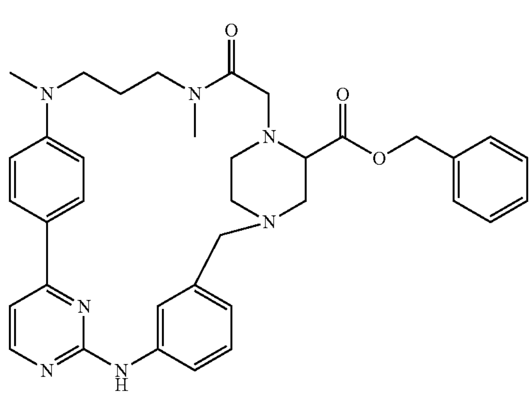 [SMILES: CN1CCCN(C)c2ccc(cc2)-c2ccnc(n2)Nc2cccc(c2)CN2CCN(CC1=O)C(C(=O)OCc1ccccc1)C2] | B7 | 3.26 | 621 | 3 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 47 | 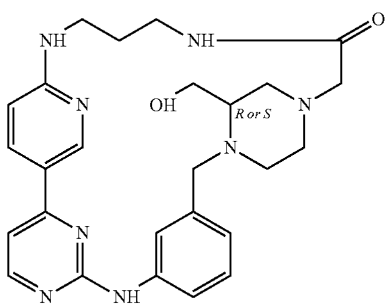 [SMILES: O=C1CN2CCN(Cc3cccc(c3)Nc3nccc(n3)-c3ccc(nc3)NCCCN1)C(CO)C2] | C5.b | 1.99 | 489 | 3 |
| 48 | 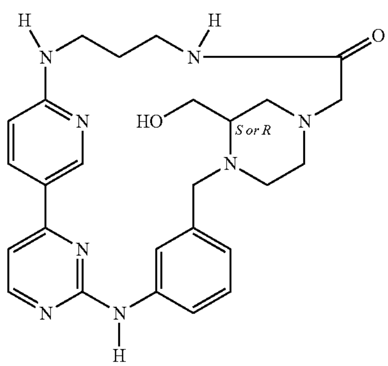 [SMILES: O=C1CN2CCN(Cc3cccc(c3)Nc3nccc(n3)-c3ccc(nc3)NCCCN1)C(CO)C2] | C5.b | 1.99 | 489 | 3 |
| 55 | 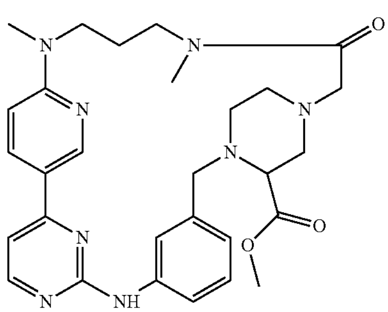 [SMILES: COC(=O)C1CN2CCN1Cc1cccc(c1)Nc1nccc(n1)-c1ccc(nc1)N(C)CCCN(C)C(=O)C2] | B5 | 2.72 | 545 | 3 |
| 101 | 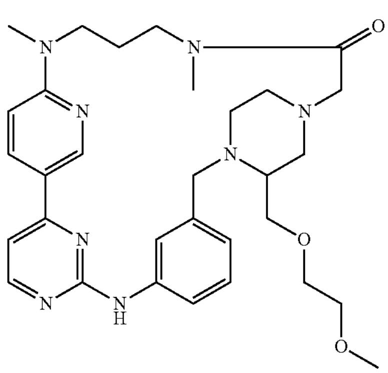 [SMILES: COCCOCC1CN2CCN1Cc1cccc(c1)Nc1nccc(n1)-c1ccc(nc1)N(C)CCCN(C)C(=O)C2] | B8 | 2.64 | 575 | 3 |

TABLE 2-continued
compounds and physico-chemical data (Co. No. means compound number)
| Co. No. | Compound Structure | Method | HPLC Rt (min) | MS M+ (H$^+$) | LC/GC/ MS Method |
|---|---|---|---|---|---|
| 97 | 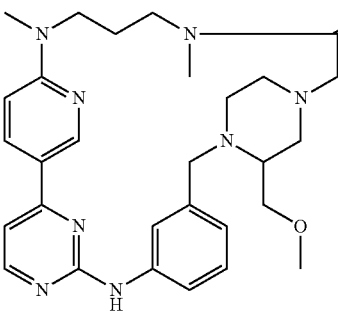 | B8 | 2.73 | 531 | 3 |
| 102 | 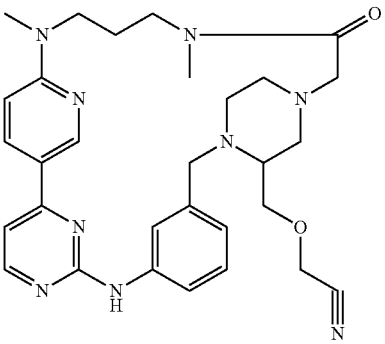 [SMILES: CN1CCCN(C)c2ccc(cn2)-c2ccnc(n2)Nc2cccc(c2)CN2CCN(CC1=O)CC2COCC#N] | B8 | 2.56 | 570 | 3 |
| 14 | 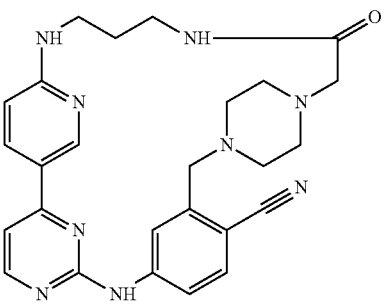 [SMILES: N#Cc1ccc2cc1CN1CCN(CC1)CC(=O)NCCCNc1ccc(cn1)-c1ccnc(n1)N2] | B1 | 0.81 | 484 | 1 |
| 93a | 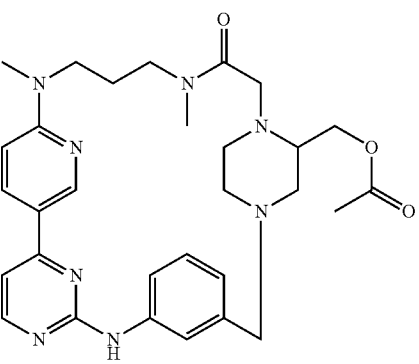 [SMILES: CC(=O)OCC1CN2CCN1CC(=O)N(C)CCCN(C)c1ccc(cn1)-c1ccnc(n1)Nc1cccc(c1)C2] | B17 | n.d. | n.d. | — |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 93 | 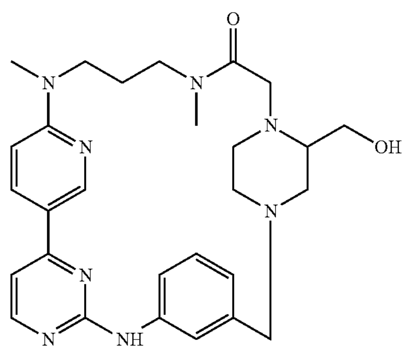 [SMILES: CN1CCCN(C)c2ccc(cn2)-c2ccnc(n2)Nc2cccc(c2)CN2CCN(CC1=O)C(CO)C2] | B17 or C4 | n.d. | n.d. | — |
| 94 | 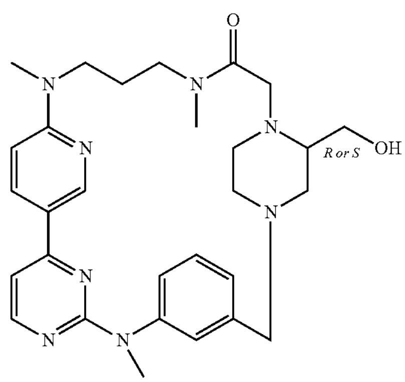 [SMILES: CN1CCCN(C)c2ccc(cn2)-c2ccnc(n2)N(C)c2cccc(c2)CN2CCN(CC1=O)C(CO)C2] | C4 | 2.33 | 517 | 3 |
| 95 | 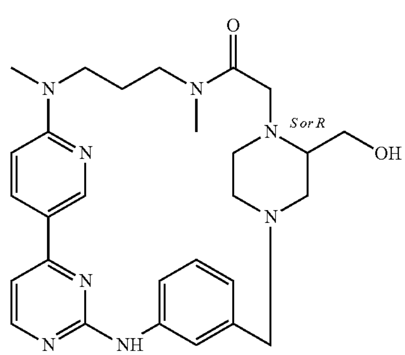 [SMILES: CN1CCCN(C)c2ccc(cn2)-c2ccnc(n2)Nc2cccc(c2)CN2CCN(CC1=O)C(CO)C2] | C4 | 2.33 | 517 | 3 |
| 136 | 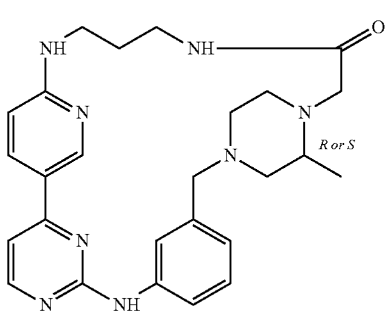 [SMILES: CC1CN2CCN1CC(=O)NCCCNc1ccc(cn1)-c1ccnc(n1)Nc1cccc(c1)C2] | C5.f | 2.31 | 473 | 3 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 137 | 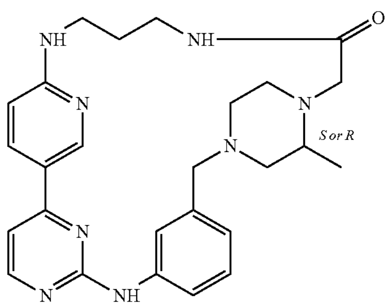 [SMILES: CC1CN2CCN1CC(=O)NCCCNc1ccc(cn1)-c1ccnc(n1)Nc1cccc(c1)C2] | C5.f | 2.32 | 473 | 3 |
| 88 | 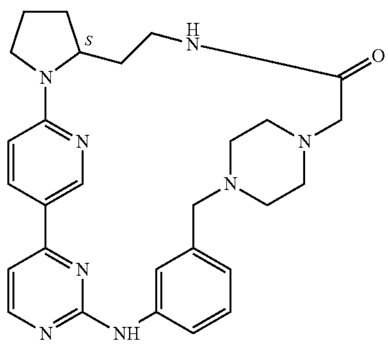 | B7 | 2.56 | 499 | 3 |
| 86 | 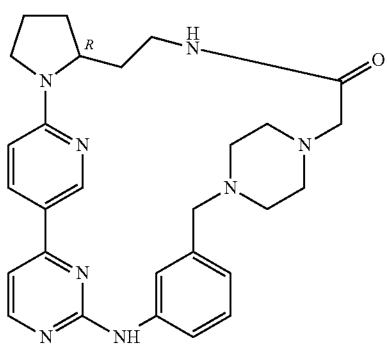 | B7 | 2.55 | 499 | 3 |
| 98 | 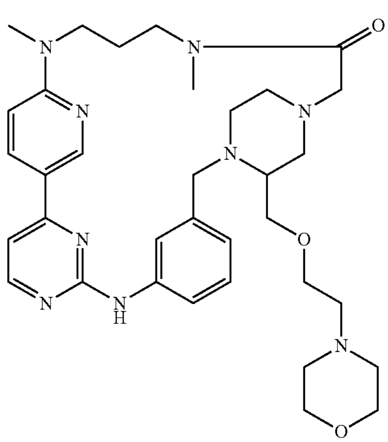 [SMILES: CN1CCCN(C)c2ccc(cn2)-c2ccnc(n2)Nc2cccc(c2)CN2CCN(CC1=O)CC2COCCN1CCOCC1] | B8 | 2.48 | 630 | 3 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 103 | 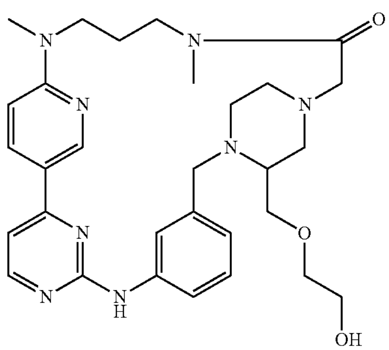 [SMILES: CN1CCCN(C)c2ccc(cn2)-c2ccnc(n2)Nc2cccc(c2)CN2CCN(CC1=O)CC2COCCO] | B8 | 2.35 | 561 | 3 |
| 108 | 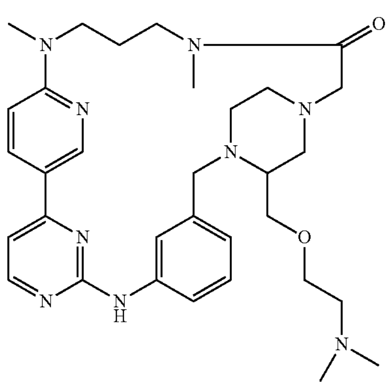 [SMILES: CN(C)CCOCC1CN2CCN1Cc1cccc(c1)Nc1nccc(n1)-c1ccc(nc1)N(C)CCCN(C)C(=O)C2] | B18 | 2.28 | 588 | 3 |
| 132 | 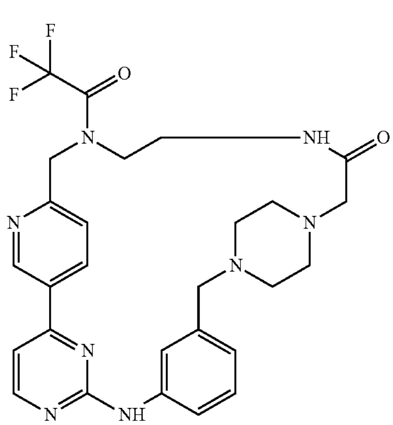 [SMILES: O=C1CN2CCN(CC2)Cc2cccc(c2)Nc2nccc(n2)-c2ccc(nc2)CN(C(=O)C(F)(F)F)CCN1] | C2.b | 0.81 | 555 | 1 |

TABLE 2-continued
compounds and physico-chemical data (Co. No. means compound number)
| Co. No. | Compound Structure | Method | HPLC Rt (min) | MS M+ (H+) | LC/GC/MS Method |
|---------|--------------------|--------|---------------|------------|-----------------|
| 106 | 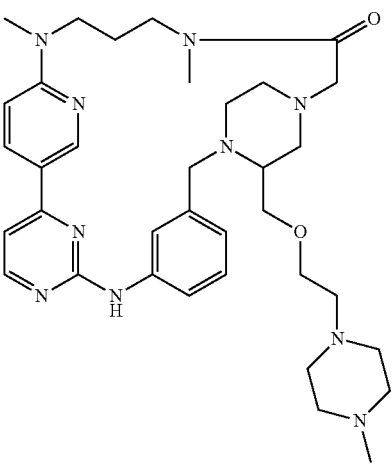 [SMILES: CN1CCN(CCOCC2CN3CCN2Cc2cccc(c2)Nc2nccc(n2)-c2ccc(nc2)N(C)CCCN(C)C(=O)C3)CC1] | B18 | 2.27 | 643 | 3 |
| 107 | 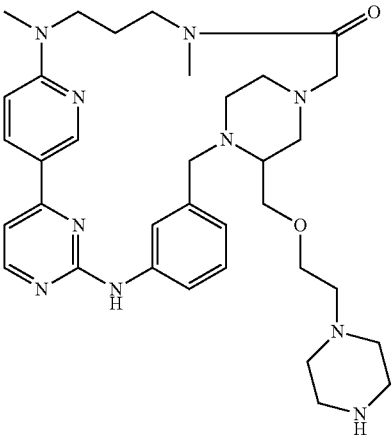 [SMILES: CN1CCCN(C)c2ccc(cn2)-c2ccnc(n2)Nc2cccc(c2)CN2CCN(CC1=O)CC2COCCN1CCNCC1] | B18 | 2.25 | 629 | 3 |
| 89 | 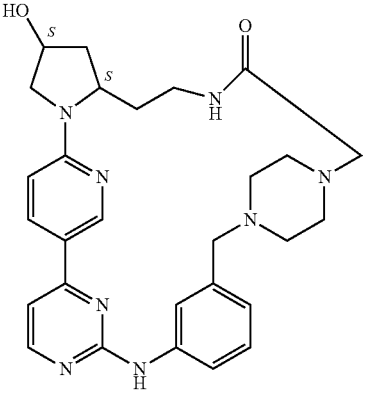 | B16 | 2.13 | 515 | 3 |

TABLE 2-continued
compounds and physico-chemical data (Co. No. means compound number)
| Co. No. | Compound Structure | Method | HPLC Rt (min) | MS M+ (H+) | LC/GC/ MS Method |
|---|---|---|---|---|---|
| 91 | 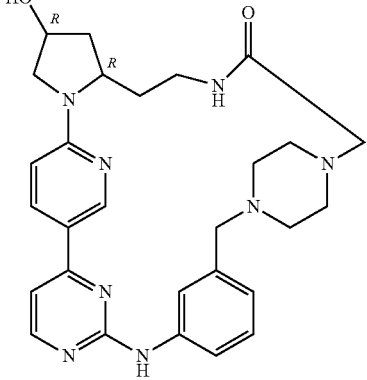 | B16 | 2.13 | 515 | 3 |
| 90 | 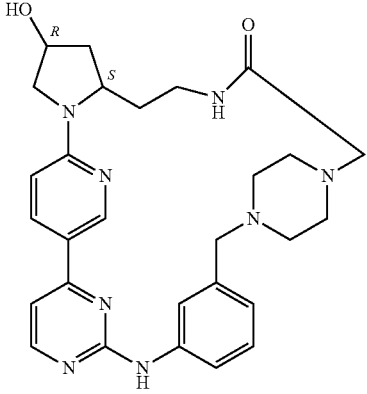 | B16 | 2.10 | 515 | 3 |
| 96 | 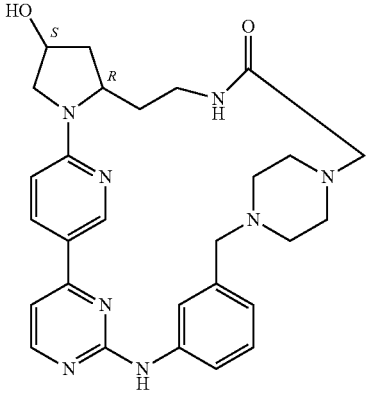 | B16 | 2.10 | 515 | 3 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 4 | 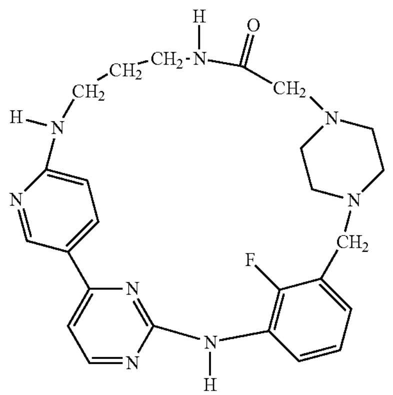 [SMILES: O=C1CN2CCN(CC2)Cc2cccc(c2F)Nc2nccc(n2)-c2ccc(nc2)NCCCN1] | B1 | 0.75 | 477 | 1 |
| 3 | 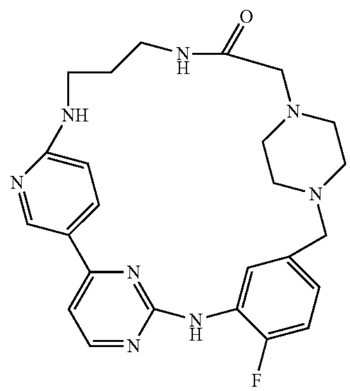 [SMILES: O=C1CN2CCN(CC2)Cc2ccc(F)c(c2)Nc2nccc(n2)-c2ccc(nc2)NCCCN1] | B1 | 0.85 | 477 | 1 |
| 2 | 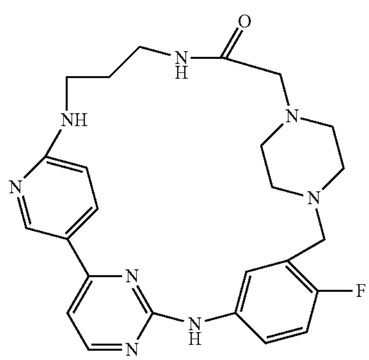 [SMILES: O=C1CN2CCN(CC2)Cc2cc(ccc2F)Nc2nccc(n2)-c2ccc(nc2)NCCCN1] | B1 | 0.83 | 477 | 1 |
| 104 | 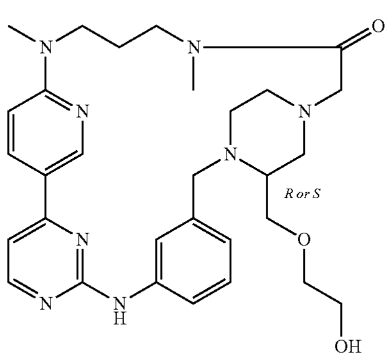 [SMILES: CN1CCCN(C)c2ccc(cn2)-c2ccnc(n2)Nc2cccc(c2)CN2CCN(CC1=O)CC2COCCO] | C5.e | 0.81 | 561 | 1 |

TABLE 2-continued
compounds and physico-chemical data (Co. No. means compound number)
| Co. No. | Compound Structure | Method | HPLC Rt (min) | MS M+ (H+) | LC/GC/MS Method |
|---|---|---|---|---|---|
| 105 | 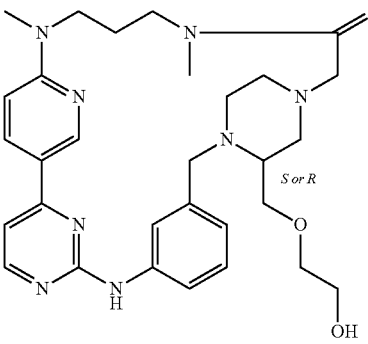 | C5.e | 0.81 | 561 | 1 |
| 99 | 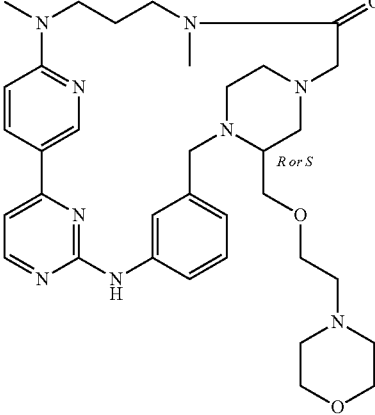 | C5.d | 0.88 | 630 | 1 |
| 100 | 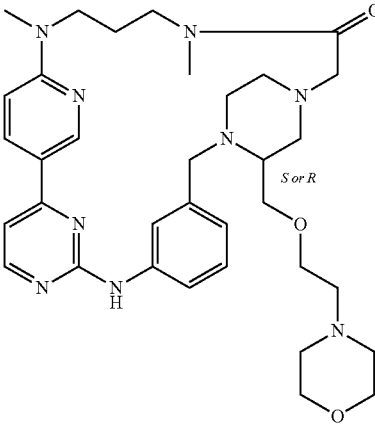 | C5.d | 0.88 | 630 | 1 |

TABLE 2-continued compounds and physico-chemical data (Co. No. means compound number)

| Co. No. | Compound Structure | Method | HPLC Rt (min) | MS M+ (H+) | LC/GC/ MS Method |
|---|---|---|---|---|---|
| 45 | 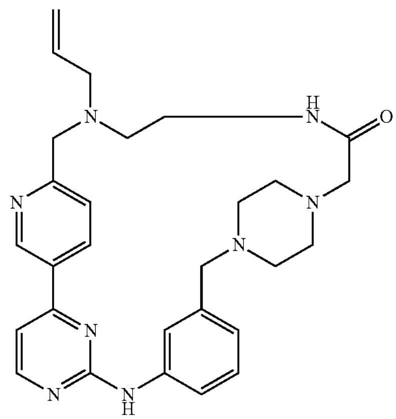 [SMILES: C=CCN1CCNC(=O)CN2CCN(CC2)Cc2cccc(c2)Nc2nccc(n2)-c2ccc(nc2)C1] | C2.a | 0.88 | 499 | 1 |
| 133 | 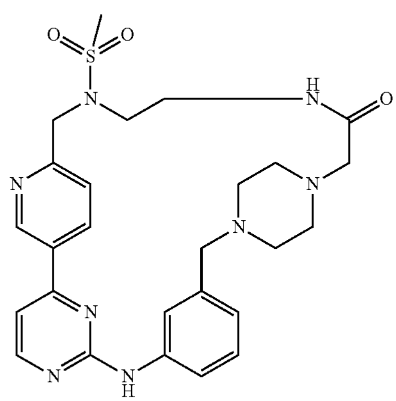 [SMILES: CS(=O)(=O)N1CCNC(=O)CN2CCN(CC2)Cc2cccc(c2)Nc2nccc(n2)-c2ccc(nc2)C1] | C2.b | 0.67 | 537 | 1 |
| 35 | 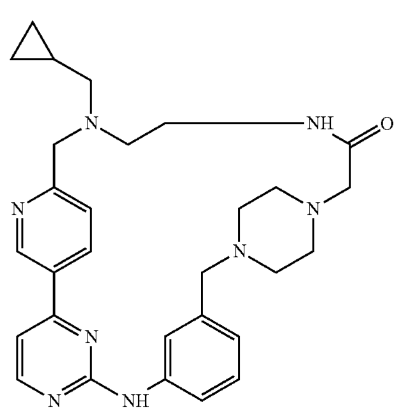 [SMILES: O=C1CN2CCN(CC2)Cc2cccc(c2)Nc2nccc(n2)-c2ccc(nc2)CN(CC2CC2)CCN1] | C2.a | 0.92 | 513 | 1 |

TABLE 2-continued
compounds and physico-chemical data (Co. No. means compound number)
| Co. No. | Compound Structure | Method | HPLC Rt (min) | MS M+ (H+) | LC/GC/ MS Method |
|---|---|---|---|---|---|
| 36 | 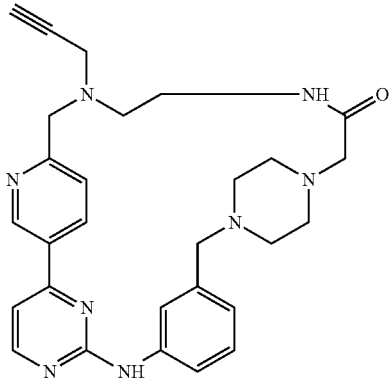 [SMILES: C#CCN1CCNC(=O)CN2CCN(CC2)Cc2cccc(c2)Nc2nccc(n2)-c2ccc(nc2)C1] | C2.a | 0.81 | 497 | 1 |
| 37 | 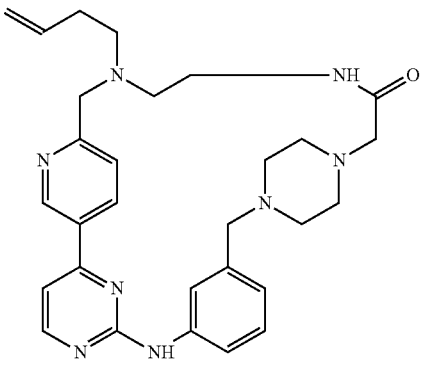 [SMILES: C=CCCN1CCNC(=O)CN2CCN(CC2)Cc2cccc(c2)Nc2nccc(n2)-c2ccc(nc2)C1] | C2.a | 0.97 | 513 | 1 |
| 41 | 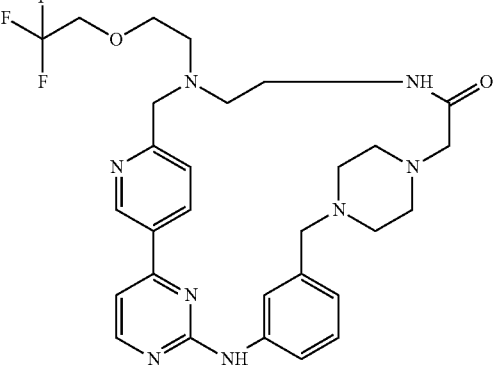 | C2.a | 0.65 | 585 | 5 |
| 42 | 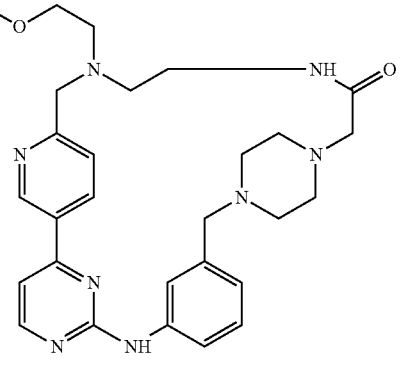 | C2.a | 0.83 | 517 | 1 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 134 | 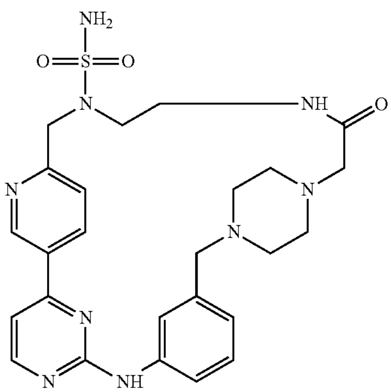 [SMILES: NS(=O)(=O)N1CCNC(=O)CN2CCN(CC2)Cc2cccc(c2)Nc2nccc(n2)-c2ccc(nc2)C1] | C2.c | 0.62 | 538 | 5 |
| 38 | 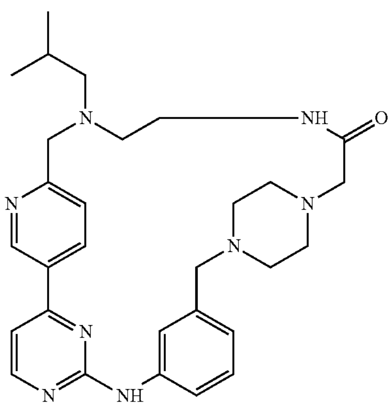 [SMILES: CC(C)CN1CCNC(=O)CN2CCN(CC2)Cc2cccc(c2)Nc2nccc(n2)-c2ccc(nc2)C1] | C2.a | 1.02 | 515 | 1 |
| 39 | 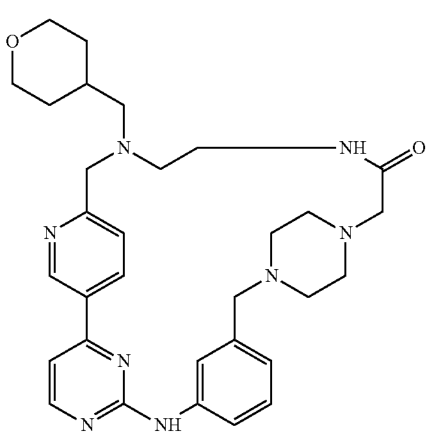 [SMILES: O=C1CN2CCN(CC2)Cc2cccc(c2)Nc2nccc(n2)-c2ccc(nc2)CN(CC2CCOCC2)CCN1] | C2.a | 0.85 | 557 | 1 |

TABLE 2-continued compounds and physico-chemical data (Co. No. means compound number)

| Co. No. | Compound Structure | Method | HPLC Rt (min) | MS M+ (H+) | LC/GC/MS Method |
|---|---|---|---|---|---|
| 40 | 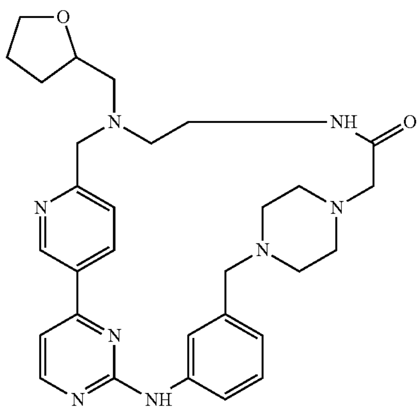 [SMILES: O=C1CN2CCN(CC2)Cc2cccc(c2)Nc2nccc(n2)-c2ccc(nc2)CN(CC2CCCO2)CCN1] | C2.a | 0.86 | 543 | 1 |
| 43 | 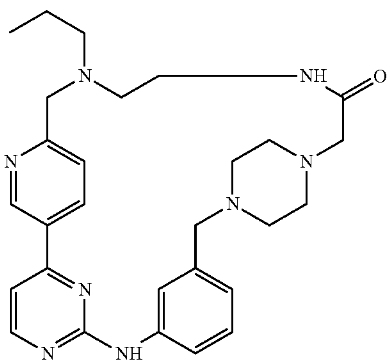 [SMILES: CCCN1CCNC(=O)CN2CCN(CC2)Cc2cccc(c2)Nc2nccc(n2)-c2ccc(nc2)C1] | C2.a | 0.92 | 501 | 1 |
| 44 | 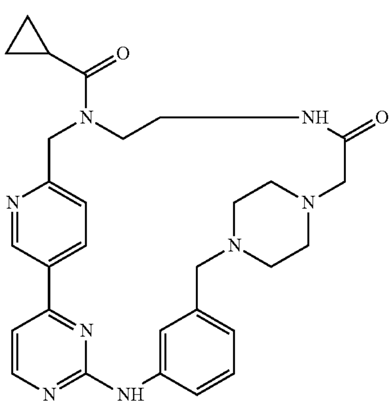 [SMILES: O=C1CN2CCN(CC2)Cc2cccc(c2)Nc2nccc(n2)-c2ccc(nc2)CN(C(=O)C2CC2)CCN1] | C2.b | 0.75 | 527 | 1 |

Melting Points (m.p.)

For compound 80, the m.p. was determined with a DSC 1 STAR$^e$ System from Mettler Toledo. The melting point was measured with a temperature gradient of 30° C./minute up to 300° C. The melting point is given as a peak value: 291.27° C.

For a number of compounds, melting points were obtained with a Kofler hot bench, consisting of a heated plate with linear temperature gradient, a sliding pointer and a temperature scale in degrees Celsius:

| Co. 23: 161° C. | Co. 48: 169° C. | Co. 86: 174° C. | Co. 88: 188° C. |
|---|---|---|---|
| Co. 89: 177° C. | Co. 90: 189° C. | Co. 91: 188° C. | Co. 96: 193° C. |

Optical Rotation (OR)

Compound 24: +41.14° (589 nm 20° C.; 0.333 w/v %; DMF)
Compound 25: −41.56° (589 nm 20° C.; 0.4115 w/v %; DMF)
Compound 47: +79.35° (589 nm; 20° C.; 0.247 w/v %; DMF)

Compound 48: −81.7° (589 nm; 20° C.; 0.235 w/v %; DMF)
Compound 52: −89.94° (589 nm; 20° C.; 0.218 w/v %; DMF)
Compound 53: +73.77° (589 nm; 20° C.; 0.183 w/v %; DMF)
Compound 61: −92.16° (589 nm; 20° C.; 0.204 w/v %; DMF)
Compound 62: +95.63° (589 nm; 20° C.; 0.252 w/v %; DMF)
Compound 89: −141.15° (589 nm; 20° C.; 0.2345 w/v %; DMF)
Compound 90: −120.00° (589 nm; 20° C.; 0.265 w/v %; DMF)
Compound 91: +141.95° (589 nm; 20° C.; 0.174 w/v %; DMF)
Compound 96: +117.91° (589 nm; 20° C.; 0.2205 w/v %; DMF)

SFC-MS

For SFC-MS, an analytical SFC system from Berger Instruments (Newark, Del., USA) was used comprising a dual pump control module (FCM-1200) for delivery of $CO_2$ and modifier, a thermal control module for column heating (TCM2100) with temperature control in the range 1-150° C. and column selection valves (Valco, VICI, Houston, Tex., USA) for 6 different columns. The photodiode array detector (Agilent 1100, Waldbronn, Germany) is equipped with a high-pressure flow cell (up to 400 bar) and configured with a CTC LC Mini PAL auto sampler (Leap Technologies, Carrboro, N.C., USA). A ZQ mass spectrometer (Waters, Milford, Mass., USA) with an orthogonal Z-electrospray interface is coupled with the SFC-system. Instrument control, data collection and processing were performed with an integrated platform consisting of the SFC ProNTo software and Masslynx software.

Co. No. 99-100: SFC-MS was carried out on a OD-H column (250×4.6 mm) (Daicel Chemical Industries Ltd) with a flow rate of 3 ml/min. Two mobile phases (mobile phase A: $CO_2$; mobile phase B: MeOH containing 0.2% isopropylamine ($iPrNH_2$)) were employed. 45% B was hold for 15 min. Column temperature was set at 30° C. Under these conditions, Co. No. 99 had a shorter $R_t$ on the column than Co. No. 100. The measurement was compared against the mixture of the compounds.

Co. No. 94-95: SFC-MS was carried out on a AD-H column (250×4.6 mm) (Daicel Chemical Industries Ltd) with a flow rate of 3 ml/min. Two mobile phases (mobile phase A: $CO_2$; mobile phase B: MeOH containing 0.3% $iPrNH_2$) were employed. 60% B was hold for 11 min. Column temperature was set at 35° C. Under these conditions, Co. No. 94 had a shorter R on the column than Co. No. 95. The measurement was compared against the mixture of the compounds.

Co. No. 136-137: SFC-MS was carried out on a AD-H column (250×4.6 mm) (Daicel Chemical Industries Ltd) with a flow rate of 3 ml/min. Two mobile phases (mobile phase A: $CO_2$; mobile phase B: EtOH containing 0.3% $iPrNH_2$) were employed. 60% B was hold for 7 min. Column temperature was set at 35° C. Under these conditions, Co. No 136 had a shorter $R_t$ on the column than Co. No 137. The measurement was compared against the mixture of the compounds.

Co. No. 104-105: SFC-MS was carried out on a OD-H column (250×4.6 mm) (Daicel Chemical Industries Ltd) with a flow rate of 3 ml/min. Two mobile phases (mobile phase A: $CO_2$; mobile phase B: MeOH containing 0.2% $iPrNH_2$) were employed. 45% B was hold for 15 min. Column temperature was set at 30° C. Under these conditions, Co. No. 104 had a shorter $R_t$ on the column than Co. No. 105. The measurement was compared against the mixture of the compounds.

NMR

For a number of compounds, $^1H$ NMR spectra were recorded on a Bruker Avance III with a 300 MHz Ultrashield magnet, on a Bruker DPX-400 spectrometer operating at 400 MHz, on a Bruker DPX-360 operating at 360 MHz, on a Bruker Avance 600 spectrometer operating at 600 MHz, or a Bruker Avance 500 III operating at 500 MHz using internal deuterium lock. As solvents CHLOROFORM-d (deuterated chloroform, $CDCl_3$) or DMSO-$d_6$ (deuterated DMSO, dimethyl-d6 sulfoxide) were used. Chemical shifts (δ) are reported in parts per million (ppm) relative to tetramethylsilane (TMS), which was used as internal standard.

Compound 1

$^1H$ NMR (600 MHz, CHLOROFORM-d) δ ppm 1.76-1.88 (m, 2H) 2.66 (br. s., 8H) 3.10 (s, 3H) 3.13-3.18 (m, 2H) 3.19 (s, 2H) 3.25 (s, 3H) 3.51 (s, 2H) 3.59-3.73 (m, 2H) 6.41 (d, J=−8.8 Hz, 1H) 6.85-6.91 (m, 1H) 7.02 (d, J=5.3 Hz, 1H) 7.09 (s, 1H) 7.11-7.16 (m, 1H) 7.27-7.33 (m, 1H) 7.99 (s, 1H) 8.08-8.16 (m, 1H) 8.32 (d, J=5.3 Hz, 1H) 8.91 (br. s., 1H)+minor rotamer Compound 87

$^1H$ NMR (500 MHz, DMSO-$d_6$) δ ppm 1.36 (br. s., 1H) 1.74-2.15 (m, 5H) 2.50-2.81 (m, 8H-partially obscured by solvent peak) 2.88 (d, J=15.4 Hz, 1H) 2.99 (d, J=15.4 Hz, 1H) 3.06-3.17 (m, 1H) 3.19-3.31 (m, 1H) 3.34-4.15 (m, 5H-partially obscured by solvent peak) 6.42 (d, J=8.9 Hz, 1H) 6.98 (d, J=7.6 Hz, 1H) 7.01 (d, J=7.6 Hz, 1H) 7.18-7.37 (m, 2H) 7.52-8.32 (m, 3H) 8.38 (d, J=5.4 Hz, 1H) 8.89 (br. s., 1H) 9.42 (s, 1H)

Compound 62

$^1H$ NMR (500 MHz, DMSO-$d_6$) δ ppm 1.17 (d, J=5.7 Hz, 3H) 1.50-1.69 (m, 2H) 2.04-2.25 (m, 2H) 2.43 (t, J=10.1 Hz, 1H) 2.49-2.57 (m, 1H-partially obscured by solvent peak) 2.65-2.95 (m, 5H) 2.98-3.14 (m, 3H) 3.37-3.47 (m, 2H-partially obscured by solvent peak) 4.04 (d, J=−11.7 Hz, 1H) 6.45 (d, J=8.8 Hz, 1H) 6.93 (d, J=7.4 Hz, 1H) 7.00 (d, J=7.4 Hz, 1H) 7.16 (d, J=5.0 Hz, 1H) 7.19-7.26 (m, 2H) 7.64-7.78 (m, 1H) 7.93-8.07 (m, 2H) 8.37 (d, J=5.4 Hz, 1H) 8.95 (br. s., 1H) 9.41 (s, 1H)

Compound 53

$^1H$ NMR (500 MHz, DMSO-$d_6$) δ ppm 1.53-2.21 (m, 4H) 2.38-2.45 (m, 1H) 2.58-3.30 (m, 13H) 3.34-4.17 (m, 7H-partially obscured by solvent peak) 4.38-4.68 (m, 1H) 6.42-7.04 (m, 3H) 7.11-7.32 (m, 2H) 7.85-8.55 (m, 3H) 8.84-9.21 (m, 1H) 9.38-9.54 (m, 1H)

Compound 47

$^1H$ NMR (500 MHz, DMSO-$d_6$) δ ppm 1.48-1.81 (m, 2H) 2.04-2.15 (m, 1H) 2.26 (t, J=9.9 Hz, 1H) 2.42-2.50 (m, 2H-partially obscured by solvent peak) 2.61-2.79 (m, 2H) 2.85-2.99 (m, 3H) 3.01-3.12 (m, 2H) 3.27-3.42 (m, 3H-partially obscured by solvent peak) 3.49-3.55 (m, 1H) 3.78-3.87 (m, 1H) 4.14 (d, J=12.0 Hz, 1H) 4.62 (t, J=5.2 Hz, 1H) 6.45 (d, J=9.1 Hz, 1H) 6.95 (d, J=7.6 Hz, 1H) 6.98 (d, J=7.6 Hz, 1H) 7.16 (d, J=5.4 Hz, 1H) 7.20-7.27 (m, 2H) 7.66-7.83 (m, 1H) 7.88-8.06 (m, 2H) 8.37 (d, J=5.4 Hz, 1H) 8.95 (s, 1H) 9.41 (s, 1H)

Compound 14

$^1H$ NMR (400 MHz, DMSO-$d_6$) δ ppm 1.60-1.70 (m, 2H) 2.54-2.61 (m, 4H) 2.68-2.77 (m, 4H) 2.92 (s, 2H) 3.20-3.28 (m, 2H) 3.41-3.50 (m, 2H) 3.53 (s, 2H) 6.50 (d, J=8.9 Hz, 1H) 6.99 (t, J=6.1 Hz, 1H) 7.19 (dd, J=8.5, 2.0 Hz, 1H) 7.23 (d, J=5.2 Hz, 1H) 7.55 (t, J=5.9 Hz, 1H) 7.63 (d, J=8.1 Hz, 1H) 7.97 (dd, J=8.9, 2.4 Hz, 1H) 8.40 (d, J=2.0 Hz, 1H) 8.43 (d, J=5.7 Hz, 1H) 9.00 (d, J=2.0 Hz, 1H) 9.69 (br. s., 1H)

Compound 88

$^1$H NMR (500 MHz, DMSO-d$_6$) δ ppm 1.36 (br. s., 1H) 1.74-2.15 (m, 5H) 2.50-2.81 (m, 8H-partially obscured by solvent peak) 2.88 (d, J=15.4 Hz, 1H) 2.99 (d, J=15.4 Hz, 1H) 3.06-3.17 (m, 1H) 3.19-3.31 (m, 1H) 3.34-4.15 (m, 5H-partially obscured by solvent peak) 6.42 (d, J=8.9 Hz, 1H) 6.98 (d, J=7.6 Hz, 1H) 7.01 (d, J=7.6 Hz, 1H) 7.18-7.37 (m, 2H) 7.52-8.32 (m, 3H) 8.38 (d, J=5.4 Hz, 1H) 8.89 (br. s., 1H) 9.42 (s, 1H)

Compound 91

$^1$H NMR (500 MHz, DMSO-d$_6$) δ ppm 1.20-1.41 (m, 1H) 1.90-2.13 (m, 4H) 2.30-2.81 (m, 8H-partially obscured by solvent peak) 2.88 (d, J=15.4 Hz, 1H) 2.98 (d, J=15.4 Hz, 1H) 3.06-3.18 (m, 1H) 3.24-3.33 (m, 2H-partially obscured by solvent peak) 3.44-3.54 (m, 1H) 3.58-3.64 (m, 1H) 3.68-4.32 (m, 1H) 4.36-4.47 (m, 1H) 4.99 (d, J=3.5 Hz, 1H) 6.42 (d, J=8.8 Hz, 1H) 6.98 (d, J=7.6 Hz, 1H) 7.01 (d, J=7.6 Hz, 1H) 7.16-7.41 (m, 2H) 7.60-8.28 (m, 3H) 8.38 (d, J=5.0 Hz, 1H) 8.88 (br. s., 1H) 9.42 (s, 1H)

Compound 96

$^1$H NMR (500 MHz, DMSO-d$_6$) δ ppm 1.88-2.18 (m, 4H) 2.31-2.81 (m, 8H-partially obscured by solvent peak) 2.86 (d, J=15.4 Hz, 1H) 2.99 (d, J=15.4 Hz, 1H) 3.08-3.18 (m, 1H) 3.20-3.30 (m, 1H) 3.35-3.36 (m, 1H-partially obscured by solvent peak) 3.36-3.84 (m, 4H) 4.39 (br. s., 1H) 5.05 (br. s., 1H) 6.42 (d, J=9.1 Hz, 1H) 6.97 (d, J=7.6 Hz, 1H) 7.01 (d, J=7.6 Hz, 1H) 7.21-7.32 (m, 2H) 7.93 (br. s, 1H) 8.06-8.34 (m, 2H) 8.38 (d, J=5.4 Hz, 1H) 8.88 (br. s., 1H) 9.42 (s, 1H)

Compound 4

$^1$H NMR (400 MHz, DMSO-d$_6$) δ ppm 1.61-1.77 (m, 2H) 2.81 (br. s., 8H) 3.10 (s, 2H) 3.19-3.28 (m, 2H) 3.32-3.40 (m, 2H) 3.81 (s, 2H) 6.42 (d, J=8.9 Hz, 1H) 7.01 (d, J=5.2 Hz, 1H) 7.13 (t, J=7.7 Hz, 1H) 7.16-7.23 (m, 1H) 7.30-7.39 (m, 1H) 7.46 (br. s., 1H) 7.79 (dd, J=8.9, 2.4 Hz, 1H) 8.30 (d, J=5.2 Hz, 1H) 8.56 (d, J=2.0 Hz, 1H)

Compound 45

$^1$H NMR (360 MHz, DMSO-d$_6$) δ ppm 2.53-2.60 (m, 8H) 2.60-2.66 (m, 2H) 2.96 (s, 2H) 3.10 (d, J=6.2 Hz, 2H) 3.23-3.33 (m, 2H) 3.38 (s, 2H) 3.75 (s, 2H) 5.14 (dd, J=10.2, 1.8 Hz, 1H) 5.22 (dd, J=17.2, 1.8 Hz, 1H) 5.77-5.89 (m, 1H) 6.95-7.02 (m, 1H) 7.02-7.09 (m, 1H) 7.26 (t, J=7.7 Hz, 1H) 7.51 (d, J=5.1 Hz, 1H) 7.61 (t, J=4.9 Hz, 1H) 7.65 (d, J=8.1 Hz, 1H) 8.12 (t, J=1.5 Hz, 1H) 8.53-8.63 (m, 2H) 9.20 (d, J=1.8 Hz, 1H) 9.70 (s, 1H)

Compound 35

$^1$H NMR (360 MHz, DMSO-d$_6$) δ ppm −0.05-0.03 (m, 2H) 0.29-0.38 (m, 2H) 0.72-0.86 (m, 1H) 2.26 (d, J=7.0 Hz, 2H) 2.48-2.63 (m, 8H) 2.66-2.75 (m, 2H) 2.92 (s, 2H) 3.24-3.28 (m, 2H) 3.32 (s, 2H) 3.73 (s, 2H) 6.95 (d, J=7.7 Hz, 1H) 6.97-7.03 (m, 1H) 7.21 (t, J=7.7 Hz, 1H) 7.46 (d, J=5.1 Hz, 1H) 7.56-7.65 (m, 2H) 8.06 (t, J=1.6 Hz, 1H) 8.52 (d, J=5.1 Hz, 1H) 8.56 (dd, J=8.4, 2.2 Hz, 1H) 9.13 (d, J=1.8 Hz, 1H) 9.65 (s, 1H)

Compound 43

$^1$H NMR (360 MHz, DMSO-d$_6$) δ ppm 0.80 (t, J=7.3 Hz, 3H) 1.37 (sxt, J=7.2 Hz, 2H) 2.38 (t, J=7.0 Hz, 2H) 2.52-2.60 (m, 8H) 2.60-2.65 (m, 2H) 2.96 (s, 2H) 3.27-3.33 (m, 2H) 3.35 (s, 2H) 3.70 (s, 2H) 6.94-7.02 (m, 1H) 7.03-7.10 (m, 1H) 7.22-7.31 (m, 1H) 7.51 (d, J=5.1 Hz, 1H) 7.56-7.67 (m, 2H) 8.12 (s, 1H) 8.53-8.63 (m, 2H) 9.19 (d, J=1.8 Hz, 1H) 9.71 (s, 1H)

Compound 2

$^1$H NMR (400 MHz, DMSO-d$_6$) δ ppm 1.58-1.70 (m, 2H) 2.52-2.60 (m, 4H) 2.64-2.72 (m, 4H) 2.90 (s, 2H) 3.17-3.24 (m, 2H) 3.37-3.45 (m, 2H) 3.46 (s, 2H) 6.47 (d, J=8.9 Hz, 1H) 6.93 (t, J=6.1 Hz, 1H) 7.03 (d, J=8.9 Hz, 1H) 7.06-7.10 (m, 1H) 7.11 (d, J=5.2 Hz, 1H) 7.54 (t, J=5.9 Hz, 1H) 7.95 (dd, J=8.9, 2.4 Hz, 1H) 8.12 (dd, J=6.9, 2.8 Hz, 1H) 8.35 (d, J=5.2 Hz, 1H) 8.95 (d, J=2.4 Hz, 1H) 9.11 (s, 1H)

Pharmacology

Biochemical EF2K Lysate-Based Kinase Assay

LN-229 cells were purchased from ATCC (CRL-2611); these are glioblastoma cells. Cell lysates from LN229 were used in this kinase assay to provide both the kinase and the substrate (EF2). The AlphaLISA p-eEF2 (Thr56) detection assay was developed using a sandwich assay format with two specific antibodies recognizing different epitopes of the target, including one antibody against the phosphorylation site of interest. One anti-eEF2 antibody was conjugated onto AlphaLISA Acceptor beads, while the second antibody was biotinylated and captured by streptavidin coated Donor beads.

Compound was mixed with LN-229 cell lysates in the presence of a kinase buffer (e.g. HEPES) at a pH of 6.6, containing 10 mM Mg$^{2+}$ (e.g. magnesium acetate) and 10 mM adenosine-tri-phosphate (ATP) and incubated at room temperature for 15 minutes. The kinase reaction was stopped with excess ethylenediaminetetraacetic acid disodium salt and the biotinylated-anti phospho eEF2 antibody (3 nM) was added for 1 hour. Then the anti-EF2 acceptor beads (10 µg/ml) as well as the streptavidin coated donor beads (20 µg/ml) were added for 1 hour, and the AlphaLISA signal was measured in an Envision instrument once, left overnight, and measured again for the final read.

EF2K Cell-Based Assay

In this assay, 2.5 mM 2-deoxyglucose was used to deplete intracellular ATP and activate 5' adenosine monophosphate-activated protein kinase (AMPK) in the immortalized epithelial breast cell lines, MCF10A. MCF 10A cells were purchased from ATCC (CRL-10317). This resulted in a rapid activation of eEF2K and an increase in phosphorylation of EF2 at Thr 56, which was determined using a phospho-specific ELISA (AlphaLISA) as described above in the lysate-based EF2k kinase assay.

MCF10A cells are seeded at a density of 1.25×10 5 Cells/ml at 100 µl/well in a 96-well plate and incubated for 24 hours (37° C., 5% CO$_2$). Compound is added for 1 hour, and cell are stimulated with 2.5 mM of 2-deoxy-glucose for 4 hours. Medium is then removed, and cells are lysed in an ice-cold buffer M-PER (Thermo Scientific, 78501), containing protease and phosphatase inhibitors. P-EF2 levels are determined in these lysates using the P-EF2 AlphaLISA described above.

Biochemical Vps34 Lipid Kinase Assay

A non-radiometric kinase assay (ADP-Glo™ Assay, Promega, Madison, Wi, USA) was used for measuring the kinase activity of the PIK3C3 lipid kinase. All kinase assays were performed in 96-well half-area microtiter plates in a 25 µl reaction volume. The reaction cocktail was pipetted in 3 steps in the following order:

10 µl of ATP solution (in assay buffer, see below)
5 µl of test sample in 5% DMSO 10 µl of enzyme/substrate mixture All lipid kinase assays contained 50 mM HEPES (4-(2-hydroxyethyl)-1-piperazineethanesulfonic acid)-NaOH, pH 7.5, 1 mM EGTA ((ethylene glycol tetraacetic acid), 100 mM NaCl, 0.03% CHAPS (3-[(3-Cholamidopropyl)dimethylammonio]-1-propanesulfonate), 2 mM DTT (Dithiothreitol), 20 µM ATP (corresponding to the apparent ATP-Km), kinase (7.6 nM) and substrate (50 µM). The assay for PIK3C3 additionally contained 3 mM MnCl$_2$.

The reaction cocktails were incubated at 30° C. for 60 minutes. The reaction was stopped with 25 µl ADP-Go™ reagent per well. Plates were incubated for 40 minutes at room temperature, followed by addition of 50 μl kinase detection reagent per well and incubation for 60 minutes at room temperature. Signal was determined with a microplate luminescence reader (Victor, Perkin Elmer). The assay was either performed using a single dose of compound (1 μM final concentration in the assay reaction) with resulting data expressed as residual activity compared to control (DMSO), or using a serial (half-log) dilution of compounds starting at 10 μM and down to 0.3 nM (final concentrations in the assay) with data expressed as the pIC50.

The results of the above described assays are shown in table 3:

($pIC_{50}$ is $-\log IC_{50}$ where $IC_{50}$ represents the concentration expressed in M at which the test compound gives 50% inhibition)

| Comp No. | eEF2K_C_alphalisa pIC50 | eEF2K_C_PThr56 pIC50 | VPS34_1microM_% of cntrl | VPS34 pIC50 |
|---|---|---|---|---|
| 1 | 7.12 | 5.53 | | 5.81 |
| 131 | 6.34 | 5.12 | 17.31 | 6.76 |
| 81 | 5.62 | 4.74 | 26.39 | 6.05 |
| 109 | 5.87 | <4.52 | 14.67 | 6.54 |
| 74 | 4.69 | | 20.73 | 6.32 |
| 31 | 6.97 | ~5.4 | 8.47 | 7.06 |
| 75 | <4.52 | <4.52 | 22.86 | 5.86 |
| 82 | 6.47 | <4.52 | 10.75 | 6.39 |
| 114 | 5.35 | 4.63 | 30.76 | |
| 83 | 5.75 | <4.52 | 3.25 | 7.16 |
| 68 | 4.70 | | 28.43 | 6.11 |
| 119 | 6.10 | 5.30 | 15.68 | 6.77 |
| 21 | 5.96 | 5.06 | 23.59 | 6.30 |
| 69 | <4.52 | | 22.76 | 5.65 |
| 30 | 4.83 | | 59.71 | |
| 121 | 4.75 | | 34.10 | |
| 79 | <4.52 | <4.52 | 24.30 | 6.22 |
| 22 | 5.14 | <4.52 | 17.27 | 5.21 |
| 128 | 5.74 | 4.58 | 5.81 | 6.99 |
| 110 | 5.83 | <4.52 | 7.68 | 6.46 |
| 77 | 5.68 | <4.52 | 6.27 | 6.89 |
| 78 | 5.92 | <4.52 | 7.48 | 6.88 |
| 125 | 4.80 | <4.52 | 28.36 | 6.47 |
| 113 | 5.55 | 5.35 | 7.65 | 6.78 |
| 129 | 6.02 | 5.03 | 9.26 | 6.33 |
| 127 | 5.43 | <4.52 | 19.23 | 6.45 |
| 111 | 5.35 | <4.52 | 1.43 | 6.77 |
| 70 | 5.22 | <4.52 | 7.38 | 7.92 |
| 112 | 5.41 | 5.13 | 6.25 | 7.22 |
| 71 | 5.12 | <4.52 | 11.99 | 7.76 |
| 73 | 5.74 | <4.52 | 19.57 | 6.39 |
| 72 | 5.42 | <4.52 | 11.46 | 6.52 |
| 124 | <4.52 | <4.52 | 53.23 | |
| 115 | 6.67 | <4.52 | 6.01 | 6.82 |
| 76 | 6.63 | | 8.71 | 6.46 |
| 130 | <4.52 | <4.52 | 21.02 | 6.62 |
| 123 | 5.06 | <4.52 | 23.62 | 5.41 |
| 23 | 6.30 | 4.65 | 7.45 | 6.82 |
| 120 | 6.76 | 4.84 | 7.29 | 6.92 |
| 29 | 4.76 | <4.52 | 5.67 | 6.70 |
| 118 | 5.10 | <4.52 | 8.10 | 6.85 |
| 28 | ~7.26 | <4.52 | 45.63 | |
| 117 | 6.46 | <4.52 | 11.72 | 6.70 |
| 67 | 6.89 | 5.41 | 32.12 | |
| 64 | 6.14 | 4.58 | 64.60 | |
| 80 | 6.76 | 5.26 | 63.22 | |
| 20 | 5.74 | <4.52 | 8.85 | 6.79 |
| 60 | 6.75 | 5.56 | 6.55 | 7.19 |
| 33 | 6.18 | 4.67 | 23.91 | 6.13 |
| 32 | 6.93 | 5.29 | 11.13 | 6.84 |
| 34 | 6.28 | ~5.14 | | 6.08 |
| 126 | 6.76 | <4.52 | 4.95 | 7.12 |
| 46 | 6.78 | 5.31 | 3.73 | 7.57 |
| 27 | 5.53 | <4.52 | 50.67 | |
| 116 | 5.11 | <4.52 | 14.00 | 6.35 |
| 85 | 5.57 | <4.52 | 47.64 | |
| 56 | 5.39 | 5.35 | 3.19 | 7.90 |
| 7 | 4.86 | <4.52 | 15.08 | 6.80 |
| 7a | 4.86 | <4.52 | 15.08 | 6.80 |
| 9 | ~5.22 | <4.52 | 8.43 | 7.01 |
| 9a | ~5.22 | <4.52 | 8.43 | 7.01 |
| 8 | 4.85 | <4.52 | 41.08 | |
| 8a | 4.85 | <4.52 | 41.08 | |
| 5 | 6.12 | 4.60 | 7.30 | 7.16 |
| 6 | 6.18 | 4.61 | 17.37 | 6.60 |
| 49 | 6.41 | 5.63 | 37.40 | |
| 59 | 6.24 | <4.52 | 3.56 | 7.41 |

-continued

| Comp No. | eEF2K_C_alphalisa pIC50 | eEF2K_C_PThr56 pIC50 | VPS34_1microM_% of cntrl | VPS34 pIC50 |
| --- | --- | --- | --- | --- |
| 25 | 5.54 | <4.52 | 6.36 | 7.11 |
| 24 | ~6.19 | 4.96 | 10.54 | 6.91 |
| 57 | 5.59 | <4.52 | | 6.53 |
| 58 | 6.93 | 5.68 | 15.91 | 6.37 |
| 51 | 6.81 | 4.81 | 14.59 | 6.32 |
| 84 | 6.54 | 5.06 | 30.59 | |
| 54 | 6.04 | <4.52 | 4.02 | 7.07 |
| 50 | 6.95 | 5.31 | 12.43 | 6.40 |
| 87 | 7.40 | 5.70 | 5.21 | 6.72 |
| 10 | 6.44 | 4.89 | 10.75 | 6.54 |
| 15 | 6.22 | 4.56 | 1.07 | 7.30 |
| 13 | 6.40 | 5.17 | 9.00 | 7.06 |
| 18 | 5.72 | <4.52 | 23.39 | 6.04 |
| 17 | 5.96 | <4.52 | 39.48 | |
| 12 | 6.68 | 4.98 | 7.68 | 6.36 |
| 66 | 7.11 | 5.38 | 6.72 | 6.85 |
| 65 | 6.78 | 5.25 | 10.79 | 6.48 |
| 62 | 7.11 | 5.69 | 166.89 | |
| 61 | 5.88 | <4.52 | 6.78 | 7.35 |
| 52 | 6.04 | <4.52 | 12.80 | 6.40 |
| 53 | 7.47 | <4.52 | 13.15 | 6.56 |
| 63 | 6.62 | <4.52 | 16.43 | 6.49 |
| 16 | 5.69 | <4.52 | 15.94 | 6.44 |
| 19 | ~5.8 | <4.52 | 87.11 | |
| 11 | 6.34 | <4.52 | 33.33 | |
| 26 | 4.83 | <4.52 | 5.23 | 6.99 |
| 92 | 7.05 | <4.52 | 38.27 | |
| 47 | >7.52 | 5.34 | 7.88 | 7.08 |
| 48 | 5.26 | <4.52 | 3.34 | 7.37 |
| 55 | 6.84 | <4.52 | | 6.05 |
| 101 | 6.77 | 4.69 | 29.36 | 6.11 |
| 97 | 6.82 | 4.65 | 24.62 | 6.27 |
| 102 | 7.09 | 4.83 | 26.45 | 6.07 |
| 14 | 7.15 | 5.12 | 3.37 | 6.98 |
| 94 | 7.17 | ~4.89 | 14.26 | 6.48 |
| 95 | 6.08 | <4.52 | 18.78 | 6.46 |
| 136 | 6.84 | ~5.07 | 3.08 | 7.78 |
| 137 | 5.71 | <4.52 | 8.17 | 7.09 |
| 88 | 8.11 | 6.02 | 17.99 | 6.19 |
| 86 | 5.31 | <4.52 | 7.25 | 7.11 |
| 98 | 6.83 | 4.56 | 33.92 | |
| 103 | 6.71 | 4.73 | 28.28 | 6.17 |
| 108 | 6.68 | 4.61 | 25.46 | 6.28 |
| 132 | 7.16 | 5.40 | 7.12 | 6.72 |
| 106 | 6.52 | 4.78 | 36.34 | |
| 107 | 6.49 | <4.52 | 32.68 | |
| 89 | ~5.2 | <4.52 | 13.56 | 7.33 |
| 91 | 7.93 | 5.85 | | 5.29 |
| 90 | 5.03 | <4.52 | 15.81 | 6.68 |
| 96 | 8.17 | 5.90 | | 6.88 |
| 4 | 7.08 | 5.06 | 29.31 | 6.32 |
| 3 | 5.78 | <4.52 | 4.43 | 7.17 |
| 2 | 7.20 | 5.24 | 4.44 | 7.00 |
| 104 | 4.75 | <4.52 | 25.12 | 6.52 |
| 105 | 7.06 | 4.75 | 28.59 | 6.01 |
| 99 | 5.62 | <4.52 | | 5.82 |
| 100 | 7.19 | 4.83 | 43.01 | |
| 45 | 8.10 | 6.66 | | 6.78 |
| 133 | 5.59 | <5 | 14.64 | 6.83 |
| 35 | 8.03 | 6.88 | | 7.11 |
| 36 | 7.36 | 5.88 | 16.04 | 6.47 |
| 37 | 8.12 | 6.74 | | 7.02 |
| 41 | ~6.35 | 5.75 | 30.81 | |
| 42 | 7.49 | 6.37 | 10.21 | 6.52 |
| 134 | 5.89 | <5 | 4.78 | 7.19 |
| 38 | 8.05 | 6.73 | | 7.11 |
| 39 | 5.92 | 5.51 | 30.67 | |
| 40 | 6.87 | ~6.09 | 17.70 | 6.65 |
| 43 | 8.21 | 6.72 | 4.32 | 6.97 |
| 44 | 7.07 | 5.62 | 10.20 | 6.52 |

Composition Examples

"Active ingredient" (a.i.) as used throughout these examples relates to a compound of Formula (I), including any tautomer or stereoisomeric form thereof, or a pharmaceutically acceptable addition salt or a solvate thereof; in particular to any one of the exemplified compounds.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:

1. A compound of Formula (I)

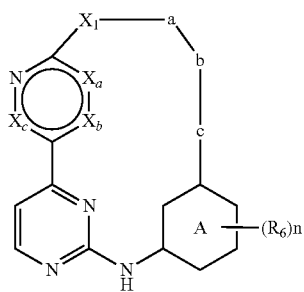

a tautomer or a stereoisomeric form thereof, wherein 
$X_a$, $X_b$ and $X_c$ each independently represent CH or N; 
—$X_1$— represents —$(CHR_{12})_s$—$NR_1$—$X_e$—$C_{1-4}$alkanediyl-$(SO_2)_{p3}$—;
wherein said $C_{1-4}$alkanediyl moiety is optionally substituted with hydroxyl or hydroxyC$_{1-4}$alkyl;
—$X_e$— represents —$C(R_2)_2$— or —C(=O)—;
a represents —$NR_4$—C(=O)—[C($R_{5b}$)$_2$]$_1$— or —$NR_4$—C($R_{5b}$)$_2$—C(=O)— or —C(=O)—$NR_4$—C($R_{5b}$)$_2$—;
b represents

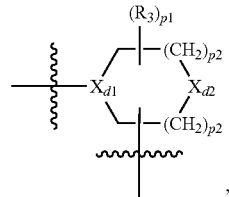

wherein said b ring may contain extra bonds to form a bridged ring system selected from 2,5-diazabicyclo[2.2.2]octanyl, 3, 8- diazabicyclo[3.2.1]octanyl, 3,6-diazabicyclo[3.1.1]heptanyl, 3, 9- diazabicyclo[3.3.1]nonyl;
$X_{d1}$ represents CH or N;
$X_{d2}$ represents CH$_2$ or NH;
provided that at least one of $X_{d1}$ and $X_{d2}$ represents nitrogen;
c represents a bond, —[C($R_{5a}$)$_2$]$_m$—, —C(=O)—, —O—, —$NR_{5a}$—, —$SO_2$—, or —SO—;
ring

represents phenyl;
$R_1$ represents $C_{2-4}$alkenyl, $C_{2-4}$alkynyl, cyanoC$_{1-4}$alkyl, —C(=O)—C$_{1-4}$alkyl, —C(=O)-haloC$_{1-4}$alkyl, hydroxyC$_{1-4}$alkyl, haloC$_{1-4}$alkyl, C$_{1-4}$alkyloxyC$_{1-4}$alkyl, haloC$_{1-4}$alkyloxyC$_{1-4}$alkyl, —C(=O)NR$_7$R$_8$, —SO$_2$—NR$_7$R$_8$, —SO$_2$—R$_9$, R$_{11}$, C$_{1-4}$alkyl substituted with R$_{11}$, —C(=O)—R$_{11}$, or —C(=O)—C$_{1-4}$alkyl-R$_{11}$;
each $R_2$ independently represents hydrogen, C$_{1-4}$alkyl, C$_{1-4}$alkyl substituted with C$_{3-6}$cycloalkyl, hydroxyC$_{1-4}$alkyl, C$_{1-4}$alkyloxyC$_{1-4}$alkyl, carboxyl, —C(=O)—O—C$_{1-4}$alkyl wherein C$_{1-4}$alkyl is optionally substituted with C$_{1-4}$alkyloxy, —C(=O)—NH$_2$, —C(=O)—NH(C$_{1-4}$alkyl) wherein C$_{1-4}$alkyl is optionally substituted with C$_{1-4}$alkyloxy, or —C(=O)—N(C$_{1-4}$alkyl)$_2$ wherein each C$_{1-4}$alkyl is optionally substituted with C$_{1-4}$alkyloxy;
or $R_1$ and one $R_2$ are taken together to form C$_{1-4}$alkanediyl or C$_{2-4}$alkenediyl, each of said C$_{1-4}$alkanediyl and C$_{2-4}$alkenediyl optionally being substituted with 1 to 4 substituents each independently selected from hydroxyl, oxo, halo, cyano, N$_3$, hydroxyC$_{1-4}$alkyl, —NR$_7$R$_8$, —SO$_2$—NR$_7$R$_8$, —NH—SO$_2$—NR$_7$R$_8$, —C(=O)—NR$_7$R$_8$, or —NH—C(=O)—NR$_7$R$_8$;
or $R_1$ and $R_{12}$ are taken together to form C$_{1-4}$alkanediyl or C$_{2-4}$alkenediyl, each of said C$_{1-4}$alkanediyl and C$_{2-4}$alkenediyl optionally being substituted with 1 to 4 substituents each independently selected from hydroxyl, oxo, halo, cyano, N$_3$, hydroxyC$_{1-4}$alkyl, —NR$_7$R$_8$, —SO$_2$—NR$_7$R$_8$, —NH—SO$_2$—NR$_7$R$_8$, —C(=O)—NR$_7$R$_8$, or —NH—C(=O)—NR$_7$R$_8$;
each $R_3$ independently represents hydrogen; oxo; hydroxyl; carboxyl; —NR$_{3a}$R$_{3b}$; —C(=O)—NR$_{3a}$R$_{3b}$; hydroxyC$_{1-4}$alkyl; haloC$_{1-4}$alkyl; —(C=O)—C$_{1-4}$alkyl; —C(=O)—O—C$_{1-4}$alkyl wherein said C$_{1-4}$alkyl may optionally be substituted with phenyl; C$_{1-4}$alkyl optionally substituted with cyano, carboxyl, C$_{1-4}$alkyloxy, —C(=O)—O—C$_{1-4}$alkyl, —O—C(=O)—C$_{1-4}$alkyl, —NR$_{3e}$R$_{3f}$, —C(=O)—NR$_{3e}$R$_{3f}$, —SO$_2$—NR$_{3e}$R$_{3f}$, Q, —C(=O)-Q, or —SO$_2$-Q; hydroxyC$_{1-4}$alkyloxyC$_{1-4}$alkyl; C$_{1-4}$alkyloxyhydroxyC$_{1-4}$alkyl; or C$_{1-4}$alkyloxyC$_{1-4}$alkyl optionally substituted with cyano, carboxyl, C$_{1-4}$alkyloxy, —C(=O)—O—C$_{1-4}$alkyl, —O—C(=O)—C$_{1-4}$alkyl, —NR$_{3e}$R$_{3f}$, —C(=O)—NR$_{3e}$R$_{3f}$, —SO$_2$—NR$_{3e}$R$_{3f}$, R$_{10}$, —C(=O)—R$_{10}$, or —SO$_2$—R$_{10}$;

or two R$_3$ substituents attached to the same carbon atom are taken together to form C$_{2-5}$alkanediyl or —(CH$_2$)$_p$—O—(CH$_2$)$_p$—;

each R$_{3a}$ and R$_{3b}$ independently represent hydrogen; —(C=O)—C$_{1-4}$alkyl; —SO$_2$—NR$_{3c}$R$_{3d}$; or C$_{1-4}$alkyl optionally substituted with C$_{1-4}$alkyloxy; or R$_{3a}$ and R$_{3b}$ are taken together with the nitrogen to which they are attached to form a 4 to 7 membered saturated monocyclic heterocyclic ring which optionally contains 1 or 2 further heteroatoms selected from N, O or SO$_2$, said heterocyclic ring being optionally substituted with 1 to 4 substituents each independently selected from C$_{1-4}$alkyl, halo, hydroxyl, or haloC$_{1-4}$alkyl;

each R$_{3c}$ and R$_{3d}$ independently represent hydrogen, C$_{1-4}$alkyl or —(C=O)—C$_{1-4}$alkyl; or R$_{3c}$ and R$_{3d}$ are taken together with the nitrogen to which they are attached to form a 4 to 7 membered saturated monocyclic heterocyclic ring which optionally contains 1 or 2 further heteroatoms selected from N, O or SO$_2$, said heterocyclic ring being optionally substituted with 1 to 4 substituents each independently selected from C$_{1-4}$alkyl, halo, hydroxyl, or haloC$_{1-4}$alkyl;

each R$_{3e}$ and R$_{3f}$ independently represent hydrogen, C$_{1-4}$alkyl optionally substituted with C$_{1-4}$alkyloxy, —(C=O)—C$_{1-4}$alkyl, or —SO$_2$—NR$_{3c}$R$_{3d}$;

R$_4$ represents hydrogen, C$_{1-4}$alkyl or C$_{1-4}$alkyloxyC$_{1-4}$alkyl;

each R$_{5a}$ independently represents hydrogen or C$_{1-4}$alkyl; or two R$_{5a}$ substituents attached to the same carbon atom are taken together to form C$_{2-5}$alkanediyl or —(CH$_2$)$_p$—O—(CH$_2$)$_p$—;

R$_{5a'}$ represents hydrogen or C$_{1-4}$alkyl;

each R$_{5b}$ independently represents hydrogen; C$_{1-4}$alkyl; C$_{1-4}$alkyl substituted with NR$_{5b1}$R$_{5b2}$; C$_{1-4}$alkyloxyC$_{1-4}$alkyl; hydroxyC$_{1-4}$alkyl; hydroxyl; C$_{3-6}$cycloalkyl; or phenyl optionally substituted with C$_{1-4}$alkyl, halo, hydroxyl or C$_{1-4}$alkyloxy; or two R$_{5b}$ substituents attached to the same carbon atom are taken together to form C$_{2-5}$alkanediyl or —(CH$_2$)$_p$—O—(CH$_2$)$_p$—;

R$_{5b1}$ and R$_{5b2}$ independently represent hydrogen, C$_{1-4}$alkyl optionally substituted with C$_{1-4}$alkyloxy, —(C=O)—C$_{1-4}$alkyl, or —SO$_2$—NR$_{5b3}$R$_{5b4}$;

R$_{5b3}$ and R$_{5b4}$ independently represent hydrogen, C$_{1-4}$alkyl or —(C=O)—C$_{1-4}$alkyl; or R$_{5b3}$ and R$_{5b4}$ are taken together with the nitrogen to which they are attached to form a 4 to 7 membered saturated monocyclic heterocyclic ring which optionally contains 1 or 2 further heteroatoms selected from N, O or SO$_2$, said heterocyclic ring being optionally substituted with 1 to 4 substituents each independently selected from C$_{1-4}$alkyl, halo, hydroxyl, or haloC$_{1-4}$alkyl;

each R$_6$ independently represents hydrogen, halo, hydroxyl, carboxyl, cyano, C$_{1-4}$alkyl, C$_{1-4}$alkyloxyC$_{1-4}$alkyl, hydroxyC$_{1-4}$alkyl, haloC$_{1-4}$alkyl, C$_{2-4}$alkenyl, C$_{2-4}$alkynyl, —NR$_{6a}$R$_{6b}$, or —C(=O)NR$_{6a}$R$_{6b}$;

each R$_{6a}$ and R$_{6b}$ independently represent hydrogen or C$_{1-4}$alkyl;

each R$_7$ and R$_8$ independently represent hydrogen, C$_{1-4}$alkyl, haloC$_{1-4}$alkyl, or C$_{3-6}$cycloalkyl; or R$_7$ and R$_8$ are taken together with the nitrogen to which they are attached to form a 4 to 7 membered saturated monocyclic heterocyclic ring which optionally contains 1 further heteroatom selected from N, O or SO$_2$, said heterocyclic ring being optionally substituted with 1 to 4 substituents each independently selected from C$_{1-4}$alkyl, halo, hydroxyl, or haloC$_{1-4}$alkyl;

R$_9$ represents C$_{1-4}$alkyl, haloC$_{1-4}$alkyl, or C$_{3-6}$cycloalkyl;

each R$_{10}$ independently represents a 4 to 7 membered saturated monocyclic heterocyclic ring containing up to 2 heteroatoms selected from N, O or SO$_2$, said heterocyclic ring being optionally substituted with 1 to 4 substituents each independently selected from C$_{1-4}$alkyl, halo, hydroxyl or haloC$_{1-4}$alkyl;

each R$_{11}$ independently represents C$_{3-6}$cycloalkyl, phenyl, or a 4 to 7 membered monocyclic heterocyclic ring containing up to 3 heteroatoms selected from N, O or SO$_2$, said heterocyclic ring being optionally substituted with 1 to 4 substituents each independently selected from C$_{1-4}$alkyl, halo, hydroxyl, or haloC$_{1-4}$alkyl;

each R$_{12}$ independently represents hydrogen or C$_{1-4}$alkyl;

Q represents a 4 to 7 membered saturated monocyclic heterocyclic ring containing up to 3 heteroatoms selected from N, O or SO$_2$, said heterocyclic ring being optionally substituted with 1 to 4 substituents each independently selected from C$_{1-4}$alkyl, halo, hydroxyl or haloC$_{1-4}$alkyl;

n represents an integer of value 1 or 2;
m represents an integer of value 1 or 2;
p represents an integer of value 1 or 2;
p1 represents an integer of value 1 or 2;
each p2 independently represents an integer of value 0, 1 or 2;
r represents an integer of value 0, 1 or 2;
each p3 independently represents an integer of value 0 or 1;
each s independently represents an integer of value 0, 1 or 2;
or a N-oxide, or a pharmaceutically acceptable addition salt thereof.

2. The compound according to claim 1, wherein
X$_a$, X$_b$ and X$_c$ each independently represent CH or N;
—X$_1$— represents —(CHR$_{12}$)$_s$—NR$_1$—X$_e$—C$_{1-4}$alkanediyl-(SO$_2$)$_{p3}$—; wherein said C$_{1-4}$alkanediyl moiety is optionally substituted with hydroxyl or hydroxyC$_{1-4}$alkyl;
—X$_e$— represents —C(R$_2$)$_2$— or —C(=O)—;
a represents —NR$_4$—C(=O)—[C(R$_{5b}$)$_2$]$_1$— or —NR$_4$—C(R$_{5b}$)$_2$—C(=O)—;
b represents

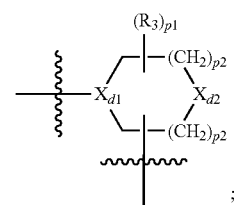

X$_{d1}$ represents CH or N; X$_{d2}$ represents NH;

c represents a bond, —[C(R$_{5a}$)$_2$]$_m$—, —C(=O)—, —SO$_2$—, or —SO—;
ring

represents phenyl;

R$_1$ represents C$_{2-4}$alkenyl, C$_{2-4}$alkynyl, cyanoC$_{1-4}$alkyl, —C(=O)—C$_{1-4}$alkyl, —C(=O)-haloC$_{1-4}$alkyl, hydroxyC$_{1-4}$alkyl, haloC$_{1-4}$alkyl, C$_{1-4}$alkyloxyC$_{1-4}$alkyl, haloC$_{1-4}$alkyloxyC$_{1-4}$alkyl, —C(=O)NR$_7$R$_8$, —SO$_2$—NR$_7$R$_8$, —SO$_2$—R$_9$, R$_{11}$, C$_{1-4}$alkyl substituted with R$_{11}$, —C(=O)—R$_{11}$, or —C(=O)—C$_{1-4}$alkyl-R$_{11}$;

R$_2$ is hydrogen;
or R$_1$ and one R$_2$ are taken together to form C$_{1-4}$alkanediyl or C$_{2-4}$alkenediyl, each of said C$_{1-4}$alkanediyl and C$_{2-4}$alkenediyl optionally being substituted with 1 to 4 hydroxyl substituents;

each R$_3$ independently represents hydrogen; oxo; hydroxyl; carboxyl; —NR$_{3a}$R$_{3b}$; —C(=O)—NR$_{3a}$R$_{3b}$; hydroxyC$_{1-4}$alkyl; haloC$_{1-4}$alkyl; —(C=O)—C$_{1-4}$ alkyl;
—C(=O)—O—C$_{1-4}$alkyl wherein said C$_{1-4}$alkyl may optionally be substituted with phenyl;
C$_{1-4}$alkyl optionally substituted with cyano, carboxyl, C$_{1-4}$alkyloxy, —C(=O)—O—C$_{1-4}$alkyl, —O—C(=O)—C$_{1-4}$alkyl, —NR$_{3e}$R$_{3f}$, —C(=O)—NR$_{3e}$R$_{3f}$, or —SO$_2$—NR$_{3e}$R$_{3f}$; hydroxyC$_{1-4}$alkyloxyC$_{1-4}$alkyl; C$_{1-4}$alkyloxyhydroxyC$_{1-4}$alkyl;
hydroxyC$_{1-4}$alkyloxyhydroxyC$_{1-4}$alkyl; or
C$_{1-4}$alkyloxyC$_{1-4}$alkyl optionally substituted with cyano, carboxyl, C$_{1-4}$alkyloxy, —C(=O)—O—C$_{1-4}$alkyl, —O—C(=O)—C$_{1-4}$alkyl, —NR$_{3e}$R$_{3f}$, —C(=O)—NR$_{3e}$R$_{3f}$, —SO$_2$—NR$_{3e}$R$_{3f}$, R$_{10}$, —C(=O)—R$_{10}$, or —SO$_2$—R$_{10}$;

each R$_{3a}$ and R$_{3b}$ independently represent hydrogen;
each R$_{3e}$ and R$_{3f}$ independently represent hydrogen, C$_{1-4}$alkyl optionally substituted with C$_{1-4}$alkyloxy, or —(C=O)—C$_{1-4}$alkyl;

R$_4$ represents hydrogen, C$_{1-4}$alkyl or C$_{1-4}$alkyloxy C$_{1-4}$alkyl;

each R$_{5a}$ independently represents hydrogen;
each R$_{5b}$ independently represents hydrogen; C$_{1-4}$alkyl; C$_{1-4}$alkyloxyC$_{1-4}$alkyl;
hydroxyC$_{1-4}$alkyl; hydroxyl; C$_{3-6}$cycloalkyl; or phenyl optionally substituted with C$_{1-4}$alkyl, halo, hydroxyl or C$_{1-4}$alkyloxy;

each R$_6$ independently represents hydrogen, halo, hydroxyl, carboxyl, cyano, C$_{1-4}$alkyl, C$_{1-4}$alkyloxy C$_{1-4}$alkyl, hydroxyC$_{1-4}$alkyl, haloC$_{1-4}$alkyl, C$_{2-4}$alkenyl, C$_{2-4}$alkynyl,
—NR$_{6a}$R$_{6b}$, or —C(=O)NR$_{6a}$R$_{6b}$;

each R$_{6a}$ and R$_{6b}$ independently represent hydrogen or C$_{1-4}$alkyl;

each R$_7$ and R$_8$ independently represent hydrogen; or
R$_7$ and R$_8$ are taken together with the nitrogen to which they are attached to form a 4 to 7 membered saturated monocyclic heterocyclic ring which optionally contains 1 further heteroatom selected from N, O or SO$_2$, said heterocyclic ring being optionally substituted with 1 to 4 substituents each independently selected from C$_{1-4}$alkyl, halo, hydroxyl, or haloC$_{1-4}$alkyl;

R$_9$ represents C$_{1-4}$alkyl or haloC$_{1-4}$alkyl;
each R$_{10}$ independently represents a 4 to 7 membered saturated monocyclic heterocyclic ring containing up to 2 heteroatoms selected from N or O, said heterocyclic ring being optionally substituted with 1 to 4 substituents each independently selected from C$_{1-4}$alkyl, halo, hydroxyl or haloC$_{1-4}$alkyl;

each R$_{11}$ independently represents C$_{3-6}$cycloalkyl, phenyl, or a 4 to 7 membered monocyclic heterocyclic ring containing up to 3 heteroatoms selected from N or O, said heterocyclic ring being optionally substituted with 1 to 4 substituents each independently selected from C$_{1-4}$alkyl, halo, hydroxyl, or haloC$_{1-4}$alkyl;

each R$_{12}$ independently represents hydrogen;
n represents an integer of value 1 or 2;
m represents an integer of value 1 or 2;
p1 represents an integer of value 1 or 2;
each p2 independently represents an integer of value 0, 1 or 2;
r represents an integer of value 1;
each p3 independently represents an integer of value 0 or 1;
each s independently represents an integer of value 0, 1 or 2.

3. The compound according to claim 1, wherein
X$_a$ is CH or N;
X$_b$ and X$_c$ represent CH;
—X$_1$— represents —(CHR$_{12}$)$_s$x—NR$_1$—X$_e$—C$_{1-4}$alkanediyl-(SO$_2$)$_{p3}$—; wherein said C$_{1-4}$alkanediyl moiety is optionally substituted with hydroxyl;
—X$_e$— represents —C(R$_2$)$_2$— or —C(=O)—;
a represents —NR$_4$—C(=O)—[C(R$_{5b}$)$_2$]$_1$— or —NR$_4$—C(R$_{5b}$)$_2$—C(=O)—;
b represents

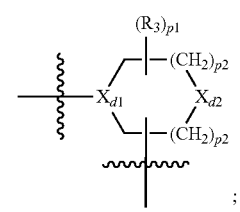

X$_{d1}$ represents CH or N;
X$_{d2}$ represents CH$_2$ or NH;
provided that at least one of X$_{d1}$ and X$_{d2}$ represents nitrogen;
c represents a bond —[C(R$_{5a}$)$_2$]$_m$—, —C(=O)—, or —SO$_2$—;
ring

represents phenyl;
R$_1$ represents C$_{2-4}$alkenyl, C$_{2-4}$alkynyl, cyanoC$_{1-4}$alkyl, —C(=O)-haloC$_{1-4}$alkyl, C$_{1-4}$alkyloxyC$_{1-4}$alkyl, haloC$_{1-4}$alkyloxyC$_{1-4}$alkyl, —SO$_2$—NR$_7$R$_8$, —SO$_2$—R$_9$, C$_{1-4}$alkyl substituted with R$_{11}$, or —C(=O)—R$_{11}$;
each R$_2$ independently represents hydrogen;

or $R_1$ and one $R_2$ are taken together to form $C_{1-4}$alkanediyl optionally being substituted with 1 hydroxyl substituent;

each $R_3$ independently represents hydrogen; oxo; hydroxyl; —C(=O)—$NR_{3a}R_{3b}$; hydroxy$C_{1-4}$alkyl; halo$C_{1-4}$alkyl; —C(=O)—O—$C_{1-4}$alkyl wherein said $C_{1-4}$alkyl may optionally be substituted with phenyl; $C_{1-4}$alkyl optionally substituted with —O—C(=O)—$C_{1-4}$alkyl; hydroxy$C_{1-4}$alkyloxy$C_{1-4}$alkyl; or $C_{1-4}$alkyloxy$C_{1-4}$alkyl optionally substituted with cyano, $C_{1-4}$alkyloxy, —$NR_{3e}R_{3f}$, or $R_{10}$;

$R_{3a}$ and $R_{3b}$ represent hydrogen;
$R_{3e}$ and $R_{3f}$ represent $C_{1-4}$alkyl;
$R_4$ represents hydrogen, $C_{1-4}$alkyl or $C_{1-4}$alkyloxy $C_{1-4}$alkyl;
$R_{5a}$ represents hydrogen;
each $R_{5b}$ independently represents hydrogen; $C_{1-4}$alkyl; $C_{1-4}$alkyloxy$C_{1-4}$alkyl;
hydroxy$C_{1-4}$alkyl; or phenyl;
each $R_6$ independently represents hydrogen, halo, hydroxyl, carboxyl, cyano, $C_{1-4}$alkyl,
or —C(=O)$NR_{6a}R_{6b}$;
each $R_{6a}$ and $R_{6b}$ independently represent hydrogen or $C_{1-4}$alkyl;
$R_7$ and $R_8$ represent hydrogen;
$R_9$ represents $C_{1-4}$alkyl;
each $R_{10}$ independently represents a 4 to 7 membered saturated monocyclic heterocyclic ring containing up to 2 heteroatoms selected from N or O, said heterocyclic ring being optionally substituted with 1 $C_{1-4}$alkyl substituent;
each $R_{11}$ independently represents $C_{3-6}$cycloalkyl, or a 4 to 7 membered monocyclic heterocyclic ring containing up to 3 oxygen atoms;
each $R_{12}$ independently represents hydrogen;
n represents an integer of value 1;
m represents an integer of value 1 or 2;
p1 represents an integer of value 1;
each p2 independently represents an integer of value 1 or 2;
r represents an integer of value 0 or 1;
each p3 independently represents an integer of value 0;
each s independently represents an integer of value 0 or 1.

4. The compound according to claim 1, wherein $X_a$, $X_b$ and $X_c$ represent CH;
—$X_1$— represents —(CHR$_{12}$)$_s$—NR$_1$—$X_e$—$C_{1-4}$alkanediyl-;
—$X_e$— represents —C(R$_2$)$_2$—;
a represents —NR$_4$—C(=O)—[C(R$_{5b}$)$_2$]$_1$— or —NR$_4$—C(R$_{5b}$)$_2$—C(=O)—;
b represents

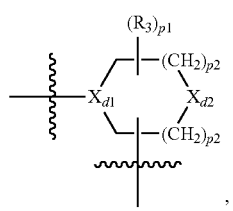

provided that the linker with the 'a substituent' is present on $X_{d2}$ or is present on a carbon atom in the alpha position of $X_{d2}$;
c represents CH$_2$ or a bond.

5. The compound according to claim 1, wherein $X_a$, $X_b$ and $X_c$ are CH;
—$X_1$— represents —CH$_2$—NR$_1$—CH$_2$—$C_{1-4}$alkanediyl-, —NR$_1$—CH$_2$—$C_{2-4}$alkanediyl-, or —$X_1$— represents one of the following groups wherein —(CH$_2$)$_2$— is attached to 'variable a':

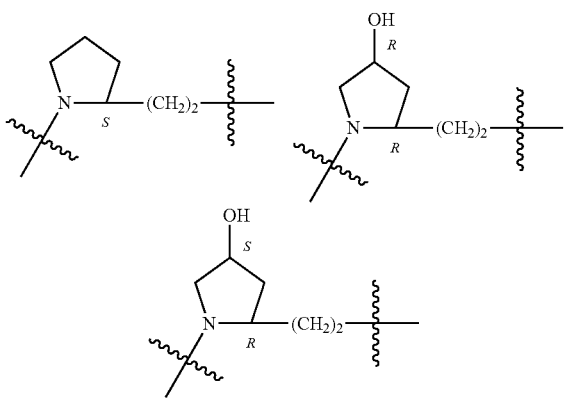

$R_1$ represents $C_{2-4}$alkenyl, $C_{2-4}$alkynyl, $C_{1-4}$alkyloxy $C_{1-4}$alkyl;
a represents —NR$_4$—C(=O)—CH$_2$—;
b represents

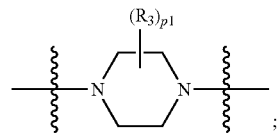

p1 is 1;
$R_3$ represents hydrogen; $C_{1-4}$alkyloxy$C_{1-4}$alkyl optionally substituted with cyano; or
hydroxy$C_{1-4}$alkyloxy$C_{1-4}$alkyl;
c is CH$_2$; and
$R_6$ represents H.

6. The compound according to claim 1, wherein if $R_1$ is taken together with one $R_2$, the bond towards the second $R_2$ substituent is oriented as shown hereunder:

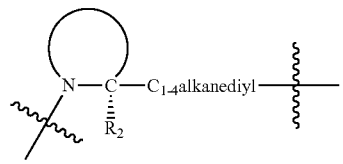

7. The compound according to claim 1, wherein b represents

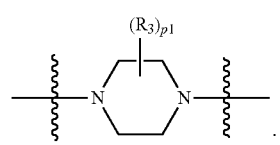

8. The compound according to claim 1, wherein
R$_1$ represents C$_{2-4}$alkenyl, C$_{2-4}$alkynyl, cyanoC$_{1-4}$alkyl, —C(=O)—C$_{1-4}$alkyl, —C(=O)-haloC$_{1-4}$alkyl, hydroxyC$_{1-4}$alkyl, haloC$_{1-4}$alkyl, C$_{1-4}$alkyloxyC$_{1-4}$alkyl, haloC$_{1-4}$alkyloxyC$_{1-4}$alkyl, —C(=O)NR$_7$R$_8$, —SO$_2$—NR$_7$R$_8$, —SO$_2$—R$_9$, R$_{11}$, C$_{1-4}$alkyl substituted with Rut, —C(=O)—R$_{11}$, or —C(=O)—C$_{1-4}$alkyl-R$_{11}$;

R$_2$ is hydrogen;

or R$_1$ and one R$_2$ are taken together to form C$_{3-4}$alkanediyl or C$_{3-4}$alkenediyl, each of said C$_{3-4}$alkanediyl and C$_{3-4}$alkenediyl optionally being substituted with 1 to 4 hydroxyl substituents.

9. The compound according to claim 1, wherein
a represents —NR$_4$—C(=O)—[C(R$_{5b}$)$_2$]—.

10. The compound according to claim 1 wherein c is CH$_2$.

11. The compound according to claim 1, wherein X$_a$, X$_b$ and X$_c$ represent CH.

12. A pharmaceutical composition comprising a pharmaceutically acceptable carrier and, as active ingredient, a therapeutically effective amount of a compound according to claim 1.

\* \* \* \* \*